US009120804B2

(12) United States Patent
Deutsch et al.

(10) Patent No.: US 9,120,804 B2
(45) Date of Patent: Sep. 1, 2015

(54) 8-SUBSTITUTED 2-AMINO-[1,2,4] TRIAZOLO [1, 5-A] PYRAZINES AS SYK TRYROSINE KINASE INHIBITORS AND GCN2 SERIN KINASE INHIBITORS

(71) Applicant: Merck Patent GmbH, Darmstadt (DE)

(72) Inventors: Carl Deutsch, Darmstadt (DE); Daniel Kuhn, Rossdorf (DE); Tatjana Ross, Eschborn (DE); Lars Burgdorf, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/379,316

(22) PCT Filed: Jan. 22, 2013

(86) PCT No.: PCT/EP2013/000189

§ 371 (c)(1),
(2) Date: Aug. 18, 2014

(87) PCT Pub. No.: WO2013/124026

PCT Pub. Date: Aug. 29, 2013

(65) Prior Publication Data

US 2015/0025058 A1 Jan. 22, 2015

(30) Foreign Application Priority Data

Feb. 21, 2012 (EP) .................................... 12001153

(51) Int. Cl.

| | |
|---|---|
| ***A61K 31/536*** | (2006.01) |
| ***A61K 31/4985*** | (2006.01) |
| ***C07D 273/01*** | (2006.01) |
| ***C07D 265/14*** | (2006.01) |
| ***C07D 487/04*** | (2006.01) |
| ***C07D 519/00*** | (2006.01) |
| ***A61K 31/496*** | (2006.01) |
| ***A61K 31/519*** | (2006.01) |
| ***A61K 31/537*** | (2006.01) |
| ***A61K 31/5377*** | (2006.01) |
| ***A61K 31/5386*** | (2006.01) |
| ***A61K 31/55*** | (2006.01) |
| ***A61K 31/5513*** | (2006.01) |

(52) U.S. Cl.

CPC ............ *C07D 487/04* (2013.01); *A61K 31/496* (2013.01); *A61K 31/519* (2013.01); *A61K 31/537* (2013.01); *A61K 31/5377* (2013.01); *A61K 31/5386* (2013.01); *A61K 31/55* (2013.01); *A61K 31/5513* (2013.01); *C07D 519/00* (2013.01)

(58) Field of Classification Search

CPC ............. A61K 31/536; A61K 31/4985; C07D 273/01; C07D 265/14

See application file for complete search history.

(56) References Cited

U.S. PATENT DOCUMENTS

| | | | | |
|---|---|---|---|---|
| 8,609,687 | B2 | 12/2013 | Zhu et al. | |
| 2010/0048557 | A1 | 2/2010 | Zhu et al. | |
| 2011/0190269 | A1 * | 8/2011 | Baumann et al. | 514/217.07 |
| 2012/0135981 | A1 | 5/2012 | Wu et al. | |
| 2012/0225855 | A1 | 9/2012 | Zhu et al. | |
| 2012/0295891 | A1 | 11/2012 | Van Brandt et al. | |
| 2012/0295901 | A1 | 11/2012 | De Cleyn et al. | |
| 2013/0225568 | A1 | 8/2013 | Burgdorf et al. | |
| 2014/0038939 | A1 | 2/2014 | Zhu et al. | |

FOREIGN PATENT DOCUMENTS

| | | | |
|---|---|---|---|
| WO | 2009155551 | A1 | 12/2009 |
| WO | 2011006903 | A1 | 1/2011 |
| WO | 2011086098 | A1 | 7/2011 |
| WO | 2011086099 | A1 | 7/2011 |
| WO | 2012025186 | A1 | 3/2012 |

OTHER PUBLICATIONS

International Search Report from PCT/EP2013/000189 dated Apr. 12, 2013.

Wermuth, Camille G. “Molecular Variations Based on Isosteric Replacements” Practice of Medicinal Chemistry, [1996], pp. 203-237.

* cited by examiner

*Primary Examiner* — Samantha Shterengarts

(74) *Attorney, Agent, or Firm* — Millen, White, Zelano & Branigan, P.C.

(57) ABSTRACT

Compounds of the formula I

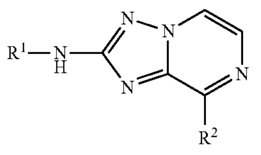

I in which $R^1$, $R^2$ and $R^4$ have the meanings indicated in Claim 1, are inhibitors of Syk, and can be employed, inter alia, for the treatment of cancer, rheumatoid arthritis and/or systemic lupus.

4 Claims, No Drawings

8-SUBSTITUTED 2-AMINO-[1,2,4] TRIAZOLO [1, 5-A] PYRAZINES AS SYK TRYROSINE KINASE INHIBITORS AND GCN2 SERIN KINASE INHIBITORS

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of signal transduction by kinases, in particular tyrosine kinases, furthermore to pharmaceutical compositions which comprise these compounds, and to the use of the compounds for the treatment of kinase-induced diseases.

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

One of the key events in the signaling pathway following the activation of mast cells is activation of the tyrosine kinase Syk. Mast cells play a critical role in asthma and allergic disorders by releasing pro-inflammatory mediators and cytokines. Antigen-mediated aggregation of FcεRJ, the high-affinity receptor for IgE, results in activation of mast cells. This triggers a series of signaling events resulting in the release of mediators, including histamine, proteases, leukotrienes and cytokines. These mediators cause increased vascular permeability, mucus production, bronchoconstriction, tissue degradation and inflammation, thus playing key roles in the etiology and symptoms of asthma and allergic disorders. Syk kinase acts as a central initiator of all subsequent signaling leading to mediator release. The critical role of Syk kinase in the signaling path was demonstrated by the complete inhibition of mediator release by a protein containing the SH2 domains of Syk kinase that functioned as an inhibitor of Syk kinase (J. A. Taylor et al, Molec. and Cell Biol, 15: 4149-4157 (1995).

Syk (Spleen-Tyrosine-Kinase) is a 72 kDa non-receptor tyrosine kinase belonging to the subfamily of intracellular tyrosine kinases that comprises ZAP70, Pyk2, Abl, Tie2, KDR and HER, among others. Syk is a major regulator of FcR (FcγRI, II, III, FcεRI, FcαR) and BCR signaling and is expressed throughout hematopoietic lineage, as well as in fibroblasts, osteoclasts, hepatocytes, epithelial and neuronal cells. In addition to the C terminal kinase domain, SYK exhibits two SH2 domains and over 10 autophosphorylation sites[1].

By means of both its SH2 domains SYK is specifically recruited to phosphorylated ITAMs (Immunoreceptor Tyrosine-based Activation Motifs present in immunoreceptors such as FcγRI, IIA, IIIA, FcαR, FcεRI and BCR, expressed by monocytes, macrophages, mast cells, neutrophils and B cells) and specifically mediates immunoreceptor signaling triggered by activation of those receptors in mast cells, B cells, macrophages, monocytes, neutrophils, eosinophils, NK cells, DC cells platelets and osteoclasts[1,2].

Upon BCR cross linking, tyrosine residues at the ITAM motifs of the cytosolic tail of the Igα/Igβ are phosphorylated by the Src-family kinase Lyn, generating docking sites for SYK that is thus recruited to the BCR immunocomplex. SYK is then phosphorylated and activated by the Src-family kinase Lyn. Upon activation, SYK will phosphorylate the adaptor protein BLNK allowing its interaction with both BTK and $PLC\gamma_2$ via their respective SH2 domains. SYK phosphorylated—and thus activated—BTK will in turn phosphorylate and activate $PLC\gamma_2$ leading to $IP_3$ formation, $Ca^{2+}$ mobilization, PKC and MAPK activation and consequent NFAT, AP-1 and NFκB transcription factor activation, resulting in activation and surface marker expression, cytokine release, survival and proliferation of B cells[3]. In mast cells, allergen activated FcεRI is phosphorylated by LYN and FYN and recruits SYK which is in turn phosphorylated by LYN and further autophosphorylated, becoming fully activated. Activated SYK phosphorylates the two adaptor molecules NTAL and LAT creating more docking sites for SH2 containing proteins such as $PLC\gamma_1$, vav, and the p85 regulatory subunit of PI3K, resulting in mast cell degranulation and cytokine production[4]. Syk's critical role in signal transduction of mast cells is confirmed by reproducible observation that the 10-15% of basophils (circulating mast cells) from human donors that cannot degranulate have reduced amounts of Syk protein[5,6]. In addition, SYK is required for the bone resorption activity of osteoclasts. Upon stimulation of osteoclasts by αvβ3 integrin, SYK becomes phosphorylated, most likely by c-Src, in a DAP-12/FcγRII dependent mechanism, leading to SPL-76 and Vav3 phosphorylation and subsequent cytoskeletal reorganisation. SYK deficient osteoclasts are inactive and show defective cytoskeletal reorganisation. In correlation with this, SYK deficient embryos show defective skeletal mass[7,8].

BCR-mediated activation of B-cells in the lymph nodes, as well as FcR-mediated activation of dendritic cells, monocytes, macrophages, neutrophils and mast cells in the joints, are essential components of the cellular patho-physiological mechanisms taking place during rheumaoid arthritis (RA). Moreover, activation of osteoclasts leads to the bone and cartilage destruction which are hallmarks of this pathology[9]. SYK signaling should therefore play a pivotal role during the development of arthritis, both at the periphery and on the site of inflammation[10]. Indeed, an orally available Syk inhibitor R406-developed by Rigel-induced a significant improvement of clinical scores and significantly reduced serum cytokine concentrations, as well as bone erosion, in a murine model of RA[11,12]. Moreover, this inhibitor has shown efficacy (ACR scores improvement) and good tolerability in RA Phase II studies in humans[13,14,15].

In SLE B cells contriubute essentially towards pathogenesis via production of autoanibodies resulting in immune complex formation, stimulation of Fc receptors and finally in an excessive and chronic activation of inflammation. In a murine model of SLE treatment with a Syk inhibitor resulted in a reduction of numbers of class-switched germinal center, marginal zone, newly formed and follicular B cells and therefore in disease mitigating effects[18].

Although TCR signals are transmited by the intracellular tyrosine kinase ZAP-70 in thymocytes and naïve T cells, several studies indicate that differentiated effector T cells, such as those involved in the pathophysiology of Multiple sclerosis (MS) or systemic lupus erythematosus (SLE), show a down regulation of the TCRzeta chain and a concomitant upregulation of the TCR/CD3 chain and its interaction with FcRγ. Those studies show that the TCR/CD3/FcRgamma complex in effector cells recruits and activates Syk, instead of ZAP-70, tyrosine kinase. This physiologic switch in TCR signaling occurs exclusively in effector, and not naive or memory T cells[16,17,18]. Not surprisingly then, SYK inhibitors have been shown to delay disease progression and to improve survival in murine models of SLE[17,18,19,20,21].

SYK inhibitors may also find a use in asthma, allergy, multiple sclerosis and other diseases such as thrombocytopenia purpura and T or B cell lymphomas[1,10,14,22-35].

Treatment of prediseased NZB/W mice with a Syk inhibitor prevented the development of renal disease demonstrated by reduced glomerular sclerosis, tubular damage, proteinuria and BUN levels[18].

REFERENCES

1. Turner, M., Schweighoffer, E., Colucci, F., Di Santo, J. P. & Tybulewicz, V. L. Tyrosine kinase SYK: essential functions for immunoreceptor signalling. *Immunol Today* 21, 148-154 (2000).
2. Ghosh, D. & Tsokos, G. C. Spleen tyrosine kinase: an Src family of non-receptor kinase has multiple functions and represents a valuable therapeutic target in the treatment of autoimmune and inflammatory diseases. *Autoimmunity* 43, 48-55.
3. Lindvall, J. M., et al. Bruton's tyrosine kinase: cell biology, sequence conservation, mutation spectrum, siRNA modifications, and expression profiling. *Immunol Rev* 203, 200-215 (2005).
4. Gilfillan, A. M. & Tkaczyk, C. Integrated signalling pathways for mast-cell activation. *Nat Rev Immunol* 6, 218-230 (2006).
5. Gomez, G., Schwartz, L. & Kepley, C. Syk deficiency in human nonreleaser lung mast cells. *Clin Immunol* 125, 112-115 (2007).
6. Kepley, C. L., Youssef, L., Andrews, R. P., Wilson, B. S. & Oliver, J. M. Syk deficiency in nonreleaser basophils. *J Allergy Clin Immunol* 104, 279-284 (1999).
7. Zou, W., et al. Syk, c-Src, the alphavbeta3 integrin, and ITAM immunoreceptors, in concert, regulate osteoclastic bone resorption. *J Cell Biol* 176, 877-888 (2007).
8. Reeve, J. L., et al. SLP-76 couples Syk to the osteoclast cytoskeleton. *J Immunol* 183, 1804-1812 (2009).
9. Klareskog, L., Catrina, A. I. & Paget, S. Rheumatoid arthritis. *Lancet* 373, 659-672 (2009).
10. Wong, B. R., Grossbard, E. B., Payan, D. G. & Masuda, E. S. Targeting Syk as a treatment for allergic and autoimmune disorders. *Expert Opin Investig Drugs* 13, 743-762 (2004).
11. Braselmann, S., et al. R406, an orally available spleen tyrosine kinase inhibitor blocks fc receptor signaling and reduces immune complex-mediated inflammation. *J Pharmacol Exp Ther* 319, 998-1008 (2006).
12. Pine, P. R., et al. Inflammation and bone erosion are suppressed in models of rheumatoid arthritis following treatment with a novel Syk inhibitor. *Clin Immunol* 124, 244-257 (2007).
13. Tomillero, A. & Moral, M. A. Gateways to clinical trials. *Methods Find Exp Clin Pharmacol* 31, 47-57 (2009).
14. Bajpai, M. Fostamatinib, a Syk inhibitor prodrug for the treatment of inflammatory diseases. *IDrugs* 12, 174-185 (2009).
15. Weinblatt, M. E., et al. Treatment of rheumatoid arthritis with a Syk kinase inhibitor: a twelve-week, randomized, placebo-controlled trial. *Arthritis Rheum* 58, 3309-3318 (2008).
16. Krishnan, S., Warke, V. G., Nambiar, M. P., Tsokos, G. C. & Farber, D. L. The FcR gamma subunit and Syk kinase replace the CD3 zeta-chain and ZAP-70 kinase in the TCR signaling complex of human effector CD4 T cells. *J Immunol* 170, 4189-4195 (2003).
17. Krishnan, S., et al. Differential expression and molecular associations of Syk in systemic lupus erythematosus T cells. *J Immunol* 181, 8145-8152 (2008).
18. Bahjat, F. R., et al. An orally bioavailable spleen tyrosine kinase inhibitor delays disease progression and prolongs survival in murine lupus. *Arthritis Rheum* 58, 1433-1444 (2008).
19. Smith, J., et al. A Spleen Tyrosine Kinase Inhibitor Reduces the Severity of Established Glomerulonephritis. *J Am Soc Nephrol* (2009).
20. Enyedy, E. J., et al. Fc epsilon receptor type I gamma chain replaces the deficient T cell receptor zeta chain in T cells of patients with systemic lupus erythematosus. *Arthritis Rheum* 44, 1114-1121 (2001).
21. Perl, A. Systems biology of lupus: mapping the impact of genomic and environmental factors on gene expression signatures, cellular signaling, metabolic pathways, hormonal and cytokine imbalance, and selecting targets for treatment. *Autoimmunity* 43, 32-47.
22. Smith, J., et al. A spleen tyrosine kinase inhibitor reduces the severity of established glomerulonephritis. *J Am Soc Nephrol* 21, 231-236.
23. Sanderson, M. P., Gelling, S. J., Rippmann, J. F. & Schnapp, A. Comparison of the anti-allergic activity of Syk inhibitors with optimized Syk siRNAs in FcepsilonRI-activated RBL-2H3 basophilic cells. *Cell Immunol* 262, 28-34.
24. Podolanczuk, A., Lazarus, A. H., Crow, A. R., Grossbard, E. & Bussel, J. B. Of mice and men: an open-label pilot study for treatment of immune thrombocytopenic purpura by an inhibitor of Syk. *Blood* 113, 3154-3160 (2009).
25. Bajpai, M., Chopra, P., Dastidar, S. G. & Ray, A. Spleen tyrosine kinase: a novel target for therapeutic intervention of rheumatoid arthritis. *Expert Opin Investig Drugs* 17, 641-659 (2008).
26. Friedberg, J. W., et al. Inhibition of Syk with fostamatinib disodium has significant clinical activity in non-Hodgkin lymphoma and chronic lymphocytic leukemia. *Blood* 115, 2578-2585.
27. Gao, C., et al. Eptifibatide-induced thrombocytopenia and thrombosis in humans require FcgammaRIIa and the integrin beta3 cytoplasmic domain. *J Clin Invest* 119, 504-511 (2009).
28. Marjon, K. D., Marnell, L. L., Mold, C. & Du Clos, T. W. Macrophages activated by C-reactive protein through Fc gamma RI transfer suppression of immune thrombocytopenia. *J Immunol* 1182, 1397-1403 (2009).
29. Chen, L., et al. SYK-dependent tonic B-cell receptor signaling is a rational treatment target in diffuse large B-cell lymphoma. *Blood* 111, 2230-2237 (2008).
30. Ponzoni, M., et al. Syk expression patterns differ among B-cell lymphomas. *Leuk Res* (2010).
31. Pechloff, K., et al. The fusion kinase ITK-SYK mimics a T cell receptor signal and drives oncogenesis in conditional mouse models of peripheral T cell lymphoma. *J Exp Med* 207, 1031-1044 (2009).
32. Uckun, F. M., Ek, R. O., Jan, S. T., Chen, C. L. & Qazi, S. Targeting SYK kinase-dependent anti-apoptotic resistance pathway in B-lineage acute lymphoblastic leukaemia (ALL) cells with a potent SYK inhibitory pentapeptide mimic. *Br J Haematol* 149, 508-517 (2010).
33. Wilcox, R. A., et al. Inhibition of Syk protein tyrosine kinase induces apoptosis and blocks proliferation in T-cell non-Hodgkin's lymphoma cell lines. *Leukemia* 24, 229-232 (2009).

34. Feldman, A. L., et al. Overexpression of Syk tyrosine kinase in peripheral T-cell lymphomas. *Leukemia* 22, 1139-1143 (2008).

35. Wang, L., et al. Alternative splicing disrupts a nuclear localization signal in spleen tyrosine kinase that is required for invasion suppression in breast cancer. *Cancer Res* 63, 4724-4730 (2003).

In addition to mast cells, Syk is expressed in other hematopoietic cells including B cells, where it is thought to play an essential role in transducing signals required for the transition of immature B cells into mature recirculating B cells (M. Turner et al, Immunology Today, 21: 148 (2000). B cells are reported to play an important role in some inflammatory conditions such as lupus (O. T. Chan etal., Immunological Rev, 169: 107-121 (1999) and rheumatoid arthritis (A. Gause et al, Biodrugs, 15(2): 73-79 (2001).

Syk was also reported to be an element of the signaling cascade in beta-amyloid and prion fibrils leading to production of neurotoxic products (C. K. Combs et al., J. Neuroscl, 19: 928-939 (1999). Furthermore, an inhibitor of Syk blocked the production of these neurotoxic products. Thus furopyridine derivatives would potentially be useful in the treatment of Alzheimer's disease and related neuroinflammatory diseases. Another report (Y. Kuno et al., Blood, 97, 1050-1055 (2001) demonstrates that Syk plays an important role in malignant progression. A TEL-Syk fusion protein was found to transform hematopoietic cells suggesting a role in the pathogenesis of hematopoietic malignancies. Therefore furopyridine derivatives may be useful in the treatment of certain types of cancers.

Other protein tyrosine kinases involved in hematologic malignancies include ABL (ABLI), ARG (ABL2), PDGFβR, PDGFaR, JAK2, TRKC, FGFRI, FGFR3, FLT3, and FRK.

The Janus kinases (JAK) are a family of tyrosine kinases consisting of JAKI, JAK2, JAK3 and TYK2. The JAKs play a critical role in cytokine signaling. The down-stream substrates of the JAK family of kinases include the signal transducer and activator of transcription (STAT) proteins. JAK/STAT signaling has been implicated in the mediation of many abnormal immune responses such as allergies, asthma, autoimmune diseases such as transplant (allograft) rejection, rheumatoid arthritis, amyotrophic lateral sclerosis and multiple sclerosis, as well as in solid and hematologic malignancies such as leukemia and lymphomas (for a review of the pharmaceutical intervention of the JAK/STAT pathway see Frank, Mol. Med. 5, 432:456 (1999), and Seidel et al, Oncogene 19, 2645-2656 (2000). JAK2 is a well validated target with strong potential in the treatment of myeloproliferative disorders (MPDs), which include polycythemia vera (PV), essential thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome and systematic mast cell disease.

Fms-like tyrosine kinase 3 (FLT3), which is also known as FLK-2 (fetal liver kinase 2) and STK-I (stem cell kinase 1), plays an important role in the proliferation and differentiation of hematopoietic stem cells. FLT3 receptor kinase is expressed in normal hematopoietic cells, placenta, gonads, and brain. However, this enzyme is expressed at very high levels on the cells of more than 80% of myelogenous patients and of a fraction of acute lymphoblastic leukemia cells. Furthermore, the enzyme can also be found on cells from patients with chronic myelogenous leukemia in lymphoid blast crisis. It has been reported that FLT3 kinase is mutated in 30% of acute myeloid leukemia (AML) and in a subset of acute lymphoblastic leukemia (ALL) as well (Gilliland et al, Blood 100, 1532-1542 (2002); Stirewalt etal, Nat. Rev. Cancer, 3, 650-665 (2003). The most common activating mutations in FLT3 are internal tandem duplications within the juxtamembrane region, while point mutations, insertions, or deletions in the kinase domain are less common. Some of these mutant FLT3 kinases are constitutively active. FLT3 mutations have been associated with a poor prognosis (Malempati et al., Blood, 104, 11 (2004). More than a dozen known FLT3 inhibitors are being developed and some have shown promising clinical effects against AML (Levis et al Int. J. Hematol, 52, 100-107 (2005).

It has been reported that some of small-molecule FLT3 inhibitors are effective in inducing apoptosis in cell lines with FLT3-activating mutations and prolonging survival of mice that express mutant FLT3 in their bone marrow cells (Levis et al, Blood, 99, 3885-3891 (2002); Kelly et al, Cancer Cell, 1, 421-432 (2002); Weisberg et al, Cancer Cell, 1, 433-443 (2002); Yee et al, Blood, 100, 2941-2949 (2002).

In particular, the present invention relates to compounds and to the use of compounds in which the inhibition, regulation and/or modulation of signal transduction by Syk plays a role.

The synthesis of small compounds which specifically inhibit, regulate and/or modulate signal transduction by tyrosine kinases in particular Syk, is therefore desirable and an aim of the present invention.

Moreover, aim of this invention is the synthesis of new compounds for the prevention and treatment of rheumatoid arthritis, systemic lupus, asthma, allergic rhinitis, ITP, multiple sclerosis, leukemia, breast cancer and maligna melanoma. Surprisingly we have identified furopyridines that inhibit selectively SYK, BTK, KDR, Src, Zap70, Fak, Pyk2, Flt3 or Jak or inhibit a selection of these kinases.

Moreover, compounds of formula I inhibit serin kinase GCN2. Many strategies of cancer treatment of solid tumors focus on the surgically removal of the tumor mass as far as possible and the subsequent eradication of any residual tumor cells by radiotherapy and chemotherapy with cytotoxic agents or inhibitors that target cancer cell pathways more specifically. However, the success of such approach is limited and often does not persist. This is mainly due to the narrow therapeutic window for such cytotoxic agents (specificity and side effects) and to the capability of cancer calls to adapt to the selective pressure applied by cytotoxic or other inhibitory agents. The survival of a small number of tumor (stem) cells that acquired resistance to the initial treatment can be sufficient to seed the regrowth of a tumor. These relapses are in most cases more difficult to treat compared to that of the initial tumors. As a consequence the more successful targeting of tumor cells may require targeting multiple survival and escape mechanism of tumor cells in parallel (Muller & Prendegast 2007).

Development of malignancies is accompanied by a major roll up of the cellular physiology. During this process several qualities are acquired by the cancer cells that are basis for immortalization or insensitivity to growth inhibitory signals. In addition the tumor cells also modify the interaction with the microenvironment and beyond. The latter area includes the strategies of tumor cells to escape from the immunological surveillance (Muller & Prendegast 2007). The immune surveillance limits malignant growth but also provides a selective pressure triggering the evolution of mechanisms for evading the immune response as reviewed by [Dunn et al. 2004]. Essentially it has been frequently observed that ablation of T cell immunity is sufficient to increase tumor incidence [Shankaran et al. 2001] and it is believed that immune escape is affecting tumor dormancy versus progression, promoting invasion and metastasis and negatively impacts on therapeutic response.

Several mechanistic studies discovered that immune escape has an important interface with metabolic alterations within the tumor microenvironment. Here important roles in mediating immune tolerance to antigens have been associated to the catabolism of the essential amino acids tryptophan and arginine, carried out by the enzymes indoleamine 2,3-dioxygenase (IDO) and arginase I (ARG), respectively (Bronte and Zanovello, 2005; Muller et al., 2005b; Muller and Prendergast, 2007; Munn and Mellor, 2007; Popovic et al., 2007).

IDO is a single-chain oxidoreductase that catalyzes the degradation of tryptophan to kynurenine. IDO is not responsible for catabolizing excess dietary tryptophan but to modulate tryptophan level in a local environment. Elevations in tryptophan catabolism in cancer patients manifest in significantly altered serum concentration of tryptophan or catabolites and this was correlated to IDO which is commonly elevated in tumors and draining lymph nodes. According to several publications IDO over-expression is associated with poor prognosis in cancer [Okamoto et al 2005; Brandacher et al, 2006].

T cells appear to be preferentially sensitive to IDO activation, such that when starved for tryptophan they cannot divide and as a result cannot become activated by an antigen presented to them. Munn and Mellor and their colleagues, revealed that IDO modulates immunity by suppressing T-cell activation and by creating peripheral tolerance to tumor antigens (Mellor and Munn, 2004). These mechanism encompass the subversion of immune cells recruited by the tumor cell to its immediate microenvironment or to the tumor-draining lymph nodes Here the tumor antigens that were scavenged by antigen-presenting cells are cross-presented to the adaptive immune system. In addition to being directly toleragenic, mature DCs have the capacity to expand regulatory Tcells (Tregs) [Moser 2003].

Beside tryptophan catabolism the conversion of arginine is increased in a tumor-conditioned microenvironment, and numerous reports indicate a role for the activation of arginases during tumor growth and development. In tumor-infiltrating myeloid cells, arginine is converted by arginase I (ARG1), arginase II (ARG2) to urea and ornithine and oxidized by the inducible form of nitric oxide synthase (NOS2) to citrulline and nitric oxide (NO).

Increased ARG activity is frequently observed in patients with colon, breast, lung, and prostate cancer [Cederbaum 2004] correlating with the over-expression of ARG and NOS found in prostate cancers [Keskinege et al. 2001, Aaltoma et al. 2001, Wang et al. 2003]. It was shown that ARG activity in infiltrating macrophages impairs antigen-specific T cell responses and the expression of the CD3 receptor. Moreover the cumulative activity of ARG and NOS in tumor associated myeloid cells can generate inhibitory signals to antigen-specific T lymphocytes that eventually lead to apoptosis [Bronte 2003 a; 2003b].

Both, the IDO and the ARG related mechanism merge at the point of sensing the depleted concentration of the respective amino acid concentration. During amino acid deprivation, the eIF2 kinase EIF2AK4 called general control nonderepressible 2 (GCN2) is interacting with the intracellular accumulating deacylated tRNA. As a consequence the GCN2 is assumed to change from an auto-inhibited to an active conformation and further activate by auto-phosphorylation. Then the only known substrate protein eIF2a becomes phosphorylated and as a consequence the complex for translation initiation is inhibited [Harding et al. 2000,]. This diminishes the general Cap-dependent translation initiation and by this the corresponding protein production. On the other hand this induces the specific expression of stress related target genes mainly by cap-independent initiation via the activating transcription factor 4 (ATF4). By expressing the respective stress response proteins, e.g. enzymes in the in amino acid metabolism, the cell tries to compensate the particular cell stress [Wek et al. 2006]. If the stress persists, the same pathway will switch to promoting cell death via transcription of the pro-apoptotic transcription factor, CCAAT/enhancer-binding protein homologous protein (CHOP) [Oyadomari 2004]. It was shown that, tryptophan starvation triggers a GCN2-dependent stress signaling pathway In T cells altering eIF2aphosphorylation and translational initiation leading to a cell growth arrest (Munn et al. 2005). Sharma, et al. [2007] published on the direct IDO-induced and GCN2-dependent activation of mature Tregs. Similarly Fallarino et al [2006] found a GCN2-dependent conversion of CD4+CD25− cells to CD25+FoxP3+ Tregs producing IL-10 and TGFβ. Rodriguez et al. [2007] identified that activation of the GCN2 pathway via tryptophan or arginine depletion in combination with TCR signaling leads to CD3ξ chain down regulation, cell cycle arrest and anergy.

Importantly the GCN2 pathway is not only important for the tumoral immune escape but also plays an active role in modulating tumor survival directly. Ye et al[2010] found that the aforementioned transcription factor ATF4 is over-expressed inhuman solid tumors, suggesting an important function in tumour progression. Amino acid and glucose deprivation are typical stresses found in solid tumours and activated the GCN2 pathway to up-regulate ATF4 target genes involved in amino acid synthesis and transport. GCN2 activation/over-expression and increased phospho-eIF2a were observed in human and mouse tumors compared with normal tissues and abrogation of ATF4 or GCN2 expression significantly inhibited tumor growth in vivo. It was concluded that the GCN2-eIF2a-ATF4 pathway is critical for maintaining metabolic homeostasis in tumor cells. Over all the present biology makes an interference with the ARG/IDO pathway attractive for braking up the tumoral immune escape by adaptive mechanism. The interference of GCN2 function is here of particular interest as it is a merging point of the two pathways, the IDO and ARG, as well as it provides additional opportunities to impede with the tumor metabolism directly.

Several pathway inhibitors are already considered as immune modulators. These inhibitors address mainly the enzymatic function of the IDO or ARG proteins (Muller and Scherle, 2006). The application of the arginase inhibitor, N-hydroxy-nor-L-Arg blocks growth of s.c. 3LL lung carcinoma in mice [Rodriguez 2004]. The NO-donating aspirins like NCX 4016 (2-(acetyloxy)benzoic acid 3-(nitrooxymethyl) phenyl ester) have been reported to interfer with the inhibitory enzymatic activities of myeloid cells. Orally administered NO aspirin normalized the immune status of tumor-bearing hosts, increased the number and function of tumor-antigen-specific T lymphocytes, and enhanced the preventive and therapeutic effectiveness of the antitumor immunity elicited by cancer vaccination (DeSanto 2005)

The substrate analogue 1 methyl-tryptophan (1 MT) and related molecules have been used widely to target IDO in the cancer context and other settings. Studies by Friberg et al. (2002) and Uyttenhove et al. (2003) demonstrated that 1 MT can limit the growth of tumors over-expressing IDO. However 1 MT was unable to elicit tumor regression in several tumor models, suggesting only modest antitumor efficacy when IDO inhibition was applied as a monotherapy. In contrast, the combinatory treatment with 1 MT and a variety of cytotoxic chemotherapeutic agents elicited regression of established MMTV-neu/HER2 tumors, which responded poorly to any single-agent therapy [Muller et al 2005a]. Immunodepletion of CD4+ or CD8+ T cells from the mice, before treatment abolished the combinatorial efficacy observed in this model, confirming the expectation that 1 MT acted indirectly through activation of T cell-mediated antitumor immunity. Important evidence that IDO targeting is essential to 1 MT action was provided by the demonstration that 1 MT lacks antitumor activity in mice that are genetically deficient for IDO [Hou et al., 2007] The inhibition of GCN2 would enable to combine the two pathway branches of amino acrid starvation induced immunoediting and would reduce the options for the tumor to circumvent the inhibition of either branch. Moreover, as detailed above, the GCN2 inhibition provides the opportunity for interfering with the tumor metabolism at the same time what may enhance the efficacy of a monotherapy or a combination therapy with other anti-cancer approaches.

LITERATURE

1. Aaltoma, S. H., P. K. Lipponen, and V. M. Kosma. 2001. Inducible nitric oxide synthase (iNOS) expression and its prognostic value in prostate cancer. Anticancer Res. 21:3101-3106.
2. Brandacher, G.; Perathoner, A.; Ladurner, R.; Schneeberger, S.; Obrist, P.; Winkler, C.; Werner, E. R.; Werner-Felmayer, G.; Weiss, H. G.; Gobel, G.; Margreiter, R.; Konigsrainer, A.; Fuchs, D.; Amberger, A. Prognostic value of indoleamine 2,3-dioxygenase expression in colorectal cancer: effect on tumorinfiltrating T cells. Clin. Cancer Res. 2006, 12, 1144-1151.
3. Bronte V, Zanovello P. (2005). Regulation of immune responses by L-arginine metabolism. Nat Rev Immunol 5: 641-654.
4. Bronte, V., P. Serafini, C. De Santo, I. Marigo, V. Tosello, A. Mazzoni, D. M. Segal, C. Staib, M. Lowel, G. Sutter, et al. 2003a. IL-4-induced arginase 1 suppresses alloreactive T cells in tumor-bearing mice. J. Immunol. 170:270-278.
5. Bronte, V., P. Serafini, A. Mazzoni, D. M. Segal, and P. Zanovello. 2003b. L-arginine metabolism in myeloid cells controls T-lymphocyte functions. Trends Immunol. 24:302-306
6. Carmela De Santo, Paolo Serafini, Ilaria Marigo, Luigi Dolcetti, Manlio Bolla, § Piero Del Soldato, Cecilia Melani, Cristiana Guiducci, Mario P. Colombo, Manuela lezzi, Piero Musiani, Paola Zanovello, and Vincenzo Bronte. Nitroaspirin corrects immune dysfunction in tumor-bearing hosts and promotes tumor eradication by cancer vaccination. Proc Natl Acad Sci USA. 2005 Mar. 15; 102(11): 4185-4190
7. Cederbaum, S. D., H. Yu, W. W. Grody, R. M. Kern, P. Yoo, and R. K. lyer. 2004. Arginases I and I I: do their functions overlap? Mol. Genet. Metab. 81:S38-44.
8. Dey, M., Cao, C., Sicheri, F. and T. E. Dever. Conserved Intermolecular Salt Bridge Required for Activation of Protein Kinases PKR, GCN2, and PERK. JBC 282(9): 6653, 2007.
9. Dunn, G. P.; Old, L. J.; Schreiber, R. D. The immunobiology of cancer immunosurveillance and immunoediting. Immunity 2004, 21, 137-148.
10. Fallarino, F. U. Grohmann, S. You, B. C. et al. The combined effects fo tryptophan starvation and tryptophan catabolites down-regulate T cell receptor zeta-chain and induce a regulatory phenotype in naïve T cells. J. Immunol. 176:6752, 2006.
11. Friberg M, Jennings R, Alsarraj M, Dessureault S, Cantor A, Extermann M et al. (2002). Indoleamine 2,3-dioxygenase contributes to tumor cell evasion of T cell-mediated rejection. Int. J Cancer 101: 151-155
12. Harding H P, Novoa I, Zhang Y, Zeng H, Wek R, Schapira M, Ron D. Regulated translation initiation controls stress-induced gene expression in mammalian cells. Mol Cell. 2000 November; 6(5):1099-108.
13. Hou D Y, Muller A J, Sharma M D, DuHadaway J, Banerjee T, Johnson M et al. (2007). Inhibition of indoleamine 2,3-dioxygenase in dendritic cells by stereoisomers of 1-methyl-tryptophan correlates with antitumor responses. Cancer Res 67: 792-801.
14. Keskinege, A., S. Elgun, and E. Yilmaz. 2001. Possible implications of arginase and diamine oxidase in prostatic carcinoma. Cancer Detect. Prev. 25:76-79.
15. Mellor A L, Munn D H. (2004). IDO expression by dendritic cells: tolerance and tryptophan catabolism. Nat Rev Immunol 4: 762-774.
16. Moser, M. Dendritic cells in immunity and tolerance-do they display opposite functions? Immunity 2003, 19, 5-8.
17. Muller, A. J. and P. A. Scherle. Targeting the mechanisms of tumoral immune tolerance with small-molecule inhibitors. Nat. Rev. Cancer. 6:613, 2006.
18. Muller A J, Prendergast G C. (2007). Indoleamine 2,3-dioxygenase in immune suppression and cancer. Curr Cancer Drug Targets 7: 31-40.
19. Muller A J, DuHadaway J B, Sutanto-Ward E, Donover P S, Prendergast G C. (2005a). Inhibition of indoleamine 2,3-dioxygenase, an immunomodulatory target of the tumor suppressor gene Bin1, potentiates cancer chemotherapy. Nature Med 11: 312-319.
20. Muller A J, Malachowski W P, Prendergast G C. (2005b). Indoleamine 2,3-dioxygenase in cancer: targeting pathological immune tolerance with small-molecule inhibitors. Expert Opin Ther Targets 9: 831-849.
21. Munn, D. H., M. D. Sharma, B. Baban, H. P. Harding, Y. Zhang, D.
Ron, A. L. Mellor. GCN2 kinase in T cells mediates proliferative arrest and anergy induction in response to indoleamine 2,3-dioxygenase. Immunity.
22:633, 2005
22. Okamoto, A.; Nikaido, T.; Ochiai, K.; Takakura, S.; Saito, M.;
Aoki, Y.; Ishii, N.; Yanaihara, N.; Yamada, K.; Takikawa, O.; Kawaguchi,
R.; Isonishi, S.; Tanaka, T.; Urashima, M. Indoleamine 2,3-dioxygenase serves as a marker of poor prognosis in gene expression profiles of serous ovarian cancer cells. Clin. Cancer Res. 2005, 11, 6030-6039.
23. Oyadomari S, Mori M. Roles of CHOP/GADD153 in endoplasmic reticulum stress. Cell Death Differ. 2004 April; 11(4):381-9.
24. G C Prendergast, Immune escape as a fundamental trait of cancer: focus on IDO. Oncogene (2008) 27, 3889-3900
25. Popovic P J, Zeh III H J, Ochoa J B. (2007). Arginine and immunity. J Nutr 137: 1681 S-1686 S.
26. Rodriguez, P. C., D. G. Quiceno, J. Zabaleta, B. Ortiz, A. H. *Zea*, M. B. Piazuelo, A. Delgado, P. Correa, J. Brayer, E. M. Sotomayor, S. Antonia, J. B. Ochoa, and A. C. Ochoa. Arginase I Production in the Tumor Microenvironment by Mature Myeloid Cells Inhibits T-Cell Receptor Expression and Antigen-Specific T-Cell Responses. Canc. Res. 64:5839, 2004
27. Rodriguez, P. C., D. G. Quiceno, and A. C. Ochoa. L-arginine availability regulates T-lymphocyte cell-cycle progresión. Blood. 109:1568, 2007.

28. Shankaran, V.; Ikeda, H.; Bruce, A. T.; White, J. M.; Swanson, P. E.; Old, L. J.; Schreiber, R. D. IFNgamma and lymphocytes prevent primary tumour development and shape tumour immunogenicity. Nature 2001, 410, 1107-1111.

29. Sharma, M. D., B. Baban, P. Chandler, D-Y. Hou, N. Singh, H. Yagita, M. Azuma, B. R. Blazar, A. L. Mellor, and D. H. Munn. Plasmacytoid dendritic cells from mouse tumor-draining lymph nodes directly activate mature Tregs via indoleamine 2,3-dioxygenase. J. Clin. Invest. 117:2570, 2007.

30. Uyttenhove C, Pilotte L, Theate I, Stroobant V, Colau D, Parmentier N et al. (2003). Evidence for a tumoral immune resistance mechanism based on tryptophan degradation by indoleamine 2,3-dioxygenase. Nat Med 9: 1269-1274

31. Wang, J., M. Torbenson, Q. Wang, J. Y. Ro, and M. Becich. 2003. Expression of inducible nitric oxide synthase in paired neoplastic and non-neoplastic primary prostate cell cultures and prostatectomy specimen. Urol. Oncol. 21:117-122.

32. Wek R C, Jiang H Y, Anthony T G. Coping with stress: eIF2 kinases and translational control. Biochem Soc Trans. 2006 February; 34 (Pt 1):7-11.

33. Ye J, Kumanova M, Hart L S, Sloane K, Zhang H, De Panis D N, Bobrovnikova-Marjon E, Diehl J A, Ron D, Koumenis C. The GCN2-ATF4 pathway is critical for tumour cell survival and proliferation in response to nutrient deprivation. EMBO J. 2010 Jun. 16; 29(12):2082-96.

It has been found that the compounds according to the invention and salts thereof have very valuable pharmacological properties while being well tolerated.

The present invention specifically relates to compounds of the formula I which inhibit, regulate and/or modulate signal transduction by Syk, to compositions which comprise these compounds, and to processes for the use thereof for the treatment of Syk-induced diseases and complaints.

The compounds of the formula I can furthermore be used for the isolation and investigation of the activity or expression of Syk. In addition, they are particularly suitable for use in diagnostic methods for diseases in connection with unregulated or disturbed Syk activity.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed are assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001, 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein, are described in the literature (for example Campos-Gonzalez, R. and Glenney, Jr., J. R. 1992, J. Biol. Chem. 267, page 14535).

For the identification of kinase inhibitors, various assay systems are available. In scintillation proximity assay (Sorg et al., J. of. Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J.).

PRIOR ART

Other heterocyclic Syk inhibitors are described in WO2008/118823, WO2009/136995, WO 2010/027500.

SUMMARY OF THE INVENTION

The invention relates to compounds of the formula I

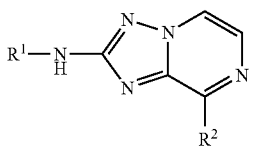

I $R^1$ denotes $Ar^1$, Carb, $Het^1$ or H, $R^2$ denotes $Ar^2$, Carb, Cyc, $Het^2$, $NR^3(CH_2)_nHet^2$, $NR^3Cyc$, $N(R^3)_2$, $NR^3(CH_2)_pN(R^3)_2$, $NR^3(CH_2)_pNR^3COA$, $NR^3SO_2A$, $NR^3SO_2Ar^3$, $NR^3SO_2Het^3$, $O(CH_2)_nHet^3$ or $NR^3Ar^3$, $Ar^1$ denotes phenyl, which is mono-, di- or trisubstituted by A, $(CH_2)_nOH$, $(CH_2)_nOA$, $(CH_2)_nHet^3$, CN, $SO_2NH_2$, $SO_2CH_3$, $SOCH_3$, Cyc, $(CH_2)_nNH_2$, $(CH_2)_nNHA$, $(CH_2)_nNA_2$ and/or $(CH_2)_nSO_3H$, $Ar^2$ denotes phenyl or biphenyl, which is unsubstituted or mono-, di- or trisubstituted by Hal, CN, $(CH_2)_nOH$, $(CH_2)_nOA$, $NHSO_2A$, $(CH_2)_nHet^3$, $[C(R^3)_2]_nNH_2$, $[C(R^3)_2]_nNHA$, $[C(R^3)_2]_nNA_2$, $SO_2CH_3$, $SO_2NH_2$ and/or $COHet^3$, $Het^1$ denotes pyridyl, benzimidazolyl, benzotriazolyl, indolyl, indazolyl, benzo[1,4]oxazinyl, 1,3- or 2,3-dihydro-indolyl, benzothiadiazolyl, 1,2,3,4-tetrahydro-quinolyl, spiro(cyclobutan-1,3'-indolyl), spiro(cyclobutan-1,3'-indolinyl), 1,4-dihydro-benzo[d][1,3]oxazinyl, 3,4-dihydro-1H-quinolyl, 3,4-dihydro-1H-quinozalinyl, chromanyl, [1,2,4]triazolo[4,3-a]pyridyl, 1,2,3,4-tetrahydro-quinoxalinyl or 2,3-dihydro-1H-2l6-benzo[c]isothiazolyl, each of which is unsubstituted or mono-, di-, tri- or tetrasubstituted A, OH, OA, $SO_2NH_2$, $(CH_2)_nNH_2$, $(CH_2)_nNHA$, $(CH_2)_nNA_2$, Hal and/or =O, $Het^2$ denotes piperidinyl, piperazinyl, pyrrolidinyl, morpholinyl, tetrahydropyranyl, pyrazolyl, indazolyl, azetidinyl, pyridyl, isoxazolyl, pyrimidinyl, furyl, thienyl, pyrido[2,3-b]pyrazinyl, 2-oxa-6-aza-spiro[3,4]octyl, 2,5-diaza-bicyclo[2.2.1]heptyl, 1,4-dioxa-7-aza-spiro[4.4]nonyl, 7,8-dihydro-5H-pyrido[4,3-d]pyrimidinyl, 1,3,7-triaza-spiro[4.5]-decyl, 2,5,7-triaza-spiro[3.4]octyl, 1,3,7-triaza-spiro[4.4]nonyl, 2-oxa-6-aza-spiro[3.3]heptyl, 2-oxa-6-aza-spiro[3.5]nonyl, 2,7-diaza-spiro[4.4]nonyl, 2,8-diaza-spiro[4.5]decyl, 3-oxa-8-aza-bicyclo[3.2.1]octyl, 1,4,6,7-tetrahydro-imidazo[4,5-c]pyridinyl, 4,5,6,7-tetrahydro-pyrazolo[1,5-a]pyrazinyl, 1,2,3,4-tetrahydro-quinolyl, quinolyl, indazolyl, diazepanyl, azepanyl, 2-oxa-3,9-diaza-spiro[5.5]undecenyl, triazolyl, 8-oxa-3-aza-bicyclo[3.2.1]octyl, 1,3,8-triaza-spiro[4.5]decenyl, 1-oxa-3,7- or 3,8-diaza-spiro[4.5]decyl, 1,3,8-triaza-spiro[4.5]decyl, 4,6-dihydro-1H-pyrrolo[3,4-c]pyrazolyl, hexahydro-pyrazino[1,2-a]pyrazinyl, tetrahydro-benzo[b]azepanyl, 2,3-dihydro-benzo[1,4]dioxinyl, 2,3-dihydro-indolyl, indolyl, 8-aza-bicyclo[3.2.1]octyl, 3,4-dihydro-2H-quinolyl, 3,4-dihydro-2H-pyrano[2,3-b]pyridyl, [1,2,4]triazolo[1,5-a]pyrazinyl, spiro[indole-3,3'-pyrrolidinyl], 6-oxa-2,9-diaza-spiro[4,5]decyl, tetrahydropyrrolo[3,4-c]pyrrolyl, 1,8-diaza-spiro[4.5]decyl, 1,2,3,4-tetrahydroisoquinolyl, 6,7-dihydro-4H-pyrazolo[5,1-c][1,4]oxazinyl, 1-aza-bicyclo[2.2.2]octyl, octahydro-isoquinolyl or 3,4-dihydro-2H-pyrido[3,2-b][1,4]oxazinyl, each of which is unsubstituted or mono-, di- or trisubstituted by Hal, A, $(CH_2)_nNH_2$, $(CH_2)_nNHA$, $(CH_2)_nNA_2$, $(CH_2)_nOH$, $(CH_2)_nOA$, $(CH_2)_nAr^3$, $(CH_2)_nHet^3$, $SO_2A$, $SO_2A$, NHCOA, NACOA, $NHSO_2A$, $NASO_2A$, COOA, $CONH_2$, COA, CONHA, COOH, $SO_2NH_2$, $SO_2NHA$, $SO_2NA_2$, $(CH_2)_nOCHO$, $NH(CH_2)_nHet^3$, CN and/or =O, $Het^3$ denotes piperidinyl, piperazinyl, pyrrolidinyl, morpholinyl, imidazolidinyl, tetrahydro-pyranyl, imidazolyl or indolinyl each of which is unsubstituted or mono-, di- or trisubstituted by A and/or =O, $R^3$ denotes H or alkyl having 1, 2, 3 or 4 C-atoms, A denotes unbranched or branched alkyl having 1-10 C atoms, in which 1-7 H atoms may be replaced by F and/or in which one or two non-adjacent $CH_2$ groups may be replaced by O and/or NH, or cyclic alkyl having 3-7 C atoms, Cyc denotes cyclic alkyl having 3-7 C atoms, which is unsubstituted or monosubstituted by $NH_2$, CN, $CONH_2$ or OH, $Ar^3$ denotes phenyl, which is unsubstituted or mono- or disubstituted by F, A, CN, $NH_2$, NHA, $NA_2$ and/or $CONH_2$, Carb denotes indanyl or 5,6,7,8-tetrahydro-naphthyl, which is unsubstituted or mono-, di-, tri- or tetrasubstituted by A, Hal denotes F, Cl, Br or I, n denotes 0, 1, 2, 3 or 4, p denotes 1, 2, 3 or 4, and pharmaceutically usable solvates, salts, tautomers and stereoisomers thereof, including mixtures thereof in all ratios.

The invention also relates to the optically active forms (stereoisomers), the enantiomers, the racemates, the diastereomers and the hydrates and solvates of these compounds.

Moreover, the invention relates to pharmaceutically acceptable derivatives of compounds of formula I.

The term solvates of the compounds is taken to mean adductions of inert solvent molecules onto the compounds which form owing to their mutual attractive force. Solvates are, for example, mono- or dihydrates or alkoxides.

It is understood, that the invention also relates to the solvates of the salts. The term pharmaceutically acceptable derivatives is taken to mean, for example, the salts of the compounds according to the invention and also so-called prodrug compounds.

As used herein and unless otherwise indicated, the term "prodrug" means a derivative of a compound of formula I that can hydrolyze, oxidize, or otherwise react under biological conditions (in vitro or in vivo) to provide an active compound, particularly a compound of formula I. Examples of prodrugs include, but are not limited to, derivatives and metabolites of a compound of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:

improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds. "Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula I and salts thereof and to a process for the preparation of compounds of the formula I and pharmaceutically usable salts, solvates, tautomers and stereoisomers thereof, characterised in that a) a compound of the formula II

II

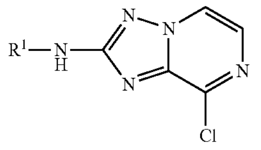

in which $R^1$ has the meaning indicated in Claim 1, is reacted with a compound of the formula III $R^2$-L III in which $R^2$ has the meaning indicated in Claim 1, and L denotes a boronic acid or a boronic acid ester group, in a Suzuki-type coupling or b) a compound of the formula II

II

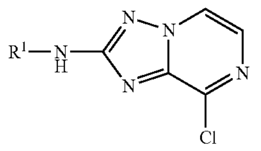

in which $R^1$ has the meaning indicated in Claim 1, is reacted with a compound of the formula III $R^2$-L III in which $R^2$ has the meaning indicated in Claim 1, and L denotes an $NH_2$ or OH and/or a base or acid of the formula I is converted into one of its salts.

Above and below, the radicals $R^1$ and $R^2$ have the meanings indicated for the formula I, unless expressly stated otherwise.

A denotes alkyl, this is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Moreover, A denotes preferably $CH_2OCH_3$, $OCH_2CH_2OCH_3$, $NHCH_2CH_2OH$, $CH_2CH_2OH$, $CH_2NHCH_2$ or $NHCH_2CH_3$.

Cyclic alkyl (cycloalkyl) preferably denotes cyclopropyl, cyclobutyl, cyclopentyl, cyclohexyl or cycloheptyl.

Cyc denotes cyclic alkyl having 3-7 C atoms, preferably denotes cyclopropyl, cyclobutyl, cyclopentyl, cyclohexyl or cycloheptyl.

$R^1$ preferably denotes denotes $Ar^1$, Carb or $Het^1$.

$Het^1$ preferably denotes 1,3-dihydro-2-oxo-indolyl.

Hal preferably denotes F, Cl or Br, but also I, particularly preferably F or Cl.

Throughout the invention, all radicals which occur more than once may be identical or different, i.e. are independent of one another.

The compounds of the formula I may have one or more chiral centres and can therefore occur in various stereoisomeric forms. The formula I encompasses all these forms.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise Use can also be made here of variants known per se which are not mentioned here in greater detail.

The starting compounds of the formulae II and III are generally known. If they are novel, however, they can be prepared by methods known per se. The pyridazinones of the formula II used are, if not commercially available, generally prepared by the method of W. J. Coates, A. McKillop, Synthesis, 1993, 334-342.

Compounds of the formula I can preferably be obtained by reacting a compound of the formula II with a compound of the formula III. In the compounds of the formula III, L preferably denotes

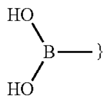

oder

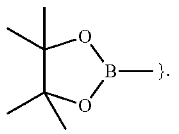

The reaction is generally carried out under conditions of a Suzuki-type coupling.

Depending on the conditions used, the reaction time is between a few minutes and 14 days, the reaction temperature is between about −30° and 140°, normally between 0° and 100°, in particular between about 60° and about 90°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to ethanole, toluene, dimethoxyethane, 1,4-dioxane and/or water.

Moreover, compounds of the formula I can preferably be obtained by reacting a compound of the formula II with a compound of the formula III wherein L preferably denotes $NH_2$ or OH. The reaction is generally carried out under conditions known to the skilled artisan and which are known and suitable for the said reaction. It is furthermore possible to convert a compound of the formula I into another compound of the formula I, for example by reducing nitro groups to amino groups (for example by hydrogenation on Raney nickel or Pd/carbon in an inert solvent, such as methanol or ethanol).

Free amino groups can furthermore be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

It is furthermore possible to convert a compound of the formula I into another compound of the formula I, for example by reducing nitro groups to amino groups (for example by hydrogenation on Raney nickel or Pd/carbon in an inert solvent, such as methanol or ethanol).

Free amino groups can furthermore be acylated in a conventional manner using an acid chloride or anhydride or alkylated using an unsubstituted or substituted alkyl halide, advantageously in an inert solvent, such as dichloromethane or THF, and/or in the presence of a base, such as triethylamine or pyridine, at temperatures between −60 and +30°.

The compounds of the formula I can furthermore be obtained by liberating them from their functional derivatives by solvolysis, in particular hydrolysis, or by hydrogenolysis.

Preferred starting materials for the solvolysis or hydrogenolysis are those which contain corresponding protected amino and/or hydroxyl groups instead of one or more free amino and/or hydroxyl groups, preferably those which carry an aminoprotecting group instead of an H atom bonded to an N atom, for example those which conform to the formula I, but contain an NHR' group (in which R' is an aminoprotecting group, for example BOC or CBZ) instead of an $NH_2$ group.

Preference is furthermore given to starting materials which carry a hydroxyl-protecting group instead of the H atom of a hydroxyl group, for example those which conform to the formula I, but contain an R"O-phenyl group (in which R" is a hydroxylprotecting group) instead of a hydroxyphenyl group.

It is also possible for a plurality of—identical or different—protected amino and/or hydroxyl groups to be present in the molecule of the starting material. If the protecting groups present are different from one another, they can in many cases be cleaved off selectively.

The term "aminoprotecting group" is known in general terms and relates to groups which are suitable for protecting (blocking) an amino group against chemical reactions, but are easy to remove after the desired chemical reaction has been carried out elsewhere in the molecule. Typical of such groups are, in particular, unsubstituted or substituted acyl, aryl, aralkoxymethyl or aralkyl groups. Since the aminoprotecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxycarbonyl, ethoxycarbonyl, 2,2,2-trichloroethoxycarbonyl, BOC and 2-iodoethoxycarbonyl; aralkoxycarbonyl, such as CBZ ("carbobenzoxy"), 4-methoxybenzyloxycarbonyl and FMOC; and arylsulfonyl, such as Mtr, Pbf and Pmc. Preferred aminoprotecting groups are BOC and Mtr, furthermore CBZ, Fmoc, benzyl and acetyl.

The term "hydroxylprotecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxylprotecting groups are not crucial since they are removed again after the desired chemical reaction or reaction sequence; preference is given to groups having 1-20, in particular 1-10, carbon atoms. Examples of hydroxylprotecting groups are, inter alia, tert-butoxycarbonyl, benzyl, p-nitrobenzoyl, p-toluenesulfonyl, tert-butyl and acetyl, where benzyl and tert-butyl are particularly preferred. The COOH groups in aspartic acid and glutamic acid are preferably protected in the form of their tert-butyl esters (for example Asp(OBut)).

The compounds of the formula I are liberated from their functional derivatives—depending on the protecting group used—for example using strong acids, advantageously using TFA or perchloric acid, but also using other strong inorganic acids, such as hydrochloric acid or sulfuric acid, strong organic carboxylic acids, such as trichloroacetic acid, or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50°, preferably between 15 and 30° (room temperature).

The BOC, OBut, Pbf, Pmc and Mtr groups can, for example, preferably be cleaved off using TFA in dichloromethane or using approximately 3 to 5N HCl in dioxane at 15-30°, and the FMOC group can be cleaved off using an approximately 5 to 50% solution of dimethylamine, diethylamine or piperidine in DMF at 15-30°.

The trityl group is employed to protect the amino acids histidine, asparagine, glutamine and cysteine. They are cleaved off, depending on the desired end product, using TFA/10% thiophenol, with the trityl group being cleaved off from all the said amino acids; on use of TFA/anisole or TFA/thioanisole, only the trityl group of His, Asn and Gin is cleaved off, whereas it remains on the Cys side chain.

The Pbf (pentamethylbenzofuranyl) group is employed to protect Arg. It is cleaved off using, for example, TFA in dichloromethane.

Hydrogenolytically removable protecting groups (for example CBZ or benzyl) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° and pressures between about 1 and 200 bar, preferably at 20-30° and 1-10 bar. Hydrogenolysis of the CBZ group succeeds well, for example, on 5 to 10% Pd/C in methanol or using ammonium formate (instead of hydrogen) on Pd/C in methanol/DMF at 20-30°.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl($C_1$-$C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula I includes isotope-labelled forms thereof. An isotope-labelled form of a compound of the formula I is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula I, a prodrug, thereof or a pharmaceutically acceptable salt of either which contains one or more of the above-mentioned isotopes and/or other isotopes of other atoms is intended to be part of the present invention. An isotope-labelled compound of the formula I can be used in a number of beneficial ways. For example, an isotope-labelled compound of the formula I into which, for example, a radioisotope, such as $^{3}H$ or $^{14}C$, has been incorporated is suitable for medicament and/or substrate tissue distribution assays. These radioisotopes, i.e. tritium ($^{3}H$) and carbon-14 ($^{14}C$), are particularly preferred owing to simple preparation and excellent detectability. Incorporation of heavier isotopes, for example deuterium ($^{2}H$), into a compound of the formula I has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula I can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^{2}H$) can also be incorporated into a compound of the formula I for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D$=2-7 are typical. If this rate difference is successfully applied to a compound of the formula I that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula I with improved stability through resistance to such oxidative metabolism. Significant improvements in the pharmacokinetic profiles of compounds of the formula I are thereby obtained, and can be expressed quantitatively in terms of increases in the in vivo half-life (t/2), concentration at maximum therapeutic effect ($C_{max}$), area under the dose response curve (AUC), and F; and in terms of reduced clearance, dose and materials costs.

The following is intended to illustrate the above: a compound of the formula I which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula I can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula I and/or pharmaceutically acceptable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986). Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of partdoses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The disclosed compounds of the formula I can be administered in combination with other known therapeutic agents including agents for the treatment of RA (rheumatoid arthritis). As used here, the term "agents for the treatment of RA" relates to any agent which is administered to a patient with RA for the purposes of treating the RA.

The medicaments below are preferably, but not exclusively, combined with the compounds of the formula I:

1. NSAIDs (non-steroidal anti-inflammatory drugs) and analgesics
2. Glucocorticoids (low oral doses)
3. Conventional disease-modifying antirheumatic drugs (DMARDs)
   - Methotrexate
   - Leflunomide
   - Sulfasalazine
   - Hydroxycloroquine
   - Azathioprine
   - Ciclosporin
   - Minocycline
   - Gold
4. Biologic response modifiers (BRMs)→target molecules/immune cells involved in the inflammatory process, and include the following agents:
   - TNF inhibitors
     - etanercept (Enbrel)
     - infliximab (Remicade)
     - adalimumab (Humira)
   - B-cell-directed therapy
     - rituximab (Rituxan)
   - T-cell/B-cell coactivation signal inhibitor
     - abatacept (Orencia)
   - IL-1 receptor antagonist
     - anakinra (Kineret)

| | MECHANISM OF ACTION |
|---|---|
| Golimumab | Fully humanized monoclonal antibody to TNF |
| Certolizumab pegol | Anti-TNF agent with just the Fab portion attached to the polyethylene glycol |
| Tocilizumab | Humanized monoclonal anti-IL-6 antibody that binds to the soluble and membrane-expresses IL-6 receptor |
| Ocrelizumab | Humanized-second generation anti-CD20 antibody that depletes B cells |
| Ofatumumab | Human monoclonal anti-CD20 IgG1 antibody |
| Denosumab | Fully humanized monoclonal antibody that binds to and inhibits the receptor activator for nuclear factor-kB ligand |
| TRU-015 | New class of CD20-directed protein therapeutics |
| Oral small molecules (JAK, Syk, MAP kinase inhibitors) | Cytoplasmic targets |
| Tolerogens (dnaJP1) | Immunotherapy based on T-cell tolerization |

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula I and/or pharmaceutically acceptable salts, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically acceptable salts, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically acceptable salts, solvates and stereoisomers thereof, including mixtures thereof in all ratios, and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula (I) can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer, metabolic conditions or conditions treatable or preventable by inhibition of a kinase or a kinase pathway, in one embodiment, the Syk, FLT-3, JAKI and/or JAK2 pathway. In one embodiment an effective amount of a compound of formula (I) is an amount that inhibits a kinase in a cell, such as, for example, in vitro or in vivo. In some embodiments, the effective amount of the compound of formula (I) inhibits the kinase in a cell by 10%, 20%, 30%, 40%, 50%, 60%, 70%, 80%, 90% or 99%, compared to the activity of the kinase in an untreated cell. The effective amount of the compound of formula (I), for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present compounds are suitable as pharmaceutical active ingredients for mammals, especially for humans, in the treatment of tyrosine kinase-induced diseases.

The present invention encompasses the use of the compounds of the formula I and/or physiologically acceptable salts and solvates thereof for the preparation of a medicament for the treatment or prevention of rheumatoid arthritis, systemic lupus, asthma, allergic rhinitis, ITP, multiple sclerosis, leukemia, breast cancer and maligna melanoma.

Examples of inflammatory diseases include rheumatoid arthritis, psoriasis, contact dermatitis, delayed hypersensitivity reaction and the like.

Also encompassed is the use of the compounds of the formula I and/or physiologically acceptable salts and solvates thereof for the preparation of a medicament for the treatment or prevention of a tyrosine kinase-induced disease or a tyrosine kinase-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The present invention also encompasses the use compounds of the formula I and/or physiologically acceptable salts and solvates thereof for the preparation of a medicament for the treatment or prevention of retinal vascularisation.

The expression "tyrosine kinase-induced diseases or conditions" refers to pathological conditions that depend on the activity of one or more tyrosine kinases. Tyrosine kinases either directly or indirectly participate in the signal transduction pathways of a variety of cellular activities, including proliferation, adhesion and migration and differentiation. Diseases associated with tyrosine kinase activity include proliferation of tumour cells, pathological neovascularisation that promotes the growth of solid tumours, ocular neovascularisation (diabetic retinopathy, age-induced macular degeneration and the like) and inflammation (psoriasis, rheumatoid arthritis and the like).

The present invention specifically relates to compounds of the formula I and pharmaceutically acceptable salts, solvates, tautomers and stereoisomers thereof, including mixtures thereof in all ratios, for the use for the treatment of diseases in which the inhibition, regulation and/or modulation inhibition of Syk plays a role.

The present invention specifically relates to compounds of the formula I and pharmaceutically acceptable salts, solvates, tautomers and stereoisomers thereof, including mixtures thereof in all ratios, for the use for the inhibition of Syk.

The present invention relates to a method of treating a proliferative, autoimmune, anti inflammatory or infectious disease disorder that comprises administering to a subject in need thereof a therapeutically effective amount of a compound of formula I.

Preferably, the present invention relates to a method wherein the disease is a cancer.

Particularly preferable, the present invention relates to a method wherein the disease is a cancer, wherein administration is simultaneous, sequential or in alternation with administration of at least one other active drug agent.

The disclosed compounds of the formula I can be administered in combination with other known therapeutic agents, including anticancer agents. As used here, the term "anticancer agent" relates to any agent which is administered to a patient with cancer for the purposes of treating the cancer.

The anti-cancer treatment defined herein may be applied as a sole therapy or may involve, in addition to the compound of the invention, conventional surgery or radiotherapy or chemotherapy. Such chemotherapy may include one or more of the following categories of anti-tumour agents:

(i) antiproliferative/antineoplastic/DNA-damaging agents and combinations thereof, as used in medical oncology, such as alkylating agents (for example cis-platin, carboplatin, cyclophosphamide, nitrogen mustard, melphalan, chloroambucil, busulphan and nitrosoureas); antimetabolites (for example antifolates such as fluoropyrimidines like 5-fluorouracil and tegafur, raltitrexed, methotrexate, cytosine arabinoside, hydroxyurea and gemcitabine); antitumour antibiotics (for example anthracyclines, like adriamycin, bleomycin, doxorubicin, daunomycin, epirubicin, idarubicin, mitomycin-C, dactinomycin and mithramycin); antimitotic agents (for example vinca alkaloids, like vincristine, vinblastine, vindesine and vinorelbine, and taxoids, like taxol and taxotere); topoisomerase inhibitors (for example epipodophyllotoxins, like etoposide and teniposide, amsacrine, topotecan, irinotecan and camptothecin) and cell-differentiating agents (for example all-trans-retinoic acid, 13-cis-retinoic acid and fenretinide);

(ii) cytostatic agents, such as antioestrogens (for example tamoxifen, toremifene, raloxifene, droloxifene and iodoxyfene), oestrogen receptor downregulators (for example fulvestrant), antiandrogens (for example bi-calutamide, flutamide, nilutamide and cyproterone acetate), LHRH antagonists or LHRH agonists (for example goserelin, leuprorelin and buserelin), progesterones (for example megestrol acetate), aromatase inhibitors (for example as anastrozole, letrozole, vorazole and exemestane) and inhibitors of 5α-reductase, such as finasteride;

(iii) agents which inhibit cancer cell invasion (for example metalloproteinase inhibitors, like marimastat, and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the antierbbl antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors, such as N-(3-chloro-4-fluorophenyl)-7-methoxy-6-(3-morpholinopropoxy) quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v)antiangiogenic agents, such as those which inhibit the effects of vascular endothelial growth factor, (for example the anti-vascular endothelial cell growth factor antibody bevacizumab [Avastin™], compounds such as those disclosed in published international patent applications WO 97/22596, WO 97/30035, WO 97/32856 and WO 98/13354) and compounds that work by other mechanisms (for example linomide, inhibitors of integrin αvβ3 function and angiostatin);

(vi) vessel-damaging agents, such as combretastatin A4 and compounds disclosed in international patent applications WO 99/02166, WO 00/40529, WO 00/41669, WO 01/92224, WO 02/04434 and WO 02/08213;

(vii) antisense therapies, for example those which are directed to the targets listed above, such as ISIS 2503, an anti-Ras antisense;

(viii) gene therapy approaches, including, for example, approaches for replacement of aberrant genes, such as aberrant p53 or aberrant BRCA1 or BRCA2, GDEPT (gene-directed enzyme pro-drug therapy) approaches, such as those using cytosine deaminase, thymidine kinase or a bacterial nitroreductase enzyme, and approaches for increasing patient tolerance to chemotherapy or radiotherapy, such as multi-drug resistance gene therapy; and (ix) immunotherapy approaches, including, for example, ex-vivo and in-vivo approaches for increasing the immunogenicity of patient tumour cells, such as transfection with cytokines, such as interleukin 2, interleukin 4 or granulocyte-macrophage colony stimulating factor, approaches for decreasing T-cell anergy, approaches using transfected immune cells, such as cytokine-transfected dendritic cells, approaches using cytokine-transfected tumour cell lines, and approaches using anti-idiotypic antibodies.

The medicaments from Table 1 below are preferably, but not exclusively, combined with the compounds of the formula I.

TABLE 1

| | | |
|---|---|---|
| Alkylating agents | Cyclophosphamide | Lomustine |
| | Busulfan | Procarbazine |
| | Ifosfamide | Altretamine |
| | Melphalan | Estramustine phosphate |
| | Hexamethylmelamine | Mechloroethamine |
| | Thiotepa | Streptozocin |
| | chloroambucil | Temozolomide |
| | Dacarbazine | Semustine |
| | Carmustine | |
| Platinum agents | Cisplatin | Carboplatin |
| | Oxaliplatin | ZD-0473 (AnorMED) |
| | Spiroplatin | Lobaplatin (Aetema) |
| | Carboxyphthalatoplatinum | Satraplatin (Johnson Matthey) |
| | Tetraplatin | BBR-3464 (Hoffmann-La Roche) |
| | Ormiplatin | SM-11355 (Sumitomo) |
| | Iproplatin | AP-5280 (Access) |
| Antimetabolites | Azacytidine | Tomudex |
| | Gemcitabine | Trimetrexate |
| | Capecitabine | Deoxycoformycin |
| | 5-fluorouracil | Fludarabine |
| | Floxuridine | Pentostatin |
| | 2-chlorodesoxyadenosine | Raltitrexed |
| | 6-Mercaptopurine | Hydroxyurea |
| | 6-Thioguanine | Decitabine (SuperGen) |
| | Cytarabine | Clofarabine (Bioenvision) |
| | 2-fluorodesoxycytidine | Irofulven (MGI Pharma) |
| | Methotrexate | DMDC (Hoffmann-La Roche) |
| | Idatrexate | Ethynylcytidine (Taiho) |

TABLE 1-continued

| | | |
|---|---|---|
| Topoisomerase inhibitors | Amsacrine | Rubitecan (SuperGen) |
| | Epirubicin | Exatecan mesylate (Daiichi) |
| | Etoposide | Quinamed (ChemGenex) |
| | Teniposide or mitoxantrone | Gimatecan (Sigma-Tau) |
| | Irinotecan (CPT-11) | Diflomotecan (Beaufour-Ipsen) |
| | 7-ethyl-10-hydroxycamptothecin | TAS-103 (Taiho) |
| | Topotecan | Elsamitrucin (Spectrum) |
| | Dexrazoxanet (TopoTarget) | J-107088 (Merck & Co) |
| | Pixantrone (Novuspharrna) | BNP-1350 (BioNumerik) |
| | Rebeccamycin analogue (Exelixis) | CKD-602 (Chong Kun Dang) |
| | BBR-3576 (Novuspharrna) | KW-2170 (Kyowa Hakko) |
| Antitumour antibiotics | Dactinomycin (Actinomycin D) | Amonafide |
| | Doxorubicin (Adriamycin) | Azonafide |
| | Deoxyrubicin | Anthrapyrazole |
| | Valrubicin | Oxantrazole |
| | Daunorubicin (Daunomycin) | Losoxantrone |
| | Epirubicin | Bleomycin sulfate (Blenoxan) |
| | Therarubicin | Bleomycinic acid |
| | Idarubicin | Bleomycin A |
| | Rubidazon | Bleomycin B |
| | Plicamycinp | Mitomycin C |
| | Porfiromycin | MEN-10755 (Menarini) |
| | Cyanomorpholinodoxorubicin | GPX-100 (Gem Pharmaceuticals) |
| | Mitoxantron (Novantron) | |
| Antimitotic agents | Paclitaxel | SB 408075 (GlaxoSmithKline) |
| | Docetaxel | E7010 (Abbott) |
| | Colchicine | PG-TXL (Cell Therapeutics) |
| | Vinblastine | IDN 5109 (Bayer) |
| | Vincristine | A 105972 (Abbott) |
| | Vinorelbine | A 204197 (Abbott) |
| | Vindesine | LU 223651 (BASF) |
| | Dolastatin 10 (NCI) | D 24851 (ASTA Medica) |
| | Rhizoxin (Fujisawa) | ER-86526 (Eisai) |
| | Mivobulin (Warner-Lambert) | Combretastatin A4 (BMS) |
| | Cemadotin (BASF) | Isohomohalichondrin-B (PharmaMar) |
| | RPR 109881A (Aventis) | ZD 6126 (AstraZeneca) |
| | TXD 258 (Aventis) | PEG-Paclitaxel (Enzon) |
| | Epothilone B (Novartis) | AZ10992 (Asahi) |
| | T 900607 (Tularik) | !DN-5109 (Indena) |
| | T 138067 (Tularik) | AVLB (Prescient NeuroPharma) |
| | Cryptophycin 52 (Eli Lilly) | Azaepothilon B (BMS) |
| | Vinflunine (Fabre) | BNP-7787 (BioNumerik) |
| | Auristatin PE (Teikoku Hormone) | CA-4-prodrug (OXiGENE) |
| | BMS 247550 (BMS) | Dolastatin-10 (NrH) |
| | BMS 184476 (BMS) | CA-4 (OXiGENE) |
| | BMS 188797 (BMS) | |
| | Taxoprexin (Protarga) | |
| Aromatase inhibitors | Aminoglutethimide | Exemestan |
| | Letrozole | Atamestan (BioMedicines) |
| | Anastrazole | YM-511 (Yamanouchi) |
| | Formestan | |
| Thymidylate synthase inhibitors | Pemetrexed (Eli Lilly) | Nolatrexed (Eximias) |
| | ZD-9331 (BTG) | CoFactor ™ (BioKeys) |
| DNA antagonists | Trabectedin (PharmaMar) | Mafosfamide (Baxter International) |
| | Glufosfamide (Baxter International) | Apaziquone (Spectrum Pharmaceuticals) |
| | Albumin + 32P (Isotope Solutions) | O6-benzylguanine (Paligent) |
| | Thymectacin (NewBiotics) | |
| | Edotreotid (Novartis) | |
| Farnesyl transferase inhibitors | Arglabin (NuOncology Labs) | Tipifarnib (Johnson & Johnson) |
| | Ionafarnib (Schering-Plough) | Perillyl alcohol (DOR BioPharma) |
| | BAY-43-9006 (Bayer) | |
| Pump inhibitors | CBT-1 (CBA Pharma) | Zosuquidar trihydrochloride (Eli Lilly) |
| | Tariquidar (Xenova) | Biricodar dicitrate (Vertex) |
| | MS-209 (Schering AG) | |

TABLE 1-continued

| | | |
|---|---|---|
| Histone acetyl transferase inhibitors | Tacedinaline (Pfizer)<br>SAHA (Aton Pharma)<br>MS-275 (Schering AG) | Pivaloyloxymethyl butyrate (Titan)<br>Depsipeptide (Fujisawa) |
| Metalloproteinase inhibitors | Neovastat (Aeterna Laboratories)<br>Marimastat (British Biotech) | CMT-3 (CollaGenex)<br>BMS-275291 (Celltech) |
| Ribonucleoside reductase inhibitors | Gallium maltolate (Titan)<br>Triapin (Vion) | Tezacitabine (Aventis)<br>Didox (Molecules for Health) |
| TNF-alpha agonists/ antagonists | Virulizin (Lorus Therapeutics)<br>CDC-394 (Celgene) | Revimid (Celgene) |
| Endothelin-A receptor antagonists | Atrasentan (Abbot)<br>ZD-4054 (AstraZeneca) | YM-598 (Yamanouchi) |
| Retinoic acid receptor agonists | Fenretinide (Johnson & Johnson)<br>LGD-1550 (Ligand) | Alitretinoin (Ligand) |
| Immunomodulators | Interferon<br>Oncophage (Antigenics)<br>GMK (Progenics)<br>Adenocarcinoma vaccine (Biomira)<br>CTP-37 (AVI BioPharma)<br>JRX-2 (Immuno-Rx)<br>PEP-005 (Peplin Biotech)<br>Synchrovax vaccines (CTL Immuno)<br>Melanoma vaccine (CTL Immuno)<br>p21-RAS vaccine (Gem-Vax) | Dexosome therapy (Anosys)<br>Pentrix (Australian Cancer Technology)<br>JSF-154 (Tragen)<br>Cancer vaccine (Intercell)<br>Norelin (Biostar)<br>BLP-25 (Biomira)<br>MGV (Progenics)<br>!3-Alethin (Dovetail)<br>CLL-Thera (Vasogen) |
| Hormonal and antihormonal agents | Oestrogens<br>Conjugated oestrogens<br>Ethynyloestradiol<br>chlorotrianisene<br>Idenestrol<br>Hydroxyprogesterone caproate<br>Medroxyprogesterone<br>Testosterone<br>Testosterone propionate<br>Fluoxymesterone<br>Methyltestosterone<br>Diethylstilbestrol<br>Megestrol<br>Tamoxifen<br>Toremofin<br>Dexamethasone | Prednisone<br>Methylprednisolone<br>Prednisolone<br>Aminoglutethimide<br>Leuprolide<br>Goserelin<br>Leuporelin<br>Bicalutamide<br>Flutamide<br>Octreotide<br>Nilutamide<br>Mitotan<br>P-04 (Novogen)<br>2-Methoxyoestradiol (Entre Med)<br>Arzoxifen (Eli Lilly) |
| Photodynamic agents | Talaporfin (Light Sciences)<br>Theralux (Theratechnologies)<br>Motexafin-Gadolinium (Pharmacyclics) | Pd-Bacteriopheophorbid (Yeda)<br>Lutetium-Texaphyrin (Pharmacyclics)<br>Hypericin |
| Tyrosine kinase inhibitors | Imatinib (Novartis)<br>Leflunomide(Sugen/Pharmacia)<br>ZDI839 (AstraZeneca)<br>Erlotinib (Oncogene Science)<br>Canertjnib (Pfizer)<br>Squalamine (Genaera)<br>SU5416 (Pharmacia)<br>SU6668 (Pharmacia)<br>ZD4190 (AstraZeneca)<br>ZD6474 (AstraZeneca)<br>Vatalanib (Novartis)<br>PKI166 (Novartis)<br>GW2016 (GlaxoSmith-Kline)<br>EKB-509 (Wyeth)<br>EKB-569 (Wyeth) | Kahalide F (PharmaMar)<br>CEP-701 (Cephalon)<br>CEP-751 (Cephalon)<br>MLN518 (Millenium)<br>PKC412 (Novartis)<br>Phenoxodiol O<br>Trastuzumab (Genentech)<br>C225 (ImClone)<br>rhu-Mab (Genentech)<br>MDX-H210 (Medarex)<br>2C4 (Genentech)<br>MDX-447 (Medarex)<br>ABX-EGF (Abgenix)<br>IMC-1C11 (ImClone) |
| Various agents | SR-27897 (CCK-A inhibitor, Sanofi-Synthelabo)<br>Tocladesine (cyclic AMP agonist, Ribapharm)<br>Alvocidib (CDK inhibitor, Aventis)<br>CV-247 (COX-2 inhibitor, Ivy Medical)<br>P54 (COX-2 inhibitor, Phytopharm)<br>CapCell ™ (CYP450 stimulant, Bavarian Nordic) | BCX-1777 (PNP inhibitor, BioCryst)<br>Ranpirnase (ribonuclease stimulant, Alfacell)<br>Galarubicin (RNA synthesis inhibitor, Dong-A)<br>Tirapazamine (reducing agent, SRI International)<br>N-Acetylcysteine (reducing agent, Zambon)<br>R-Flurbiprofen (NF-kappaB inhibitor, Encore) |

TABLE 1-continued

| | |
|---|---|
| GCS-IOO (gal3 antagonist, GlycoGenesys) | 3CPA (NF-kappaB inhibitor, Active Biotech) |
| G17DT immunogen (gastrin inhibitor, Aphton) | Seocalcitol (vitamin D receptor agonist, Leo) |
| Efaproxiral (oxygenator, Allos Therapeutics) | 131-I-TM-601 (DNA antagonist, TransMolecular) |
| PI-88 (heparanase inhibitor, Progen) | Eflornithin (ODC inhibitor, ILEX Oncology) |
| Tesmilifen (histamine antagonist, YM BioSciences) | Minodronic acid (osteoclast inhibitor, Yamanouchi) |
| Histamine (histamine H2 receptor agonist, Maxim) | Indisulam (p53 stimulant, Eisai) |
| Tiazofurin (IMPDH inhibitor, Ribapharm) | Aplidin (PPT inhibitor, PharmaMar) |
| Cilengitide (integrin antagonist, Merck KGaA) | Rituximab (CD20 antibody, Genentech) |
| SR-31747 (IL-1 antagonist, Sanofi-Synthelabo) | Gemtuzumab (CD33 antibody, Wyeth Ayerst) |
| CCI-779 (mTOR kinase inhibitor, Wyeth) | PG2 (haematopoiesis promoter, Pharmagenesis) |
| Exisulind (PDE-V inhibitor, Cell Pathways) | Immunol ™ (triclosan mouthwash, Endo) |
| CP-461 (PDE-V inhibitor, Cell Pathways) | Triacetyluridine (uridine prodrug, Wellstat) |
| AG-2037 (GART inhibitor, Pfizer) | SN-4071 (sarcoma agent, Signature BioScience) |
| WX-UK1 (plasminogen activator inhibitor, Wilex) | TransMID-107 ™ (immunotoxin, KS Biomedix) |
| PBI-1402 (PMN stimulant, ProMetic LifeSciences) | PCK-3145 (apoptosis promoter, Procyon) |
| Bortezomib (proteasome inhibitor, Millennium) | Doranidazole (apoptosis promoter, Pola) |
| SRL-172 (T-cell stimulant, SR Pharma) | CHS-828 (cytotoxic agent, Leo) |
| TLK-286 (glutathione-S transferase inhibitor, Telik) | Trans-retinic acid (differentiator, NIH) |
| PT-100 (growth factor agonist, Point Therapeutics) | MX6 (apoptosis promoter, MAXIA) |
| Midostaurin (PKC inhibitor, Novartis) | Apomine (apoptosis promoter, ILEX Oncology) |
| Bryostatin-1 (PKC stimulant, GPC Biotech) | Urocidin (apoptosis promoter, Bioniche) |
| CDA-II (apoptosis promoter, Everlife) | Ro-31-7453 (apoptosis promoter, La Roche) |
| SDX-101 (apoptosis promoter, Salmedix) | Brostallicin (apoptosis promoter, Pharmacia) |
| Ceflatonin (apoptosis promoter, ChemGenex) | |

The present invention specifically relates to compounds of the formula I and pharmaceutically acceptable salts, solvates, tautomers and stereoisomers thereof, including mixtures thereof in all ratios, for the use for the treatment of rheumatoid arthritis, systemic lupus, asthma, allergic rhinitis, ITP, multiple sclerosis, leukemia, breast cancer, maligna melanoma.

The present invention specifically relates to methods for treating or preventing an inflammatory condition, immunological condition, autoimmune condition, allergic condition, rheumatic condition, thrombotic condition, cancer, infection, neurodegenerative disease, neuroinflammatory disease, cardiovascular disease or metabolic condition, comprising administering to a subject in need thereof an effective amount of a compound of formula I or a pharmaceutically acceptable salt, tautomer, stereoisomer or solvate thereof.

In another aspect provided herein are methods of inhibiting a kinase in a cell expressing said kinase, comprising contacting said cell with an effective amount of a compound of formula I or a pharmaceutically acceptable salt, tautomer, stereoisomer or solvate thereof. In one embodiment the kinase is Syk, FLT3, JAK1 or JAK2 or JAK3 or BTK, or mutants or isoforms thereof, or combinations of two or more thereof.

Representative immunological conditions that compounds of formula I are useful for treating or preventing include, but are not limited to, Behçet's syndrome, non-allergy mast cell diseases (e.g., mastocytosis and treatment of anaphylaxis), ankylosing spondylitis, osteoarthritis, rheumatoid arthritis (RA), multiple sclerosis, lupus, inflammatory bowel disease, ulcerative colitis, Crohn's disease, myasthenia gravis, Grave's disease, transplant rejection, humoral transplant rejection, non-humoral transplant rejection, cellular transplant rejection, immune thrombocytopenic purpura (ITP), idiopathic thrombocytopenic purpura, diabetes, immunological response to bacterial, parasitic, helminth infestation or viral infection, eczema, dermatitis, graft versus host disease, Goodpasture's disease, hemolytic disease of the newborn, autoimmune hemolytic anemia, anti-phospholipid syndrome, ANCA-associated vasculitis, Churg-Strauss syndrome, Wegeners granulomatosus, pemphigus vulgaris, serum sickness, mixed cryoglobulinemia, peripheral neuropathy associated with IgM antibody, microscopic polyangiitis, Hashimoto's thyroiditis, Sjogrens syndrome, fibrosing conditions (such as those dependent on the innate or adaptive immune systems or local mesenchyma cells) or primary biliary cirrhosis.

Representative autoimmune conditions that compounds of formula I are useful for treating or preventing include, but are not limited to, autoimmune hemolytic anemia (A1 HA), Behçet's syndrome, Crohn's disease, type I diabetes, Goodpasture's disease, Grave's disease, Hashimoto's thyroiditis, idiopathic thrombocytopenic purpura, lupus, multiple sclerosis, amyotrophic lateral sclerosis, myasthenia gravis, pemphigus vulgaris, primary biliary cirrhosis, rheumatoid arthritis, scleroderma, Sjogren's syndrome, ulcerative colitis, or Wegeners granulomatosus.

Representative allergic conditions that compounds of formula I are useful for treating or preventing include, but are not limited to, anaphylaxis, hay fever, allergic conjunctivitis, allergic rhinitis, allergic asthma, atopic dermatitis, eczema, urticaria, mucosal disorders, tissue disorders and certain gastrointestinal disorders.

Representative rheumatic conditions that compounds of formula I are useful for treating or preventing include, but are not limited to, rheumatoid arthritis, gout, ankylosing spondylitis, or osteoarthritis.

Representative inflammatory conditions that compounds of formula I are useful for treating or preventing include, but are not limited to, non-ANCA (anti-neutrophil cytoplasmic autoantibody) vasculitis (e.g., wherein Syk function is associated with neutrophil adhesion, diapedesis and/or activation), psoriasis, asthma, allergic rhinitis, allergic conjunctivitis, chronic urticaria, hives, anaphylaxis, bronchitis, chronic obstructive pulmonary disease, cystic fibrosis, inflammatory bowel disease, irritable bowel syndrome, gout, Crohn's disease, mucous colitis, ulcerative colitis, allergy to intestinal antigens (such as gluten enteropathy), diabetes (e.g., Type I diabetes and Type II diabetes) and obesity. In some embodiments, the inflammatory condition is a dermatologic condition, such as, for example, psoriasis, urticaria, hives, eczema, scleroderma, or dermatitis. In other embodiments, the inflammatory condition is an inflammatory pulmonary condition, such as, for example, asthma, bronchitis, chronic obstructive pulmonary disease (COPD), or adult/acute respiratory distress syndrome (ARDS). In other embodiments, the inflammatory condition is a gastrointestinal condition, such as, for example, inflammatory bowel disease, ulcerative colitis, Crohn's disease, idiopathic inflammatory bowel disease, irritable bowel syndrome, or spastic colon.

Representative infections that compounds of formula I are useful for treating or preventing include, but are not limited to, bacterial, parasitic, prion, viral infections or helminth infestation.

Representative cancers that compounds of formula I are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Representative cardiovascular diseases that compounds of formula I are useful for treating or preventing include, but are not limited to, restenosis, atherosclerosis and its consequences such as stroke, myocardial infarction, ischemic damage to the heart, lung, gut, kidney, liver, pancreas, spleen or brain.

Representative metabolic conditions that compounds of formula I are useful for treating or preventing include, but are not limited to, obesity and diabetes (e.g., Type I and II diabetes). In a particular embodiment, provided herein are methods for the treatment or prevention of insulin resistance. In certain embodiments, provided herein are methods for the treatment or prevention of insulin resistance that leads to diabetes (e.g., Type II diabetes). In another embodiment, provided herein are methods for the treatment or prevention of syndrome X or metabolic syndrome. In another embodiment, provided herein are methods for the treatment or prevention of Type II diabetes, Type I diabetes, slow-onset Type I diabetes, diabetes insipidus (e.g., neurogenic diabetes insipidus, nephrogenic diabetes insipidus, dipsogenic diabetes insipidus, or gestagenic diabetes insipidus), diabetes mellitus, gestational diabetes mellitus, polycystic ovarian syndrome, maturity-onset diabetes, juvenile diabetes, insulin-dependant diabetes, non-insulin dependant diabetes, malnutrition-related diabetes, ketosis-prone diabetes, pre-diabetes (e.g., impaired glucose metabolism), cystic fibrosis related diabetes, hemochromatosis and ketosis-resistant diabetes.

Representative neurodegenerative and neuroinflammatory diseases that compounds of formula I are useful for treating or preventing include, but are not limited to, Huntington's disease, Alzheimer's disease, viral (e.g., HIV) or bacterial-associated encephalitis and damage.

In another embodiment, provided herein are methods for the treatment or prevention of fibrotic diseases and disorders. In a particular embodiment, provided herein are methods for the treatment or prevention of idiopathic pulmonary fibrosis, myelofibrosis, hepatic fibrosis, steatofibrosis and steatohepatitis.

In another embodiment, provided herein are methods for the treatment or prevention of diseases associated with thrombotic events such as but not limited to atherosclerosis, myocardial infarction and ischemic stroke.

The present invention specifically relates to compounds of the formula I and pharmaceutically acceptable salts, solvates, tautomers and stereoisomers thereof, including mixtures thereof in all ratios, for the use for the treatment and/or prevention of inflammatory conditions, immunological conditions, autoimmune conditions, allergic conditions, rheumatic conditions, thrombotic conditions, cancer, infections, neurodegenerative diseases, neuroinflammatory diseases, cardiovascular diseases, and metabolic conditions, the methods comprising administering to a subject in need thereof an effective amount of a compound of claim 1.

Moreover, the present invention specifically relates to compounds for the use for the treatment and/or prevention of cancer, where the cancer to be treated is a solid tumour or a tumour of the blood and immune system.

Moreover, the present invention specifically relates to compounds, for the use for the treatment and/or prevention of cancer, where the where the tumour originates from the group of acute myeloid leukaemia, chronic myeloid leukaemia, acute lymphatic leukaemia and/or chronic lymphatic leukaemia.

Moreover, the present invention specifically relates to compounds, for the use for the treatment and/or prevention of cancer, where the solid tumour originates from the group of tumours of the epithelium, the bladder, the stomach, the kidneys, of head and neck, the esophagus, the cervix, the thyroid, the intestine, the liver, the brain, the prostate, the uro-genital tract, the lymphatic system, the stomach, the larynx, the bones, including chondosarcoma and Ewing sarcoma, germ cells, including embryonal tissue tumours, and/or the lung, from the group of monocytic leukaemia, lung adenocarcinoma, small-cell lung carcinomas, pancreatic cancer, glioblastomas, neurofibroma, angiosarcoma, breast carcinoma and/or maligna melanoma.

Moreover, the present invention specifically relates to for the use for the treatment and/or prevention of diseases selected from the group rheumatoid arthritis, systemic lupus, asthma, multiple sclerosis, osteoarthritis, ischemic injury, giant cell arteritis, inflammatory bowel disease, diabetes, cystic fibrosis, psoriasis, Sjögrens syndrom and transplant organ rejection.

Moreover, the present invention specifically relates to compounds for the use for the treatment and/or prevention of diseases selected from the group Alzheimer's disease, Down's syndrome, hereditary cerebral hemorrhage with amyloidosis-Dutch Type, cerebral amyloid angiopathy, Creutzfeldt-Jakob disease, frontotemporal dementias, Huntington's disease, Parkinson's disease.

Moreover, the present invention specifically relates to compounds for the use for the treatment and/or prevention of diseases selected from the group

*leishmania*, mycobacteria, including *M. leprae, M. tuberculosis* and/or *M. avium, leishmania, plasmodium*, human immunodeficiency virus, Epstein Barr virus, Herpes simplex virus, hepatitis C virus.

The following abbreviations refer respectively to the definitions below:

aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), AcOH (acetic acid), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethylcarbodiimide), ESI (Electro-spray ionization), EtOAc (ethyl acetate), $Et_2O$ (diethyl ether), EtOH (ethanol), HATU (dimethylamino-([1,2,3]triazolo[4,5-b]pyridin-3-yloxy)-methylene]-dimethylammonium hexafluorophosphate), HPLC (High Performance Liquid Chromatography), i-PrOH (2-propanol), $K_2CO_3$ (potassium carbonate), LC (Liquid Chromatography), MeOH (methanol), $MgSO_4$ (magnesium sulfate), MS (mass spectrometry), MTBE (Methyl tert-butyl ether), $NaHCO_3$ (sodium bicarbonate), $NaBH_4$ (sodium borohydride), NMM (N-methyl morpholine), NMR (Nuclear Magnetic Resonance), PyBOP (benzotriazole-1-yl-oxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Description of the In Vitro Assays

SYK Flash Plate Assay

The kinase assay is performed either as 384-well Flashplate assay (for e.g. Topcount measurement) or as 384-well Image-Flashplate assay (for LEADseeker measurement).

2.5 nM SYK, 400 nM Biotin-Aha-Aha-KEDPDYEWPSAKK and 10 μM ATP (spiked with 0.3 μCi 33P-ATP/well) are incubated in a total volume of 50 μl (60 mM Hepes, 10 mM $MgCl_2$, 1.2 mM Dithiothreitol, 0.02% Brij35, 0.1% BSA, pH 7.5) with or without test compound for 1 hours at 30° C. The reaction is stopped with 25 μl 200 mM EDTA. After 30 Min at 30° C. the liquid is removed and each well washed thrice with 100 μl 0.9% sodium chloride solution. Non-specific reaction is determined in presence of 0.1 PIM Staurosporine. Radioactivity is measured with Topcount (when using Flashplates) or with LEADseeker (when using Image-Flashplates) respectively. Results (e.g. IC50-values) are calculated with program tools provided by the IT-department (e.g. Symyx Assay Explorer, Genedata Screener).

In Vivo Assays

CIA

For induction of collagen-induced arthritis (CIA) male DBA/1 mice are injected with 500 μl pristane i.p. on day −21. On day 0 mice are immunized with 100 μg chicken collagen type II (CII) in Complete Freund's Adjuvant (CFA) intradermally, distributed over pinnae and one site on the back on day 0. On day 21, mice will receive an i.p. booster immunization (100 μg) with soluble CII in PBS. Dosing of Syk inhibitor will be prophylactic: starting day 0 and continued until day 10 and before boost starting on day 20 and continued until day 30. Compounds will be administered orally twice a day at doses of 3, 10 and 30 mg/kg.

Body weight and clinical score will be recorded on a daily basis. Arthritis severity is graded using a clinical scoring system based on the assessment of inflammation in individual paws. The scale for this clinical score ranges from 0-4 for each individual paw.

GIA

For induction of Glucose-6-phosphate isomerase-induced arthritis (GIA) female DBA/1 mice are immunized with 100 μg G6PI in Complete Freund's Adjuvant (CFA) intradermally, distributed over pinnae and one site on the back on day 0. Dosing of Syk inhibitor will be prophylactic starting day 0 and continued until day 14. Compounds will be administered orally twice a day at doses of 3, 10 and 30 mg/kg.

Body weight and clinical score will be recorded on a daily basis. Arthritis severity is graded using a clinical scoring system based on the assessment of inflammation in individual paws. The scale for this clinical score ranges from 0-4 for each individual paw.

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation. Rf values on silica gel; eluent: ethyl acetate/methanol 9:1.

HPLC data provided in the examples described below (Retentiontime given) are obtained as followed.

Method A: 1 min 99% A. In 2.5 min from 99% A to 100% B; followed by 1.5 min 100% B and 1 min 99% A; Column Chromolith SpeedRod RP-18e; 50-4.6 mm; detection 220 nM (Solvent A: H20 (0.1% TFA), Solvent B: ACN (0.1% TFA);

Method A: Column: XBridge C8 (50×4.6 mm, 3.5 μm); A—0.1% TFA in $H_2O$, B—0.1% TFA in ACN: Flow—2.0 mL/min.

LCMS data provided in the examples are given with retention time, purity and/or mass in m/z. The results are obtained as followed: Mass spectrum: LC/MS Waters ZMD (ESI) or Hewlett Packard System of the HP 1100 series (Ion source: Electrospray (positive mode); Scan: 100-1000 m/z; Fragmentation-voltage: 60 V; Gas-temperature: 300° C., DAD: 220 nm. Flow rate: 2.4 ml/Min. The used splitter reduced the flow rate after the DAD for the MS to 0.75 ml/Min; Column: Chromolith Speed ROD RP-18e 50-4.6; Solvent: LiChrosolv-quality from the company Merck KGaA or as mentionend in the method Method A: Column: XBridge C8 (50×4.6 mm, 3.5 μm), +ve mode; A—0.1% TFA in $H_2O$, B—0.1% TFA in ACN: Flow—2.0 ml/min; Column: XBridge C8 (50×4.6 mm 3.5 Um, +ve mode Method B_Column: XBridge C8 (50×4.6 mm, 3.5 m), −ve mode; A—0.1% $NH_4HCO_3$ in $H_2O$, B-ACN: Flow—1.0 mL/min.

Method C: Column: Chromolith SpeedROD RP-18e 50-4.6 mm; SolentA: water+0.05% formic acid; SolventB: acetonitrile+0.04% formic acid, Flow: 2.4 ml/min; Gradient: within 2.8 min from 4% B to 100% B Method D: Column: Chromolith Speed Rod RP18e-50-4.6; Flow: 2.4 ml/min; Solvent A: Wasser+0.1% TFA; Solvent B: Acetonitril+0.1% TFA; WL: 220 nm Gradient: within 2.6 min: from 4% B to 100% B, followed by 0.7 min 100% B Preparative HPLC is performed on a Agilent 1200. Column: Chromolith prep RP 18e Merck KGaA. Mobile phase: 0.1% formic acid in water/0.1% formic acid in acetonitrile.

$^1$H NMR is recorded on Bruker DPX-300, DRX-400 or AVII-400 spectrometer, using residual signal of deuterated solvent as internal reference. Chemical shifts (δ) are reported in ppm relative to the residual solvent signal (δ=2.49 ppm for 1H NMR in DMSO-$d_6$). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

The microwave chemistry is performed on a single mode microwave reactor Emrys™ Optimiser from Personal Chemistry.

EXAMPLES

Preparation of Reactants

2-(2-Chloro-4-isothiocyanato-phenylsulfanyl)-1-methyl-4,5-dihydro-1H-imidazole ("A1")

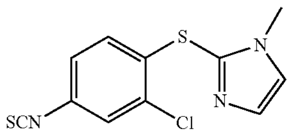

To a stirred solution of 3-chloro-4-(1-methyl-4,5-dihydro-1H-imidazol-2-ylsulfanyl)-phenylamine (5.0 g, 21 mmol) and diisopropylethylamine (5.37 g, 41.6 mmol) in dry tetrahydrofuran at 0° C. under $N_2$ inert atmosphere, thiophosgene (2.39 g, 21 mmol) in tetrahydrofuran is added dropwise and stirred for 20 minutes. When the reaction is completed, the reaction mixture is concentrated at room temperature and taken in dichloromethane (100 mL), washed with water (2×50 mL) and dried over anhydrous $MgSO_4$ to get the product as a brown solid (5.8 g, 99%). TLC: pet ether/ethyl acetate (8/2) $R_f$—0.4. LCMS (method A): mass found (M+H$^+$, 282.0), Rt (min): 3.43, area % 71.5 (max); $^1$H NMR (400 MHz, DMSO-$d_6$): δ 7.72 (d, J=2.16 Hz, 1H), 7.57 (s, 1H), 7.31 (m, 1H), 7.28 (m, 1H), 6.43 (d, J=8.56 Hz, 1H), 3.61 (s, 3H).

2,2-Difluoro-6-isothiocyanato-4H-benzo[1,4]oxazin-3-one ("A2")

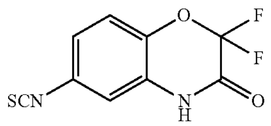

Intermediate "A2" is prepared as a brown solid (2.2 g, 91%) following the protocol used for the intermediate "A1" starting from 6-amino-2,2-difluoro-4H-benzo[1,4]oxazin-3-on. TLC: pet ether/ethyl acetate (8/2) $R_f$—0.2; $^1$H NMR (400 MHz, DMSO-$d_6$): δ 12.13 (br s, 1H), 7.37 (d, J=8.8 Hz, 1H), 7.21 (m, 1H), 7.04 (s, 1H).

1-Benzyl-6-isothiocyanato-1H-indazole ("A3")

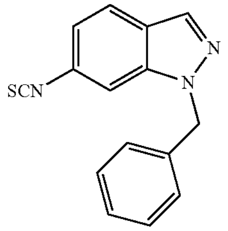

Intermediate "A3" is prepared as a brown solid (2.9 g, 98%) following the protocol used for the intermediate "A1" starting from 1-benzyl-1H-indazol-6-ylamine. TLC: pet ether/ethyl acetate (8/2) $R_f$—0.4. LCMS (method B): mass found (M+H$^+$, 266.2), Rt (min): 4.58 area % 94.8 (max); $^1$H NMR (400 MHz, DMSO-$d_6$): δ 8.16 (s, 1H), 7.97 (s, 1H), 7.82 (d, J=8.52 Hz, 1H), 7.24 (m, 5H), 7.15 (m, 1H), 5.64 (s, 2H).

6-Isothiocyanato-2,2-dimethyl-4H-pyrido[3,2-b]oxazin-3-one ("A4")

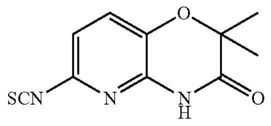

Intermediate "A4" is prepared as a brown solid (2.0 g, 83%) following the protocol used for the intermediate A1 starting from 6-amino-2,2-dimethyl-4H-pyrido[3,2-b]oxazin-3-one. TLC: pet ether/ethyl acetate (8/2) $R_f$—0.4. LCMS (method A): mass found (M+H$^+$, 236.0), Rt (min): 4.12 area % 83.8 (max), 82.18 (220 nm); $^1$H NMR (400 MHz, DMSO-$d_6$): δ 11.44 (br s, 1H), 7.43 (d, J=8.24 Hz, 1H), 6.99 (d, J=8.24 Hz, 1H), 1.42 (s, 6H).

N-(tert.-Butoxycarbonyl)-O-(mesitylsulfonyl)-hydroxylamine

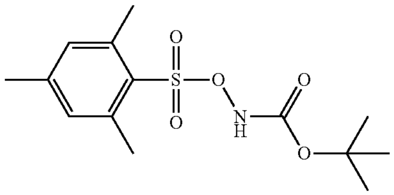 [SMILES: Cc1cc(C)c(S(=O)(=O)ONC(=O)OC(C)(C)C)c(C)c1]

To a solution of 2-mesitylene sulphonyl chloride (2.0 g, 9.14 mmol) in dry THF (50 mL), is added N-Boc-hydroxylamine (1.21 g, 9.14 mmol) and cooled to 0° C. under $N_2$ atmosphere. The reaction mixture is stirred for 5 minutes. To this mixture triethylamine (1.1 g, 11 mmol) is added slowly over 10 minutes. The reaction mixture is stirred for 1 hour at 0° C. and upon completion, the solvent removed in vacuo. The residue is redissolved in dichloromethane (50 mL) and washed with water (2×50 mL), 10% aqueous $NaHCO_3$ (50 mL) and dried over $MgSO_4$. It is then concentrated under reduced pressure at room temperature to get the product as an off white solid; (2.1 g, 73%). TLC: pet ether/ethyl acetate (8/2) $R_f$—0.4. $^1$H NMR (DMSO-$d_6$; 400 MHz): δ 11.16 (s, 1H), 7.12 (s, 2H), 2.49 (s, 6H), 2.28 (s, 3H), 1.23 (s, 9H).

2-[(Aminoxy)-sulfonyl]-1,3,5-trimethylbenzene

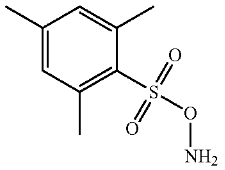

To the solid product N-(tert.-butoxycarbonyl)-O-(mesitylsulfonyl)-hydroxylamine (2.1 g, 6.6 mmol) is added trifluoroacetic acid (20 mL) slowly at 0° C. under a nitrogen atmosphere. The reaction mixture is stirred for 30 minutes followed slowly by water (60 mL). The reaction is left at 0° C. for 15 minutes. The solid precipitated is filtered and washed several times with water until the pH of the filtrate was neutral. The white solid (1.4 g, 98%) is dried in the Buchner funnel and used immediately for the next reaction; $^1$H NMR (400 MHz, DMSO-$d_6$): δ6.73 (s, 2H), 2.48 (s, 6H), 2.15 (s, 3H).

1,2-Diamino-3-chloro-pyrazinium mesitylenate

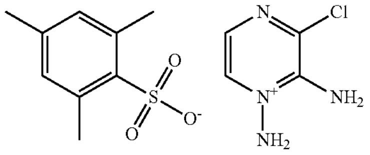

To a solution of 2-amino-3-chloro-pyrazine (1.4 g, 11 mmol) in dry dichloromethane (25 mL) at 0° C. under $N_2$ atmosphere is added 2-[(aminoxy)-sulfonyl]-1,3,5-trimethylbenzene (2.91 g, 13.5 mmol) over 10 minutes. The reaction mixture is stirred for 30 minutes at RT. To this reaction mixture, diethyl ether (100 mL) is added and stirred for 15 minutes. The solid precipitated is filtered and washed with diethyl ether to afford the product as a light brown solid (3 g, 80%); $^1$H NMR (DMSO-$d_6$, 400 MHz): δ 9.07 (br s, 2H), 8.11 (d, J=4.28 Hz, 1H), 7.78 (d, J=4.2 Hz, 1H), 7.28 (s, 1H), 6.72 (s, 1H), 2.48 (s, 6H), 2.15 (s, 3H).

8-Chloro-[1,2,4]triazolo[1,5-a]pyrazin-2-yl-(3,5-dimethyl-phenyl)-amine ("B1")

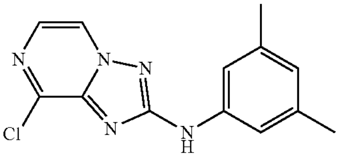 [SMILES: Cc1cc(C)cc(Nc2nc3c(Cl)nccn3n2)c1]

To a solution of 3,5-dimethylisothiocyanate (200 mg, 1.2 mmol) in dichloromethane and N,N-dimethylformamide (1:1) (5.0 mL) are added 1,2-diamino-3-chloro-pyrazinium mesitylenate (0.59 g, 0.0017 mol) and diisopropylethylamine (791 mg, 6.1 mmol). The reaction mixture is stirred for 1 hour. EDCI (93 mg, 5 mmol) is added and the solution stirred for 2 hours at room temperature before being concentrated to dryness. The residue is taken up in water and stirred for 5 minutes and the solid precipitated was filtered, washed with water, dried to get the product as a light brown solid (0.25 g, 75%). TLC: pet ether/ethyl acetate (6/4) $R_f$—0.4. LCMS (method A): mass found (M+H$^+$, 274.0), Rt (min): 4.47 area % 98.0 (max), 98.47 (254 nm); $^1$H NMR (400 MHz, DMSO-$d_6$): δ 9.99 (s, 1H), 8.95 (d, J=4.28 Hz, 1H), 7.91 (d, J=4.32 Hz, 1H), 7.28 (s, 2H), 6.58 (s, 1H), 2.24 (s, 6H).

8-Chloro-[1,2,4]triazolo[1,5-a]pyrazin-2-yl-(3,5-dimethoxy-phenyl)-amine ("B2")

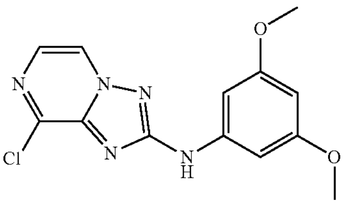 [SMILES: COc1cc(Nc2nc3c(Cl)nccn3n2)cc(OC)c1]

To a solution of 3,5-dimethoxyisothiocyanate (0.4 g, 2 mmol) in dichloromethane and N, N-dimethylformamide (1:1) (25.0 mL) are added 1,2-diamino-3-chloro-pyrazinium mesitylenate (0.98 g, 2.8 mmol) and diisopropylethyl-amine (1.32 g, 10 mmol). The reaction mixture is stirred for 1 hour, followed by addition of EDCI (0.79 g, 4 mmol). The reaction is stirred for 5 hours at room temperature and concentrated to dryness. The residue is taken up in water and stirred for 15 minutes. The solid precipitated is filtered, washed with water, dried to get the product as a light brown solid (0.5 g, 80%). TLC: chloroform/methanol (9/1) $R_f$—0.5. LCMS (method A): mass found (M+H$^+$, 306.0), Rt (min): 3.81 area % 98.7 (max), 98.77 (254 nm); $^1$H NMR (400 MHz, DMSO-$d_6$): δ

10.10 (s, 1H), 8.95 (d, J=4.32 Hz, 1H), 7.91 (d, J=4.32 Hz, 1H), 6.91 (m, 2H), 6.13 (m, 1H), 3.73 (s, 6H).

8-Chloro-[1,2,4]triazolo[1,5-a]pyrazin-2-yl-(3-trifluoromethyl-phenyl)-amine ("B3")

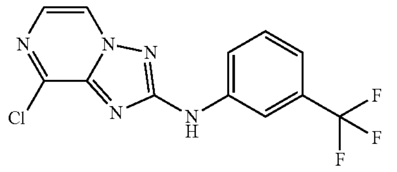 [SMILES: FC(F)(F)c1cccc(Nc2nc3c(Cl)nccn3n2)c1]

To a solution of 3-(trifluoromethyl)isothiocyanate (0.6 g, 3 mmol) in dichloromethane and N,N-dimethylformamide (1:1) (25.0 mL) are added 1,2-diamino-3-chloro-pyrazinium mesitylenate (1.42 g, 4.1 mmol) and diisopropylethyl-amine (1.9 g, 14.5 mmol). It is stirred for 1 hour, EDCI (1.12 g, 6 mmol) added and the reaction mixture stirred for 2 hours at room temperature. When the reaction is completed, it is concentrated to dryness and the residue that was taken up in water stirred for 5 minutes. The solid precipitated is filtered, washed with water, dried to get the product as a light brown solid (0.8 g, 87%). TLC: chloroform/methanol (9.5/0.5) $R_f$—0.5. LCMS (method A): mass found ($M+H^+$, 314.0), Rt (min): 4.75 area % 95.9 (max), 96.13 (254 nm); $^1H$ NMR (400 MHz, DMSO-$d_6$): δ 10.55 (s, 1H), 9.00 (d, J=4 Hz, 1H), 8.07 (s, 1H), 7.97 (d, J=4.32 Hz, 1H), 7.90 (d, J=7.92 Hz, 1H), 7.56 (t, J=8.04 Hz, 1H), 7.27 (d, J=7.64 Hz, 1H).

8-Chloro-[1,2,4]triazolo[1,5-a]pyrazin-2-yl-m-tolyl-amine ("B4")

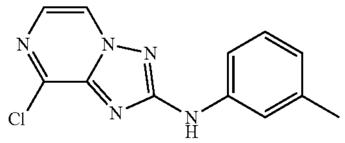 [SMILES: Cc1cccc(Nc2nc3c(Cl)nccn3n2)c1]

To a solution of m-tolylisothiocyanate (0.25 g, 1.6 mmol) in dichloromethane and N,N-dimethylformamide (1:1) (15.0 mL), 1,2-diamino-3-chloro-pyrazinium mesitylenate (0.8 g, 2.3 mmol), diisopropylethylamine (1.07 g, 8.3 mmol) are added and stirred for 1 hour. EDCI (0.64 g, 3.3 mol) is added and stirred for 6 hours at room temperature. The reaction mixture is concentrated to dryness and the residue taken up in water. It is stirred for 5 minutes and the solid precipitated is filtered, washed with water, dried to get the product as a light brown solid (0.35 g, 80.8%). TLC: chloroform/methanol (9.5/0.5) $R_f$—0.5. LCMS (method A): mass found ($M+H^+$, 260.0), Rt (min): 4.13 area % 97.4 (max), 97.11 (254 nm); $^1H$ NMR (400 MHz, DMSO-$d_6$): δ 10.07 (s, 1H), 8.94 (d, J=4.32 Hz, 1H), 7.92 (d, J=4.28 Hz, 1H), 7.50 (d, J=8.12 Hz, 1H), 7.43 (s, 1H), 7.19 (t, J=7.76 Hz, 1H), 6.75 (d, J=7.4 Hz, 1H), 2.29 (s, 3H).

8-Chloro-[1,2,4]triazolo[1,5-a]pyrazin-2-yl-phenyl-amine ("B5")

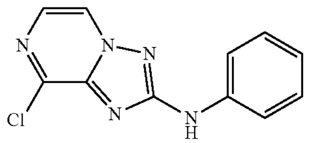 [SMILES: Clc1nccn2nc(Nc3ccccc3)nc12]

To a solution of phenylisothiocyanate (0.25 g, 1.8 mmol) in dichloromethane and N,N-dimethylformamide (1:1) (15.0 mL), 1,2-diamino-3-chloro-pyrazinium mesitylenate (0.89 g, 2.5 mmol), diisopropylethylamine (1.19 g, 9.2 mmol) are added and stirred for 1 hour. EDCI (0.7 g, 3.7 mmol) is added and stirred for 6 hours at room temperature. The reaction mixture is concentrated and the residue is taken in water and stirred for 5 minutes, the solid precipitated is filtered, washed with water, dried to get the product as a light brown solid (0.4 g, 88%). TLC: chloroform/methanol (9.5/0.5) $R_f$—0.5. LCMS (method A): mass found ($M+H^+$, 246.0), Rt (min): 3.74 area % 98.2 (max), 98.39 (254 nm); $^1H$ NMR (400 MHz, DMSO-$d_6$): δ 10.14 (s, 1H), 8.95 (d, J=4.28 Hz, 1H), 7.93 (d, J=4.28 Hz, 1H), 7.67 (m, 2H), 7.32 (t, J=8.63 Hz, 2H), 6.94 (t, J=7.32 Hz, 1H).

Examples "B6"-"B9" are prepared following the above procedures.

[3-Chloro-4-(1-methyl-1H-imidazol-2-ylsulfanyl)-phenyl]-(8-chloro-[1,2,4]triazolo[1,5-a]pyrazin-2-yl)-amine ("B6")

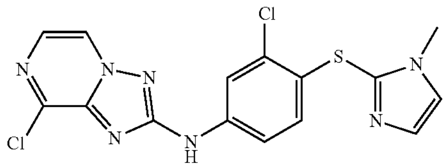 [SMILES: Cn1ccnc1Sc1ccc(Nc2nc3c(Cl)nccn3n2)cc1Cl]

Light brown solid, 49.5 mg (yield: 73.2%), HPLC purity: 94.1%, Rt: 2.9 min, observed $[M+H]^+$ 392.0; $^1H$ NMR (400 MHz, DMSO-$d_6$) δ 10.45 (s, 1H), 8.97 (d, J=4.28 Hz, 1H), 7.95 (d, J=4.36 Hz, 1H), 7.91 (d, J=2.2 Hz, 1H), 7.46 (m, 2H), 7.10 (s, 1H), 6.70 (d, J=8.72 Hz, 1H), 3.62 (s, 3H). 6-(8-Chloro-[1,2,4]triazolo[1,5-a]pyrazin-2-ylamino)-2,2-difluoro-4H-benzo[1,4]oxazin-3-one ("B7")

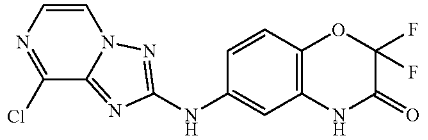 [SMILES: O=C1Nc2cc(Nc3nc4c(Cl)nccn4n3)ccc2OC1(F)F]

Off white solid, 16.9 mg (yield: 72.2%), HPLC purity: 97%, Rt: 3.85 min, observed $[M+H]^+$ 353.0; $^1H$ NMR (400 MHz, DMSO-$d_6$) δ 11.99 (br s, 1H), 10.31 (s, 1H), 8.88 (d, J=4.12 Hz, 1H), 7.94 (d, J=4.08 Hz, 1H), 7.49 (s, 1H), 7.41 (d, J=8.84 Hz, 1H), 7.26 (m, 1H).

6-(8-Chloro-[1,2,4]triazolo[1,5-a]pyrazin-2-ylamino)-2,2-dimethyl-4H-pyrido[3,2-b][1,4]oxazin-3-one ("B8")

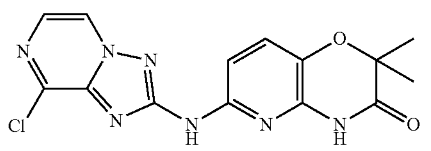 [SMILES: CC1(C)Oc2ccc(Nc3nc4c(Cl)nccn4n3)nc2NC1=O]

Light brown solid, 25.8 mg (yield: 71.4%), HPLC purity: 98.6%, Rt: 3.47 min, observed $[M+H]^+$ 346.0; $^1H$ NMR (400 MHz, DMSO-$d_6$) δ 11.00 (br s, 1H), 10.29 (s, 1H), 8.95 (d, J=4.32 Hz, 1H), 7.95 (d, J=4.36 Hz, 1H), 7.64 (d, J=8.68 Hz, 1H), 7.41 (d, J=8.64 Hz, 1H), 1.39 (s, 6H).

(1-Benzyl-1H-indazol-6-yl)-(8-chloro-[1,2,4]triazolo[1,5-a]pyrazin-2-yl)-amine ("B9")

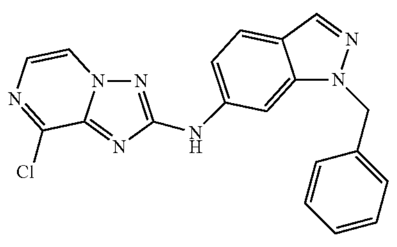 [SMILES: Clc1nccn2nc(Nc3ccc4cnn(Cc5ccccc5)c4c3)nc12]

Light brown solid, 43.5 mg (yield: 75.3%), HPLC purity: 97.2%, Rt: 4.28 min, observed $[M+H]^+$ 376.0; $^1H$ NMR (400 MHz, DMSO-$d_6$) δ 10.37 (s, 1H), 8.96 (d, J=4.28 Hz, 1H), 8.13 (s, 1H), 7.97 (m, 2H), 7.68 (d, J=8.72 Hz, 1H), 7.26 (m, 6H), 5.56 (s, 2H).

4-(4-Isothiocyanato-phenyl)-morpholine

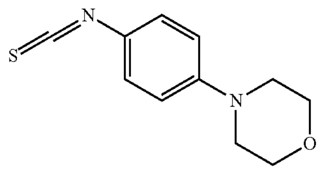 [SMILES: S=C=Nc1ccc(N2CCOCC2)cc1]

To a stirring solution of 4-morpholino-4-yl-phenylamine (2 g, 11.22 mmol) and diisopropylethylamine (2.89 g, 22.42 mmol) in dry dichloromethane (100 ml) at 0° C. under $N_2$, thiophosgene (1.54 g, 13.46 mmol) in dichloromethane is added dropwise and stirred for 30 minutes. The reaction mixture is quenched with water (100 ml) and the layers are separated, the organic layer is washed with water (50 ml×2) and dried over anhydrous $MgSO_4$ to get the product as brown crystalline solid (2.4 g, 97.56%); TLC: pet ether/ethyl acetate (6/4)

$R_f$—0.5;

$^1H$-NMR (400 MHz, DMSO-$d_6$): δ [ppm] 7.29 (d, J=6.92 Hz, 2H), 6.95 (d, J=6.96 Hz, 2H), 3.71 (t, J=4.96 Hz, 4H), 3.14 (t, J=4.84 Hz, 4H).

(8-Chloro-[1,2,4]triazolo[1,5-a]pyrazin-2-yl-(4-morpholin-4-yl-phenyl)-amine

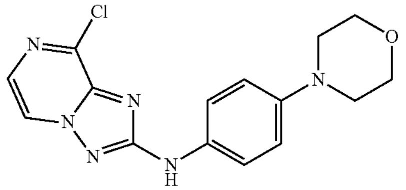 [SMILES: Clc1nccn2nc(Nc3ccc(N4CCOCC4)cc3)nc12]

To a solution of 4-morpholinophenylisothiocyanate (2 g, 8.99 mmol) in dry dichloromethane (200 ml), 1,2-diaminopyrazinium mesitylenate (3.86 g, 11.24 mmol), diisopropylethylamine (5.81 g, 44.99 mmol) and EDCI (3.44 g, 17.98 mmol) are added and stirred for 6 hours. The reaction mixture is concentrated and the residue is taken in water (100 ml), triturated and filtered, washed with water (50 ml×2) and dried, the crude solid is purified by silica column using (60-120) mesh to get the titled product as light brown solid (2.5 g, 84.17%); TLC: chloroform/methanol (9.5/0.5) $R_f$—0.3; HPLC puritiy (method A) 98%; Rt (min): 2.21; LCMS: mass found (M+, 331.0), Rt (min): 2.08;

$^1H$-NMR (400 MHz, DMSO-$d_6$): δ [ppm] 9.85 (s, 1H), 8.90 (d, J=4.32 Hz, 1H), 7.90 (d, J=4.32 Hz, 1H), 7.52 (dd, J=7.04, 2.00 Hz, 2H), 6.93 (d, J=9.04 Hz, 2H), 3.73 (t, J=4.92 Hz, 4H), 3.02 (t, J=4.80 Hz, 4H).

(8-Chloro-[1,2,4]triazolo[1,5-a]pyrazin-2-yl-(6-methoxy-pyridin-3-yl)-amine

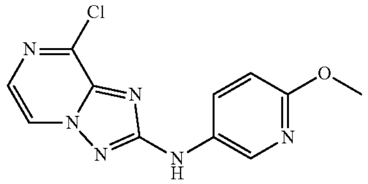 [SMILES: COc1ccc(Nc2nc3c(Cl)nccn3n2)cn1]

To a solution of 2-methoxypyridyl-5-isothiocyanate (3 g, 18.07 mmol) in dry dichloromethane (200 ml), 1,2-diaminopyrazinium mesitylenate (7.77 g, 22.5 mmol), diisopropylethylamine (11.67 g, 90.35 mmol) and EDCI (3.44 g, 36.14 mmol) are added and stirred for 6 hours. The reaction mixture is concentrated and the residue is taken in water (100 ml), triturated and filtered, washed with water (50 ml×2) and 50% diethylether in hexane to get the titled product as light brown solid (4 g, 80.32%); TLC: chloroform/methanol (9.5/0.5) $R_f$—0.3; HPLC purity (method A) 98%, Rt (min): 2.41; LCMS: mass found (M+, 277.0), Rt (min): 2.36);

$^1H$-NMR (400 MHz, DMSO-$d_6$): δ [ppm] 10.02 (s, 1H), 8.91 (d, J=4.32 Hz, 1H), 8.46 (d, J=2.72 Hz, 1H), 7.97 (dd, J=8.88, 2.84 Hz, 1H), 7.93 (d, J=4.32 Hz, 1H), 6.83 (d, J=8.88 Hz, 1H), 3.81 (s, 3H).

5-Isothiocyanato-1,3-dihydro-indol-2-one

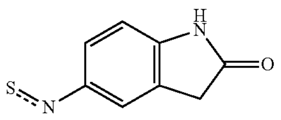

To a stirring solution of 5-amino-1,3-dihydro-indol-2-one hydrochloride (2 g, 10.83 mmol) and diisopropylethylamine (4.19 g, 32.49 mmol) in dry dichloromethane (100 ml) at 0° C. under $N_2$, thiophosgene (1.49 g, 10.83 mmol) in dichloromethane is added dropwise and stirred for 30 minutes. The reaction mixture is quenched with water (100 ml) and the layers are separated, the organic layer is washed with water (50 ml×2) and dried over anhydrous $MgSO_4$ to get the product as brown crystalline solid (2.03 g, 99.02%); TLC: chloroform/methanol (9.5/0.5) $R_f$—0.5;

$^1$H-NMR (400 MHz, DMSO-$d_6$): δ [ppm] 10.60 (s, 1H), 7.31 (s, 1H), 7.25 (d, J=7.88 Hz, 1H), 6.82 (d, J=8.24 Hz, 1H), 3.50 (s, 2H).

5-(8-Chloro-[1,2,4]triazolo[1,5-a]pyrazin-2-ylamino)-1,3-dihydro-indol-2-one

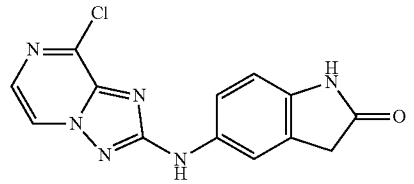 [SMILES: O=C1Cc2cc(Nc3nc4c(Cl)nccn4n3)ccc2N1]

To a solution of 5-isothiocyanato-1,3-dihydro-indol-2-one (2.3 g, 12.09 mmol) in dry dichloromethane (200 ml), 1,2-diamino-pyrazinium mesitylenate (5.21 g, 15.12 mmol), diisopropylethylamine (7.81 g, 60.45 mmol) and EDCI (4.63 g, 24.18 mmol) are added and stirred for 6 hours. The reaction mixture is concentrated and the residue is taken in water (100 ml), triturated and filtered, the crude solid is purified by silica column using (60-120) mesh to get the titled product as yellow solid (2.0 g, 55%);

TLC: chloroform/methanol (9.5/0.5)

$R_f$—0.3; HPLC purity (method A): 97%, Rt (min): 2.40; LCMS: mass found (M+, 301.0), Rt (min): 2.36;

$^1$H-NMR (400 MHz, DMSO-$d_6$): δ [ppm] 10.24 (s, 1H), 9.95 (s, 1H), 8.92 (d, J=4.32 Hz, 1H), 7.91 (d, J=4.28 Hz, 1H), 7.56 (s, 1H), 7.44 (dd, J=8.38, 2.20 Hz, 1H), 6.77 (d, J=8.36 Hz, 1H), 3.49 (s, 2H).

MC825_scaffold

Step 1-IS08115-029

O-(2,2-dimethylpropanoyl)-N-[(mesitylsulfonyl)oxy]hydroxylamine

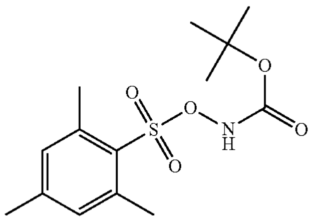 [SMILES: Cc1cc(C)c(S(=O)(=O)ONC(=O)OC(C)(C)C)c(C)c1]

Procedure: To a solution of 2-mestylenesulphonylchloride (5 g, 22.8 mmol) in dry tetrahydrofuran (75 mL), N-boc-hydroxylamine (3.34 g, 25.1 mmol) is added and cooled to 0° C. Triethylamine (3.8 mL, 27.4 mmol) is added slowly over 10 min. The reaction mixture is stirred for 1 h at 0° C. The reaction mixture is concentrated and the residue is taken in dichloromethane (75 mL) and washed with water (2×75 mL), an aqueous solution of $NaHCO_3$ (10%, 75 mL) and dried over $MgSO_4$ and concentrated to get the product. Yield: 96% (7 g, off white solid). $^1$H NMR (400 MHz, DMSO-$d_6$): δ [ppm] 11.16 (s, 1H), 7.12 (s, 2H), 2.49 (s, 6H), 2.28 (s, 3H), 1.23 (s, 9H).

Step 2-IS08115-031

2-[(aminooxy)sulfonyl]-1,3,5-trimethylbenzene

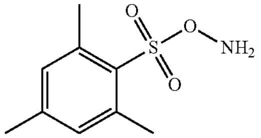

Procedure: To a solid product of O-(2,2-dimethylpropanoyl)-N-[(mesitylsulfonyl)oxy]hydroxylamine (10 g, 31.7 mmol) trifluoroacetic acid (60 mL) is added slowly at 0° C. The reaction mixture is stirred for 30 minutes. After the completion of the reaction (monitored by TLC), cold water is added slowly and stirred for 15 minutes. The solid precipitated is filtered and washed several times with water until the pH becomes neutral. The solid is dried and used for next step immediately. Yield: 73% (~5 g, white solid). $^1$H NMR (400 MHz, DMSO-$d_6$): δ [ppm] 6.73 (s, 2H), 2.48 (s, 6H), 2.15 (s, 3H).

Step 3-IS08115-032

1,2-diamino-3-chloro-pyrazinium mesitylenate

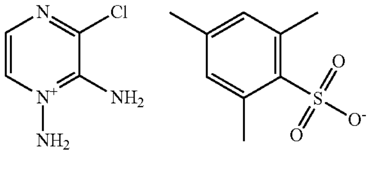

Procedure: To a solution of 2-amino-3-chloropyrazine (3 g, 23.1 mmol) in dry dichloromethane (50 mL) at RT, 2-[(aminooxy)sulfonyl]-1,3,5-trimethylbenzene (7.5 g, 34.7 mmol) is added. The reaction mixture is stirred for 3 h at RT. The reaction mixture is concentrated to minimum, cold diethyl ether (50 mL) is added and stirred for 15 min. The solid precipitated is filtered and washed with cold diethyl ether to get the product. Yield: 88% (7 g, off white solid). $^1$H NMR (400 MHz, DMSO-$d_6$): δ [ppm] 9.07 (br s, 2H), 8.11 (d, J=4.3 Hz, 1H), 7.78 (d, J=4.2 Hz, 1H), 7.28 (s, 1H), 6.72 (s, 1H), 2.48 (s, 6H), 2.15 (s, 3H).

MC825_SC01

Step 1-FS08115-048

(8-Chloro-[1,2,4]triazolo[1,5-a]pyrazin-2-yl)-(4-methoxy-phenyl)-amine

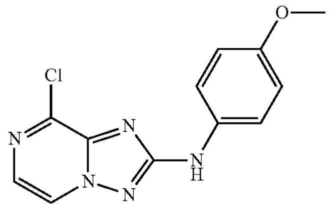 [SMILES: COc1ccc(Nc2nc3c(Cl)nccn3n2)cc1]

Procedure: To a solution of 4-methoxyphenylisothiocyanate (0.6 g, 3.63 mmol) in dry dichloromethane (30 mL), 1,2-diamino-3-chloro-pyrazinium mesitylenate (1.56 g, 4.54 mmol) and diisopropylethylamine (3.15 mL, 18.1 mmol) are added and stirred for 1 h. EDC.HCl (1.38 g, 7.26 mmol) is added and stirred for 6 hours. After completion of the reaction (monitored by TLC), the reaction mixture is concentrated to get the crude product. The crude product is purified by column chromatography (silica gel, Ethyl acetate/Pet Ether gradient elution). Yield: 80% (800 mg, off white solid). LCMS: (Method A) 276.0 (M+H), RT. 3.4 min, 99.0% (Max), 98.7% (254 nm). $^1$H NMR (400 MHz, DMSO-$d_6$): δ [ppm] 9.90 (s, 1H), 8.92 (d, J=4.3 Hz, 1H), 7.91 (d, J=4.2 Hz, 1H), 7.57 (dd, J=2.2, 6.8 Hz, 2H), 6.92 (dd, J=2.2, 6.8 Hz, 2H), 3.72 (s, 3H). HPLC: (Method A) RT 3.5 min, 99.1% (Max), 99.2% (254 nm).

MC825_010

(8-Biphenyl-2-yl-[1,2,4]triazolo[1,5-a]pyrazin-2-yl)-(4-methoxy-phenyl)-amine (C1")

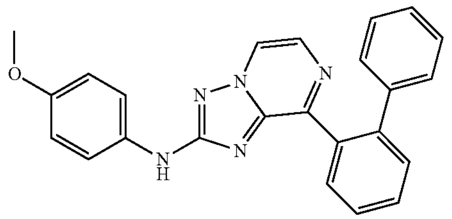 [SMILES: COc1ccc(Nc2nc3c(-c4ccccc4-c4ccccc4)nccn3n2)cc1]

Procedure: To a solution of (8-Chloro-[1,2,4]triazolo[1,5-a]pyrazin-2-yl)-(4-methoxy-phenyl)-amine (100 mg, 0.36 mmol) in acetonitrile/water (9:1, 4 mL), biphenyl boronic acid (108 mg, 0.54 mmol), 2-dicyclohexylphosphino-2,4,6-triisopropylbiphenyl (8 mg, 0.02 mmol), palladium acetate (4 g, 0.02 mmol) and potassium carbonate (151 mg, 1.1 mmol) were added, degassed briefly and irradiated in microwave at 120° C. for 40 min. After completion of the reaction (monitored by TLC), the reaction mixture was passed through celite, washed with dichloromethane/methanol (1:1, 10 mL), the filtrate was concentrated to get the crude product. The crude product was purified by column chromatography (silica gel, MeOH/DCM gradient elution). Yield: 5% (11 mg, pale yellow solid). LCMS: (Method A) 394 (M+H), RT. 4.8 min, 95.78% (Max). 96.60% (254 nm); $^1$H NMR (400 MHz, DMSO-$d_6$): δ [ppm] 9.58 (s, 1H), 8.76 (d, J=4.32 Hz, 1H), 7.99 (d, J=4.32 Hz, 1H), 7.70 (dd, J=7.88, 1.08 Hz, 1H), 7.64-7.55 (m, 1H), 7.45 (t, J=1.44 Hz, 2H), 7.44 (dd, J=6.86, 2.24 Hz, 2H), 7.19-7.10 (m, 5H), 6.86 (d, J=2.20 Hz, 2H), 3.70 (s, 3H). HPLC: (Method A) RT 4.8 min, 95.88% (Max), 96.08% (254 nm).

MC825_028

(4-Methoxy-phenyl)-[8-(1-methyl-1H-pyrazol-4-yl)-[1,2,4]triazolo[1,5-a]pyrazin-2-yl]-amine ("C2")

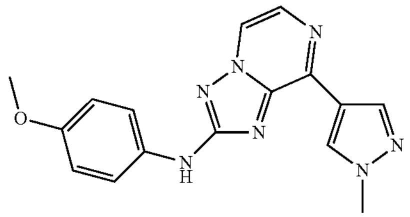 [SMILES: COc1ccc(Nc2nc3c(-c4cnn(C)c4)nccn3n2)cc1]

Synthesized as described for MC825_010

Yield: 12% (14 mg, Yellow solid). LCMS: (Method A) 322 (M+H), RT. 3.4 min, 92.08% (Max). 94.91% (254 nm); $^1$H NMR (400 MHz, DMSO-$d_6$): δ [ppm] 9.71 (s, 1H), 8.68 (d, J=4.28 Hz, 1H), 8.64 (s, 1H), 8.37 (s, 1H), 8.02 (d, J=4.28 Hz, 1H), 7.63 (d, J=9.04 Hz, 2H), 6.93 (d, J=9.04 Hz, 2H), 3.98 (s, 3H), 3.73 (s, 3H), HPLC: (Method A) RT 3.3 min, 94.64% (Max), 94.3% (254 nm).

MC825_SC02

Step 1-FS08115-049

(8-Chloro-[1,2,4]triazolo[1,5-a]pyrazin-2-yl)-(2,5-dimethoxy-phenyl)-amine

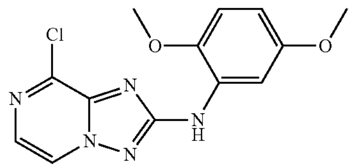 [SMILES: COc1ccc(OC)c(Nc2nc3c(Cl)nccn3n2)c1]

Synthesized using the procedure as described for MC825_SC01_Step1.

Yield: 24% (29 mg, off white solid). LCMS: (Method A) 306.0 (M+H), RT. 3.9 min, 98.3% (Max), 98.8% (254 nm).

$^1$H NMR (400 MHz, DMSO-$d_6$): δ [ppm] 8.97 (d, J=4.3 Hz, 1H), 8.71 (s, 1H), 7.95 (d, J=4.3 Hz, 1H), 7.81 (d, J=2.9 Hz, 1H), 6.96 (d, J=8.8 Hz, 1H), 6.55 (dd, J=2.9, 8.8 Hz, 1H), 3.80 (s, 3H), 3.73 (s, 3H). HPLC: (Method A) RT 4.0 min, 98.7% (Max), 98.5% (254 nm).

MC825_011

(8-Biphenyl-2-yl-[1,2,4]triazolo[1,5-a]pyrazin-2-yl)-(2,5-dimethoxy-phenyl)-amine ("C3")

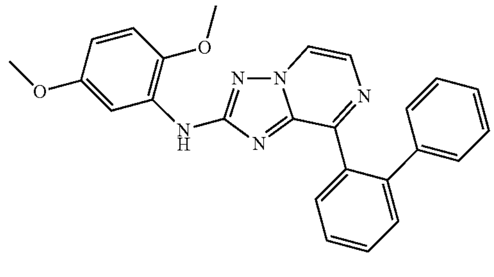 [SMILES: COc1ccc(OC)c(Nc2nc3c(-c4ccccc4-c4ccccc4)nccn3n2)c1]

Synthesized as described for MC825_010

Yield: 7% (15.3 mg, Yellow solid). LCMS: (Method A) 424.3 (M+H), RT. 5.1 min, 97.80% (Max). 97.73% (254 nm); $^1$H NMR (400 MHz, DMSO-$d_6$): δ [ppm] 8.82 (d, J=4.36 Hz, 1H), 8.31 (s, 1H), 8.03 (d, J=4.36 Hz, 1H), 7.77 (d, J=3.00 Hz, 1H), 7.72 (dd, J=7.20, 2.36 Hz, 1H), 7.64-7.60 (m, 1H), 7.55-7.51 (m, 2H), 7.17-7.07 (m, 5H), 6.90 (d, J=8.84 Hz, 1H), 6.48 (dd, J=8.80, 3.00 Hz, 1H), 3.76 (s, 3H), 3.71 (s, 3H). HPLC: (Method A) RT 5.2 min, 95.63% (Max), 96.94% (254 nm).

MC825_027

(2,5-Dimethoxy-phenyl)-[8-(1-methyl-1H-pyrazol-4-yl)-[1,2,4]triazolo[1,5-a]pyrazin-2-yl]-amine ("C4")

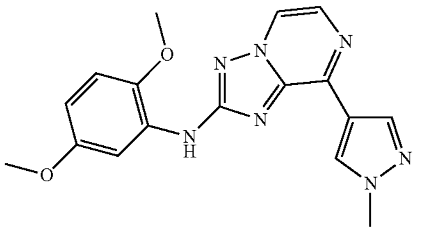 [SMILES: COc1ccc(OC)c(Nc2nc3c(-c4cnn(C)c4)nccn3n2)c1]

Synthesized as described for MC825_010 Yield: 6.5% (11 mg, Yellow solid). LCMS: (Method A) 352.3 (M+H), RT. 3.7 min, 96.47% (Max). 96.43% (254 nm); $^1$H NMR (400 MHz, DMSO-$d_6$): δ [ppm] 8.74 (t, J=8.16 Hz, 2H), 8.36 (d, J=11.64 Hz, 2H), 8.07 (d, J=4.32 Hz, 1H), 7.96 (d, J=2.96 Hz, 1H), 6.97 (d, J=8.84 Hz, 1H), 6.52 (dd, J=8.82, 3.00 Hz, 1H), 3.97 (s, 3H), 3.84 (s, 3H), 3.77 (s, 3H). HPLC: (Method A) RT 3.7 min, 96.24% (Max), 96.92% (254 nm).

MC825_SC03

Step 1-FS08115-050

(8-Chloro-[1,2,4]triazolo[1,5-a]pyrazin-2-yl)-(3,4-dimethoxy-phenyl)-amine

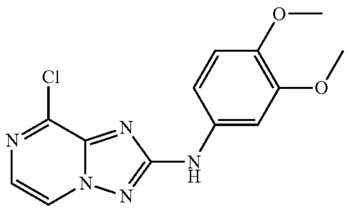 [SMILES: COc1ccc(Nc2nc3c(Cl)nccn3n2)cc1OC]

Synthesized using the procedure as described for MC825_SC01_Step1.

Yield: 29% (74 mg, yellow solid). LCMS: (Method A) 306.0 (M+H), RT. 3.1 min, 98.3% (Max), 99.1% (254 nm). $^1$H NMR (400 MHz, DMSO-$d_6$): δ [ppm] 9.89 (s, 1H), 8.92 (d, J=4.3 Hz, 1H), 7.92 (d, J=6.1 Hz, 1H), 7.32 (d, J=2.5 Hz, 1H), 7.22 (dd, J=8.60, 2.50 Hz, 1H), 6.93 (d, J=8.7 Hz, 1H), 3.77 (s, 3H), 3.72 (s, 3H). HPLC: (Method A) RT 3.2 min, 99.6% (Max), 99.8% (254 nm).

MC825_007

(8-Biphenyl-2-yl-[1,2,4]triazolo[1,5-a]pyrazin-2-yl)-(3,4-dimethoxy-phenyl)-amine ("C5")

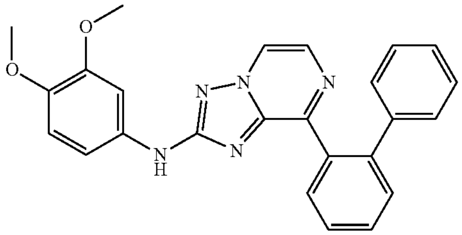 [SMILES: COc1ccc(Nc2nc3c(-c4ccccc4-c4ccccc4)nccn3n2)cc1OC]

Synthesized as described for MC825_010

Yield: 16.7% (34.9 mg, Pale yellow solid). LCMS: (Method A) 424.3 (M+H), RT. 4.5 min, 98.94% (Max). 99.92% (254 nm); $^1$H NMR (400 MHz, DMSO-$d_6$): δ [ppm] 9.61 (s, 1H), 8.76 (d, J=3.98 Hz, 1H), 7.97 (d, J=4.32 Hz, 1H), 7.73 (t, J=1.04 Hz, 1H), 7.59-7.63 (m, 1H), 7.52 (dd, J=7.48, 1.36 Hz, 2H), 7.27 (d, J=2.48 Hz, 1H), 7.19 (t, J=1.72 Hz, 3H), 7.15-7.11 (m, 3H), 6.89-6.86 (m, 1H), 3.71 (s, 3H), 3.69 (s, 3H). HPLC: (Method A) RT 4.6 min, 99.45% (Max), 99.75% (254 nm).

MC825_031

(3,4-Dimethoxy-phenyl)-[8-(1-methyl-1H-pyrazol-4-yl)-[1,2,4]triazolo[1,5-a]pyrazin-2yl]-amine ("C6")

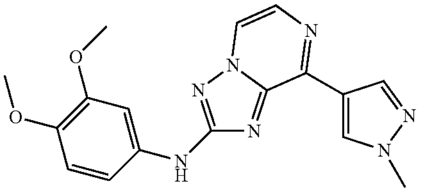 [SMILES: COc1ccc(Nc2nc3c(-c4cnn(C)c4)nccn3n2)cc1OC]

Synthesized as described for MC825_010

Yield: 55% (95 mg, Yellow solid). LCMS: (Method A) 352.3 (M+H), RT. 3.0 min, 98.78% (Max). 99.06% (254 nm); $^1$H NMR (400 MHz, DMSO-$d_6$): δ [ppm] 9.72 (s, 1H), 8.68 (d, J=4.32 Hz, 1H), 8.65 (s, 1H), 8.39 (d, J=0.44 Hz, 1H), 8.03 (d, J=4.32 Hz, 1H), 7.52 (d, J=2.48 Hz, 1H), 7.20 (dd, J=8.68, 2.52 Hz, 1H), 6.93 (d, J=8.76 Hz, 1H), 3.97 (s, 3H), 3.91 (s, 3H), 3.72 (s, 3H). HPLC: (Method A) RT 3.0 min, 97.52% (Max), 98.55% (254 nm).

MC825_SC04

Step 1-FS08115-051

(8-Chloro-[1,2,4]triazolo[1,5-a]pyrazin-2-yl)-(3-methoxy-phenyl)-amine

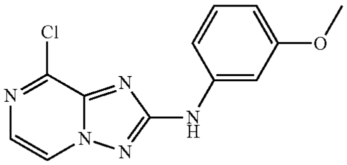 [SMILES: COc1cccc(Nc2nc3c(Cl)nccn3n2)c1]

Synthesized using the procedure as described for MC825_SC01_Step1.

Yield: 34% (145 mg, off white solid). LCMS: (Method A) 276.0 (M+H), RT. 3.6 min, 98.1% (Max), 98.4% (254 nm). $^1$H NMR (400 MHz, DMSO-$d_6$): δ [ppm] 10.14 (s, 1H), 8.96 (d, J=4.3 Hz, 1H), 7.94 (d, J=4.2 Hz, 1H), 7.36-7.35 (t, J=1.2 Hz, 1H), 7.21 (dd, J=4.0, 0.9 Hz, 2H), 6.55-6.52 (m, 1H), 3.75 (s, 3H). HPLC: (Method A) RT 3.8 min, 99.1% (Max), 99.2% (254 nm).

MC825_008

(8-Biphenyl-2-yl-[1,2,4]triazolo[1,5-a]pyrazin-2-yl)-(3-methoxy-phenyl)-amine ("C7")

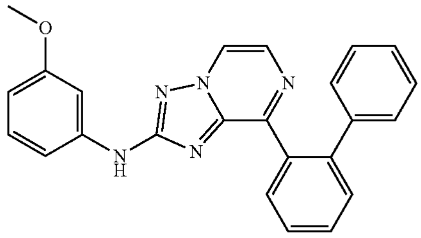 [SMILES: COc1cccc(Nc2nc3c(-c4ccccc4-c4ccccc4)nccn3n2)c1]

Synthesized as described for MC825_010

Yield: 43% (123 mg, Yellow solid). LCMS: (Method A) 394 (M+H), RT. 4.9 min, 98.25% (Max). 98.97% (254 nm); $^1$H NMR (400 MHz, DMSO-$d_6$): δ [ppm] 9.85 (s, 1H), 8.82 (d, J=4.32 Hz, 1H), 8.02 (d, J=4.32 Hz, 1H), 7.74 (d, J=7.52 Hz, 1H), 7.63 (t, J=6.48 Hz, 1H), 7.55 (t, J=7.40 Hz, 2H), 7.30 (s, 1H), 7.20-7.09 (m, 7H), 6.50 (dd, J=7.92, 2.16 Hz, 1H), 3.74 (s, 3H).

HPLC: (Method A) RT 5.0 min, 99.02% (Max), 99.20% (254 nm).

MC825_030

(3-Methoxy-phenyl)-[8-(1-methyl-1H-pyrazol-4-yl)-[1,2,4]triazolo[1,5-a]pyrazin-2-yl]-amine ("C8")

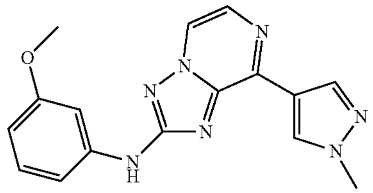 [SMILES: COc1cccc(Nc2nc3c(-c4cnn(C)c4)nccn3n2)c1]

Synthesized as described for MC825_010

Yield: 35% (69.5 mg, pale yellow solid). LCMS: (Method A) 322.3 (M+H), RT. 3.5 min, 95.35% (Max). 96.72% (254 nm); $^1$H NMR (400 MHz, DMSO-$d_6$): δ [ppm] 9.96 (s, 1H), 8.74 (d, J=4.32 Hz, 1H), 8.67 (s, 1H), 8.41 (s, 1H), 8.07 (d, J=4.28 Hz, 1H), 7.50 (d, J=2.04 Hz, 1H), 7.24 (d, J=7.84 Hz, 2H), 6.54 (d, J=7.28 Hz, 1H), 3.99 (s, 3H), 3.77 (s, 3H).;

HPLC: (Method A) RT 3.6 min, 98.12% (Max), 98.34% (254 nm).

MC825_SC05

Step 1-IS08115-044

1-Isothiocyanato-2,3-dimethoxy-benzene

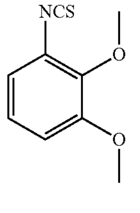

Procedure: To a solution of 2,3-dimethoxy-phenylamine (1 g, 6.52 mmol) in dry dichloromethane (25 mL) at 0° C., diisopropylethylamine (2.3 mL, 13 mmol) is added and stirred for 5 min. Thiophosgene (0.55 mL, 7.2 mmol) is added and stirred at 0° C. for 30 min. After completion of the reaction (monitored by TLC), the reaction mixture is quenched with cold water, separated the layer, washed the organic layer with water (3×25 mL), brine, dried over $MgSO_4$ and concentrated to get the product. Yield: 55% (0.7 g, colourless gum). $^1$H NMR (400 MHz, DMSO-$d_6$): δ [ppm] 7.09-7.06 (m, 2H), 6.89-6.86 (m, 1H), 3.82 (s, 3H), 3.81 (s, 3H).

Step 2-FS08115-045

(8-Chloro-[1,2,4]triazolo[1,5-a]pyrazin-2-yl)-(2,3-dimethoxy-phenyl)-amine

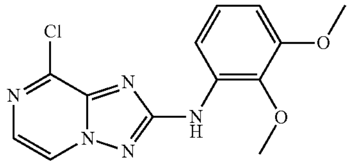

Synthesized using the procedure as described for MC825_SC01_Step1.

Yield: 43% (378 mg, white solid). LCMS: (Method A) 306.0 (M+H), RT. 3.8 min, 98.7% (Max), 99.5% (254 nm). $^1$H NMR (400 MHz, DMSO-$d_6$): δ [ppm] 9.03 (s, 1H), 8.96 (d, J=4.3 Hz, 1H), 7.96 (d, J=4.2 Hz, 1H), 7.79 (dd, J=8.3, 1.2 Hz, 1H), 7.07 (t, J=8.2 Hz, 1H), 6.74 (dd, J=8.3, 1.2 Hz, 1H), 3.83 (s, 3H), 3.77 (s, 3H). HPLC: (Method A) RT 3.9 min, 99.7% (Max), 99.7% (254 nm).

MC825_012

(8-Biphenyl-2-yl-[1,2,4]triazolo[1,5-a]pyrazin-2-yl)-(2,3-dimethoxy-phenyl)-amine ("C9")

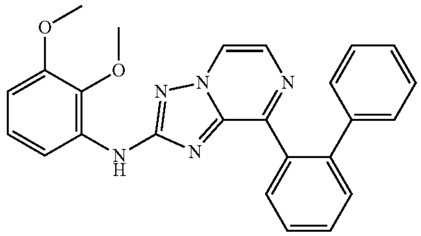 [SMILES: COc1cccc(Nc2nc3c(-c4ccccc4-c4ccccc4)nccn3n2)c1OC]

Synthesized as described for MC825_010

Yield: 15% (42 mg, pale brown solid). LCMS: (Method A) 424.3 (M+H), RT. 5.0 min, 94.50% (Max). 96.31% (254 nm); $^1$H NMR (400 MHz, DMSO-$d_6$): δ [ppm] 8.80 (d, J=4.36 Hz, 1H), 8.58 (s, 1H), 8.04 (d, J=4.36 Hz, 1H), 7.71 (d, J=1.64 Hz, 1H), 7.69-7.60 (m, 2H), 7.55-7.51 (m, 2H), 7.18-7.10 (m, 5H), 7.08-7.02 (m, 1H), 6.67 (dd, J=8.32, 1.20 Hz, 1H), 3.79 (s, 3H), 3.71 (s, 3H). HPLC: (Method A) RT 5.1 min, 95.12% (Max), 95.56% (254 nm).

MC825_032

(2,3-Dimethoxy-phenyl)-[8-(1-methyl-1H-pyrazol-4-yl)-[1,2,4]triazolo[1,5-a]pyrazin-2-yl]-amine ("C10")

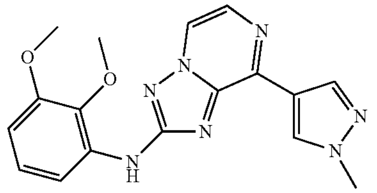 [SMILES: COc1cccc(Nc2nc3c(-c4cnn(C)c4)nccn3n2)c1OC]

Synthesized as described for MC825_010

Yield: 24% (56 mg, pale brown solid). LCMS: (Method A) 352.3 (M+H), RT. 3.6 min, 94.27% (Max). 94.56% (254 nm); $^1$H NMR (400 MHz, DMSO-$d_6$): δ [ppm] 8.71 (d, J=4.40 Hz, 2H), 8.61 (s, 1H), 8.38 (d, J=0.52 Hz, 1H), 8.06 (d, J=4.32 Hz, 1H), 7.90 (dd, J=8.32, 1.28 Hz, 1H), 7.09 (t, J=8.32 Hz, 1H), 6.72 (dd, J=8.36, 1.28 Hz, 1H), 3.98 (s, 3H), 3.82 (s, 3H), 3.80 (s, 3H). HPLC: (Method A) RT 3.6 min, 94.40% (Max), 94.73% (254 nm).

MC825_SC06

Step 1-IS08027-086

6-Nitro-1-(2-trimethylsilanyl-ethoxymethyl)-1H-indazole

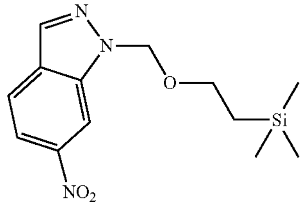 [SMILES: C[Si](C)(C)CCOCn1ncc2ccc([N+](=O)[O-])cc21]

Procedure: To a suspension of sodium hydride (60%) (1.46 g, 36.7 mmol) in dry N,N-dimethylformamide (75 mL) at 0° C., a solution of 6-nitroindazole (5 g, 30.6 mmol) in dry N,N-dimethylformamide (25 mL) is added and stirred for 1 h. (2-(chloromethoxy)ethyl)trimethylsilane (5.4 mL, 30.6 mmol) is added and stirred at RT for 30 min. After completion of the reaction (monitored by TLC), the reaction mixture is quenched with cold water and concentrated, the residue is taken in ethylacetate, washed with water (2×75 mL), brine, dried over $MgSO_4$ and concentrated to get the crude product. The crude product is purified by column chromatography (silica gel, EA/PE gradient elution) to get the mixture of regioisomers.

Yield: 73% (6.6 g, reddish brown oil). LCMS: (Method A) 294.0 (M+H), RT. 5.5, 5.6 min, 46.4, 53.3% (Max).

Step 2-IS08027-096

1-(2-Trimethylsilanyl-ethoxymethyl)-1H-indazol-6-ylamine

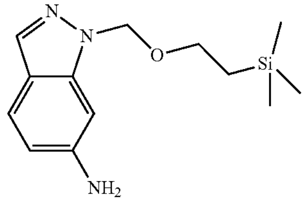 [SMILES: C[Si](C)(C)CCOCn1ncc2ccc(N)cc21]

Procedure: To a solution of 6-Nitro-1-(2-trimethylsilanyl-ethoxymethyl)-1H-indazole (6.6 g, 22.5 mmol) in absolute alcohol (100 mL) Pd/C (10%, 0.66 g) is added and stirred under hydrogen pressure of 1 Kg/cm$^3$. The reaction mixture is filtered through celite and washed with absolute alcohol (100 mL). The filtrate is concentrated to get the product. Yield: 94% (5.6 g, reddish brown oil). LCMS: (Method A) 294.0 (M+H), RT. 3.4, 3.5 min, 21.9, 67.2% (Max), 15.6, 64.5% (254 nm).

Step 3-IS08027-097

6-Isothiocyanato-1-(2-trimethylsilanyl-ethoxymethyl)-1H-indazole

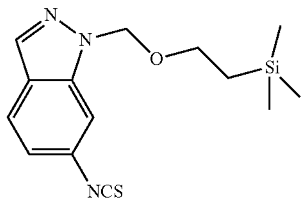

Procedure: To a solution of 1-(2-trimethylsilanyl-ethoxymethyl)-1H-indazol-6-ylamine (5.5 g, 20.8 mmol) in dry dichloromethane (75 mL) at 0° C., diisopropylethylamine (7.2 mL, 41.8 mmol) is added and stirred for 5 min. Thiophosgene (1.82 mL, 23 mmol) is added and stirred at 0° C. for 30 min. After completion of the reaction (monitored by TLC), the reaction mixture is quenched with cold water, separated the layer, washed the organic layer with water (3×75 mL), brine, dried over $MgSO_4$ and concentrated to get the product. Yield: 98% (6.3 g, reddish brown oil).

LCMS: (Method A) 416.0 (M+H), RT. 4.8, 5.1 min, 13.3, 84% (Max), 15.3, 83.4% (254 nm).

Step 4-IS08027-098

(8-Chloro-[1,2,4]triazolo[1,5-a]pyrazin-2-yl)-[1-(2-trimethylsilanyl-ethoxymethyl)-1H-indazol-6-yl]-amine

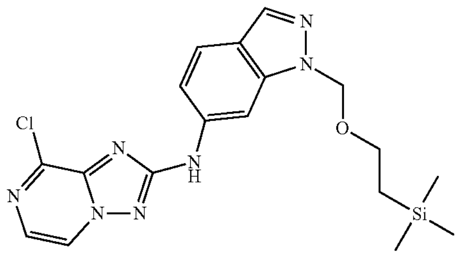 [SMILES: C[Si](C)(C)CCOCn1ncc2ccc(Nc3nc4c(Cl)nccn4n3)cc21]

Synthesized using the procedure as described for MC825_SC01_Step1.

Yield: 58% (5 g, yellow solid). LCMS: (Method A) 416.0 (M+H), RT. 4.8, 5.1 min, 13.3, 84.0% (Max), 15.3, 83.4% (254 nm). $^1$H NMR (400 MHz, DMSO-$d_6$): δ [ppm] 10.43 (s, 1H), 8.96 (d, J=4.3 Hz, 1H), 8.17-8.16 (m, 1H), 8.00-7.95 (m, 2H), 7.68-7.70 (m, 1H), 7.37-7.34 (m, 1H), 5.67 (s, 2H), 3.55 (t, J=8.0 Hz, 2H), 0.83 (t, J=7.7 Hz, 2H), −0.12 (s, 9H).

MC825_016

(8-Biphenyl-2-yl-[1,2,4]triazolo[1,5-a]pyrazin-2-yl)-(1H-indazol-6-yl)-amine ("C11")

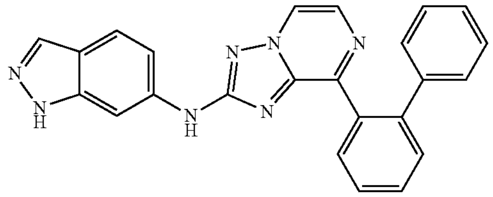 [SMILES: c1ccc(-c2ccccc2-c2nccn3nc(Nc4ccc5cn[nH]c5c4)nc23)cc1]

Synthesized as described for MC825_010, the final compound is obtained after deprotection of SEM group with TBAF in THF. Yield: 8% (12.7 mg, off white solid). LCMS: (Method A) 404.3 (M+H), RT. 3.9 min, 94.83% (Max). 94.44% (254 nm); $^1$H NMR (400 MHz, DMSO-$d_6$: δ [ppm] 12.84 (s, 1H), 10.20 (s, 1H), 8.81 (d, J=4.32 Hz, 1H), 7.96 (s, 1H), 7.90 (s, 1H), 7.74 (t, J=1.08 Hz, 1H), 7.64-7.54 (m, 5H), 7.15-7.11 (m, 6H). HPLC: (Method A) RT 4.0 min, 94.63% (Max), 94.03% (254 nm).

MC825_037

(1H-Indazol-6-yl)-[8-(1-methyl-1H-pyrazol-4-yl)-[1,2,4]triazolo[1,5-a]pyrazin-2-yl]-amine ("C12")

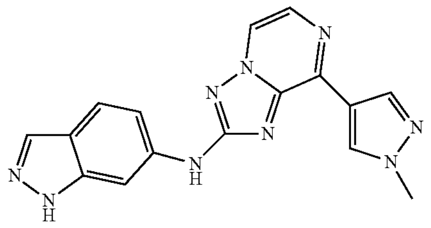 [SMILES: Cn1cc(-c2nccn3nc(Nc4ccc5cn[nH]c5c4)nc23)cn1]

Synthesized as described for MC825_010, the final compound is obtained after deprotection of SEM group with TBAF in THF. Yield: 12% (17 mg, pale yellow solid). LCMS: (Method A) 332.3 (M+H), RT. 2.7 min, 96.20% (Max). 97.96% (254 nm); $^1$H NMR (400 MHz, DMSO-$d_6$: δ [ppm] 12.86 (s, 1H), 10.13 (s, 1H), 8.73 (d, J=4.28 Hz, 1H), 8.68 (s, 1H), 8.41 (d, J=0.36 Hz, 1H), 8.17 (s, 1H), 8.08 (d, J=4.32 Hz, 1H), 7.93 (s, 1H), 7.65 (d, J=8.68 Hz, 1H), 7.27 (dd, J=8.76, 1.80 Hz, 1H), 4.01 (s, 3H). HPLC: (Method A) RT 2.6 min, 97.75% (Max), 98.73% (254 nm).

MC825_SC07

Step 1-IS08149-040

3-Isothiocyanato-benzenesulfonamide

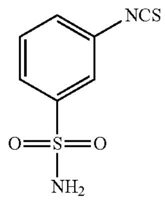

Synthesized using the procedure as described for MC825_SC05_Step 1.

Yield: 80% (1 g, brown solid). $^1$H NMR (400 MHz, DMSO-$d_6$): δ [ppm] 7.80-7.76 (m, 2H), 7.65-7.64 (m, 2H), 7.51 (br s, 2H).

Step 2-FS08115-047

3-(8-Chloro-[1,2,4]triazolo[1,5-a]pyrazin-2-ylamino)-benzene sulfonamide

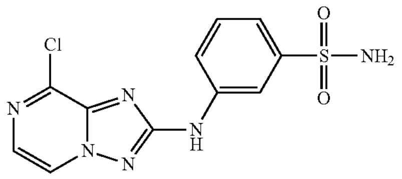 [SMILES: NS(=O)(=O)c1cccc(Nc2nc3c(Cl)nccn3n2)c1]

Synthesized using the procedure as described for MC825_SC01_Step1.

Yield: 20% (14 mg, light orange solid). LCMS: (Method A) 325.0 (M+H), RT. 2.5 min, 95.1% (Max), 93.3% (254 nm). $^1$H NMR (400 MHz, DMSO-$d_6$): δ [ppm] 10.50 (s, 1H), 8.96 (d, J=4.3 Hz, 1H), 8.12 (t, J=1.9 Hz, 1H), 7.97 (d, J=4.3 Hz, 1H), 7.93-7.90 (m, 1H), 7.53 (t, J=8.0 Hz, 1H), 7.42-7.39 (m, 1H), 7.36 (br s, 2H). HPLC: (Method A) RT 2.5 min, 95.9% (Max), 93.9% (254 nm).

MC825_020

3-(8-Biphenyl-2-yl-[1,2,4]triazolo[1,5-a]pyrazin-2-ylamino)-benzenesulfonamide ("C13")

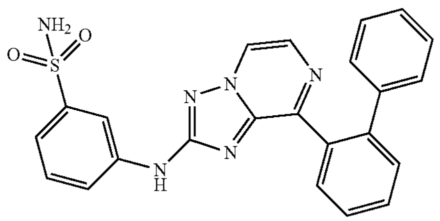 [SMILES: NS(=O)(=O)c1cccc(Nc2nc3c(-c4ccccc4-c4ccccc4)nccn3n2)c1]

Synthesized as described for MC825_010

Yield: 11% (22.5 mg, off white solid). LCMS: (Method A) 443 (M+H), RT. 3.9 min, 96.2% (Max). 96.5% (254 nm); $^1$H NMR (400 MHz, DMSO-$d_6$: δ [ppm] 10.22 (s, 1H), 8.81 (d, J=4.4 Hz, 1H), 8.06 (d, J=4.3 Hz, 1H), 8.01 (t, J=1.8 Hz, 1H), 7.81 (d, J=1.4 Hz, 1H), 7.79 (d, J=1.4 Hz, 1H), 7.74 (t, J=8.1 Hz, 1H), 7.65-7.61 (m, 2H), 7.56-7.46 (m, 1H), 7.37-7.31 (m, 3H), 7.17-7.11 (m, 5H). HPLC: (Method A) RT 4.0 min, 96.7% (Max), 95.8% (254 nm).

MC825_033

3-[8-(1-Methyl-1H-pyrazol-4-yl)-[1,2,4]triazolo[1,5-a]pyrazin-2-ylamino]-benzenesulfonamide ("C14")

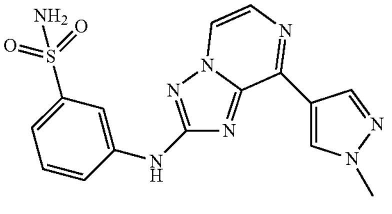 [SMILES: Cn1cc(-c2nccn3nc(Nc4cccc(S(N)(=O)=O)c4)nc23)cn1]

Synthesized as described for MC825_010

Yield: 2.6% (9 mg, off white solid). LCMS: (Method A) 371 (M+H), RT. 2.5 min, 97.0% (Max). 96.2% (254 nm); $^1$H NMR (400 MHz, DMSO-$d_6$): δ [ppm] 10.36 (s, 1H), 8.80 (s, 1H), 8.72 (dd, J=4.6, 4.3 Hz, 2H), 8.34 (s, 1H), 8.09 (d, J=4.3 Hz, 1H), 7.69 (td, J=4.46, 1.4 Hz, 1H), 7.52 (t, J=8.0 Hz, 1H), 7.53-7.41 (m, 1H), 7.42-7.36 (m, 2H), 4.00 (s, 3H). HPLC: (Method A) RT 2.6 min, 97.5% (Max), 96.9% (254 nm).

MC825_SC08

Step 1-IS08149-041

4-Isothiocyanato-benzenesulfonamide

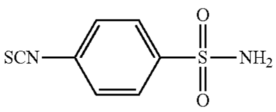

Synthesized using the procedure as described for MC825_SC05_Step 1.

Yield: 80% (1 g, brown solid). $^1$H NMR (400 MHz, DMSO-$d_6$): δ [ppm] 7.86-7.83 (m, 2H), 7.62-7.59 (m, 2H), 7.49 (br s, 2H).

Step 2-FS08149-042

4-(8-Chloro-[1,2,4]triazolo[1,5-a]pyrazin-2-ylamino)-benzenesulfonamide

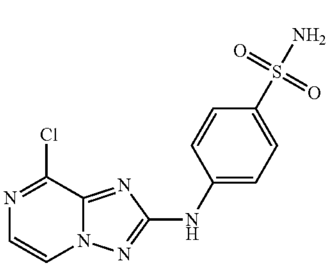 [SMILES: NS(=O)(=O)c1ccc(Nc2nc3c(Cl)nccn3n2)cc1]

Synthesized using the procedure as described for MC825_SC01_Step1.

Yield: 40% (1 g, brown solid). LCMS: (Method A) 325.0 (M+H), RT. 2.3 min, 91.1% (Max), 84.0% (254 nm). $^1$H NMR (400 MHz, DMSO-$d_6$): δ [ppm] 10.62 (s, 1H), 9.00 (d, J=4.3 Hz, 1H), 7.99 (d, J=4.3 Hz, 1H), 7.76-7.81 (m, 4H), 7.20 (br s, 2H). HPLC: (Method A) RT 2.5 min, 89.2% (Max), 87.9% (254 nm).

MC825_001

4-(8-Biphenyl-2-yl-[1,2,4]triazolo[1,5-a]pyrazin-2-ylamino)-benzenesulfonamide ("C15")

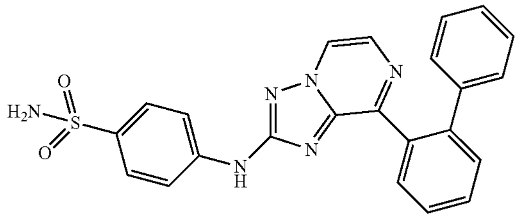 [SMILES: NS(=O)(=O)c1ccc(Nc2nc3c(-c4ccccc4-c4ccccc4)nccn3n2)cc1]

Synthesized as described for MC825_010

Yield: 5.6% (11.5 mg, off white solid). LCMS: (Method A) 443.0 (M+H), RT. 3.8 min, 97.1% (Max). 97.2% (254 nm); $^1$H NMR (400 MHz, $CDCl_3$): δ [ppm] 8.32 (d, J=4.3 Hz, 1H), 8.09 (d, J=4.3 Hz, 1H), 7.88 (d, J=8.8 Hz, 2H), 7.75 (d, J=7.0 Hz, 1H), 7.62-7.54 (m, 5H), 7.16-7.14 (m, 5H). HPLC: (Method A) RT 3.9 min, 95.5% (Max), 94% (254 nm).

MC825_021

4-[8-(1-Methyl-1H-pyrazol-4-yl)-[1,2,4]triazolo[1,5-a]pyrazin-2-ylamino]-benzenesulfonamide ("C16")

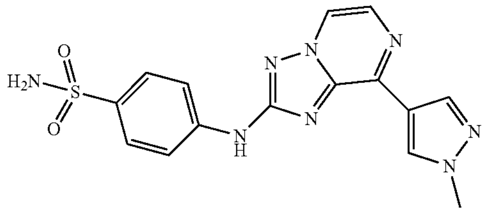 [SMILES: Cn1cc(-c2nccn3nc(Nc4ccc(S(N)(=O)=O)cc4)nc23)cn1]

Synthesized as described for MC825_010

Yield: 3% (9 mg, off white solid). LCMS: (Method A) 371.0 (M+H), RT. 2.5 min, 95.9% (Max). 92.6% (254 nm); $^1$H NMR (400 MHz, DMSO-$d_6$): δ [ppm] 10.43 (s, 1H), 8.76 (d, J=4.3 Hz, 1H), 8.68 (s, 1H), 8.39 (s, 1H), 8.10 (d, J=4.3 Hz, 1H), 7.86 (d, J=9.0 Hz, 2H), 7.79 (d, J=8.9 Hz, 2H), 7.18 (s, 2H), 3.99 (s, 3H). HPLC: (Method A) RT 2.5 min, 97.2% (Max), 92.9% (254 nm).

MC825_SC09

Step 1-IS08027-080

4-(3-Isothiocyanato-phenyl)-morpholine

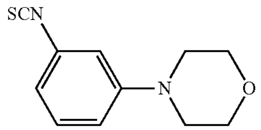

Synthesized using the procedure as described for MC825_SC05_Step 1.

Yield: 73% (0.9 g, brown oil). $^1$H NMR (400 MHz, DMSO-$d_6$): δ [ppm] 7.26 (t, J=7.9 Hz, 1H), 6.97-6.94 (m, 2H), 6.83-6.80 (m, 1H), 3.71 (t, J=4.7 Hz, 4H), 3.13 (t, J=4.8 Hz, 4H).

Step 2-FS08115-053

(8-Chloro-[1,2,4]triazolo[1,5-a]pyrazin-2-yl)-(3-morpholin-4-yl-phenyl)-amine

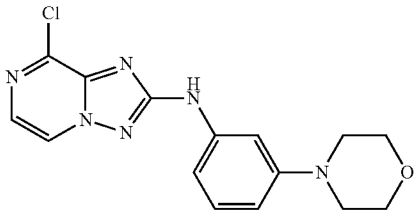 [SMILES: Clc1nccn2nc(Nc3cccc(N4CCOCC4)c3)nc12]

Synthesized using the procedure as described for MC825_SC01_Step1.

Yield: 37% (500 mg, yellow solid). LCMS: (Method A) 331.0 (M+H), RT. 2.5 min, 99.2% (Max), 99.5% (254 nm). $^1$H NMR (400 MHz, DMSO-$d_6$): δ [ppm] 10.00 (s, 1H), 8.95 (d, J=4.3 Hz, 1H), 7.93 (d, J=4.3 Hz, 1H), 7.26 (d, J=1.9 Hz, 1H), 7.20-7.14 (m, 2H), 6.55-6.58 (m, 1H), 3.76 (t, J=4.8 Hz, 4H), 3.10 (t, J=4.7 Hz, 4H). HPLC: (Method A) RT 2.6 min, 99.7% (Max), 99.7% (254 nm).

MC825_014

(8-Biphenyl-2-yl-[1,2,4]triazolo[1,5-a]pyrazin-2-yl)-(3-morpholin-4-yl-phenyl)-amine ("C17")

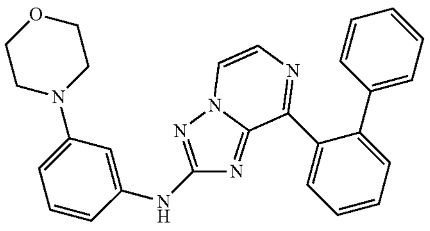 [SMILES: c1ccc(-c2ccccc2-c2nccn3nc(Nc4cccc(N5CCOCC5)c4)nc23)cc1]

Synthesized as described for MC825_010

Yield: 25% (68 mg, pale yellow solid). LCMS: (Method A) 449.3 (M+H), RT. 4.0 min, 96.0% (Max). 97.3% (254 nm); $^1$H NMR (400 MHz, DMSO-$d_6$): δ [ppm] 9.86 (s, 1H), 8.78 (d, J=4.3 Hz, 1H), 7.99 (d, J=4.3 Hz, 1H), 7.73 (d, J=7.8 Hz, 1H), 7.65-7.60 (m, 1H), 7.55-7.51 (m, 2H), 7.33 (s, 1H), 7.18-7.08 (m, 6H), 6.99-7.01 (m, 1H), 6.49 (dd, J=2.0, 8.2 Hz, 1H), 3.73 (t, J=4.9 Hz, 4H), 3.04 (t, J=4.7 Hz, 4H). HPLC: (Method A) RT 4.0 min, 99.1% (Max), 99.3% (254 nm).

MC825_041

[8-(1-Methyl-1H-pyrazol-4-yl)-[1,2,4]triazolo[1,5-a]pyrazin-2-yl]-(3-morpholin-4-yl-phenyl)-amine ("C18")

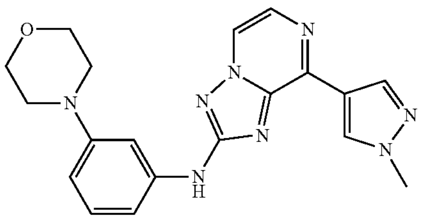 [SMILES: Cn1cc(-c2nccn3nc(Nc4cccc(N5CCOCC5)c4)nc23)cn1]

Synthesized as described for MC825_010

Yield: 20% (46 mg, brown solid). LCMS: (Method A) 377.3 (M+H), RT. 2.6 min, 97.7% (Max). 94.8% (254 nm); $^1$H NMR (400 MHz, DMSO-$d_6$): δ [ppm] 9.80 (s, 1H), 8.70 (d, J=4.3 Hz, 1H), 8.64 (s, 1H), 8.40 (d, J=0.5 Hz, 1H), 8.04 (d, J=4.3 Hz, 1H), 7.46 (d, J=1.8 Hz, 1H), 7.19-7.14 (m, 2H), 6.57-6.54 (m, 1H), 3.97 (s, 3H), 3.77 (t, J=4.8 Hz, 4H), 3.16-3.12 (m, 4H).

HPLC: (Method A) RT 2.6 min, 98.99% (Max), 97.49% (254 nm).

MC825_SC10

Step 1-IS08027-081

5-Isothiocyanato-benzo[1,2,5]thiadiazole

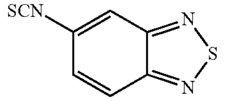

Synthesized using the procedure as described for MC825_SC05_Step 1.

Yield: 79% (1.5 g, light brown solid). $^1$H NMR (400 MHz, DMSO-$d_6$): δ [ppm] 8.23-8.23 (m, 1H), 8.16 (dd, J=0.6, 9.2 Hz, 1H), 7.75 (dd, J=2.0, 9.2 Hz, 1H).

Step 2-FS08027-082

Benzo[1,2,5]thiadiazol-5-yl-(8-chloro-[1,2,4]triazolo[1,5-a]pyrazin-2-yl)-amine

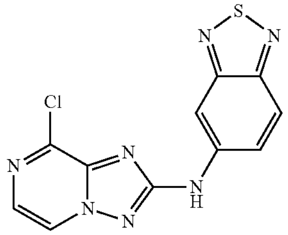 [SMILES: Clc1nccn2nc(Nc3ccc4nsnc4c3)nc12]

Synthesized using the procedure as described for MC825_SC01_Step1.

Yield: 42% (1 g, brown solid). LCMS: (Method A) 304.0 (M+H), RT. 3.6 min, 90.9% (Max), 97.9% (254 nm). $^1$H NMR (400 MHz, DMSO-$d_6$): δ [ppm] 10.85 (s, 1H), 9.11 (d, J=4.3 Hz, 1H), 8.58 (d, J=1.7 Hz, 1H), 8.02-8.05 (m, 2H), 7.79-7.76 (m, 1H).

MC825_013

Benzo[1,2,5]thiadiazol-5-yl-(8-biphenyl-2-yl-[1,2,4]triazolo[1,5-a]pyrazin-2-yl)-amine ("C19")

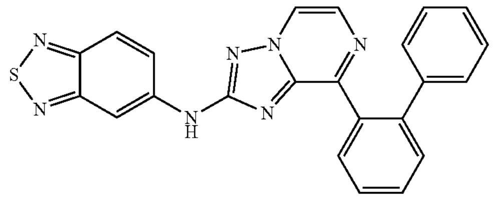 [SMILES: c1ccc(-c2ccccc2-c2nccn3nc(Nc4ccc5nsnc5c4)nc23)cc1]

Synthesized as described for MC825_010

Yield: 9% (18.8 mg, pale yellow solid). LCMS: (Method A) 422.0 (M+H), RT. 4.9 min, 98.6% (Max). 99.5% (254 nm); $^1$H NMR (400 MHz, DMSO-$d_6$): δ [ppm] 10.53 (s, 1H), 8.95 (d, J=4.4 Hz, 1H), 8.46 (d, J=1.7 Hz, 1H), 8.13 (d, J=4.3 Hz, 1H), 7.98 (d, J=9.4 Hz, 1H), 7.76-7.74 (m, 1H), 7.68-7.64 (m, 2H), 7.61-7.55 (m, 2H), 7.15-7.09 (m, 5H). HPLC: (Method A) RT 4.9 min, 98.4% (Max), 98.7% (254 nm).

MC825_SC11

Step 1-IS08027-087

1-Methyl-6-nitro-1H-indazole

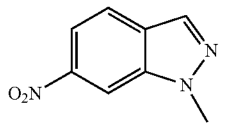

Procedure: To a suspension of sodium hydride (60%) (1.1 g, 29.4 mmol) in dry N,N-dimethylformamide (75 mL) at 0° C., a solution of 6-nitroindazole (4 g, 24.5 mmol) in dry N,N-dimethylformamide (25 mL) is added and stirred for 1 h. Iodomethane (1.8 mL, 29.4 mmol) ias added and stirred at RT for 30 min. After completion of the reaction (monitored by TLC), the reaction mixture is quenched with cold water and concentrated, the residue is taken in ethylacetate, washed with water (2×75 mL), brine, dried over $MgSO_4$ and concentrated to get the crude product. The crude product is purified by column chromatography (silica gel, EA/PE gradient elution). The required regioisomer has to be taken for the next step. Yield: 46% (2 g, yellow solid).

$^1H$ NMR (400 MHz, DMSO-$d_6$): δ [ppm] 8.59 (s, 2H), 7.97-7.94 (m, 1H), 7.81-7.78 (m, 1H), 4.27 (s, 3H).

Step 2-IS08027-093

1-Methyl-1H-indazol-6-ylamine

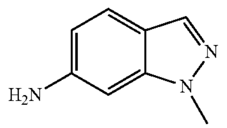

Synthesized using the procedure as described for MC825_SC06_Step 2.

Yield: 90% (1.5 g, white solid). LCMS: (Method A) 148.3 (M+H), RT. 0.6 min, 92.7% (Max).

Step 3-IS08027-094

6-Isothiocyanato-1-methyl-1H-indazole

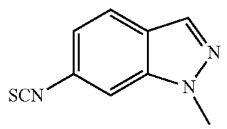

Synthesized using the procedure as described for MC825_SC06_Step 3.

Yield: 75% (1.5 g, brown solid). LCMS: (Method A) 190.0 (M+H), RT. 3.9 min, 95.6% (Max).

Step 4-FS08027-095

(8-Chloro-[1,2,4]triazolo[1,5-a]pyrazin-2-yl)-(1-methyl-1H-indazol-6-yl)-amine

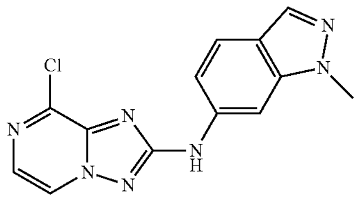 [SMILES: Cn1ncc2ccc(Nc3nc4c(Cl)nccn4n3)cc21]

Synthesized using the procedure as described for MC825_SC01_Step1.

Yield: 31% (750 mg, yellow solid). LCMS: (Method A) 300.0 (M+H), RT. 2.3 min, 98.4% (Max), 99.6% (254 nm). $^1H$ NMR (400 MHz, DMSO-$d_6$): δ [ppm] 10.17 (s, 1H), 9.00 (d, J=4.3 Hz, 1H), 8.20 (s, 1H), 8.13 (s, 1H), 7.95 (d, J=4.3 Hz, 1H), 7.60 (d, J=8.8 Hz, 1H), 7.12 (dd, J=8.9, 1.8 Hz, 1H), 4.09 (s, 3H). HPLC: (Method A) RT 2.4 min, 98.9% (Max), 99.1% (254 nm).

MC825_018

(8-Biphenyl-2-yl-[1,2,4]triazolo[1,5-a]pyrazin-2-yl)-(1-methyl-1H-indazol-6-yl)-amine ("C20")

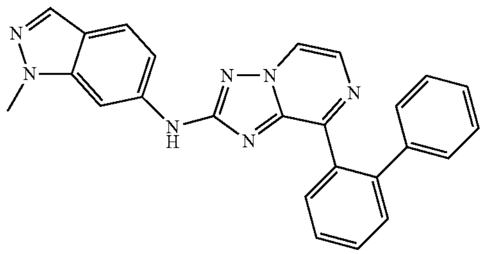 [SMILES: Cn1ncc2ccc(Nc3nc4c(-c5ccccc5-c5ccccc5)nccn4n3)cc21]

Synthesized as described for MC825_010

Yield: 22% (61 mg, pale yellow solid). LCMS: (Method A) 418.2 (M+H), RT. 3.7 min, 98.8% (Max). 99.6% (254 nm); $^1H$ NMR (400 MHz, DMSO-$d_6$): δ [ppm] 9.86 (s, 1H), 8.85 (d, J=4.3 Hz, 1H), 8.16 (s, 1H), 8.16-8.02 (m, 2H), 7.72 (t, J=1.1 Hz, 1H), 7.65-7.61 (m, 1H), 7.57-7.53 (m, 3H), 7.19-7.10 (m, 5H), 7.09-7.00 (m, 1H), 4.09 (s, 3H). HPLC: (Method A) RT 3.6 min, 99.7% (Max), 99.6% (254 nm).

MC825_039

(1-Methyl-1H-indazol-6-yl)-[8-(1-methyl-1H-pyrazol-4-yl)-[1,2,4]triazolo[1,5-a]pyrazin-2-yl]-amine ("C21")

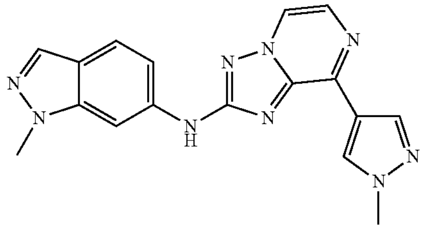 [SMILES: Cn1cc(-c2nccn3nc(Nc4ccc5cnn(C)c5c4)nc23)cn1]

Synthesized as described for MC825_010

Yield: 72% (166 mg, pale yellow solid). LCMS: (Method A) 346.3 (M+H), RT. 2.4 min, 99.0% (Max). 98.6% (254 nm);

$^1H$ NMR (400 MHz, DMSO-$d_6$): δ [ppm] 9.95 (s, 1H), 8.77 (d, J=4.3 Hz, 1H), 8.66 (s, 1H), 8.43 (s, 1H), 8.18 (t, J=0.7 Hz, 2H), 8.06 (d, J=4.3 Hz, 1H), 7.60 (d, J=9.0 Hz, 1H), 7.20 (dd, J=1.8, 9.0 Hz, 1H), 4.10 (s, 3H), 3.98 (s, 3H). HPLC: (Method A) RT 2.4 min, 96.5% (Max), 97.9% (254 nm).

MC825_SC12

Step 1-IS08115-060

1-Isothiocyanato-4-methanesulfonyl-benzene

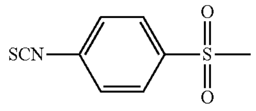

Synthesized using the procedure as described for MC825_SC05_Step 1.

Yield: 80% (2 g, light brown solid). $^1H$ NMR (400 MHz, DMSO-$d_6$): δ [ppm] 7.98 (dd, J=1.9, 6.7 Hz, 2H), 7.67 (dd, J=1.9, 6.7 Hz, 2H), 3.25 (s, 3H).

Step 2-FS08115-061

(8-Chloro-[1,2,4]triazolo[1,5-a]pyrazin-2-yl)-(4-methanesulfonyl-phenyl)-amine

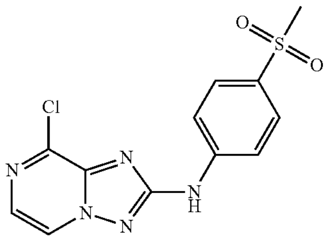 [SMILES: CS(=O)(=O)c1ccc(Nc2nc3c(Cl)nccn3n2)cc1]

Synthesized using the procedure as described for MC825_SC01_Step1.

Yield: 44% (1.8 g, yellow solid). LCMS: (Method A) 324.0 (M+H), RT. 2.8 min, 98.6% (Max), 95.8% (254 nm). $^1H$ NMR (400 MHz, DMSO-$d_6$): δ [ppm] 10.77 (s, 1H), 9.01 (d, J=4.3 Hz, 1H), 8.00 (d, J=4.3 Hz, 1H), 7.87 (s, 4H), 3.15 (s, 3H). HPLC: (Method A) RT 2.9 min, 99.0% (Max), 98.2% (254 nm).

MC825__006

(8-Biphenyl-2-yl-[1,2,4]triazolo[1,5-a]pyrazin-2-yl)-(4-methanesulfonyl-phenyl)-amine ("C22")

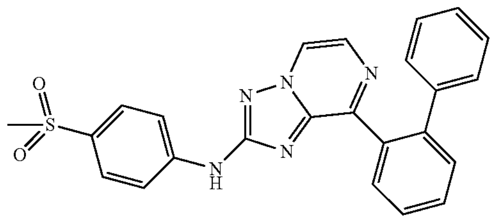 [SMILES: CS(=O)(=O)c1ccc(Nc2nc3c(-c4ccccc4-c4ccccc4)nccn3n2)cc1]

Synthesized as described for MC825__010

Yield: 80% (275 mg, off white solid). LCMS: (Method A) 442 (M+H), RT. 4.2 min, 98.53% (Max). 96.90% (254 nm); $^1H$ NMR (400 MHz, DMSO-$d_6$): δ [ppm] 10.52 (s, 1H), 8.87 (d, J=4.32 Hz, 1H), 8.11 (d, J=4.36 Hz, 1H), 7.84-7.80 (m, 2H), 7.73 (dd, J=7.14, 1.64 Hz, 3H), 7.66-7.62 (m, 1H), 7.58-7.53 (m, 2H), 7.18-7.10 (m, 5H), 3.14 (s, 3H). HPLC: (Method A) RT 4.2 min, 99.35% (Max), 97.70% (254 nm).

MC825__026

(4-Methanesulfonyl-phenyl)-[8-(1-methyl-1H-pyrazol-4-yl)-[1,2,4]triazolo[1,5-a]pyrazin-2-yl]-amine ("C23")

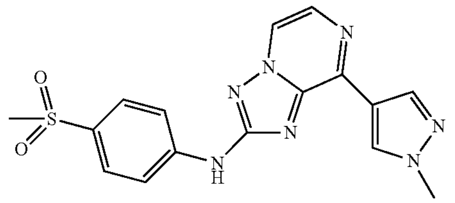 [SMILES: Cn1cc(-c2nccn3nc(Nc4ccc(S(C)(=O)=O)cc4)nc23)cn1]

Synthesized as described for MC825__010

Yield: 36.5% (104 mg, Yellow solid). LCMS: (Method A) 370 (M+H), RT. 2.8 min, 97.59% (Max). 97.47% (254 nm); $^1H$ NMR (400 MHz, DMSO-$d_6$): δ [ppm] 10.59 (s, 1H), 8.77 (d, J=4.32 Hz, 1H), 8.68 (s, 1H), 8.39 (s, 1H), 8.11 (d, J=4.36 Hz, 1H), 7.96-7.87 (m, 4H), 4.00 (s, 3H), 3.15 (s, 3H).

HPLC: (Method A) RT 2.8 min, 98.75% (Max), 98.32% (254 nm).

MC825_SC13

Step 1-FS08115-073

(8-Chloro-[1,2,4]triazolo[1,5-a]pyrazin-2-yl)-(2-methoxy-phenyl)-amine

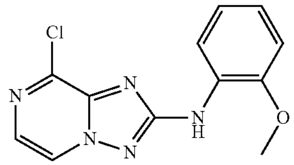 [SMILES: COc1ccccc1Nc1nc2c(Cl)nccn2n1]

Synthesized using the procedure as described for MC825_SC01_Step1.

Yield: 50% (500 mg, white solid). LCMS: (Method A) 276.0 (M+H), RT. 3.9 min, 96.6% (Max), 98.4% (254 nm). $^1H$ NMR (400 MHz, DMSO-$d_6$): δ [ppm] 8.93 (d, J=4.3 Hz, 1H), 8.69 (s, 1H), 8.06 (dd, J=7.5, 2.0 Hz, 1H), 7.93 (d, J=4.3 Hz, 1H), 7.06-6.99 (m, 3H), 3.85 (s, 3H). HPLC: (Method A) RT 4.0 min, 98.4% (Max), 99.0% (254 nm).

MC825__009

(8-Biphenyl-2-yl-[1,2,4]triazolo[1,5-a]pyrazin-2-yl)-(2-methoxy-phenyl)-amine ("C24")

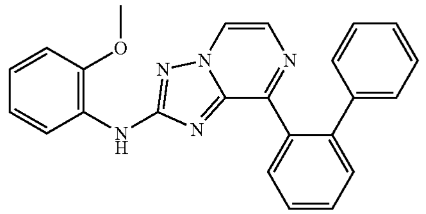 [SMILES: COc1ccccc1Nc1nc2c(-c3ccccc3-c3ccccc3)nccn2n1]

Synthesized as described for MC825__010

Yield: 11% (40 mg, Yellow solid). LCMS: (Method A) 394 (M+H), RT. 5.1 min, 98.86% (Max). 99.35% (254 nm); $^1H$ NMR (400 MHz, DMSO-$d_6$): δ [ppm] 8.79 (s, 1H), 8.83 (s, 1H), 8.03 (d, J=4.32 Hz, 1H), 7.97-7.94 (m, 1H), 7.71-7.69 (m, 1H), 7.62-7.60 (m, 1H), 7.56-7.52 (m, 2H), 7.18-7.08 (m, 5H), 7.01-6.93 (m, 3H), 3.81 (s, 3H). HPLC: (Method A) RT 5.2 min, 98.79% (Max), 98.87% (254 nm).

MC825__029

(2-Methoxy-phenyl)-[8-(1-methyl-1H-pyrazol-4-yl)-[1,2,4]triazolo[1,5-a]pyrazin-2-yl]-amine ("C25")

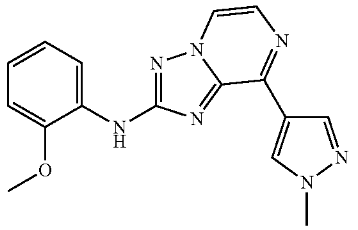 [SMILES: COc1ccccc1Nc1nc2c(-c3cnn(C)c3)nccn2n1]

Synthesized as described for MC825__010

Yield: 34% (99.9 mg, off white solid; LCMS: (Method A) 322 (M+H), RT. 3.8 min, 98.07% (Max). 99.10% (254 nm); $^1$H NMR (400 MHz, DMSO-$d_6$): δ [ppm] 8.71 (d, J=4.20 Hz, 2H), 8.36 (s, 1H), 8.31 (s, 1H), 8.20 (dd, J=7.38, 1.80 Hz, 1H), 8.05 (d, J=4.32 Hz, 1H), 7.06 (dd, J=7.30, 2.24 Hz, 1H), 7.02-6.98 (m, 2H), 3.98 (s, 3H), 3.89 (s, 3H). HPLC: (Method A) RT 3.9 min, 99.10% (Max), 98.75% (254 nm).

MC825_SC14

Step 1-IS08149-051

1-Methyl-4-nitro-1H-pyrazole

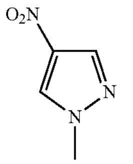

Procedure: To a solution of 4-nitro-1H-pyrazole (5 g, 44.2 mmol) in dry acetonitrile (100 mL), cesium carbonate (28.8 g, 88.4 mmol) and iodomethane (4.1 mL, 66.3 mmol) are added and heated to 70° C. for 2 h. The reaction mixture is concentrated and the residue is taken in ethylacetate, washed with water (2×75 mL), brine, dried over $MgSO_4$ and concentrated to get the product. Yield: 53% (3 g, yellow solid). LCMS: (Method A) 128.0 (M+H), RT. 1.3 min, 99.4% (Max), 98.6% (254 nm). $^1$H NMR (400 MHz, DMSO-$d_6$): δ [ppm] 8.83 (s, 1H), 8.22 (s, 1H), 3.90 (s, 3H).

Step 2-IS08115-071

1-Methyl-1H-pyrazol-4-ylamine

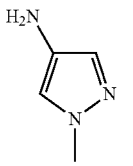

Synthesized using the procedure as described for MC825_SC06_Step 2.

Yield: 100% (2 g, white gummy solid). $^1$H NMR (400 MHz, DMSO-$d_6$): δ [ppm] 6.95 (s, 1H), 6.85 (s, 1H), 4.34 (s, 2H), 3.63 (s, 3H).

Step 3-IS08115-072

4-Isothiocyanato-1-methyl-1H-pyrazole

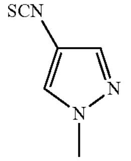

Synthesized using the procedure as described for MC825_SC06_Step 3.

Yield: 70% (2 g, brown gummy solid). $^1$H NMR (400 MHz, DMSO-$d_6$): δ [ppm] 7.93 (s, 1H), 7.42 (s, 1H), 3.78 (s, 3H).

Step 4-FS08115-074

(8-Chloro-[1,2,4]triazolo[1,5-a]pyrazin-2-yl)-(1-methyl-1H-pyrazol-4-yl)-amine

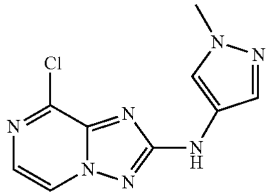 [SMILES: Cn1cc(Nc2nc3c(Cl)nccn3n2)cn1]

Synthesized using the procedure as described for MC825_SC01_Step1.

Yield: 40% (500 mg, light brown solid). LCMS: (Method A) 250.0 (M+H), RT. 2.0 min, 95.9% (Max), 98.5% (254 nm). $^1$H NMR (400 MHz, DMSO-$d_6$): δ [ppm] 9.69 (s, 1H), 8.85 (d, J=4.0 Hz, 1H), 7.88 (d, J=4.3 Hz, 1H), 7.79 (s, 1H), 7.45 (s, 1H), 3.81 (s, 3H). HPLC: (Method A) RT 2.1 min, 95.6% (Max), 98.7% (254 nm).

MC825__034

(1-Methyl-1H-pyrazol-4-yl)-[8-(1-methyl-1H-pyrazol-4-yl)-[1,2,4]triazolo[1,5-a]pyrazin-2-yl]-amine ("C26")

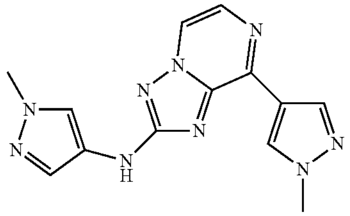 [SMILES: Cn1cc(Nc2nc3c(-c4cnn(C)c4)nccn3n2)cn1]

Synthesized as described for MC825__010

Yield: 22% (65 mg, Yellow solid). LCMS: (Method A) 296 (M+H), RT. 2.2 min, 98.69% (Max). 98.55% (254 nm); H NMR (400 MHz, DMSO-$d_6$: δ [ppm] 9.54 (s, 1H), 8.63 (t, J=4.36 Hz, 2H), 8.35 (d, J=0.52 Hz, 1H), 8.00 (d, J=4.28 Hz, 1H), 7.84 (s, 1H), 7.49 (d, J=0.64 Hz, 1H), 3.98 (s, 3H), 3.83 (s, 3H). HPLC: (Method A) RT 2.3 min, 97.66% (Max), 98.48% (254 nm).

MC825_SC15

Step 1-IS08149-057

4-Hydroxy-piperidine-1-carboxylic acid tert-butyl ester

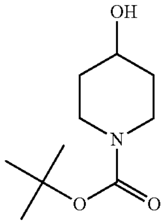

Procedure: To a solution of 1-boc-4-piperidone (5 g, 25.1 mmol) in absolute alcohol (100 mL) at 0° C., sodium borohydride (1.4 g, 37.6 mmol) is added and stirred at RT for 2 h. After completion of the reaction (monitored by TLC), the reaction mixture is quenched with cold water and concentrated, the residue is taken in ethylacetate (75 mL), washed with water (2×75 mL), brine, dried over $MgSO_4$ and concentrated to get the product. Yield: 97% (4.9 g, white solid). $^1H$ NMR (400 MHz, DMSO-$d_6$): δ [ppm] 4.68 (d, J=4.2 Hz, 1H), 3.67-3.57 (m, 3H), 2.93-2.91 (m, 2H), 1.69-1.64 (m, 2H), 1.37 (s, 9H), 1.28-1.19 (m, 2H).

Step 2-IS08149-058

4-(4-Nitro-pyrazol-1-yl)-piperidine-1-carboxylic acid tert-butyl ester

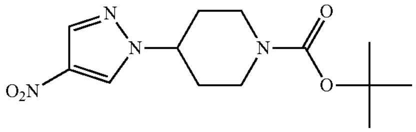 [SMILES: CC(C)(C)OC(=O)N1CCC(n2cc([N+](=O)[O-])cn2)CC1]

Procedure: To a solution of 4-hydroxy-piperidine-1-carboxylic acid tert-butyl ester (5.6 g, 48.6 mmol) in dry tetrahydrofuran (150 mL) at 0° C., 4-nitro-1H-pyrazole (3.1 g, 27.4 mmol) and triphenylphosphine (8.6 g, 32.9 mmol) are added and stirred for 5 min. ditert-butylazodicarboxylate (8.2 g, 35.6 mmol) is added dropwise slowly and the reaction mixture is allowed to reach RT and stirred for 16 h. After completion of the reaction (monitored by TLC), the reaction mixture is concentrated to get the crude product. The crude product is purified by column chromatography (silica gel, EA/PE gradient elution). Yield: 59% (4.8 g, light brown solid). $^1H$ NMR (400 MHz, DMSO-$d_6$): δ [ppm] 8.94 (s, 1H), 8.27 (s, 1H), 4.48-4.42 (m, 1H), 4.05-4.02 (m, 2H), 2.89-2.87 (m, 2H), 2.04-2.01 (m, 2H), 1.85-1.75 (m, 2H), 1.39 (s, 9H).

Step 3-IS08115-078-A 4-(4-Amino-pyrazol-1-yl)-piperidine-1-carboxylic acid tert-butyl ester

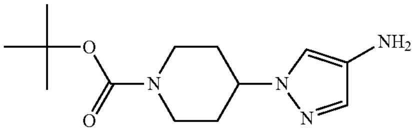 [SMILES: CC(C)(C)OC(=O)N1CCC(n2cc(N)cn2)CC1]

Synthesized using the procedure as described for MC825_SC06_Step 2. The product obtained is taken for the next step.

Yield: 100% (1.8 g, white gummy solid).

Step 4-IS08115-078-B 4-(4-Isothiocyanato-pyrazol-1-yl)-piperidine-1-carboxylic acid tert-butyl ester

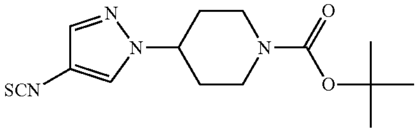

Synthesized using the procedure as described for MC825_SC06_Step 3.

Yield: 70% (1.4 g, colourless gummy solid). $^1H$ NMR (400 MHz, DMSO-$d_6$): δ [ppm] 8.25 (s, 1H), 7.76 (s, 1H), 4.35-4.29 (m, 1H), 4.02-3.99 (m, 2H), 2.87-2.85 (m, 2H), 1.98-1.94 (m, 2H), 1.73-1.67 (m, 2H), 1.39 (s, 9H).

Step 5-IS08115-079

4-[4-(8-Chloro-[1,2,4]triazolo[1,5-a]pyrazin-2-ylamino)-pyrazol-1-yl]-piperidine-1-carboxylic acid tert-butyl ester

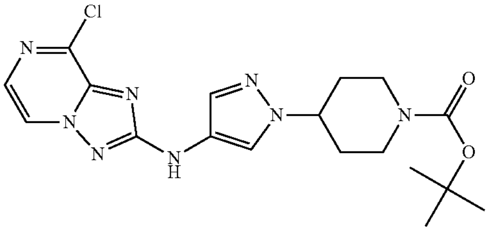 [SMILES: CC(C)(C)OC(=O)N1CCC(n2cc(Nc3nc4c(Cl)nccn4n3)cn2)CC1]

Synthesized using the procedure as described for MC825_SC01_Step1.

Yield: 73% (1 g, light brown solid). LCMS: (Method A) 419.3 (M+H), RT. 3.9 min, 99.2% (Max), 99.6% (254 nm). $^1H$ NMR (400 MHz, DMSO-$d_6$): δ [ppm] 9.69 (s, 1H), 8.85 (d, J=4.3 Hz, 1H), 7.88 (d, J=4.3 Hz, 1H), 7.85 (s, 1H), 7.50 (s, 1H), 4.36-4.33 (m, 1H), 4.05-4.01 (m, 2H), 2.90-2.88 (m, 2H), 1.99-1.97 (m, 2H), 1.80-1.71 (m, 2H), 1.41 (s, 9H).

Step 6-FS08115-085

(8-Chloro-[1,2,4]triazolo[1,5-a]pyrazin-2-yl)-(1-piperidin-4-yl-1H-pyrazol-4-yl)-amine. hydrochloride

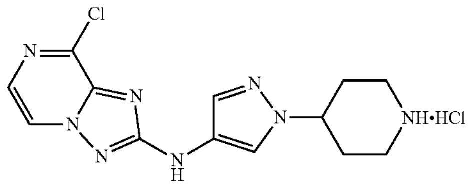

Procedure: To a solution of 4-[4-(8-chloro-[1,2,4]triazolo[1,5-a]pyrazin-2-ylamino)-pyrazol-1-yl]-piperidine-1-carboxylic acid tert-butyl ester (100 mg, 0.24 mmol) in dry 1,4 dioxane (3 mL) at 0° C., HCl in 1,4 dioxane (3 mL) is added and stirred for 2 h at RT. The reaction mixture is concentrated and the residue is triturated with diethylether and filtered to get the product.

Yield: 17% (13 mg, light brown solid). LCMS: (Method A) 319.0 (M+H), RT. 1.7 min, 96.7% (Max), 97.8% (254 nm). $^1$H NMR (400 MHz, DMSO-$d_6$): δ [ppm] 9.77 (s, 1H), 9.02 (br s, 1H), 8.85 (d, J=4.3 Hz, 1H), 8.76 (br s, 1H), 7.90 (d, J=4.3 Hz, 1H), 7.85 (s, 1H), 7.54 (s, 1H), 4.50-4.45 (m, 1H), 3.40-3.36 (m, 2H), 3.05-3.03 (m, 2H), 2.17-2.11 (m, 4H). HPLC: (Method A) RT 1.7 min, 97.0% (Max), 97.1% (254 nm).

MC825_019

(8-Biphenyl-2-yl-[1,2,4]triazolo[1,5-a]pyrazin-2-yl)-(1-piperidin-4-yl-1H-pyrazol-4-yl)-amine)hydrochloride ("C27")

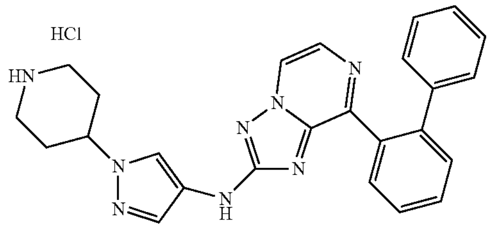 [SMILES: c1ccc(-c2ccccc2-c2nccn3nc(Nc4cnn(C5CCNCC5)c4)nc23)cc1 ; Cl]

Synthesized as described for MC825_010, the final compound is obtained after deprotection of BOC group with HCl in Dioxane as reported for MC825_SC15 step 6. Yield: 6% (25.5 mg, Reddish brown solid); LCMS: (Method A) 437 (M+H), RT. 3.1 min, 93.70% (Max). 93.41% (254 nm); $^1$H NMR (400 MHz, DMSO-$d_6$): δ [ppm] 9.43 (s, 1H), 8.95 (d, J=8.44 Hz, 1H), 8.68 (dd, J=4.36, 9.72 Hz, 2H), 7.98 (d, J=4.32 Hz, 1H), 7.71 (t, J=6.72 Hz, 2H), 7.64-7.60 (m, 1H), 7.60-7.52 (m, 2H), 7.44 (d, J=0.52 Hz, 1H), 7.16 (s, 3H), 4.48-4.40 (m, 1H), 3.38 (t, J=5.36 Hz, 2H), 3.09-3.02 (m, 2H), 2.16-2.08 (m, 4H). HPLC: (Method A) RT 3.1 min, 94.47% (Max), 92.20% (254 nm).

MC825_035

[8-(1-Methyl-1H-pyrazol-4-yl)-[1,2,4]triazolo[1,5-a]pyrazin-2-yl]-(1-piperidin-4-yl-1H-pyrazol-4-yl)-amine hydrochloride ("C28")

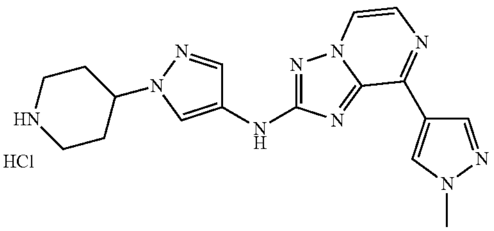 [SMILES: Cl ; Cn1cc(-c2nccn3nc(Nc4cnn(C5CCNCC5)c4)nc23)cn1]

Synthesized as described for MC825_010, the final compound is obtained after deprotection of BOC group with HCl in Dioxane as reported for MC825_SC15 step 6. Yield: 10% (47.8 mg, yellow solid). LCMS: (Method A) 365.3 (M+H), RT. 1.9 min, 94.67% (Max). 97.57% (254 nm); $^1$H NMR (400 MHz, DMSO-$d_6$): δ [ppm] 9.54 (s, 1H), 8.63 (d, J=4.20 Hz, 2H), 8.35 (d, J=7.36 Hz, 1H), 8.00 (d, J=4.28 Hz, 1H), 7.87 (d, J=0.80 Hz, 1H), 7.53 (d, J=0.64 Hz, 1H), 4.21-4.13 (m, 1H), 3.97 (s, 3H), 3.05-3.02 (m, 2H), 2.62 (d, J=2.28 Hz, 2H), 1.96 (d, J=2.32 Hz, 2H), 1.80 (t, J=7.96 Hz, 2H); HPLC: (Method A) RT 1.9 min, 93.73% (Max), 95.79% (254 nm).

MC825_SC16

Step 1-IS08115-070

N2-Methyl-4-nitro-benzene-1,2-diamine

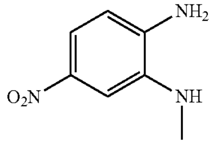

Procedure: To a solution of 4-nitro-benzene-1,2-diamine (5 g, 32.6 mmol) in dry N,N-dimethylformamide (30 mL), iodomethane (1.6 mL, 26.1 mmol) and saturated sodium carbonate solution (8 ml) are added and stirred at RT for 12 h. The reaction mixture is concentrated at high vacuum pump and diluted with ethylacetate (75 mL), washed with water (2×75 mL), brine, dried over $MgSO_4$ and concentrated to get the crude product. The crude product is purified by column chromatography (silica gel, EA/PE gradient elution). Yield: 55% (3 g, reddish brown solid); LCMS: (Method A) 166.0 (M−H), RT. 3.9 min, 98.5% (Max), 98.1% (254 nm). $^1$H NMR (400 MHz, DMSO-$d_6$): δ [ppm] 7.71 (dd, J=2.4, 8.5 Hz, 1H), 7.54 (d, J=2.4 Hz, 1H), 6.68 (d, J=8.5 Hz, 1H), 3.82 (br s, 3H), 2.94 (s, 3H).

Step 2-IS08115-084

1-Methyl-6-nitro-1H-benzotriazole

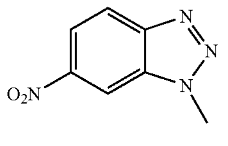

Procedure: To a solution of N2-methyl-4-nitro-benzene-1,2-diamine (1 g, 6 mmol) in aqueous HCl (5M, 20 mL) at −5° C., an aqueous solution of sodium nitrite (0.82 g, 11.9 mmol)

is added dropwise slowly and the reaction mixture is allowed to reach RT and stirred for 12 h. After completion of the reaction (monitored by TLC), the reaction mixture is basified with an aqueous solution of ammonium hydroxide (25%) to pH 8. The reaction mixture is extracted with ethylacetate (50 mL), washed with water (2×50 mL), brine, dried over $MgSO_4$ and concentrated to get the product. Yield: 94% (1 g, reddish brown solid). LCMS: (Method A) 179.0 (M+H), RT. 2.4 min, 98.0% (Max), 98.4% (254 nm). $^1$H NMR (400 MHz, DMSO-$d_6$): δ [ppm] 8.98 (d, J=2.0 Hz, 1H), 8.28 (d, J=9.0 Hz, 1H), 8.22-8.19 (m, 1H), 4.45 (s, 3H).

Step 3-IS08115-086-A

3-Methyl-3H-benzotriazol-5-ylamine

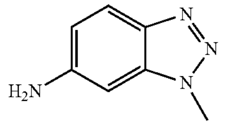

Synthesized using the procedure as described for MC825_SC06_Step 2. The product obtained was taken for the next step.

Yield: 96% (0.8 g, reddish brown solid).

Step 4-IS08115-086-B

6-Isothiocyanato-1-methyl-1H-benzotriazole

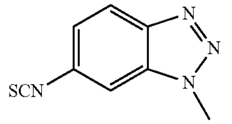

Synthesized using the procedure as described for MC825_SC06_Step 3.

Yield: 70% (0.7 g, brown solid). LCMS: (Method A) 191.0 (M+H), RT. 3.7 min, 98.6% (Max), 98.1% (220 nm). $^1$H NMR (400 MHz, DMSO-$d_6$): δ [ppm] 8.10-8.07 (m, 2H), 7.42-7.40 (m, 1H), 4.28 (s, 3H).

Step 5-FS08115-087

(8-Chloro-[1,2,4]triazolo[1,5-a]pyrazin-2-yl)-(3-methyl-3H-benzotriazol-5-yl)-amine

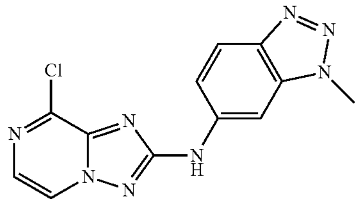 [SMILES: Cn1nnc2ccc(Nc3nc4c(Cl)nccn4n3)cc21]

Synthesized using the procedure as described for MC825_SC01_Step1.

Yield: 47% (0.5 g, brown solid). LCMS: (Method A) 301.0 (M+H), RT. 2.7 min, 97.2% (Max), 97.1% (254 nm). $^1$H NMR (400 MHz, DMSO-$d_6$): δ [ppm] 10.62 (s, 1H), 9.01 (d, J=4.3 Hz, 1H), 8.16 (d, J=2.1 Hz, 1H), 7.99 (d, J=4.3 Hz, 1H), 7.95 (d, J=8.9 Hz, 1H), 7.51 (dd, J=9.0, 1.9 Hz, 1H), 4.24 (s, 3H). HPLC: (Method A) RT 2.9 min, 96.8% (Max), 96.5% (254 nm).

MC825_015

8-Biphenyl-2-yl-[1,2,4]triazolo[1,5-a]pyrazin-2-yl)-(3-methyl-3H-benzotriazol-5-yl)-amine ("C29")

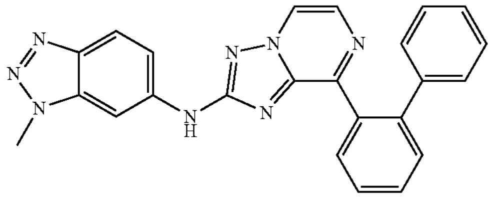 [SMILES: Cn1nnc2ccc(Nc3nc4c(-c5ccccc5-c5ccccc5)nccn4n3)cc21]

Synthesized as described for MC825_010

Yield: 26% (55 mg, Pale brown solid). LCMS: (Method A) 419 (M+H), RT. 4.1 min, 98.86% (Max). 99.35% (254 nm); $^1$H NMR (400 MHz, DMSO-$d_6$): δ [ppm] 10.33 (s, 1H), 8.86 (d, J=4.32 Hz, 1H), 8.08 (dd, J=5.98, 4.36 Hz, 2H), 7.90 (t, J=0.48 Hz, 1H), 7.79 (d, J=1.36 Hz, 1H), 7.77-7.77 (m, 1H), 7.67-7.54 (m, 2H), 7.40 (dd, J=9.04, 1.96 Hz, 1H), 7.18 (t, J=1.56 Hz, 5H), 4.23 (s, 3H). HPLC: (Method A) RT 4.1 min, 98.48% (Max), 99.00% (254 nm).

MC825_036

(3-Methyl-3H-benzotriazol-5-yl)-[8-(1-methyl-1H-pyrazol-4-yl)-[1,2,4]triazolo[1,5-a]pyrazin-2-yl]-amine ("C30")

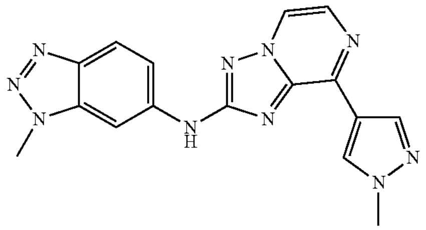 [SMILES: Cn1cc(-c2nccn3nc(Nc4ccc5nnn(C)c5c4)nc23)cn1]

Synthesized as described for MC825_010

Yield: 52% (90 mg, pale brown solid). LCMS: (Method A) 347 (M+H), RT. 4.0 min, 95.97% (Max) 94.27% (254 nm); $^1$H NMR (400 MHz, DMSO-$d_6$): δ [ppm] 10.44 (s, 1H), 8.77 (t, J=4.52 Hz, 2H), 8.40 (d, J=2.72 Hz, 2H), 8.11 (d, J=4.40 Hz, 1H), 7.95 (d, J=8.96 Hz, 1H), 7.49 (dd, J=1.36, 9.02 Hz, 1H), 4.30 (s, 3H), 4.01 (s, 3H). HPLC: (Method A) RT 2.7 min, 94.15% (Max), 93.93% (254 nm).

MC825_005

Step 1-IS08149-083

3-Biphenyl-2-yl-pyrazin-2-ylamine

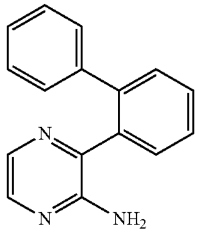 [SMILES: Nc1nccnc1-c1ccccc1-c1ccccc1]

Procedure: To a solution of 2-amino-3-chloropyrazine (1.0 g, 7.7 mmol) in 1,4-dioxane/water (9:1, 20 mL), biphenyl boronic acid (2.3 g, 11.6 mmol), 2-dicyclohexylphosphino-2,4,6-trisiopropylbiphenyl (0.22 g, 0.46 mmol), palladium acetate (0.05 g, 0.23 mmol) and potassium carbonate (3.2 g, 23.1 mmol) are added, degassed briefly and heated in sealed tube at 90° C. for 6 h. After completion of the reaction (monitored by TLC), the reaction mixture is passed through celite, washed with dichloromethane/methanol (1:1, 50 mL), the filtrate is concentrated to get the crude product. The crude product is purified by column chromatography (silica gel, MeOH/DCM gradient elution). Yield: 52% (1 g, light brown solid); LCMS: (Method A) 248.3 (M+H), RT. 2.7 min, 91.2% (Max). $^1$H NMR (400 MHz, DMSO-$d_6$): δ [ppm] 7.81 (d, J=2.7 Hz, 1H), 7.70 (d, J=2.7 Hz, 1H), 7.56-7.45 (m, 3H), 7.38-7.36 (m, 1H), 7.24-7.19 (m, 3H), 7.15-7.13 (m, 2H), 5.61 (brs, 2H).

Step 2-IS08149-083

8-Biphenyl-2-yl-[1,2,4]triazolo[1,5-a]pyrazin-2-ylamine

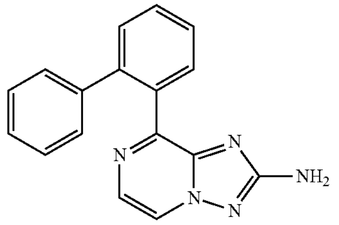 [SMILES: Nc1nc2c(-c3ccccc3-c3ccccc3)nccn2n1]

Procedure: To a solution of 3-biphenyl-2-yl-pyrazin-2-ylamine (1 g, 4.04 mmol) in dry tetrahydrofuran (25 mL), ethoxycarbonylisothiocyanate (0.63 g, 4.85 mmol) is added and heated to 50° C. for 12 h. The reaction mixture is concentrated and suspended in mixture of ethanol/methanol (1:1, 50 mL), hydroxylamine hydrochloride (1.8 g, 26.4 mmol) and diisopropylethylamine (2.7 mL, 15.8 mmol) are added and heated to 80° C. for 3 h. After the completion of the reaction (monitored by TLC), the reaction mixture is concentrated and the residue is taken in water, extracted with dichloromethane (30 mL), washed with water (2×30 mL), brine, dried over $MgSO_4$ and concentrated to get the crude product. The crude product is purified by column chromatography (silica gel, MeOH/DCM gradient elution). Yield: 72% (0.8 g, light brown solid). LCMS: (Method A) 288.3 (M+H), RT. 3.2 min, 95.9% (Max). $^1$H NMR (400 MHz, DMSO-$d_6$): δ [ppm] 8.54 (s, 1H), 7.82 (d, J=4.3 Hz, 1H), 7.66-7.63 (m, 1H), 7.60-7.55 (m, 1H), 7.51-7.47 (m, 2H), 7.19-7.13 (m, 3H), 7.05-7.03 (m, 2H), 6.34 (br s, 2H).

Step 3-IS08149-085

(8-Biphenyl-2-yl-[1,2,4]triazolo[1,5-a]pyrazin-2-yl)-(4-methanesulfinyl-phenyl)-amine ("C31")

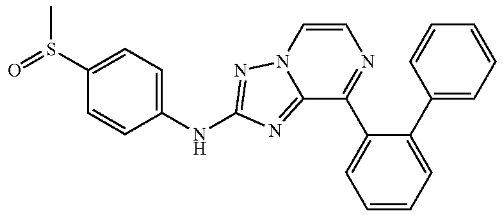 [SMILES: CS(=O)c1ccc(Nc2nc3c(-c4ccccc4-c4ccccc4)nccn3n2)cc1]

Procedure: To a solution of 8-biphenyl-2-yl-[1,2,4]triazolo[1,5-a]pyrazin-2-ylamine (150 mg, 0.52 mmol) in dry t-butanol (5 mL), 1-bromo-4-methanesulfinyl-benzene (303 mg, 0.0.78 mmol), 2-dicyclohexylphosphino-2'-(N,N-dimethylamino)biphenyl (20 mg, 0.05 mmol), tris(dibenzelideneacetone)-dipalladium(0) (20 mg, 0.02 mmol) and sodiumhexamethyldisilylamide (1M/THF) (0.8 mL, 0.78 mmol) are added, degassed briefly and irradiated in microwave 150° C. for 1 h. After completion of the reaction (monitored by TLC), the reaction mixture is filtered through celite washed with dichloromethane/methanol (1:1, 10 mL), the filtrate is concentrated to get the crude product. The crude product is purified by column chromatography (silica gel, MeOH/DCM gradient elution). Yield: 14% (32 mg, pale yellow solid). LCMS: (Method A) 426.0 (M+H), RT. 3.8 min, 93.0% (Max), 93.3% (254 nm). $^1$H NMR (400 MHz, DMSO-$d_6$): δ [ppm] 10.21 (s, 1H), 8.84 (d, J=4.4 Hz, 1H), 8.07 (d, J=4.4 Hz, 1H), 7.73-7.69 (m, 3H), 7.66-7.83 (m, 5H), 7.18-7.70 (m, 5H), 2.66 (s, 3H).

HPLC: (Method A) RT 3.7 min, 95.38% (Max), 95.0% (254 nm).

MC825_025

Step 1-IS08149-084

3-(1-Methyl-1H-pyrazol-4-yl)-1,2-dihydro-pyrazin-2-ylamine

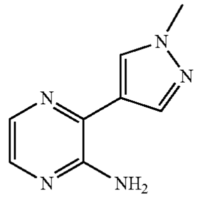

Synthesized using the procedure as described for MC825_005_Step1.

Yield: 68% (1.1 g, light brown solid). LCMS: (Method B) 176.0 (M+H), RT. 2.4 min, 93.6% (Max), 94.9% (254 nm). $^1$H NMR (400 MHz, DMSO-$d_6$): δ [ppm] 8.25 (s, 1H), 7.93 (s, 1H), 7.82 (d, J=2.6 Hz, 1H), 7.79 (d, J=2.6 Hz, 1H), 6.05 (br s, 2H), 3.88 (s, 3H).

Step 2-IS08149-086

8-(1-Methyl-1H-pyrazol-4-yl)-[1,2,4]triazolo[1,5-a]pyrazin-2-ylamine

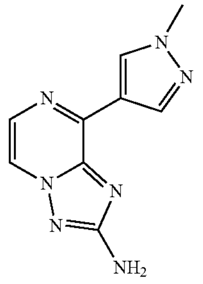 [SMILES: Cn1cc(-c2nccn3nc(N)nc23)cn1]

Synthesized using the procedure as described for M825_005_Step 2.

Yield: 44% (0.6 g, light brown solid). LCMS: (Method A) 216.0 (M+H), RT. 1.5 min, 99.9% (Max). $^1$H NMR (400

MHz, DMSO-$d_6$): δ [ppm] 8.59 (s, 1H), 8.49 (d, J=4.3 Hz, 1H), 8.29 (s, 1H), 7.91 (d, J=4.3 Hz, 1H), 6.45 (br s, 2H), 3.95 (s, 3H).

Step-3

(4-Methanesulfinyl-phenyl)-[8-(1-methyl-1H-pyrazol-4-yl)-[1,2,4]triazolo[1,5-a]pyrazin-2-yl]-amine ("C32")

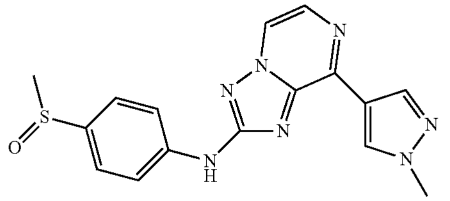 [SMILES: Cn1cc(-c2nccn3nc(Nc4ccc(S(C)=O)cc4)nc23)cn1]

Synthesized using the procedure as described for MC825_005_Step 3.

Yield: 14% (47 mg, off white solid). LCMS: (Method A) 354 (M+H), RT. 2.52 min, 99.07% (Max). 99.04% (254 nm); $^1$H NMR (400 MHz, DMSO-$d_6$): δ [ppm] 10.34 (s, 1H), 8.76 (d, J=4.28 Hz, 1H), 8.67 (s, 1H), 8.39 (s, 1H), 8.09 (d, J=4.32 Hz, 1H), 7.92 (d, J=8.76 Hz, 2H), 7.67 (d, J=8.72 Hz, 2H), 3.99 (s, 3H), 2.72 (s, 3H). HPLC: (Method A) RT 2.4 min, 99.57% (Max), 99.32% (254 nm).

MC825_022

Step 1-IS08391-054

6-Bromo-2-chloromethyl-1H-benzoimidazole

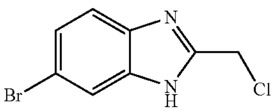 [SMILES: ClCc1nc2ccc(Br)cc2[nH]1]

Procedure: To a solution of 4-bromobenzene-1,2-diamine (3 g, 16 mmol) in absolute alcohol (50 mL), ethyl-2-chloro-acetimidate.hydrochloride (5 g, 32 mmol) is added and stirred at RT for 12 h. After completion of the reaction (monitored by TLC), the reaction mixture is concentrated under vacuo. The residue is taken in dichloromethane (60 mL), washed with water, brine, dried over $MgSO_4$ and concentrated to get the crude product. The crude product is purified by column chromatography (silica gel, EA/PE gradient elution). Yield: 30% (1.2 g, pale brown solid). LCMS: (Method A) 246.0 (M+H), RT. 2.3 min, 97.4% (Max), 97.5% (254 nm). $^1$H NMR (400 MHz, DMSO-$d_6$): δ [ppm] 7.76 (s, 1H), 7.52 (d, J=8.5 Hz, 1H), 7.34 (dd, J=8.5, 1.8 Hz, 1H), 4.91 (s, 2H).

Step 2-IS08391-055

(6-Bromo-1H-benzoimidazol-2-ylmethyl)-dimethyl-amine

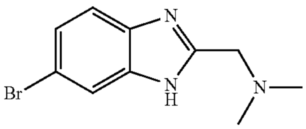

Procedure: To a solution of 6-bromo-2-chloromethyl-1H-benzoimidazole (1.2 g, 4.8 mmol) in dry tetrahydrofuran (20 mL), dimethylamine (40%, 5 mL) is added and stirred at RT for 2 h in a sealed tube. After completion of the reaction (monitored by TLC), the reaction mixture is concentrated under vacuo. The residue is taken in dichloromethane (30 mL), washed with water, brine, dried over $MgSO_4$ and concentrated to get the product. Yield: 69% (0.85 g, brown solid). $^1$H NMR (400 MHz, DMSO-$d_6$): δ [ppm] 13.41 (br s, 1H), 7.95 (s, 1H), 7.68 (d, J=8.3 Hz, 1H), 7.44 (dd, J=1.5, 8.6 Hz, 1H), 5.00 (s, 2H), 3.26 (s, 6H).

Step 3-IS08391-056

[6-Bromo-1-(2-trimethylsilanyl-ethoxymethyl)-1H-benzoimidazol-2-ylmethyl]-dimethyl-amine

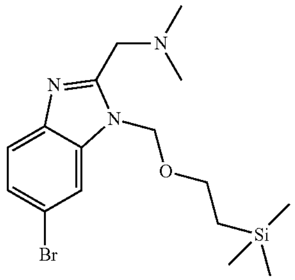 [SMILES: CN(C)Cc1nc2ccc(Br)cc2n1COCC[Si](C)(C)C]

Procedure: To a suspension of sodium hydride (60%) (0.15 g, 3.8 mmol) in dry N,N-dimethylformamide (15 mL) at 0° C., a solution of (6-bromo-1H-benzoimidazol-2-ylmethyl)-dimethyl-amine (0.8 g, 3.17 mmol) in dry N,N-dimethylformamide (10 mL) is added and stirred for 1 h. (2-(chloromethoxy)-ethyl)trimethylsilane (5.4 mL, 30.6 mmol) is added and stirred at RT for 30 min. After completion of the reaction (monitored by TLC), the reaction mixture is quenched with cold water and concentrated at high vacuum, the residue is taken in ethylacetate, washed with water (2×25 mL), brine, dried over $MgSO_4$ and concentrated to get the crude product. The crude product is purified by column chromatography (silica gel, MeOH/DCM gradient elution) to get the mixture of regioisomers. Yield: 49% (0.6 g, brown gummy solid). LCMS: (Method A) 384.0 (M+H), RT. 4.5 min, 85.3% (Max), 88.7% (254 nm). $^1$H NMR (400 MHz, DMSO-$d_6$): δ [ppm] 7.86-7.80 (m, 1H), 7.60-7.55 (m, 1H), 7.35-7.32 (m, 1H), 5.69 (s, 2H), 3.69-3.68 (m, 2H), 3.53-3.48 (m, 2H), 2.20 (s, 6H), 0.84-0.80 (m, 2H), −0.10 (s, 9H).

Step 4-IS08555-005

[2-Dimethylaminomethyl-3-(2-trimethylsilanyl-ethoxymethyl)-3H-benzoimidazol-5-yl]-[8-(1-methyl-1H-pyrazol-4-yl)-[1,2,4]triazolo[1,5-a]pyrazin-2-yl]-amine

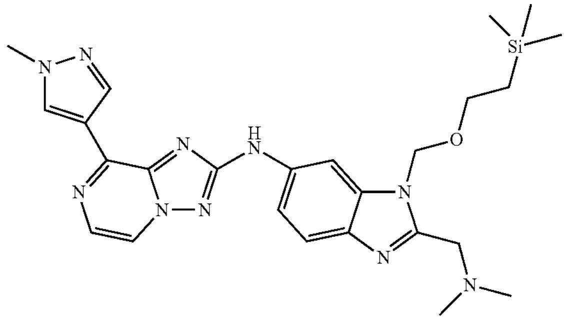

Procedure: To a solution of 8-(1-methyl-1H-pyrazol-4-yl)-[1,2,4]triazolo[1,5-a]pyrazin-2-ylamine (50 mg, 0.23 mmol)

in dry t-butanol (3 mL), [6-bromo-1-(2-trimethylsilanyl-ethoxymethyl)-1H-benzoimidazol-2-ylmethyl]-dimethyl-amine (130 mg, 0.35 mmol), 2-dicyclohexylphosphino-2'-(N,N-dimethyl-amino)biphenyl (9 mg, 0.02 mmol), tris (dibenzelideneacetone)dipalladium (0) (9 mg, 0.09 mmol) and sodiumhexamethyldisilylamide (1M/THF) (0.47 mL, 0.46 mmol) are added, degassed briefly and irradiated in microwave 150° C. for 1 h. After completion of the reaction (monitored by TLC), the reaction mixture is filtered through celite washed with dichloromethane/methanol (1:1, 10 mL), the filtrate is concentrated to get the crude product. The crude product is purified by column chromatography (silica gel, MeOH/DCM gradient elution). Yield: 21% (25 mg, pale brown liquid). LCMS: (Method A) 519.3 (M+H), RT. 3.6, 3.8 min, 45.3, 45.8% (Max).

Step 5-FS08555-008

(2-Dimethylaminomethyl-3H-benzoimidazol-5-yl)-[8-(1-methyl-1H-pyrazol-4-yl)-[1,2,4]triazolo[1,5-a] pyrazin-2-yl]-amine ("C33")

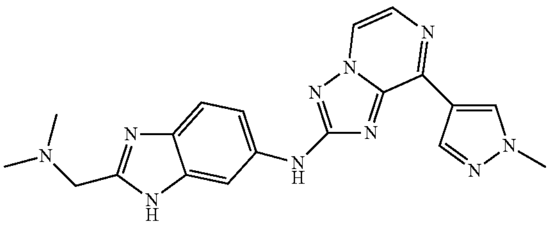

Procedure: To a solution of 2-dimethylaminomethyl-1-(2-trimethylsilanyl-ethoxymethyl)-1H-benzoimidazol-5-yl]-[8-(1-methyl-1H-pyrazol-4-yl)-[1,2,4]triazolo[1,5-a] pyrazin-2-yl]-amine (25 mg, 0.24 mmol) in dry methanol (3 mL), HCl in methanol (3 mL) is added and irradiated in microwave at 70° C. for 1 h. After completion of the reaction (monitored by TLC), the reaction mixture is concentrated under vacuo. The residue is taken in dichloromethane (15 mL), washed with water, brine, dried over $MgSO_4$ and concentrated to get the crude product. The crude product is purified by column chromatography (silica gel, MeOH/DCM gradient elution). Yield: 12% (16 mg, pale yellow solid). LCMS: (Method A) 389 (M+H), RT. 2.3 min, 97.88% (Max). 99.00% (254 nm); $^1$H NMR (400 MHz, DMSO-$d_6$): δ [ppm] 12.21 (s, 1H), 9.86 (s, 1H), 8.68 (m, 2H), 8.42 (s, 1H), 8.04 (t, J=4.32 Hz, 2H), 7.45-7.35 (m, 2H), 3.99 (s, 3H), 3.63 (s, 2H), 2.24 (s, 6H). HPLC: (Method A) RT 2.0 min, 98.91% (Max), 99.19% (254 nm).

MC825_043

Step 1-IS08391-077

2-(4-Bromo-2-nitro-phenyl)-malonic acid dimethyl ester

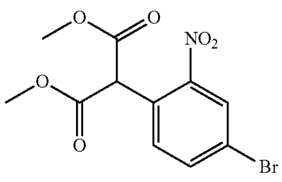 [SMILES: COC(=O)C(C(=O)OC)c1ccc(Br)cc1[N+](=O)[O-]]

Procedure: To a suspension of sodium hydride (60%) (2.13 g, 53.3 mmol) in dry N,N-dimethylformamide (50 mL) at 0° C., a solution of dimethylmalonate (12 mL, 104.2 mmol) in dry N,N-dimethylformamide (20 mL) is added. The reaction mixture is heated to 100° C. for 20 min. 2,5-dibromonitrobenzene (5 g, 17.8 mmol) in dry N,N-dimethylformamide (20 mL) is added dropwise at RT and is heated to 100° C. for 3 h. After completion of the reaction (monitored by TLC), the reaction mixture is cooled to 0° C. and quenched with cold water. The reaction mixture is concentrated at high vacuum, the residue is taken in ethylacetate (75 mL), washed with water (2×75 mL), brine, dried over $MgSO_4$ and concentrated to get the crude product. The crude product is purified by column chromatography (silica gel, EA/PE gradient elution). Yield: 80% (4.7 g, light orange solid). LCMS: (Method B) 330.0 (M−H), RT. 5.8 min, 91.1% (Max), 90.8% (254 nm). $^1$H NMR (400 MHz, DMSO-$d_6$): δ [ppm] 8.30 (d, J=2.16 Hz, 1H), 8.01 (dd, J=8.3, 2.1 Hz, 1H), 7.50 (d, J=8.3 Hz, 1H), 5.49 (s, 1H), 3.69 (s, 6H).

Step 2-IS08391-079

4-Bromo-2-nitro-benzoic acid methyl ester

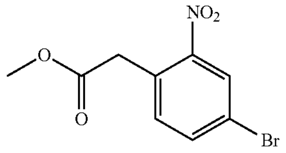

Procedure: To a solution of 2-(4-bromo-2-nitro-phenyl)-malonic acid dimethyl ester (4.7 g, 14.2 mmol) in DMSO (10 mL), lithium chloride (1.2 g, 28.4 mmol) and water (0.3 mL) are added and heated to 100° C. for 24 h. After completion of the reaction (monitored by TLC), the reaction mixture is concentrated under high vacuum. The residue is diluted with dichloromethane (50 mL), washed with water, brine, dried over $MgSO_4$ and concentrated to get the crude product. The crude product is purified by column chromatography (silica gel, EA/PE gradient elution). Yield: 20% (0.8 gm, light brown solid). LCMS: (Method B) 274.0 (M−H), RT. 5.8 min, 94.0% (Max). $^1$H NMR (400 MHz, DMSO-$d_6$): δ [ppm] 8.28 (d, J=2.1 Hz, 1H), 7.96 (dd, J=8.2, 2.0 Hz, 1H), 7.54 (d, J=8.2 Hz, 1H), 4.06 (s, 2H), 3.61 (s, 3H).

Step 3-IS08391-082

2-(4-Bromo-2-nitro-phenyl)-2-methyl-propionic acid methyl ester

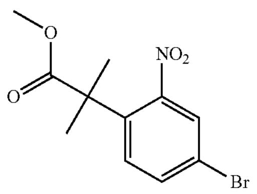 [SMILES: COC(=O)C(C)(C)c1ccc(Br)cc1[N+](=O)[O-]]

Procedure: To a suspension of sodium hydride (60%) (0.28 g, 7.22 mmol) in dry N,N-dimethylformamide (15 mL) at 0° C., 4-bromo-2-nitro-benzoic acid methyl ester (0.8 g, 2.9 mmol), iodomethane (0.72 mL, 11.5 mmol) and 18-crown-6 (0.8 g, 0.3 mmol) are added and stirred at RT for 2 h. After completion of the reaction (monitored by TLC), the reaction mixture is cooled to 0° C. and quenched with cold water. The reaction mixture is concentrated at high vacuum, the residue is taken in ethylacetate (30 mL), washed with water (2×30 mL), brine, dried over $MgSO_4$ and concentrated to get the crude product. The crude product is purified by column chromatography (silica gel, EA/PE gradient elution). Yield: 91% (0.8 g, brown oil). LCMS: (Method B) 301.0 (M−H), RT. 6.2 min, 96.3% (Max), 93.5% (254 nm). $^1$H NMR (400 MHz, DMSO-$d_6$): δ [ppm] 8.14 (d, J=2.2 Hz, 1H), 7.94 (dd, J=8.6, 2.2 Hz, 1H), 7.71 (d, J=8.6 Hz, 1H), 3.53 (s, 3H), 1.56 (s, 6H).

Step 4-IS08391-083

6-Bromo-3,3-dimethyl-1,3-dihydro-indol-2-one

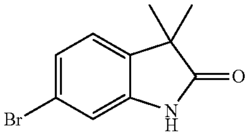

Procedure: To a solution of 2-(4-Bromo-2-nitro-phenyl)-2-methyl-propionic acid methyl ester (0.6 g, 1.96 mmol) in glacial acetic acid (10 mL), iron powder (0.55 g, 9.8 mmol) ias added and heated to 100° C. for 2 h. After completion of the reaction (monitored by TLC), the reaction mixture is concentrated at high vacuum, diluted with dichloromethane and passed through celite. The filtrate is concentrated to get the crude product. The crude product is purified by column chromatography (silica gel, EA/PE gradient elution). Yield: 35% (210 mg, white solid). LCMS: (Method B) 240.0 (M−H), RT. 5.1 min, 99.5% (Max), 99.0% (254 nm). $^1$H NMR (400 MHz, DMSO-$d_6$): δ [ppm] 10.45 (s, 1H), 7.24 (d, J=7.9 Hz, 1H), 7.13 (dd, J=7.8, 1.7 Hz, 1H), 6.97 (d, J=1.8 Hz, 1H), 1.22 (s, 6H).

Step 5-FS08391-085

3,3-Dimethyl-6-[8-(1-methyl-1H-pyrazol-4-yl)-[1,2,4]triazolo[1,5-a]pyrazin-2-ylamino]-1,3-dihydro-indol-2-one ("C34")

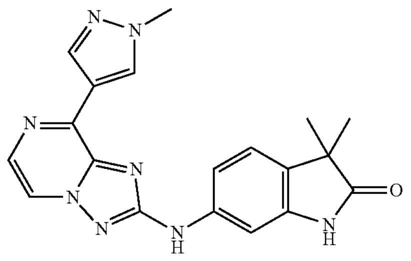 [SMILES: Cn1cc(-c2nccn3nc(Nc4ccc5c(c4)NC(=O)C5(C)C)nc23)cn1]

Synthesized using the procedure as described for MC825_005_Step 3.

Yield: 17% (15 mg, white solid). LCMS: (Method A) 375.0 (M+H), RT. 3.1 min, 98.3% (Max), 99.4% (254 nm). $^1$H NMR (400 MHz, DMSO-$d_6$): δ [ppm] 10.37 (s, 1H), 9.92 (s, 1H), 8.67 (d, J=4.3 Hz, 1H), 8.66 (s, 1H), 8.38 (s, 1H), 8.05 (d, J=4.3 Hz, 1H), 7.40 (d, J=1.8 Hz, 1H), 7.26 (dd, J=8.1, 1.9 Hz, 1H), 7.19 (d, J=8.0 Hz, 1H), 3.99 (s, 3H), 1.23 (s, 6H). HPLC: (Method A) RT 3.3 min, 99.7% (Max), 99.7% (254 nm).

MC825_044

4-(8-Biphenyl-2-yl-[1,2,4]triazolo[1,5-a]pyrazin-2-ylamino)-2-hydroxybenzonitrile ("C35")

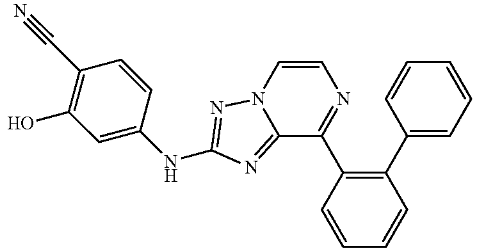 [SMILES: N#Cc1ccc(Nc2nc3c(-c4ccccc4-c4ccccc4)nccn3n2)cc1O]

Synthesized using the procedure as described for MC825_005_Step 3.

Yield: 16% (22 mg, off white solid). LCMS: (Method A) 405.2 (M+H), RT. 4.4 min, 99.5% (Max), 97.3% (254 nm). $^1$H NMR (400 MHz, $CDCl_3$): δ [ppm] 8.16-8.13 (m, 1H), 7.79-7.65 (m, 1H), 7.63-7.53 (m, 4H), 7.42-7.37 (m, 2H), 7.18-7.14 (m, 6H), 6.95-6.93 (m, 1H). HPLC: (Method A) RT 4.4 min, 97.4% (Max), 96.1% (254 nm).

MC825_045

Step 1-FS08555-007

2-Hydroxy-4-[8-(1-methyl-1H-pyrazol-4-yl)-[1,2,4]triazolo[1,5-a]pyrazin-2-ylamino]-benzonitrile ("C36")

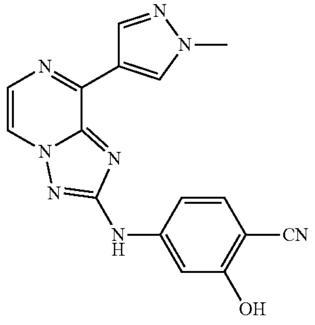 [SMILES: Cn1cc(-c2nccn3nc(Nc4ccc(C#N)c(O)c4)nc23)cn1]

Synthesized using the procedure as described for MC825_005_Step 3.

Yield: 5% (6 mg, off white solid). LCMS: (Method A) 333.2 (M+H), RT. 3.4 min, 99.6% (Max), 98.9% (254 nm). $^1$H NMR (400 MHz, DMSO-$d_6$): δ [ppm] 11.04 (s, 1H), 10.44 (s, 1H), 8.71 (d, J=4.3 Hz, 1H), 8.68 (s, 1H), 8.41 (s, 1H), 8.10 (d, J=4.3 Hz, 1H), 7.57 (d, J=1.9 Hz, 1H), 7.51 (d, J=8.6 Hz, 1H), 7.20 (dd, J=8.6, 1.9 Hz, 1H), 3.99 (s, 3H). HPLC: (Method A) RT 3.0 min, 99.7% (Max), 98.7% (254 nm).

Synthesis of 8-Iodo-[1,2,4]triazolopyrazin-2-ylamine

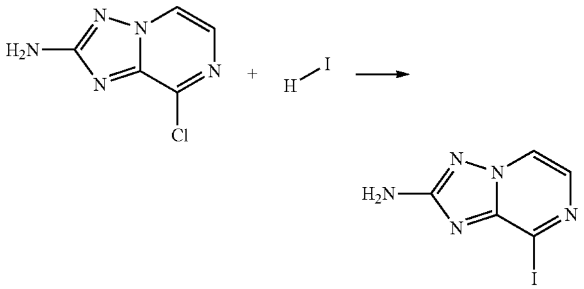

8-Chloro-[1,2,4]triazolo[1,5-a]pyrazin-2-ylamine (5.500 g; 32.43 mmol) is suspended in water (40.0 ml) before HI (67%, 21.855 ml; 194 mmol) is added. The mixture is stirred at 50° C. for 16 h and monitored by HPLC. The mixture is cooled to Rt, diluted with water. After adding NaOH till pH 14 is reached, the resulting suspension is cooled to 0° C. and all solids are filtered off giving 8-Iodo-[1,2,4]triazolo[1,5-a]pyrazin-2-ylamine (7.850 g; 30.074 mmol) as a yellow solid.

General Procedure for Suzuki-Miyaura Coupling 1

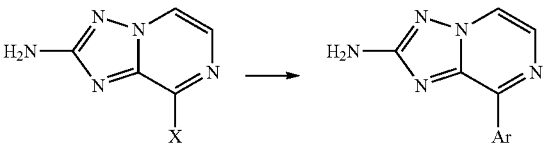

1 eq. 8-Halo-[1,2,4]triazolopyrazin-2-ylamine, 1.1 eq boronic acid (or corresponding boronic ester), 0.03 eq. palladium(II)acetate, 0.06 eq X-Phos and 2 eq. potassiumcarbonate are given into a microwavetube charged with a stir bar. The tube is sealed, evacuated and backfilled with argon. A mixture of acetonitrile and water (2:1 v/v, 4 mL/mmol) (briefly degassed by bubbling argon under ultra-sonic irradtion through the mixture for 10 min or evacuating and backfilling with argon) is added under nitrogene via syringe. The tube is heated at 150° C. under microwave irradiation for an appropriate time and monitored by HPLC-MS. Upon completion, the mixture is diluted with ethylacetate, filtered over a plug of Celite and evaporated under reduced pressure.

The crude product is loaded on silica and purified via column chromatography.

General Procedure for Buchwald-Hartwig Amination 2

1 eq. of Triazolopyrazine, 1.1 eq. halogene coupling partner and 0.03 eq. chloro[2-dicyclohexylphosphino)-3,6-dimethoxy-2,'-4'-6'-tri-isopropyl-1,'1-biphenyl[2-(2amino-ethyl)phenyl)Pd(II) (Brettphose-Precat) in a screw capped or microwave vial are dissolved in tert.-butanol (5 mL/mmol). The mixture is degassed by evacuating and backfilling with nitrogene for 3 times before LHMDS (2 eq. 1.1 M in THF) is added and the reaction mixture is heated to 110° C. and monitored by HPLC. Upon completion, the mixture is quenched with water, diluted with ethylacetate and filtered over celite. The solvent is removed in Vaccuum and the residue purified via chromatography or prep. HPLC.

General Procedure for Nucleophilic Aromatic Substitution 3

To a microwave vial stir bar is added 1 eq. of triazolopyrazine, 1.1 eq. of the corresponding amine and potassium carbonate (2 eq). N,N-dimethylformamide (3 mL/mmol) is added and the suspension heated in the microwave at 180° C. The reaction is monitored by HPLC. Upon completion, the mixtured is diluted with ethylacetate, filtered over celite and concentrated. The residue is purified via column chromatography or prep. HPLC.

N-(4-morpholinophenyl)-8-pyrido[2,3-b]pyrazin-7-yl-[1,2,4]triazolo[1,5-a]pyrazin-2-amine ("C37")

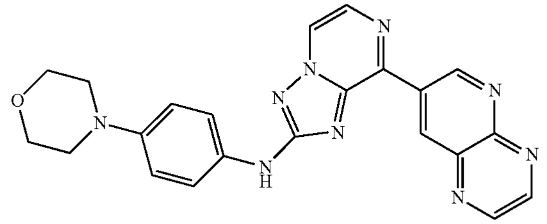 [SMILES: c1cn2nc(Nc3ccc(N4CCOCC4)cc3)nc2c(-c2cnc3nccnc3c2)n1]

8-Iodo-[1,2,4]triazolo[1,5-a]pyrazin-2-ylamine, 7-(4,4,5,5-tetramethyl-[1,3,2]dioxaborolan-2-yl)-pyrido[2,3-b]pyrazine (1.1 eq), palladium(II) acetate (0.03 eq.), potassium carbonate (3 eq.) are combined and suspended in acetonitrile and water. The suspension is purged with $N_2$ and 2-(dicyclohexylphosphino)-2',4',6'-triisopropylbiphenyl (0.1 eq) is added. The reaction vessel is sealed under $N_2$ and heated by microwave irradiation to 150° C. for 1 h. The crude material is purified via flash chromatography and used in the next step.

8-Pyrido[2,3-b]pyrazin-7-yl-[1,2,4]triazolo[1,5-a]pyrazin-2-ylamine, 4-(4-chloro-phenyl)-morpholine (1.1 eq.), chloro[2-(dicyclohexylphosphino)-3,6-dimethoxy-2'-4'-6'-tri-i-propyl-1,1'-biphenyl]2-(2-aminoethyl)phenyl)Pd (II) (0.25 eq), 2-(dicyclohexylphosphino)-3,6-dimethoxy-2'-4'-6'-tri-i-propyl-1,1'-biphenyl; BrettPhos (0.25 eq.) are combined and suspended in t-butanol. The suspension is purged with $N_2$ and lithium bis(trimethylsilyl)amide, (3 eq; 20% (ca 1.06M) solution in THF/ethylbenzene) is added. The vessel is sealed under $N_2$ and heated to 65° C. for 2 h and then to 110° C. for 2 h. The mixture is filtered and concentrated. Purification via prep. HPLC gives the title compound.

HPLC purity (Method C): 100%, Rt: 1.76 min, observed [M+H]=426.2;

$^1$H NMR (500 MHz, DMSO-$d_6$) δ [ppm] 10.30-10.26 (d, J=2.4 Hz, 1H), 9.98-9.92 (m, 2H), 9.24-9.16 (m, 2H), 9.06-9.02 (d, J=4.2 Hz, 1H), 8.39-8.34 (d, J=4.2 Hz, 1H), 7.67-7.61 (d, J=9.0 Hz, 2H), 7.01-6.96 (d, J=9.0 Hz, 2H), 3.79-3.71 (m, 4H), 3.10-3.04 (m, 4H).

8-(4-methylsulfonylphenyl)-N-(4-morpholinophenyl)-[1,2,4]triazolo[1,5-a]pyrazin-2-amine ("C38")

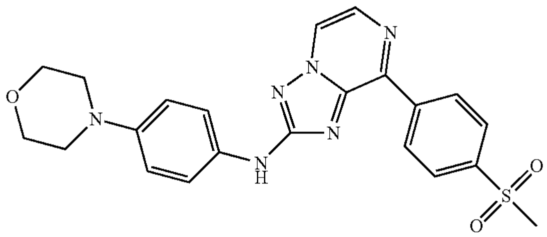 [SMILES: CS(=O)(=O)c1ccc(-c2nccn3nc(Nc4ccc(N5CCOCC5)cc4)nc23)cc1]

Synthesis analogous to "C37" using 2-(4-methanesulfonyl-phenyl)-4,4,5,5-tetramethyl-[1,3,2]dioxaborolane for the Suzuki-coupling.

LCMS purity (Method C): 100%, Rt: 1.84 min, observed [M+H]=451.2; $^1$H NMR (500 MHz, DMSO-$d_6$) δ [ppm] 9.86-9.82 (s, 1H), 8.98-8.92 (m, 3H), 8.29-8.25 (d, J=4.2 Hz, 1H), 8.17-8.12 (d, J=8.6 Hz, 2H), 7.65-7.59 (d, J=9.0 Hz, 2H), 7.00-6.94 (d, J=9.0 Hz, 2H), 3.78-3.72 (m, 5H), 3.08-3.02 (m, 3H).

8-[4-(morpholinomethyl)phenyl]-N-(4-morpholinophenyl)-[1,2,4]triazolo[1,5-a]pyrazin-2-amine ("C39")

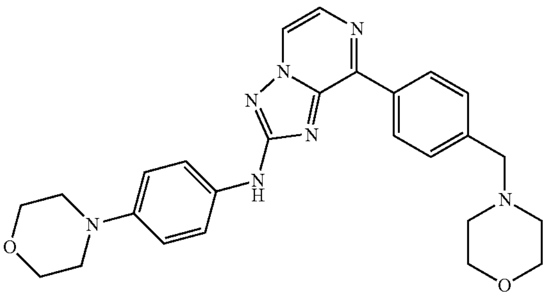 [SMILES: c1cn2nc(Nc3ccc(N4CCOCC4)cc3)nc2c(-c2ccc(CN3CCOCC3)cc2)n1]

The title compound is obtained by following general procedure 1 using 4-[4-(4,4,5,5-tetramethyl-[1,3,2]dioxaborolan-2-yl)-benzyl]-morpholine and 8-iodo-[1,2,4]triazolopyrazin-2-ylamine as coupling partners in the Suzuki Miyaura coupling.

Buchwald amination is performed analogously to "C37".

LCMS purity (Method C): 100%, Rt: 1.35 min, observed [M+H]=472.2;

$^1$H NMR (500 MHz, DMSO-$d_6$) δ [ppm] 9.77-9.73 (s, 1H), 8.87-8.83 (d, J=4.2 Hz, 1H), 8.72-8.67 (d, J=8.3 Hz, 2H), 8.22-8.17 (d, J=4.2 Hz, 1H), 7.65-7.59 (d, J=9.0 Hz, 2H), 7.56-7.50 (d, J=8.4 Hz, 2H), 7.00-6.94 (d, J=9.1 Hz, 2H), 3.79-3.73 (m, 5H), 3.64-3.59 (m, 5H), 3.59-3.56 (s, 2H), 3.08-3.02 (m, 4H), 2.44-2.39 (m, 4H).

[8-(3-fluoro-4-morpholin-4-ylmethyl-phenyl)-[1,2,4]triazolo[1,5-a]pyrazin-2-yl]-(4-morpholin-4-yl-phenyl)-amine ("C40")

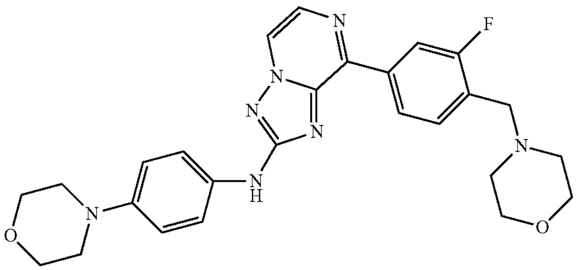 [SMILES: Fc1cc(-c2nccn3nc(Nc4ccc(N5CCOCC5)cc4)nc23)ccc1CN1CCOCC1]

Following general procedure 1 with 4-[2-fluoro-4-(4,4,5,5-tetramethyl-[1,3,2]dioxaborolan-2-yl)-benzyl]-morpholine and 8-iodo-[1,2,4]triazolopyrazin-2-ylamine as coupling partners and general procedure 2 for the Buchwald-Hartwig amination with 4-(4-chloro-phenyl)-morpholine gives the title compound as a solid.

LCMS purity (Method C): 100%, Rt: 1.42 min, observed [M+H]=490.2; $^1$H NMR (500 MHz, DMSO-$d_6$) δ [ppm] 9.81-9.77 (s, 1H), 8.93-8.88 (d, J=4.2 Hz, 1H), 8.62-8.51 (m, 2H), 8.24-8.19 (d, J=4.2 Hz, 1H), 7.68-7.59 (m, 3H), 7.00-6.94 (m, 2H), 3.78-3.74 (m, 5H), 3.65-3.62 (s, 2H), 3.62-3.58 (m, 4H), 3.08-3.03 (m, 4H), 2.48-2.42 (m, 4H).

morpholin-4-yl-{4-[2-(4-morpholin-4-yl-phenylamino)-[1,2,4]triazolo[1,5-a]pyrazin-8-yl]-phenyl}-methanone ("C41")

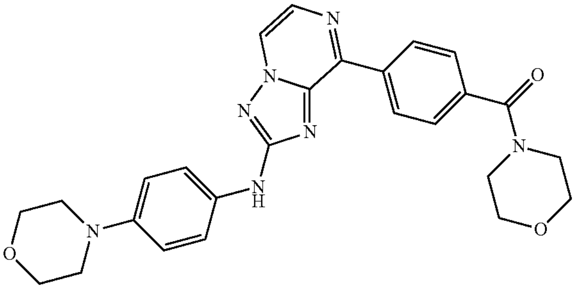 [SMILES: O=C(c1ccc(-c2nccn3nc(Nc4ccc(N5CCOCC5)cc4)nc23)cc1)N1CCOCC1]

Morpholin-4-yl-[4-(4,4,5,5-tetramethyl-[1,3,2]dioxaborolan-2-yl)-phenyl]-methanone is reacted with 8-iodo-[1,2,4]triazolo[1,5-a]pyrazin-2-ylamine using general procedure 1 prior to amination using general procedure 2. LCMS purity (Method C): 100%, Rt: 1.71 min, observed [M+H]=486.2; $^1$H NMR (500 MHz, DMSO-$d_6$) δ [ppm] 9.83-9.79 (s, 1H), 8.93-8.88 (d, J=4.2 Hz, 1H), 8.83-8.77 (d, J=8.4 Hz, 2H), 8.26-8.21 (d, J=4.2 Hz, 1H), 7.67-7.59 (m, 3H), 7.00-6.94 (d, J=9.1 Hz, 2H), 3.79-3.74 (m, 4H), 3.08-3.02 (m, 4H).

N-{4-[2-(4-morpholin-4-yl-phenylamino)-[1,2,4]triazolo[1,5-a]pyrazin-8-yl]-phenyl}-methanesulfonamide ("C42")

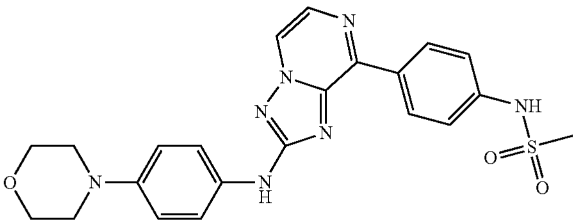 [SMILES: CS(=O)(=O)Nc1ccc(-c2nccn3nc(Nc4ccc(N5CCOCC5)cc4)nc23)cc1]

Reaction of N-[4-(4,4,5,5-tetramethyl-[1,3,2]dioxaborolan-2-yl)-phenyl]-methanesulfonamide with 8-iodo-[1,2,4]triazolo[1,5-a]pyrazin-2-ylamine analogously to general procedure 1 gives N-[4-(2-amino-[1,2,4]triazolo[1,5-a]pyrazin-8-yl)-phenyl]-methanesulfonamide which is reacted with 4-(4-chloro-phenyl)-morpholine to give the title compound as a solid.

LCMS purity (Method C): 100%, Rt: 1.80 min, observed [M+H]=466.2; $^1$H NMR (500 MHz, DMSO-$d_6$) δ [ppm] 9.77-9.72 (s, 1H), 8.87-8.81 (m, 1H), 8.76-8.69 (m, 1H), 8.21-8.15 (m, 1H), 7.66-7.59 (m, 2H), 7.44-7.36 (m, 1H), 7.02-6.94 (m, 2H), 3.80-3.73 (m, 4H), 3.15-3.08 (d, J=0.9 Hz, 3H), 3.08-3.02 (m, 4H).

4-[2-(3,5-dimethoxy-phenylamino)-[1,2,4]triazolo[1,5-a]pyrazin-8-yl]-piperazin-2-one ("C43")

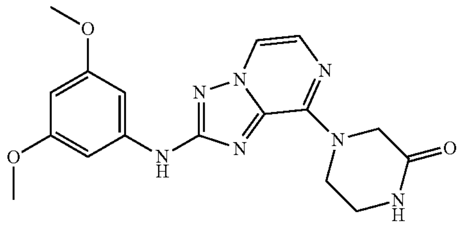 [SMILES: COc1cc(Nc2nc3c(N4CCNC(=O)C4)nccn3n2)cc(OC)c1]

Piperazin-2-one (1.1 eq), 8-chloro-[1,2,4]triazolo[1,5-a]pyrazin-2-ylamine (1 eq) are dissolved in DMF and heated to 180° C. in a microwave for 1 h following general procedure 3. The intermediate is reacted with 1-chloro-3,5-dimethoxy-benzene under amination conditions as described in general procedure 3 giving the title compound as a solid.

LCMS purity (Method C): 100%, Rt: 1.79 min, observed [M+H]=370.2; $^1$H NMR (500 MHz, DMSO-$d_6$) δ [ppm] 9.76-9.71 (s, 1H), 8.24-8.18 (d, J=4.4 Hz, 1H), 8.14-8.09 (s, 1H), 7.62-7.56 (d, J=4.4 Hz, 1H), 6.96-6.90 (d, J=2.2 Hz, 2H), 6.10-6.04 (t, J=2.2 Hz, 1H), 4.61-4.56 (s, 2H), 4.36-4.28 (m, 2H), 3.76-3.71 (s, 6H).

(3,5-dimethoxy-phenyl)-(8-morpholin-4-yl-[1,2,4]triazolo[1,5-a]pyrazin-2-yl)-amine ("C44")

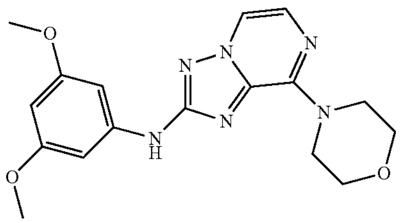 [SMILES: COc1cc(Nc2nc3c(N4CCOCC4)nccn3n2)cc(OC)c1]

(3,5-Dimethoxy-phenyl)-(8-morpholin-4-yl-[1,2,4]triazolo[1,5-a]pyrazin-2-yl)-amine is synthesized analogously to "C43" using morpholine instead of piperazin-2-one as reactionpartner in step 1.

LCMS purity (Method C): 100%, Rt: 2.10 min, observed [M+H]=357.2; $^1$H NMR (500 MHz, DMSO-$d_6$) δ [ppm] 9.70-9.65 (s, 1H), 8.22-8.16 (d, J=4.4 Hz, 1H), 7.60-7.54 (d, J=4.4 Hz, 1H), 6.94-6.89 (d, J=2.2 Hz, 2H), 6.10-6.04 (t, J=2.2 Hz, 1H), 4.11-4.04 (m, 4H), 3.77-3.73 (m, 4H), 3.73-3.71 (s, 6H).

1-[2-(3,5-dimethoxy-phenylamino)-[1,2,4]triazolo[1,5-a]pyrazin-8-yl]-piperidine-3-carboxylic acid (2-hydroxy-ethyl)-amide ("C45")

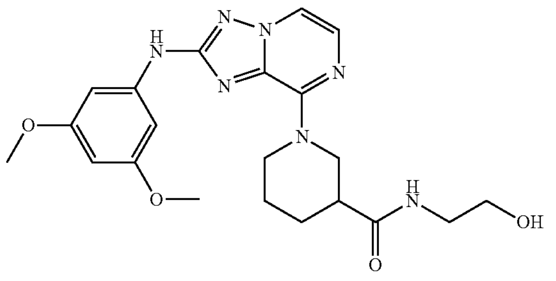 [SMILES: COc1cc(Nc2nc3c(N4CCCC(C(=O)NCCO)C4)nccn3n2)cc(OC)c1]

The title compound is prepared analogously to "C44" using N-(2-hydroxy-ethyl)piperidine-3-carboxamide as nucleophile instead of morpholine in the first step.

LCMS purity (Method C): 100%, Rt: 1.80 min, observed [M+H]=442.2;

$^1$H NMR (500 MHz, DMSO-$d_6$) δ [ppm] 9.67-9.62 (s, 1H), 8.16-8.10 (d, J=4.3 Hz, 1H), 7.89-7.82 (m, 1H), 7.59-7.53 (d, J=4.4 Hz, 1H), 6.95-6.89 (d, J=2.2 Hz, 2H), 6.10-6.04 (t, J=2.2 Hz, 1H), 5.22-5.15 (d, J=12.4 Hz, 2H), 5.12-5.05 (d, J=13.1 Hz, 1H), 4.72-4.64 (t, J=5.4 Hz, 1H), 3.75-3.70 (s, 6H), 3.17-3.09 (m, 2H), 2.49-2.38 (m, 2H), 1.96-1.87 (m, 5H), 1.77-1.69 (d, J=10.5 Hz, 1H), 1.61-1.50 (m, 3H).

(3,5-dimethoxy-phenyl)-[8-(4-methyl-piperazin-1-yl)-[1,2,4]triazolo[1,5-a]pyrazin-2-yl]-amine ("C46")

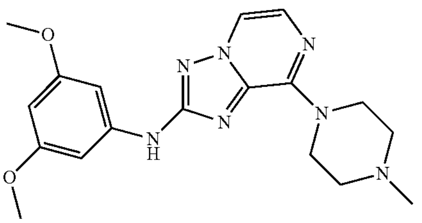

The title compound is prepared analogously to "C44" using N-methylpiperazine as nucleophile instead of morpholine in the first step.

LCMS purity (Method C): 100%, Rt: 1.46 min, observed [M+H]=370.2; $^1$H NMR (500 MHz, DMSO-$d_6$) δ [ppm] 9.69-9.64 (s, 1H), 8.19-8.12 (m, 2H), 7.58-7.52 (d, J=4.4 Hz, 1H), 6.95-6.89 (d, J=2.2 Hz, 2H), 6.10-6.04 (t, J=2.2 Hz, 1H), 4.13-4.05 (m, 4H), 3.75-3.70 (s, 6H), 2.48-2.45 (m, 4H), 2.27-2.22 (s, 3H).

1-[2-(3,5-dimethoxy-phenylamino)-[1,2,4]triazolo[1,5-a]pyrazin-8-vl]-piperidine-3-carboxylic acid ("C47")

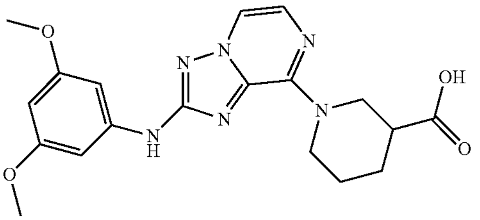 [SMILES: COc1cc(Nc2nc3c(N4CCCC(C(=O)O)C4)nccn3n2)cc(OC)c1]

The title compound is prepared analogously to "C44" using piperidine-3-carboxylic acid as nucleophile instead of morpholine in the first step.

LCMS purity (Method C): 100%, Rt: 2.02 min, observed [M+H]=399.2; $^1$H NMR (500 MHz, DMSO-$d_6$) δ [ppm] 9.67-9.62 (s, 1H), 8.17-8.11 (d, J=4.3 Hz, 1H), 7.58-7.52 (d, J=4.3 Hz, 1H), 6.95-6.90 (d, J=2.2 Hz, 2H), 6.09-6.03 (t, J=2.2 Hz, 1H), 5.08-4.92 (m, 2H), 3.75-3.70 (s, 6H), 2.08-1.99 (m, 1H), 1.81-1.63 (m, 2H), 1.63-1.53 (m, 1H).

{4-[2-(2-methyl-1H-benzoimidazol-5-ylamino)-[1,2,4]triazolo[1,5-a]pyrazin-8-yl]-phenyl}-morpholin-4-yl-methanone("C48")

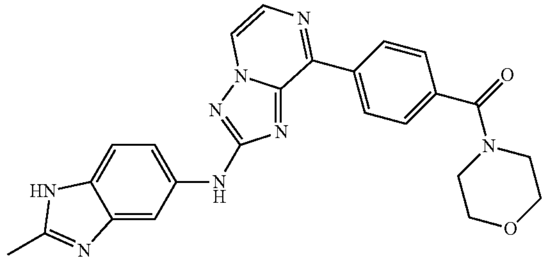 [SMILES: Cc1nc2cc(Nc3nc4c(-c5ccc(C(=O)N6CCOCC6)cc5)nccn4n3)ccc2[nH]1]

[4-(2-Amino-[1,2,4]triazolo[1,5-a]pyrazin-8-yl)-phenyl]-morpholin-4-yl-methanone (see "C41", 5-bromo-2-methyl- 1-(2-trimethylsilanyl-ethoxymethyl)-1H-benzoimidazole (1.1 eq.), chloro[2-(dicyclohexylphosphino)-3,6-dimethoxy-2'-4'-6'-tri-i-propyl-1,1'-biphenyl]2-(2-aminoethyl)phenyl) Pd(II) (0.03 eq), 2-(dicyclohexylphosphino)-3,6-dimethoxy-2'-4'-6'-tri-i-propyl-1,1'-biphenyl (0.03 eq) are dissolved in dry t-butanol under nitrogene, before lithium bis(trimethylsilyl)amide, (3 eq., 20% (ca 1.06M) solution in THF/ethylbenzene) is added. The resulting mixture is heated to 110° C. for 1 h. Work-up as described in general procedure 3 gives the SEM-protected intermediate. (4-{2-[2-Methyl-1-(2-trimethylsilanyl-ethoxymethyl)-1H-benzoimidazol-5-ylamino]-[1,2,4]triazolo[1,5-a]pyrazin-8-yl}-phenyl)-morpholin-4-yl-methanone is dissolved in ethanol. Concentrated HCl is added and the reaction mixture is heated to 65° C. for 4 h and monitored by LCMS. Upon completion, the mixture is neutralized with saturated $NaHCO_3$-solution and the layers are separated, the aqueous phase is 3 times extracted with DCM. The combined organic phases are dried with $Na_2SO_4$ and concentrated. Purification gives the title compound as a solid.

LCMS purity (Method C): 100%, Rt: 1.37 min, observed [M+H]=455.2; $^1$H NMR (500 MHz, DMSO-$d_6$) δ [ppm] 10.00-9.96 (s, 1H), 8.95-8.90 (d, J=4.2 Hz, 1H), 8.86-8.80 (d, J=8.0 Hz, 2H), 8.28-8.23 (d, J=4.2 Hz, 1H), 8.06-8.02 (s, 1H), 7.69-7.63 (d, J=8.0 Hz, 2H), 7.43-7.38 (d, J=6.8 Hz, 2H), 3.66-3.62 (bs, 8H), 2.51-2.47 (s, 4H).

1-[2-(3,5-dimethoxy-phenylamino)-[1,2,4]triazolo[1,5-a]pyrazin-8-yl]-4-(2-hydroxy-ethyl)-piperidin-4-ol ("C49")

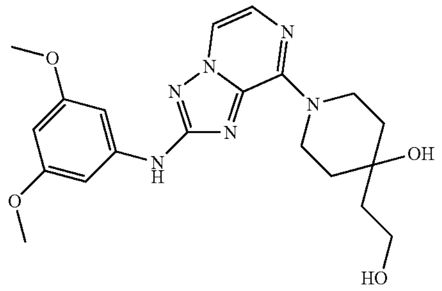 [SMILES: COc1cc(Nc2nc3c(N4CCC(O)(CCO)CC4)nccn3n2)cc(OC)c1]

The title compound is prepared analogously to "C44" using 4-(2-hydroxy-ethyl)piperidin-4-ol as nucleophile instead of morpholine in the first step.

LCMS purity (Method C): 100%, Rt: 1.72 min, observed [M+H]=415.2; $^1$H NMR (500 MHz, DMSO-$d_6$) δ [ppm] 9.65-9.60 (s, 1H), 8.12-8.06 (d, J=4.3 Hz, 1H), 7.55-7.49 (d, J=4.3 Hz, 1H), 6.95-6.90 (d, J=2.2 Hz, 2H), 6.09-6.03 (t, J=2.2 Hz, 1H), 4.82-4.74 (d, J=12.8 Hz, 2H), 4.43-4.31 (m, 2H), 3.75-3.70 (s, 6H), 3.62-3.52 (m, 3H), 1.66-1.55 (m, 6H).

[8-(4-amino-piperidin-1-yl)-[1,2,4]triazolo[1,5-a]pyrazin-2-yl]-(3,5-dimethoxy-phenyl)-amine ("C50")

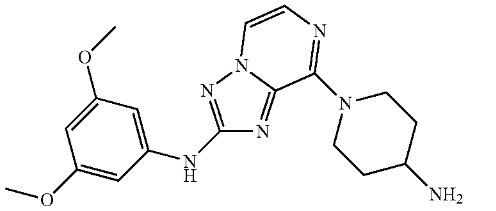 [SMILES: COc1cc(Nc2nc3c(N4CCC(N)CC4)nccn3n2)cc(OC)c1]

The title compound is prepared analogously to "C44" using tert-butyl N-(4-piperidyl)carbamate as nucleophile instead of morpholine in the first step. Cleavage of the Boc-protecting group under standard conditions gives [8-(4-amino-piperidin-1-yl)-[1,2,4]triazolo[1,5-a]pyrazin-2-yl]-(3,5-dimethoxy-phenyl)-amine as a solid.

LCMS purity (Method C): 100%, Rt: 1.47 min, observed [M+H]=370.2; $^1$H NMR (500 MHz, DMSO-$d_6$) δ [ppm] 9.68-9.63 (s, 3H), 8.38-8.33 (s, 3H), 8.18-8.12 (d, J=4.4 Hz, 3H), 7.59-7.53 (d, J=4.4 Hz, 3H), 6.95-6.90 (d, J=2.2 Hz, 6H), 6.10-6.04 (m, 3H), 5.12-5.04 (d, J=13.3 Hz, 6H), 3.26-3.14 (m, 8H), 2.56-2.51 (s, 1H), 1.98-1.90 (d, J=12.3 Hz, 6H), 1.54-1.40 (m, 6H).

1-{4-[2-(3,5-dimethoxy-phenylamino)-[1,2,4]triazolo[1,5-a]pyrazin-8-yl]-piperazin-1-yl}-ethanone ("C51")

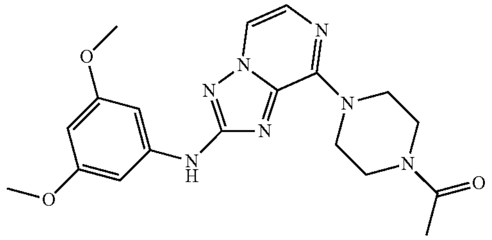 [SMILES: COc1cc(Nc2nc3c(N4CCN(C(C)=O)CC4)nccn3n2)cc(OC)c1]

N-(3,5-dimethoxyphenyl)-8-piperazin-1-yl-[1,2,4]triazolo[1,5-a]pyrazin-2-amine (synthesized as described earlier) is converted into the acetate using standard conditions.

LCMS purity (Method C): 100%, Rt: 1.90 min, observed [M+H]=398.2; $^1$H NMR (500 MHz, DMSO-$d_6$) δ [ppm] 9.71-9.67 (s, 1H), 8.23-8.18 (d, J=4.4 Hz, 1H), 7.61-7.56 (d, J=4.4 Hz, 1H), 6.95-6.90 (d, J=2.2 Hz, 2H), 6.10-6.05 (m, 1H), 5.77-5.73 (s, 1H), 4.14-4.05 (m, 3H), 3.75-3.71 (s, 6H), 3.64-3.58 (m, 3H), 2.09-2.05 (s, 3H).

(3,5-dimethoxy-phenyl)-[8-(4-methanesulfonyl-piperazin-1-yl)-[1,2,4]triazolo[1,5-a]pyrazin-2-yl]-amine ("C52")

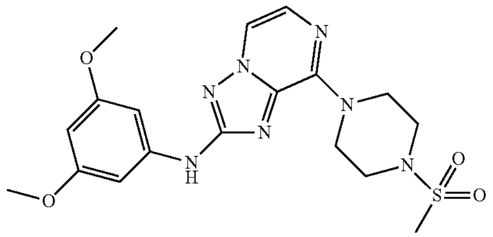 [SMILES: COc1cc(Nc2nc3c(N4CCN(S(C)(=O)=O)CC4)nccn3n2)cc(OC)c1]

N-(3,5-dimethoxyphenyl)-8-piperazin-1-yl-[1,2,4]triazolo[1,5-a]pyrazin-2-amine (synthesized as described earlier) was converted into the mesylate by treatment with Methanesulfonylchloride under standard conditions.

LCMS purity (Method C): 100%, Rt: 2.1 min, observed [M+H]=434.2; $^1$H NMR (500 MHz, DMSO-$d_6$) δ [ppm] 9.72-9.68 (s, 1H), 8.25-8.20 (d, J=4.4 Hz, 1H), 7.62-7.57 (d, J=4.4 Hz, 1H), 6.94-6.90 (d, J=2.2 Hz, 2H), 6.10-6.06 (t, J=2.2 Hz, 1H), 5.76-5.72 (s, 0H), 4.25-4.19 (m, 4H), 3.75-3.71 (s, 6H), 3.29-3.26 (m, 6H), 2.93-2.89 (s, 3H).

N-{1-[2-(3,5-dimethoxy-phenylamino)-[1,2,4]triazolo[1,5-a]pyrazin-8-yl]-piperidin-4-yl}-methane-sulfonamide ("C53")

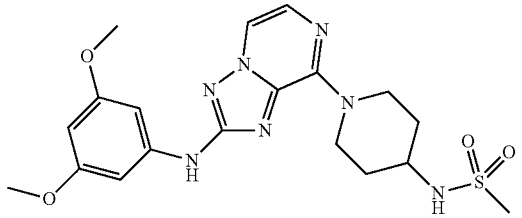 [SMILES: COc1cc(Nc2nc3c(N4CCC(NS(C)(=O)=O)CC4)nccn3n2)cc(OC)c1]

[8-(4-Amino-piperidin-1-yl)-[1,2,4]triazolo[1,5-a]pyrazin-2-yl]-(3,5-dimethoxy-phenyl)-amine was converted into the title compound using standard conditions.

LCMS purity (Method C): 100%, Rt: 2.0 min, observed [M+H]=448.2; $^1$H NMR (500 MHz, DMSO-$d_6$) δ [ppm] 9.69-9.64 (s, 1H), 8.18-8.12 (d, J=4.3 Hz, 1H), 7.59-7.53 (d, J=4.4 Hz, 1H), 7.17-7.10 (d, J=7.3 Hz, 1H), 6.96-6.91 (d, J=2.2 Hz, 2H), 6.11-6.05 (t, J=2.2 Hz, 1H), 5.04-4.95 (d, J=13.4 Hz, 2H), 3.76-3.71 (s, 6H), 3.56-3.47 (s, 1H), 3.00-2.95 (s, 3H), 2.01-1.93 (d, J=12.2 Hz, 2H), 1.59-1.46 (m, 2H).

(3,5-dimethoxy-phenyl)-[8-(3-phenyl-piperazin-1-yl)-[1,2,4]triazolo[1,5-a]pyrazin-2-yl]-amine ("C54")

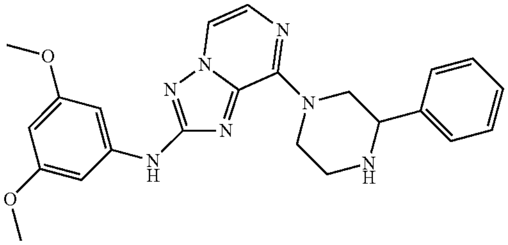 [SMILES: COc1cc(Nc2nc3c(N4CCNC(c5ccccc5)C4)nccn3n2)cc(OC)c1]

8-Chloro-[1,2,4]triazolo[1,5-a]pyrazin-2-ylamine and tert-butyl 3-phenyl-piperazine-1-carboxylate were coupled according general procedure 3. The intermediate was isolated and Buchwald Hartwig Amination following general procedure 2 with 1-chloro-3,5-dimethoxy-benzene gave the title compound as a solid.

LCMS purity (Method C): 100%, Rt: 1.65 min, observed [M+H]=432.2; $^1$H NMR (500 MHz, DMSO-$d_6$) δ [ppm] 9.63-9.59 (s, 1H), 8.17-8.12 (m, 2H), 7.58-7.54 (d, J=4.4 Hz, 1H), 7.51-7.45 (m, 2H), 7.40-7.27 (m, 3H), 6.91-6.87 (d, J=2.2 Hz, 2H), 6.08-6.03 (t, J=2.2 Hz, 1H), 5.22-5.12 (m, 2H), 3.88-3.81 (m, 1H), 3.18-3.08 (m, 2H), 3.02-2.88 (m, 2H).

(3,5-dimethoxy-phenyl)-[8-(4-methyl-2-phenyl-piperazin-1-yl)-[1,2,4]triazolo[1,5-a]pyrazin-2-yl]-amine ("C55")

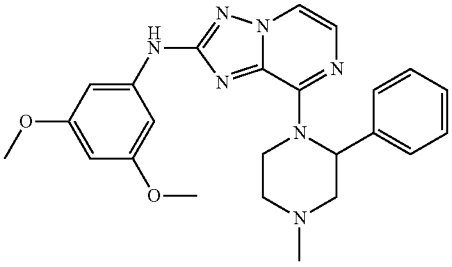 [SMILES: COc1cc(Nc2nc3c(N4CCN(C)CC4c4ccccc4)nccn3n2)cc(OC)c1]

8-Chloro-[1,2,4]triazolo[1,5-a]pyrazin-2-ylamine and 1-methyl-3-phenyl-piperazine are coupled according general procedure 3. The intermediate is isolated and Buchwald Hartwig Amination following general procedure 2 with 1-chloro-3,5-dimethoxy-benzene gives the title compound as a solid.

LCMS purity (Method C): 100%, Rt: 1.68 min, observed [M+H]=446.2;

$^1$H NMR (500 MHz, DMSO-$d_6$) δ [ppm] 9.68-9.64 (s, 2H), 8.19-8.14 (m, 2H), 7.58-7.53 (d, J=4.4 Hz, 2H), 7.47-7.42 (m, 4H), 7.33-7.26 (m, 3H), 7.24-7.18 (m, 1H), 6.92-6.87 (d, J=2.2 Hz, 4H), 6.08-6.03 (m, 2H), 3.69-3.65 (s, 12H), 2.87-2.81 (d, J=11.9 Hz, 1H), 2.50-2.43 (m, 2H), 2.25-2.21 (s, 5H), 2.19-2.10 (m, 2H).

1-{4-[2-(3,5-dimethoxy-phenylamino)-[1,2,4]triazolo[1,5-a]pyrazin-8-yl]-piperazin-1-yl}-2-hydroxy-ethanone ("C56")

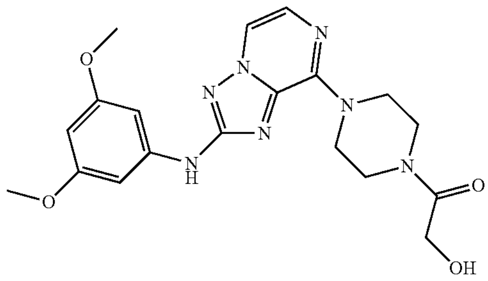 [SMILES: COc1cc(Nc2nc3c(N4CCN(C(=O)CO)CC4)nccn3n2)cc(OC)c1]

Reaction of 3,5-dimethoxy-phenyl)-(8-piperazin-1-yl-[1,2,4]triazolo[1,5-a]pyrazin-2-yl)-amine, synthesized as described earlier, with 2-hydroxyacetic acid under standard conditions gives the title compound as a solid.

LCMS purity (Method C): 100%, Rt: 1.80 min, observed [M+H]=414.2; $^1$H NMR (500 MHz, DMSO-$d_6$) δ [ppm] 9.71-9.67 (s, 1H), 8.23-8.18 (d, J=4.4 Hz, 1H), 7.61-7.56 (d, J=4.4 Hz, 1H), 6.94-6.90 (d, J=2.2 Hz, 2H), 6.10-6.06 (m, 1H), 4.66-4.60 (m, 1H), 4.19-4.15 (d, J=5.5 Hz, 2H), 4.13-4.08 (m, 4H), 3.75-3.71 (s, 6H), 3.66-3.62 (s, 2H), 3.55-3.50 (d, J=5.3 Hz, 2H).

(2-methyl-1H-benzoimidazol-5-yl)-[8-(4-morpholin-4-ylmethyl-phenyl)-[1,2,4]triazolo[1,5-a]pyrazin-2-yl]-amine ("C57")

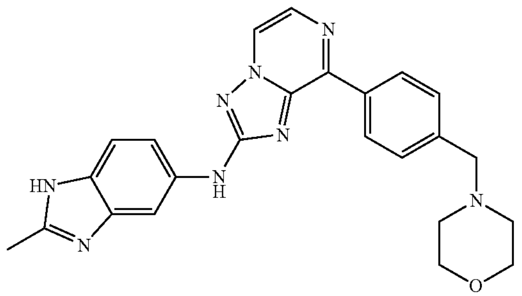 [SMILES: Cc1nc2cc(Nc3nc4c(-c5ccc(CN6CCOCC6)cc5)nccn4n3)ccc2[nH]1]

The title compound is synthesized analogously to "C49" with 4-[4-(4,4,5,5-tetramethyl-[1,3,2]dioxaborolan-2-yl)-benzyl]-morpholine as coupling partner in the Suzuki reaction.

LCMS purity (Method C): 100%, Rt: 1.10 min, observed [M+H]=441.2; $^1$H NMR (500 MHz, DMSO-$d_6$) δ [ppm] 9.98-9.94 (s, 1H), 8.90-8.85 (d, J=4.2 Hz, 1H), 8.76-8.70 (m, 2H), 8.24-8.20 (d, J=4.2 Hz, 1H), 8.17-8.13 (s, 1H), 8.08-8.04 (d, J=1.8 Hz, 1H), 7.60-7.54 (m, 2H), 7.47-7.38 (m, 2H), 3.67-3.61 (m, 3H), 3.54-3.49 (d, J=4.2 Hz, 4H), 3.42-3.38 (s, 4H), 2.57-2.53 (s, 2H), 2.49-2.47 (s, 2H).

[8-(4-methanesulfonyl-phenyl)-[1,2,4]triazolo[1,5-a]pyrazin-2-yl]-(2-methyl-1H-benzoimidazol-5-yl)-amine ("C58")

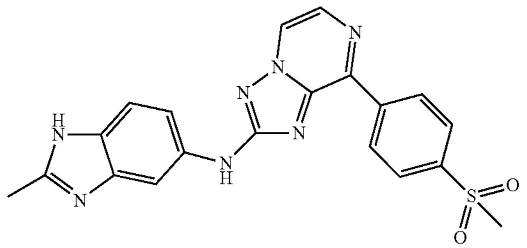 [SMILES: Cc1nc2cc(Nc3nc4c(-c5ccc(S(C)(=O)=O)cc5)nccn4n3)ccc2[nH]1]

[8-(4-Methanesulfonyl-phenyl)-[1,2,4]triazolo[1,5-a]pyrazin-2-yl]-(2-methyl-1H-benzoimidazol-5-yl)-amine is synthesized analogously to "C49" and "C38".

LCMS purity (Method C): 100%, Rt: 1.41 min, observed [M+H]=420.0; $^1$H NMR (500 MHz, DMSO-$d_6$) δ [ppm] 10.01-9.97 (s, 1H), 9.02-8.96 (m, 3H), 8.33-8.25 (m, 2H), 8.20-8.15 (m, 2H), 8.08-8.01 (m, 2H), 7.42-7.37 (m, 2H), 3.34-3.32 (s, 3H), 2.49-2.46 (s, 3H).

[8-(3-fluoro-4-morpholin-4-ylmethyl-phenyl)-[1,2,4]triazolo[1,5-a]pyrazin-2-yl]-(2-methyl-1H-benzoimidazol-5-yl)-amine ("C59")

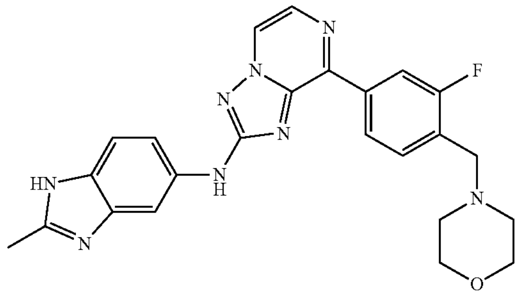 [SMILES: Cc1nc2cc(Nc3nc4c(-c5ccc(CN6CCOCC6)c(F)c5)nccn4n3)ccc2[nH]1]

The title compound is synthesized analogously to "C49" and "C38".

LCMS purity (Method C): 100%, Rt: 1.15 min, observed [M+H]=459.2; $^1$H NMR (500 MHz, DMSO-$d_6$) δ [ppm] 9.95-9.91 (s, 1H), 8.94-8.89 (d, J=4.2 Hz, 1H), 8.63-8.54 (m, 2H), 8.26-8.21 (m, 1H), 8.01-7.97 (s, 1H), 7.69-7.62 (m, 1H), 7.41-7.37 (m, 2H), 3.64-3.63 (s, 2H), 3.62-3.60 (m, 4H), 2.49-2.47 (s, 3H), 2.47-2.43 (m, 7H).

6-[8-(1-methyl-1H-pyrazol-4-yl)-[1,2,4]triazolo[1,5-a]pyrazin-2-ylamino]-1,3-dihydro-indol-2-one ("C60")

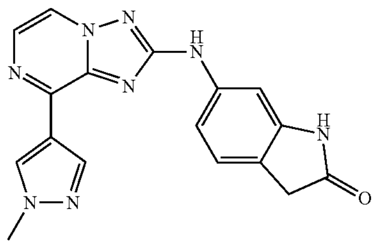 [SMILES: Cn1cc(-c2nccn3nc(Nc4ccc5c(c4)NC(=O)C5)nc23)cn1]

8-(1-methylpyrazol-4-yl)-[1,2,4]triazolo[1,5-a]pyrazin-2-amine, synthesized as described earlier, is coupled with 6-chloro-oxindol according to general procedure 2.

LCMS purity (Method C): 100%, Rt: 1.56 min, observed [M+H]=347.2; $^1$H NMR (400 MHz, DMSO-$d_6$) δ [ppm] 10.49-10.44 (s, 1H), 9.98-9.93 (s, 1H), 8.76-8.69 (m, 2H), 8.48-8.42 (m, 1H), 8.15-8.08 (d, J=4.3 Hz, 1H), 7.48-7.43 (d, J=2.0 Hz, 1H), 7.35-7.27 (m, 1H), 7.23-7.16 (d, J=8.1 Hz, 1H), 4.08-4.03 (s, 3H), 3.49-3.44 (s, 2H).

2-{4-[8-(1-methyl-1H-pyrazol-4-yl)-[1,2,4]triazolo[1,5-a]pyrazin-2-ylamino]-phenyl}-propan-2-ol ("C61")

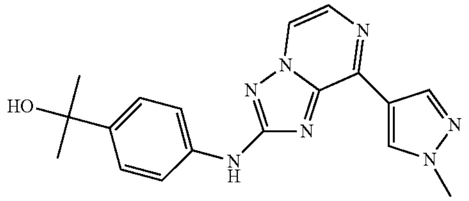 [SMILES: Cn1cc(-c2nccn3nc(Nc4ccc(C(C)(C)O)cc4)nc23)cn1]

2-(4-Bromophenyl)propan-2-ol and 8-(1-methylpyrazol-4-yl)-[1,2,4]triazolo[1,5-a]pyrazin-2-amine are reacted under Buchwald Hartwig conditions as described in general procedure 2.

LCMS purity (Method C): 100%, Rt: 1.71 min, observed [M+H]=350.2; $^1$H NMR (400 MHz, DMSO-$d_6$) δ [ppm] 9.84-9.79 (s, 1H), 8.74-8.64 (m, 2H), 8.43-8.37 (d, J=0.7 Hz, 1H), 8.08-8.02 (d, J=4.3 Hz, 1H), 7.69-7.62 (d, J=8.7 Hz, 2H), 7.46-7.39 (d, J=8.7 Hz, 2H), 4.90-4.85 (s, 1H), 4.02-3.97 (s, 3H), 1.46-1.41 (s, 7H).

(4-tert-butyl-phenyl)-[8-(1-methyl-1H-pyrazol-4-yl)-[1,2,4]triazolo[1,5-a]pyrazin-2-yl]-amine ("C62")

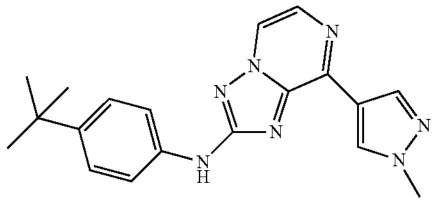 [SMILES: Cn1cc(-c2nccn3nc(Nc4ccc(C(C)(C)C)cc4)nc23)cn1]

8-(1-Methylpyrazol-4-yl)-[1,2,4]triazolo[1,5-a]pyrazin-2-amine, as described earlier, is coupled with 1-bromo-4-tert-butyl-benzene according to general procedure 2.

LCMS purity (Method C): 100%, Rt: 2.46 min, observed [M+H]=348.2; $^1$H NMR (400 MHz, DMSO-$d_6$) δ [ppm] 9.81-9.76 (s, 1H), 8.72-8.63 (m, 2H), 8.42-8.37 (d, J=0.7 Hz, 1H), 8.07-8.01 (d, J=4.3 Hz, 1H), 7.69-7.62 (d, J=8.7 Hz, 2H), 7.39-7.32 (d, J=8.7 Hz, 2H), 4.02-3.97 (s, 3H), 1.31-1.26 (s, 9H).

1-{4-[8-(1-methyl-1H-pyrazol-4-yl)-[1,2,4]triazolo[1,5-a]pyrazin-2-ylamino]-phenyl}-cyclopropanecarbonitrile ("C63")

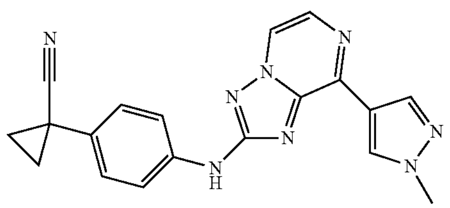 [SMILES: Cn1cc(-c2nccn3nc(Nc4ccc(C5(C#N)CC5)cc4)nc23)cn1]

Reaction of 8-(1-methylpyrazol-4-yl)-[1,2,4]triazolo[1,5-a]pyrazin-2-amine with 1-(4-chlorophenyl)-1-cyclopropanecarbonitrile following general procedure 2 gives the title compound as a solid.

LCMS purity (Method D): 100%, Rt: 2.00 min, observed [M+H]=357.1;

$^1$H NMR (500 MHz, DMSO-$d_6$) δ [ppm] 10.04-10.00 (s, 1H), 8.74-8.69 (d, J=4.3 Hz, 1H), 8.68-8.64 (s, 1H), 8.41-8.37 (d, J=0.8 Hz, 1H), 8.09-8.04 (d, J=4.3 Hz, 1H), 7.78-7.72 (d, J=8.7 Hz, 2H), 7.35-7.30 (d, J=8.7 Hz, 2H), 4.01-3.97 (s, 3H), 1.72-1.65 (m, 2H), 1.47-1.41 (m, 2H).

1-{4-[8-(1-methyl-1H-pyrazol-4-yl)-[1,2,4]triazolo [1,5-a]pyrazin-2-ylamino]-phenyl}-cyclopropanecarboxylic acid amide ("C64")

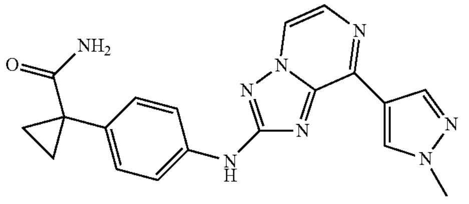 [SMILES: Cn1cc(-c2nccn3nc(Nc4ccc(C5(C(N)=O)CC5)cc4)nc23)cn1]

1-{4-[8-(1-Methyl-1H-pyrazol-4-yl)-[1,2,4]triazolo[1,5-a]pyrazin-2-ylamino]-phenyl}-cyclopropanecarbonitrile is dissolved in methanol before potassiumcarbonate (5 eq.), DMSO (3.5 eq) and hydrogeneperoxide (30% solution, 5.eq) are added. The mixture is stirred for 5 h and monitored via LCMS MS. DMSO (3.5 eq) and hydrogeneperoxide (30% solution, 5.eq) ares added and the mixture iss stirred at rt for 16 h. The mixture is concentrated and the crude material purified via column chromatographie. LCMS purity (Method D): 100%, Rt: 1.70 min, observed [M+H]=375.1;

$^1$H NMR (500 MHz, DMSO-$d_6$) δ [ppm] 9.98-9.94 (s, 1H), 8.74-8.69 (d, J=4.3 Hz, 1H), 8.68-8.64 (s, 1H), 8.41-8.37 (d, J=0.7 Hz, 1H), 8.08-8.03 (d, J=4.3 Hz, 1H), 7.74-7.69 (d, J=8.6 Hz, 2H), 7.36-7.30 (d, J=8.6 Hz, 2H), 7.01-6.97 (s, 1H), 6.05-6.01 (s, 1H), 4.01-3.97 (s, 3H), 1.35-1.28 (m, 2H), 0.97-0.90 (m, 2H).

1-{4-[8-(1H-pyrazol-4-yl)-[1,2,4]triazolo[1,5-a] pyrazin-2-ylamino]-phenyl}-cyclopropanecarbonitrile ("C65")

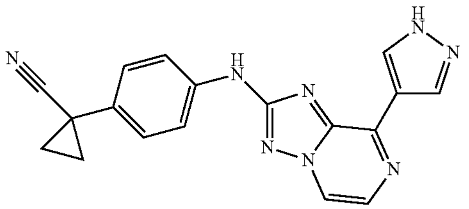 [SMILES: N#CC1(c2ccc(Nc3nc4c(-c5cn[nH]c5)nccn4n3)cc2)CC1]

8-Chloro-[1,2,4]triazolo[1,5-a]pyrazin-2-ylamine is reacted first with 4-(4,4,5,5-tetramethyl-1,3,2-dioxaborolan-2-yl)-1H-pyrazole using general procedure 1 and then with 1-(4-chlorophenyl)-1-cyclopropanecarbonitrile following general procedure 2.

LCMS purity (Method D): 100%, Rt: 1.84 min, observed [M+H]=343.1;

$^1$H NMR (500 MHz, DMSO-$d_6$) δ [ppm] 13.37-13.33 (s, 1H), 10.03-9.99 (s, 1H), 8.74-8.69 (m, 2H), 8.46-8.42 (d, J=2.0 Hz, 1H), 8.09-8.04 (d, J=4.3 Hz, 1H), 7.78-7.72 (d, J=8.7 Hz, 2H), 7.35-7.29 (d, J=8.7 Hz, 2H), 1.72-1.65 (m, 2H), 1.48-1.41 (m, 2H).

1-{4-[8-(1H-pyrazol-4-yl)-[1,2,4]triazolo[1,5-a] pyrazin-2-ylamino]-phenyl}-cyclopropanecarboxylic acid amide ("C66")

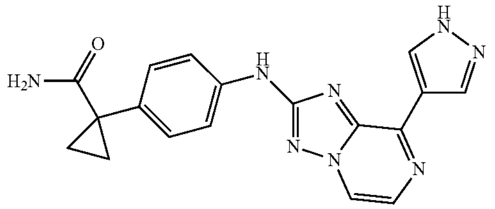 [SMILES: NC(=O)C1(c2ccc(Nc3nc4c(-c5cn[nH]c5)nccn4n3)cc2)CC1]

Saponification of 1-{4-[8-(1H-Pyrazol-4-yl)-[1,2,4]triazolo[1,5-a]pyrazin-2-ylamino]-phenyl}-cyclopropanecarbonitrile analogously to "C64" gives the title compound as as a solid.

LCMS purity (Method D): 100%, Rt: 1.56 min, observed [M+H]=361.1;

$^1$H NMR (500 MHz, DMSO-$d_6$) δ [ppm] 13.38-13.34 (s, 1H), 9.96-9.92 (s, 1H), 8.75-8.69 (m, 2H), 8.46-8.42 (s, 1H), 8.09-8.04 (d, J=4.3 Hz, 1H), 7.74-7.69 (m, 2H), 7.35-7.29 (m, 2H), 7.00-6.96 (s, 1H), 6.06-6.02 (s, 1H), 1.34-1.28 (m, 2H), 0.97-0.91 (m, 2H).

3,3-dimethyl-6-[8-(1H-pyrazol-4-yl)-[1,2,4]triazolo [1,5-a]pyrazin-2-ylamino]-1,3-dihydro-indol-2-one ("C67")

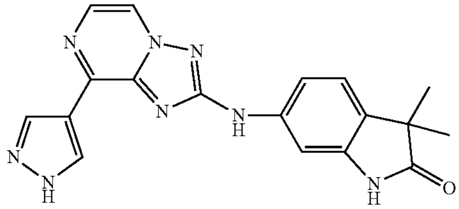 [SMILES: CC1(C)C(=O)Nc2cc(Nc3nc4c(-c5cn[nH]c5)nccn4n3)ccc21]

8-(1H-Pyrazol-4-yl)-[1,2,4]triazolo[1,5-a]pyrazin-2-amine synthesized as descried earlier, is reacted with 6-chloro-3,3-dimethyl-1,3-dihydro-indol-2-one under Buchwald Hartwig conditions using general procedure 2.

LCMS purity (Method C): 100%, Rt: 1.67 min, observed [M+H]=361.2;

$^1$H NMR (500 MHz, DMSO-$d_6$) δ [ppm] 13.43-13.39 (s, 1H), 10.43-10.39 (s, 1H), 9.94-9.90 (s, 1H), 8.78-8.74 (s, 1H), 8.73-8.68 (d, J=4.3 Hz, 1H), 8.50-8.46 (s, 1H), 8.11-8.06 (d, J=4.3 Hz, 1H), 7.44-7.39 (d, J=1.9 Hz, 1H), 7.34-7.28 (m, 1H), 7.25-7.19 (d, J=8.1 Hz, 1H), 1.28-1.24 (s, 6H).

3,3-dimethyl-6-[8-(1,3,5-trimethyl-1H-pyrazol-4-yl)-[1,2,4]triazolo[1,5-a]pyrazin-2-ylamino]-1,3-dihydro-indol-2-one ("C68")

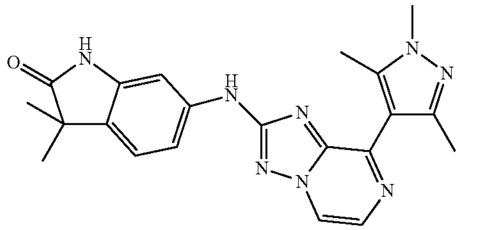 [SMILES: Cc1nn(C)c(C)c1-c1nccn2nc(Nc3ccc4c(c3)NC(=O)C4(C)C)nc12]

8-(1,3,5-Trimethylpyrazol-4-yl)-[1,2,4]triazolo[1,5-a]pyrazin-2-amine, synthesized by reaction of 8-chloro-[1,2,4]triazolo[1,5-a]pyrazin-2-ylamine with (1,3,5-trimethylpyrazol-4-yl)boronic acid following procedure 1, is coupled with 6-chloro-3,3-dimethyl-1,3-dihydro-indol-2-one under Buchwald Hartwig conditions using general procedure 2.

LCMS purity (Method D): 100%, Rt: 1.69 min, observed [M+H]=419.1;

$^1$H NMR (500 MHz, DMSO-$d_6$) δ [ppm] 10.36-10.31 (s, 1H), 9.83-9.78 (s, 1H), 8.76-8.70 (d, J=4.3 Hz, 1H), 8.17-8.11 (d, J=4.3 Hz, 1H), 7.36-7.31 (d, J=1.9 Hz, 1H), 7.27-7.20 (m, 1H), 7.20-7.12 (m, 1H), 3.80-3.75 (s, 3H), 2.39-2.34 (s, 3H), 2.28-2.23 (s, 3H), 1.25-1.20 (s, 6H).

6-[8-(1,3-dimethyl-1H-pyrazol-4-yl)-[1,2,4]triazolo[1,5-a]pyrazin-2-ylamino]-3,3-dimethyl-1,3-dihydro-indol-2-one ("C69")

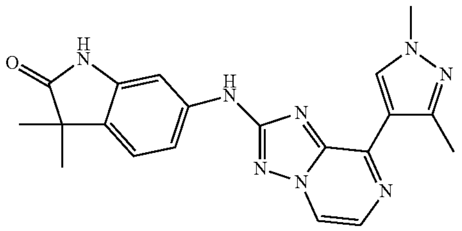 [SMILES: Cc1nn(C)cc1-c1nccn2nc(Nc3ccc4c(c3)NC(=O)C4(C)C)nc12]

The title molecule is synthesized analogously" to "C68" but using 1,3-dimethyl-4-(4,4,5,5-tetramethyl-[1,3,2]dioxaborolan-2-yl)-1H-pyrazole as boronic acid in the first Suzuki-reaction.

LCMS purity (Method C): 100%, Rt: 1.90 min, observed [M+H]=389.2;

$^1$H NMR (500 MHz, DMSO-$d_6$) δ [ppm] 10.34-10.29 (s, 1H), 9.89-9.84 (s, 1H), 8.81-8.76 (s, 1H), 8.65-8.59 (d, J=4.3 Hz, 1H), 8.10-8.04 (d, J=4.4 Hz, 1H), 7.42-7.36 (d, J=1.9 Hz, 1H), 7.30-7.15 (m, 2H), 3.95-3.90 (s, 3H), 2.60-2.55 (s, 3H), 1.27-1.22 (s, 6H).

6-[8-(4-Methanesulfonyl-phenyl)-[1,2,4]triazolo[1,5-a]pyrazin-2-ylamino]-3,3-dimethyl-1,3-dihydro-indol-2-one ("C70")

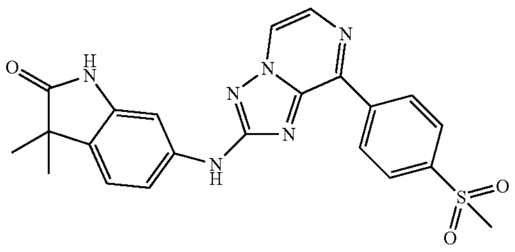 [SMILES: CC1(C)C(=O)Nc2cc(Nc3nc4c(-c5ccc(S(C)(=O)=O)cc5)nccn4n3)ccc21]

8-(4-Methanesulfonyl-phenyl)-[1,2,4]triazolo[1,5-a]pyrazin-2-ylamine, synthesized as described earlier, is coupled with 6-chloro-3,3-dimethyl-1,3-dihydro-indol-2-one under Buchwald Hartwig conditions using general procedure 2.

LCMS purity (Method C): 100%, Rt: 1.95 min, observed [M+H]=449.0;

$^1$H NMR (400 MHz, DMSO-$d_6$) δ [ppm] 10.42-10.37 (s, 1H), 10.13-10.08 (s, 1H), 9.02-8.94 (m, 3H), 8.35-8.29 (d, J=4.2 Hz, 1H), 8.23-8.15 (d, J=8.6 Hz, 2H), 7.47-7.41 (d, J=2.0 Hz, 1H), 7.34-7.27 (m, 1H), 7.26-7.19 (m, 1H), 3.35-3.32 (s, 3H), 1.27-1.25 (m, 6H).

3-hydroxy-3-methyl-6-[8-(1-methyl-1H-pyrazol-4-yl)-[1,2,4]triazolo[1,5-a]pyrazin-2-ylamino]-1,3-dihydro-indol-2-one ("C71")

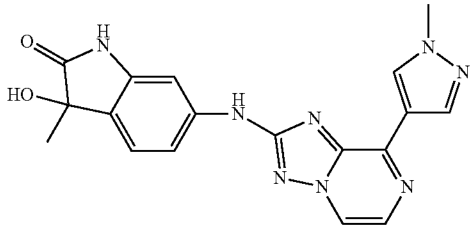 [SMILES: Cn1cc(-c2nccn3nc(Nc4ccc5c(c4)NC(=O)C5(C)O)nc23)cn1]

8-(1-Methylpyrazol-4-yl)-[1,2,4]triazolo[1,5-a]pyrazin-2-amine is reacted with 6-bromo-3-hydroxy-3-methyl-1,3-dihydro-indol-2-one, available via addition of methymagnesiumbromide to 6-bromo-Isatin, to give the title compound as a solid.

LCMS purity (Method D): 100%, Rt: 1.51 min, observed [M+H]=377.1;

$^1$H NMR (500 MHz, DMSO-$d_6$) δ [ppm] 10.26-10.22 (s, 1H), 9.98-9.94 (s, 1H), 8.70-8.64 (m, 2H), 8.41-8.37 (d, J=0.7 Hz, 1H), 8.08-8.04 (d, J=4.3 Hz, 1H), 7.39-7.35 (d, J=1.9 Hz, 1H), 7.30-7.19 (m, 2H), 5.71-5.67 (s, 1H), 4.02-3.98 (s, 3H), 1.38-1.34 (s, 3H).

2-{6-[8-(1-methyl-1H-pyrazol-4-yl)-[1,2,4]triazolo[1,5-a]pyrazin-2-ylamino]-1H-indazol-3-yl}-propan-2-ol ("C72")

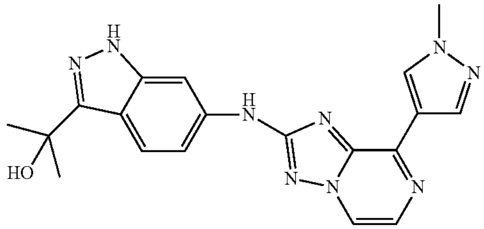 [SMILES: Cn1cc(-c2nccn3nc(Nc4ccc5c(C(C)(C)O)n[nH]c5c4)nc23)cn1]

2-(6-Bromo-1H-indazol-3-yl)-propan-2-ol is synthesized via the following sequence:

6-Bromo-1H-indole-2,3-dione is treated with sodiumhydroxide (1.1 eq) in water at 30° C. till all solids are dissolved. Sodiumnitrite (1.1 eq) dissolved in a little amount of water is added slowly at this temperature and the solution is stirred for additional 30 minutes. The mixture is slowly added to a solution of sulfuric acid (1.9 eq) in water at 0° C. keeping the internal temperature below 10° C. After additional 20 minutes at this temperature, a mixture of tin(II)chloride (2.4 eq) in water and hydrochloric acid is added slowly. After 2 h of stirring at 0° C. workup by filtration over celite, washing with acetone and removing the solvent in vacuum gives the intermediate carboxylic acid.

6-Bromo-1H-indazole-3-carboxylic acid is converted into the corresponding methylester following standard procedures. 6-Bromo-1H-indazole-3-carboxylic acid methyl ester is treated with methylmagnesiumbromide (6.6 eq) at 0° C. and then slowly warmed to RT. Upon completion, the mixture is quenched with saturated ammonium chloride, and the crude material is purified via chromatography. Reaction of 8-(1-methyl-1H-pyrazol-4-yl)-[1,2,4]triazolo[1,5-a]pyrazin-2-ylamine and 2-(6-bromo-1H-indazol-3-yl)-propan-2-ol gives the title compound as a solid.

LCMS purity (Method D): 100%, Rt: 1.58 min, observed [M+H]=390.1;

$^1$H NMR (500 MHz, DMSO-$d_6$) δ [ppm] 12.42-12.38 (s, 1H), 10.07-10.03 (s, 1H), 8.74-8.66 (m, 2H), 8.44-8.40 (s, 1H), 8.10-8.05 (m, 2H), 7.91-7.85 (d, J=8.8 Hz, 1H), 7.25-7.19 (m, 1H), 5.12-5.08 (s, 1H), 4.03-3.99 (s, 3H), 1.61-1.57 (s, 6H).

6-[8-((R)-3-hydroxy-pyrrolidin-1-yl)-[1,2,4]triazolo[1,5-a]pyrazin-2-ylamino]-3,3-dimethyl-1,3-dihydro-indol-2-one ("C73")

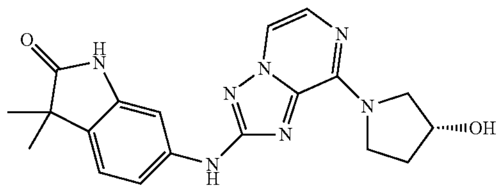 [SMILES: CC1(C)C(=O)Nc2cc(Nc3nc4c(N5CC[C@@H](O)C5)nccn4n3)ccc21]

(R)-1-(2-Amino-[1,2,4]triazolo[1,5-a]pyrazin-8-yl)-pyrrolidin-3-ol, synthesized by reaction of 8-chloro-[1,2,4]triazolo[1,5-a]pyrazin-2-ylamine and (R)-pyrrolidin-3-ol following general procedure 3, is coupled with 6-chloro-3,3-dimethyl-1,3-dihydro-indol-2-one under Buchwald Hartwig conditions using general procedure 2.

LCMS purity (Method C): 100%, Rt: 1.41 min, observed [M+H]=380.2;

$^1$H NMR (500 MHz, DMSO-$d_6$) δ [ppm] 10.30-10.26 (s, 1H), 9.59-9.55 (s, 1H), 7.96-7.91 (d, J=4.4 Hz, 1H), 7.50-7.45 (d, J=4.4 Hz, 1H), 7.34-7.30 (d, J=2.0 Hz, 1H), 7.24-7.18 (m, 1H), 7.16-7.10 (d, J=8.1 Hz, 1H), 5.01-4.97 (d, J=3.6 Hz, 1H), 4.46-4.40 (m, 1H), 3.95-3.88 (s, 5H), 3.20-3.15 (d, J=5.3 Hz, 2H), 2.07-1.98 (m, 1H), 1.97-1.90 (m, 1H), 1.24-1.20 (s, 6H).

6-[8-(3-hydroxy-azetidin-1-yl)-[1,2,4]triazolo[1,5-a]pyrazin-2-ylamino]-3,3-dimethyl-1,3-dihydro-indol-2-one ("C74")

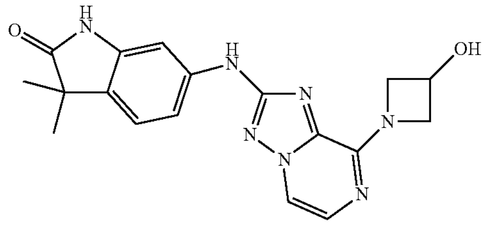 [SMILES: CC1(C)C(=O)Nc2cc(Nc3nc4c(N5CC(O)C5)nccn4n3)ccc21]

1-(2-Amino-[1,2,4]triazolo[1,5-a]pyrazin-8-yl)-azetidin-3-ol, available by nucleophilic substitution of 8-chloro-[1,2,4]triazolo[1,5-a]pyrazin-2-ylamine with azetidin-3-ol using general procedure 3, is reacted under amination conditions described in general procedure 2 with 6-chloro-3,3-dimethyl-1,3-dihydro-indol-2-one giving the title compound as a solid.

LCMS purity (Method D): 100%, Rt: 1.44 min, observed [M+H]=366.1;

$^1$H NMR (500 MHz, DMSO-$d_6$) δ [ppm] 10.37-10.24 (s, 1H), 9.69-9.57 (s, 1H), 8.10-7.93 (d, J=4.5 Hz, 1H), 7.52-7.43 (d, J=4.4 Hz, 1H), 7.39-7.31 (d, J=2.0 Hz, 1H), 7.21-7.17 (m, 1H), 7.16-7.11 (m, 1H), 4.73-4.61 (m, 1H), 4.61-4.49 (d, J=3.3 Hz, 1H), 4.18-4.04 (m, 1H), 3.24-3.13 (s, 1H), 1.27-1.18 (s, 6H).

cis-6-[8-(4-hydroxy-cyclohexylamino)-[1,2,4]triazolo[1,5-a]pyrazin-2-ylamino]-3,3-dimethyl-1,3-dihydro-indol-2-one ("C75")

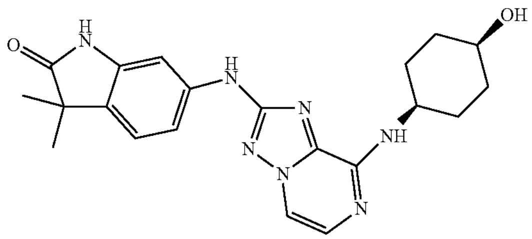 [SMILES: CC1(C)C(=O)Nc2cc(Nc3nc4c(N[C@H]5CC[C@@H](O)CC5)nccn4n3)ccc21]

The title compound is obtained using the procedure as described for "C74" using cis-4-amino-cyclohexanol as coupling partner in the nucleophilic substitution.

LCMS purity (Method C): 100%, Rt: 1.50 min, observed [M+H]=408.2; $^1$H NMR (500 MHz, DMSO-$d_6$) δ [ppm] 10.31-10.17 (s, 1H), 9.60-9.44 (s, 1H), 8.06-7.82 (d, J=4.5 Hz, 1H), 7.54-7.44 (d, J=4.5 Hz, 1H), 7.33-7.26 (dd, J=8.1, 2.0 Hz, 1H), 7.25-7.21 (d, J=2.0 Hz, 1H), 7.18-7.08 (d, J=8.1 Hz, 1H), 6.70-6.56 (d, J=7.7 Hz, 1H), 4.44-4.36 (d, J=3.1 Hz, 1H), 3.83-3.71 (d, J=3.7 Hz, 1H), 3.22-3.14 (d, J=5.2 Hz, 4H), 1.91-1.79 (m, 2H), 1.73-1.62 (m, 4H), 1.62-1.49 (m, 2H), 1.28-1.20 (s, 6H).

trans-6-[8-(4-hydroxy-cyclohexylamino)-[1,2,4]triazolo[1,5-a]pyrazin-2-ylamino]-3,3-dimethyl-1,3-dihydro-indol-2-one ("C76")

The title compound is obtained using the procedure as described for "C74" using trans-4-amino-cyclohexanol as coupling partner in the nucleophilic substitution.

LCMS purity (Method C): 100%, Rt: 1.50 min, observed [M+H]=408.2;

$^1$H NMR (500 MHz, DMSO-$d_6$) δ [ppm] 10.27-10.23 (s, 1H), 9.44-9.40 (s, 1H), 7.96-7.91 (d, J=4.5 Hz, 1H), 7.48-7.43 (d, J=4.5 Hz, 1H), 7.32-7.26 (dd, J=8.1, 2.0 Hz, 1H), 7.23-7.19 (d, J=2.0 Hz, 1H), 7.17-7.11 (d, J=8.1 Hz, 1H), 6.83-6.78 (d, J=8.1 Hz, 1H), 4.60-4.53 (m, 1H), 4.01-3.93 (m, 1H), 3.49-3.40 (m, 2H), 3.40-3.36 (s, 1H), 3.20-3.15 (d, J=5.3 Hz, 1H), 1.99-1.84 (m, 4H), 1.52-1.42 (m, 2H), 1.34-1.23 (m, 2H), 1.23-1.21 (s, 6H).

3,3-dimethyl-6-[8-(piperidin-3-ylamino)-[1,2,4]triazolo[1,5-a]pyrazin-2-ylamino]-1,3-dihydro-indol-2-one ("C77")

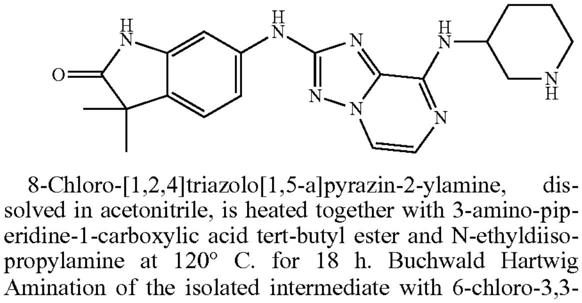

8-Chloro-[1,2,4]triazolo[1,5-a]pyrazin-2-ylamine, dissolved in acetonitrile, is heated together with 3-amino-piperidine-1-carboxylic acid tert-butyl ester and N-ethyldiisopropylamine at 120° C. for 18 h. Buchwald Hartwig Amination of the isolated intermediate with 6-chloro-3,3-dimethyl-1,3-dihydro-indol-2-one using general procedure 1, gives, after cleaving the Boc-group under standard conditions, the title compound.

LCMS purity (Method C): 100%, Rt: 1.53 min, observed [M+H]=393.2;

$^1$H NMR (500 MHz, DMSO-$d_6$) δ [ppm] 10.29-10.25 (s, 1H), 9.45-9.41 (s, 1H), 8.20-8.16 (s, 1H), 8.05-8.00 (d, J=4.5 Hz, 1H), 7.50-7.45 (d, J=4.5 Hz, 1H), 7.33-7.27 (m, 1H), 7.27-7.19 (m, 2H), 7.17-7.12 (d, J=8.1 Hz, 1H), 4.42-4.36 (m, 1H), 3.15-3.14 (s, 2H), 2.95-2.87 (m, 1H), 2.81-2.77 (s, 1H), 2.00-1.95 (d, J=4.8 Hz, 1H), 1.89-1.83 (m, 1H), 1.76-1.68 (m, 2H), 1.25-1.21 (s, 6H).

6-[8-(cyclohexyl-methyl-amino)-[1,2,4]triazolo[1,5-a]pyrazin-2-ylamino]-3,3-dimethyl-1,3-dihydro-indol-2-one ("C78")

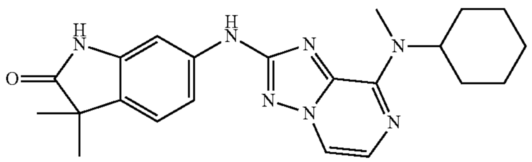 [SMILES: CN(c1nccn2nc(Nc3ccc4c(c3)NC(=O)C4(C)C)nc12)C1CCCCC1]

The title compound is synthesized using the sequence described for "C76" using cyclohexyl-methyl-amine as reaction partner in the nucleophilic substitution.

LCMS purity (Method C): 100%, Rt: 1.85 min, observed [M+H]=406.2.

6-[8-(4-hydroxy-2-phenyl-pyrrolidin-1-yl)-[1,2,4]triazolo[1,5-a]pyrazin-2-ylamino]-3,3-dimethyl-1,3-dihydro-indol-2-one ("C79")

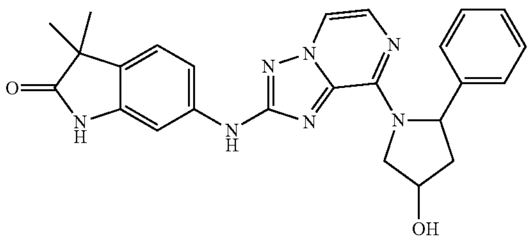 [SMILES: CC1(C)C(=O)Nc2cc(Nc3nc4c(N5CC(O)CC5c5ccccc5)nccn4n3)ccc21]

LCMS purity (Method C): 100%, Rt: 1.87 min, observed [M+H]=456.2;

$^1$H NMR (500 MHz, DMSO-$d_6$) δ [ppm] 10.30-10.26 (s, 1H), 9.59-9.55 (s, 1H), 7.96-7.91 (d, J=4.4 Hz, 1H), 7.38-7.34 (s, 1H), 7.32-7.26 (s, 1H), 7.27-7.23 (d, J=4.3 Hz, 4H), 7.22-7.18 (m, 1H), 7.17-7.10 (m, 2H), 4.46-4.39 (m, 1H), 4.35-4.31 (s, 1H), 2.45-2.37 (m, 1H), 1.98-1.94 (s, 1H), 1.25-1.21 (d, J=1.3 Hz, 6H).

2,2-dimethyl-6-[8-(1-methyl-1H-pyrazol-4-yl)-[1,2,4]triazolo[1,5-a]pyrazin-2-ylamino]-4H-benzo[1,4]oxazin-3-one ("C80")

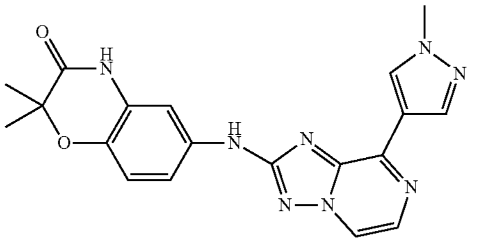 [SMILES: Cn1cc(-c2nccn3nc(Nc4ccc5c(c4)NC(=O)C(C)(C)O5)nc23)cn1]

8-(1-Methyl-1H-pyrazol-4-yl)-[1,2,4]triazolo[1,5-a]pyrazin-2-ylamine is coupled with 6-chloro-2,2-dimethyl-4H-benzo[1,4]oxazin-3-one, available by reaction of 2-amino-4-chlorphenol with 2-bromo-2-methyl-propanoyl bromide under basic conditions, using general procedure 2 gave the title compound as a solid.

LCMS purity (Method D): 100%, Rt: 1.88 min, observed [M+H]=391.1;

$^1$H NMR (500 MHz, DMSO-$d_6$) δ [ppm] 10.71-10.67 (s, 1H), 9.83-9.79 (s, 1H), 8.69-8.62 (m, 2H), 8.42-8.38 (s, 1H), 8.07-8.03 (d, J=4.3 Hz, 1H), 7.42-7.38 (d, J=2.5 Hz, 1H), 7.28-7.22 (m, 1H), 6.94-6.89 (d, J=8.6 Hz, 1H), 4.02-3.98 (s, 3H), 1.42-1.38 (s, 6H).

3,3-dimethyl-6-[8-(2-oxa-6-aza-spiro[3.4]oct-6-yl)-[1,2,4]triazolo[1,5-a]pyrazin-2-ylamino]-1,3-dihydro-indol-2-one ("C81")

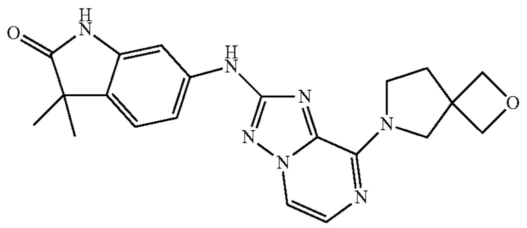 [SMILES: CC1(C)C(=O)Nc2cc(Nc3nc4c(N5CCC6(COC6)C5)nccn4n3)ccc21]

Following the same sequence as described for "C76", but using 2-oxa-6-aza-spiro[3.4]octane as nucleophile in the first step, the title compound is obtained as a solid.

LCMS purity (Method C): 100%, Rt: 1.52 min, observed [M+H]=406.2;

$^1$H NMR (500 MHz, DMSO-$d_6$) δ [ppm] 10.30-10.25 (s, 1H), 9.61-9.56 (s, 1H), 7.99-7.93 (d, J=4.4 Hz, 1H), 7.50-7.44 (d, J=4.4 Hz, 1H), 7.34-7.28 (d, J=1.9 Hz, 1H), 7.24-7.17 (m, 1H), 7.16-7.09 (m, 1H), 4.65-4.59 (d, J=6.1 Hz, 2H), 4.59-4.52 (d, J=6.1 Hz, 2H), 4.20-4.15 (s, 2H), 3.91-3.86 (s, 2H), 3.20-3.14 (d, J=4.5 Hz, 1H), 2.32-2.23 (m, 2H), 1.25-1.20 (s, 6H).

3-hydroxy-3-isopropyl-6-[8-(1-methyl-1H-pyrazol-4-yl)-[1,2,4]triazolo[1,5-a]pyrazin-2-ylamino]-1,3-dihydro-indol-2-one ("C82")

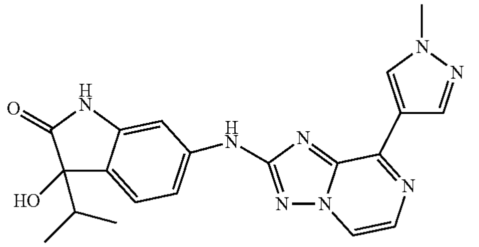 [SMILES: CC(C)C1(O)C(=O)Nc2cc(Nc3nc4c(-c5cnn(C)c5)nccn4n3)ccc21]

Addition of isopropylmagnesiumchloride to 6-bromoisatin at −78° C. in THF gives after usual workup 6-bromo-3-hydroxy-3-isopropyl-1,3-dihydro-indol-2-one which is reacted with 8-(1-methyl-1H-pyrazol-4-yl)-[1,2,4]triazolo[1,5-a]pyrazin-2-ylamine using general procedure 2 to give the title compound as a solid.

LCMS purity (Method C): 100%, Rt: 1.70 min, observed [M+H]=405.2;

$^1$H NMR (500 MHz, DMSO-$d_6$) δ [ppm] 10.26-10.22 (s, 1H), 10.00-9.96 (s, 1H), 8.70-8.64 (m, 2H), 8.41-8.37 (d, J=0.7 Hz, 1H), 8.09-8.04 (d, J=4.3 Hz, 1H), 7.39-7.34 (d, J=2.0 Hz, 1H), 7.29-7.23 (m, 1H), 7.21-7.15 (d, J=8.1 Hz, 1H), 5.63-5.59 (s, 1H), 4.02-3.98 (s, 3H), 2.12-2.02 (m, 1H), 1.03-0.97 (d, J=6.8 Hz, 3H), 0.68-0.63 (d, J=6.8 Hz, 3H).

6-[8-((S)-3-hydroxy-pyrrolidin-1-yl)-[1,2,4]triazolo[1,5-a]pyrazin-2-ylamino]-3,3-dimethyl-1,3-dihydro-indol-2-one ("C83")

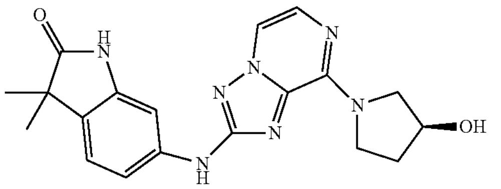 [SMILES: CC1(C)C(=O)Nc2cc(Nc3nc4c(N5CC[C@H](O)C5)nccn4n3)ccc21]

The compound is synthesized using the procedure described for 6-[8-((R)-3-hydroxy-pyrrolidin-1-yl)-[1,2,4]triazolo[1,5-a]pyrazin-2-ylamino]-3,3-dimethyl-1,3-dihydro-indol-2-one with (S)-3-hydroxy-pyrrolidin as nuceophile.

LCMS purity (Method C): 100%, Rt: 1.42 min, observed [M+H]=380.2;

$^1$H NMR (500 MHz, DMSO-$d_6$) δ [ppm] 10.38-10.18 (s, 1H), 9.70-9.46 (s, 1H), 8.07-7.83 (d, J=4.4 Hz, 1H), 7.56-7.40 (d, J=4.4 Hz, 1H), 7.39-7.29 (d, J=2.0 Hz, 1H), 7.26-7.17 (dd, J=8.1, 2.0 Hz, 1H), 7.17-7.07 (m, 1H), 5.09-4.89 (d, J=3.6 Hz, 1H), 4.55-4.36 (m, 1H), 3.98-3.77 (s, 3H), 2.18-1.82 (m, 1H), 1.31-1.13 (s, 6H).

6-[8-((S)-2-hydroxymethyl-pyrrolidin-1-yl)-[1,2,4]triazolo[1,5-a]pyrazin-2-ylamino]-3,3-dimethyl-1,3-dihydro-indol-2-one ("C84")

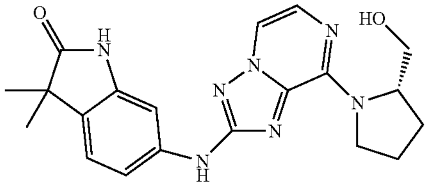 [SMILES: CC1(C)C(=O)Nc2cc(Nc3nc4c(N5CCC[C@H]5CO)nccn4n3)ccc21]

The title compound is synthesized using the sequence described for "C76" using (S)-(+)-2-(hydroxymethyl)-Pyrrolidin as reaction partner in the nucleophilic substitution.

LCMS purity (Method C): 100%, Rt: 1.52 min, observed [M+H]=394.2;

$^1$H NMR (500 MHz, DMSO-$d_6$) δ [ppm] 10.26-10.22 (s, 1H), 9.57-9.53 (s, 1H), 7.98-7.94 (d, J=4.3 Hz, 1H), 7.51-7.46 (d, J=4.4 Hz, 1H), 7.34-7.30 (d, J=1.9 Hz, 1H), 7.26-7.20 (m, 1H), 7.16-7.10 (d, J=8.1 Hz, 1H), 4.79-4.73 (m, 1H), 4.73-4.69 (s, 1H), 4.11-4.04 (m, 1H), 4.04-4.01 (s, 1H), 3.94-3.90 (s, 1H), 3.72-3.64 (m, 1H), 3.54-3.45 (m, 1H), 3.20-3.15 (d, J=5.2 Hz, 2H), 2.11-2.04 (m, 2H), 2.00-1.92 (m, 2H), 1.25-1.21 (s, 6H).

The following compounds are synthesized using one of the following sequences:

Sequence A:

8-Chloro-[1,2,4]triazolo[1,5-a]pyrazin-2-ylamine is dissolved in DMF or acetonitrile. An appropriate base (e.g. $Cs_2CO_3$, $K_2CO_3$ or N-Ethyldiisopropylamine; 2.5 eq.) and the necessary nucleophile (1.5 eq) are added and the mixture is heated to 130° C. (in acetonitrile) or 180° C. in DMF by conventional heating or by microwave irradiation and monitored via LCMS. Upon completion, usual workup (e.g. filtration over Celite as well as purification via chromatography) gives the desired 8-substituted triazolopyrazine.

This intermediate is reacted with 6-chloro-3,3-dimethyl-1,3-dihydro-indol-2-one under Buchwald-Hartwig conditions in tert-butanol with chloro[2-(Dicyclohexylphosphino)-3,6-dimethoxy-2'-4'-6'-tri-i-propyl-1,1'-biphenyl]2-(2-aminoethyl)phenyl)Pd(II) (0.05 eq) as catalyst and LHMDS (2 eq.) as base at 110° C. and monitored via LCMS.

Workup and purification via prep. LCMS or column chromatography gives the desired compounds.

In some cases an additonal deprotection step is necessary to obtain the desired product.

Sequence B:

6-[(8-Chloro-[1,2,4]triazolo[1,5-a]pyrazin-2-yl)amino]-3,3-dimethyl-indolin-2-one available by methods described earlier is reacted with the desired nucleophile (1.5 eq) in DMF or acetonitrile with an appropriate base (e.g. $Cs_2CO_3$, $K_2CO_3$ or N-ethyldiisopropylamine; 2.5 eq.) at 130° C. or 180° C. by conventional heating or by microwave irradiation and monitored via LCMS.

Workup and purification via prep. LCMS or column chromatography gives the desired compounds.

In some cases an additonal deprotection step is necessary to obtain the desired product.

3,3-dimethyl-6-[8-((S)-piperidin-3-ylamino)-[1,2,4]triazolo[1,5-a]pyrazin-2-ylamino]-1,3-dihydro-indol-2-one ("C85")

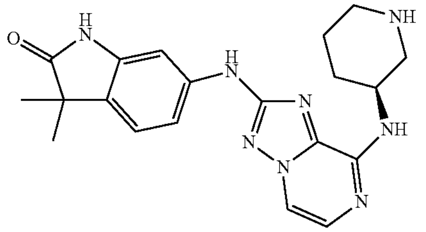 [SMILES: CC1(C)C(=O)Nc2cc(Nc3nc4c(N[C@H]5CCCNC5)nccn4n3)ccc21]

LCMS purity (Method C): 100%, Rt: 1.42 min, observed [M+H]=393.2; $^1$H NMR (500 MHz, DMSO-$d_6$) δ [ppm] 10.29-10.25 (s, 1H), 9.44-9.40 (s, 1H), 8.21-8.17 (s, 2H), 8.04-7.99 (d, J=4.5 Hz, 1H), 7.50-7.45 (d, J=4.5 Hz, 1H), 7.33-7.20 (m, 3H), 7.17-7.11 (d, J=8.1 Hz, 1H), 4.43-4.36 (m, 1H), 3.36-3.30 (d, J=8.9 Hz, 1H), 3.17-3.10 (d, J=12.7 Hz, 1H), 2.96-2.88 (m, 1H), 2.81-2.77 (s, 1H), 2.02-1.94 (m, 1H), 1.89-1.83 (m, 1H), 1.76-1.68 (m, 2H), 1.24-1.21 (s, 6H).

6-[8-((S)-3-amino-pyrrolidin-1-yl)-[1,2,4]triazolo[1,5-a]pyrazin-2-ylamino]-3,3-dimethyl-1,3-dihydro-indol-2-one ("C86")

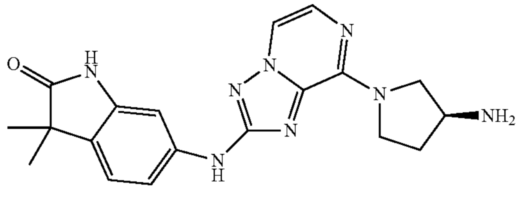 [SMILES: CC1(C)C(=O)Nc2cc(Nc3nc4c(N5CC[C@H](N)C5)nccn4n3)ccc21]

LCMS purity (Method C): 100%, Rt: 1.30 min, observed [M+H]=379.2;

$^1$H NMR (500 MHz, DMSO-$d_6$) δ [ppm] 10.29-10.24 (s, 1H), 9.58-9.53 (s, 1H), 7.94-7.88 (d, J=4.4 Hz, 1H), 7.49-7.43

(d, J=4.4 Hz, 1H), 7.34-7.29 (d, J=2.0 Hz, 1H), 7.23-7.16 (m, 1H), 7.15-7.08 (m, 1H), 4.34-4.26 (t, J=5.1 Hz, 1H), 3.64-3.57 (m, 1H), 3.50-3.38 (m, 1H), 2.12-2.02 (m, 1H), 1.79-1.69 (m, 1H), 1.24-1.19 (s, 6H).

3,3-dimethyl-6-[8-((R)-piperidin-3-ylamino)-[1,2,4]triazolo[1,5-a]pyrazin-2-ylamino]-1,3-dihydro-indol-2-one ("C87")

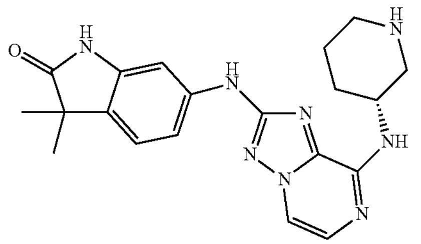 [SMILES: CC1(C)C(=O)Nc2cc(Nc3nc4c(N[C@@H]5CCCNC5)nccn4n3)ccc21]

LCMS purity (Method C): 100%, Rt: 1.52 min, observed [M+H]=393.2; $^1$H NMR (500 MHz, DMSO-$d_6$) δ [ppm] 10.30-10.26 (s, 1H), 9.45-9.41 (s, 1H), 8.23-8.19 (s, 2H), 8.03-7.98 (d, J=4.5 Hz, 1H), 7.49-7.44 (d, J=4.5 Hz, 1H), 7.32-7.26 (dd, J=8.1, 2.0 Hz, 1H), 7.23-7.11 (m, 3H), 4.37-4.30 (m, 1H), 3.28-3.23 (d, J=3.8 Hz, 1H), 3.10-3.03 (d, J=12.7 Hz, 1H), 2.90-2.82 (m, 1H), 2.79-2.70 (m, 1H), 1.98-1.92 (m, 1H), 1.86-1.79 (m, 1H), 1.75-1.61 (m, 2H), 1.24-1.20 (s, 6H).

3,3-dimethyl-6-[8-(methyl-piperidin-3-yl-amino)-[1,2,4]triazolo[1,5-a]pyrazin-2-ylamino]-1,3-dihydro-indol-2-one ("C88")

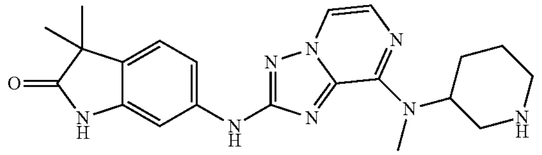 [SMILES: CN(c1nccn2nc(Nc3ccc4c(c3)NC(=O)C4(C)C)nc12)C1CCCNC1]

LCMS purity (Method C): 100%, Rt: 1.33 min, observed [M+H]=407.2;

$^1$H NMR (500 MHz, DMSO-$d_6$) δ [ppm] 10.33-10.28 (s, 1H), 9.46-9.41 (s, 1H), 8.36-8.31 (s, 2H), 7.98-7.92 (d, J=4.5 Hz, 1H), 7.48-7.41 (m, 2H), 7.33-7.26 (m, 1H), 7.24-7.19 (d, J=1.9 Hz, 1H), 7.17-7.10 (d, J=8.1 Hz, 1H), 2.79-2.66 (m, 1H), 2.15-2.06 (m, 1H), 1.84-1.70 (m, 2H), 1.62-1.51 (m, 1H), 1.25-1.20 (s, 6H).

6-[(1S,4S)-8-(2,5-diaza-bicyclo[2.2.1]hept-2-yl)-[1,2,4]triazolo[1,5-a]pyrazin-2-ylamino]-3,3-dimethyl-1,3-dihydro-indol-2-one ("C89")

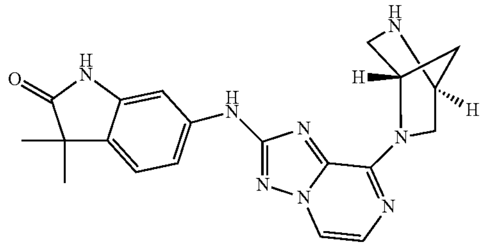 [SMILES: CC1(C)C(=O)Nc2cc(Nc3nc4c(N5C[C@@H]6C[C@H]5CN6)nccn4n3)ccc21]

LCMS purity (Method C): 100%, Rt: 1.51 min, observed [M+H]=437.2;

$^1$H NMR (500 MHz, DMSO-$d_6$) δ [ppm] 10.33-10.29 (s, 1H), 9.64-9.60 (s, 1H), 8.26-8.22 (s, 1H), 8.03-7.98 (d, J=4.4 Hz, 1H), 7.52-7.47 (d, J=4.4 Hz, 1H), 7.35-7.31 (d, J=1.9 Hz, 1H), 7.21-7.10 (m, 2H), 4.02-3.98 (s, 1H), 3.16-3.10 (d, J=9.5 Hz, 1H), 3.09-3.03 (d, J=10.2 Hz, 1H), 2.00-1.94 (d, J=9.8 Hz, 1H), 1.87-1.81 (d, J=10.2 Hz, 1H), 1.24-1.20 (s, 6H).

6-[8-(1H-indazol-4-yl)-[1,2,4]triazolo[1,5-a]pyrazin-2-ylamino]-3,3-dimethyl-1,3-dihydro-indol-2-one ("C90")

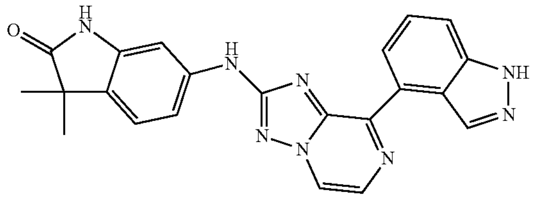 [SMILES: CC1(C)C(=O)Nc2cc(Nc3nc4c(-c5cccc6[nH]ncc56)nccn4n3)ccc21]

LCMS purity (Method D): 100%, Rt: 1.92 min, observed [M+H]=411.1;

$^1$H NMR (400 MHz, DMSO-$d_6$) δ [ppm] 13.32-13.27 (s, 1H), 10.37-10.32 (s, 1H), 10.05-10.00 (s, 1H), 8.98-8.91 (d, J=7.3 Hz, 1H), 8.89-8.81 (m, 2H), 8.38-8.32 (d, J=4.2 Hz, 1H), 7.80-7.73 (d, J=8.2 Hz, 1H), 7.65-7.56 (m, 1H), 7.41-7.36 (d, J=2.0 Hz, 1H), 7.35-7.28 (m, 1H), 7.24-7.17 (d, J=8.1 Hz, 1H), 1.27-1.22 (s, 6H).

3,3-dimethyl-6-[8-(2-oxa-6-aza-spiro[3.3]hept-6-yl)-[1,2,4]triazolo[1,5-a]pyrazin-2-ylamino]-1,3-dihydro-indol-2-one ("C91")

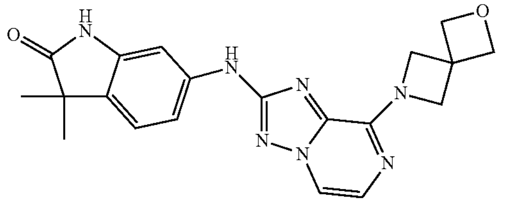 [SMILES: CC1(C)C(=O)Nc2cc(Nc3nc4c(N5CC6(COC6)C5)nccn4n3)ccc21]

LCMS purity (Method C): 100%, Rt: 1.52 min, observed [M+H]=392.2;

$^1$H NMR (400 MHz, DMSO-$d_6$) δ [ppm] 10.34-10.30 (s, 1H), 9.66-9.62 (s, 1H), 8.05-8.00 (d, J=4.5 Hz, 1H), 7.51-7.46 (d, J=4.5 Hz, 1H), 7.42-7.37 (d, J=1.9 Hz, 1H), 7.21-7.11 (m, 2H), 4.79-4.75 (s, 4H), 4.54-4.50 (s, 4H), 1.25-1.21 (s, 6H).

3,3-dimethyl-6-[8-(2-oxa-6-aza-spiro[3.5]non-6-yl)-[1,2,4]triazolo[1,5-a]pyrazin-2-ylamino]-1,3-dihydro-indol-2-one ("C92")

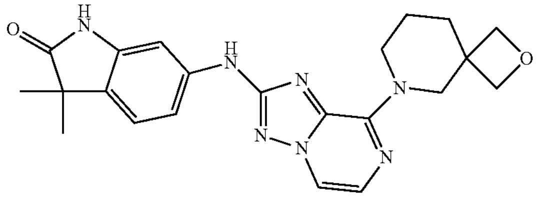 [SMILES: CC1(C)C(=O)Nc2cc(Nc3nc4c(N5CCCC6(COC6)C5)nccn4n3)ccc21]

LCMS purity (Method D): 100%, Rt: 2.13 min, observed [M+H]=420.1;

$^1$H NMR (500 MHz, DMSO-$d_6$) δ [ppm] 10.16-10.12 (s, 1H), 9.71-9.67 (s, 1H), 8.12-8.08 (d, J=4.3 Hz, 1H), 7.57-7.52

(d, J=4.4 Hz, 1H), 7.38-7.33 (d, J=2.0 Hz, 1H), 7.27-7.21 (m, 1H), 7.16-7.11 (d, J=8.1 Hz, 1H), 4.41-4.36 (d, J=5.9 Hz, 2H), 4.35-4.33 (s, 2H), 4.33-4.30 (d, J=5.9 Hz, 2H), 4.00-3.94 (m, 2H), 1.95-1.89 (m, 2H), 1.63-1.57 (m, 2H), 1.24-1.20 (s, 6H).

6-{8-[(2-hydroxy-ethyl)-piperidin-4-yl-amino]-[1,2,4]triazolo[1,5-a]pyrazin-2-ylamino}-3,3-dimethyl-1,3-dihydro-indol-2-one ("C93")

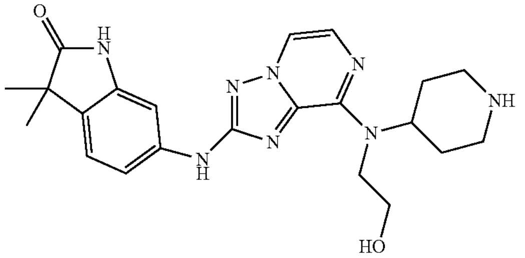 [SMILES: CC1(C)C(=O)Nc2cc(Nc3nc4c(N(CCO)C5CCNCC5)nccn4n3)ccc21]

LCMS purity (Method C): 100%, Rt: 1.40 min, observed [M+H]=437.2;

$^1$H NMR (500 MHz, DMSO-$d_6$) δ [ppm] 10.30-10.26 (s, 1H), 9.68-9.64 (s, 1H), 8.29-8.25 (s, 1H), 8.11-8.06 (d, J=4.4 Hz, 1H), 7.56-7.51 (d, J=4.4 Hz, 1H), 7.29-7.25 (d, J=2.0 Hz, 1H), 7.23-7.17 (m, 1H), 7.16-7.11 (m, 1H), 5.06-4.98 (m, 2H), 3.54-3.48 (m, 2H), 3.27-3.18 (m, 2H), 2.77-2.71 (m, 2H), 2.02-1.95 (m, 1H), 1.41-1.37 (s, 2H), 1.26-1.20 (s, 8H).

6-[8-((R)-3-amino-piperidin-1-yl)-[1,2,4]triazolo[1,5-a]pyrazin-2-ylamino]-3,3-dimethyl-1,3-dihydro-indol-2-one ("C94")

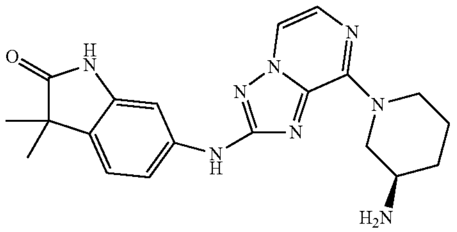 [SMILES: CC1(C)C(=O)Nc2cc(Nc3nc4c(N5CCC[C@@H](N)C5)nccn4n3)ccc21]

LCMS purity (Method C): 100%, Rt: 1.40 min, observed [M+H]=393.2; $^1$H NMR (500 MHz, DMSO-$d_6$) δ [ppm] 10.30-10.26 (s, 1H), 9.67-9.63 (s, 1H), 8.08-8.03 (d, J=4.3 Hz, 1H), 7.54-7.50 (d, J=4.4 Hz, 1H), 7.29-7.25 (d, J=2.0 Hz, 1H), 7.25-7.19 (m, 1H), 7.17-7.11 (m, 1H), 5.04-4.97 (m, 1H), 4.88-4.80 (m, 1H), 3.23-3.13 (m, 1H), 2.95-2.86 (dd, J=12.6, 9.5 Hz, 1H), 2.79-2.71 (m, 1H), 1.95-1.88 (m, 1H), 1.83-1.75 (m, 1H), 1.57-1.46 (m, 1H), 1.35-1.26 (m, 3H), 1.25-1.21 (s, 6H).

7-[2-(3,3-dimethyl-2-oxo-2,3-dihydro-1H-indol-6-ylamino)-[1,2,4]triazolo[1,5-a]pyrazin-8-yl]-2,7-diaza-spiro[4.4]nonane-1,3-dione ("C95")

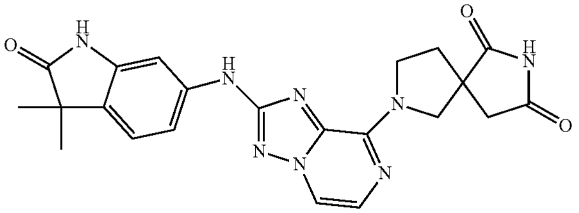 [SMILES: CC1(C)C(=O)Nc2cc(Nc3nc4c(N5CCC6(CC(=O)NC6=O)C5)nccn4n3)ccc21]

LCMS purity (Method C): 100%, Rt: 1.51 min, observed [M+H]=447.2;

$^1$H NMR (500 MHz, DMSO-$d_6$) δ [ppm] 11.33-11.29 (s, 1H), 10.30-10.26 (s, 1H), 9.60-9.56 (s, 1H), 8.02-7.97 (d, J=4.4 Hz, 1H), 7.52-7.47 (d, J=4.4 Hz, 1H), 7.33-7.28 (d, J=2.0 Hz, 1H), 7.23-7.17 (m, 1H), 7.16-7.11 (m, 1H), 4.13-4.09 (s, 1H), 2.90-2.83 (m, 1H), 2.81-2.74 (m, 1H), 2.39-2.28 (m, 1H), 2.23-2.14 (m, 1H), 1.25-1.21 (s, 6H).

3,3-dimethyl-6-[8-(3-oxa-8-aza-bicyclo[3.2.1 l]oct-8-yl)-[1,2,4]triazolo[1,5-a]pyrazin-2-ylamino]-1,3-dihydro-indol-2-one ("C96")

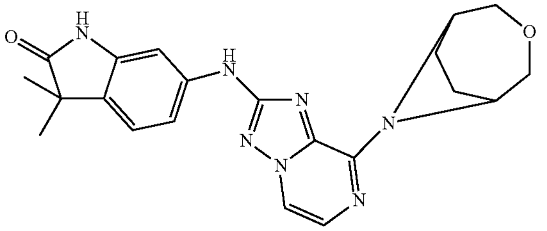 [SMILES: CC1(C)C(=O)Nc2cc(Nc3nc4c(N5C6CCC5COC6)nccn4n3)ccc21]

LCMS purity (Method C): 100%, Rt: 1.71 min, observed [M+H]=406.2;

$^1$H NMR (500 MHz, DMSO-$d_6$) δ [ppm] 10.33-10.29 (s, 1H), 9.68-9.64 (s, 1H), 8.13-8.08 (d, J=4.4 Hz, 1H), 7.59-7.54 (d, J=4.4 Hz, 1H), 7.31-7.27 (d, J=1.9 Hz, 1H), 7.21-7.12 (m, 2H), 5.24-5.20 (s, 2H), 3.78-3.71 (m, 2H), 3.68-3.61 (m, 2H), 2.57-2.53 (s, 1H), 2.08-1.96 (m, 3H), 1.25-1.21 (s, 6H).

6-[8-(trans-3-amino-cyclobutylamino)-[1,2,4]triazolo[1,5-a]pyrazin-2-ylamino]-3,3-dimethyl-1,3-dihydro-indol-2-one ("C97")

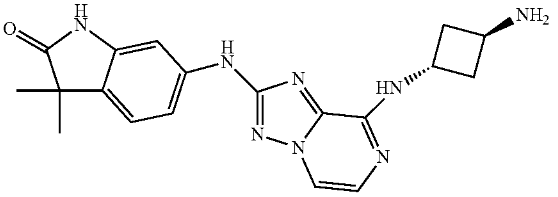 [SMILES: CC1(C)C(=O)Nc2cc(Nc3nc4c(N[C@H]5C[C@H](N)C5)nccn4n3)ccc21]

LCMS purity (Method C): 100%, Rt: 1.45 min, observed [M+H]=379.2.

6-[8-(cis-3-amino-cyclobutylamino)-[1,2,4]triazolo[1,5-a]pyrazin-2-ylamino]-3,3-dimethyl-1,3-dihydro-indol-2-one ("C98")

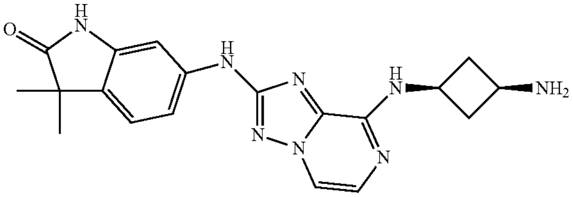 [SMILES: CC1(C)C(=O)Nc2cc(Nc3nc4c(N[C@H]5C[C@@H](N)C5)nccn4n3)ccc21]

LCMS purity (Method C): 100%, Rt: 1.46 min, observed [M+H]=379.2;

$^1$H NMR (500 MHz, DMSO-$d_6$) δ [ppm] 10.29-10.25 (s, 1H), 9.46-9.42 (s, 1H), 8.24-8.20 (s, 2H), 8.01-7.96 (d, J=4.5 Hz, 1H), 7.47-7.41 (m, 2H), 7.33-7.27 (m, 1H), 7.26-7.22 (d, J=2.0 Hz, 1H), 7.16-7.11 (d, J=8.1 Hz, 1H), 4.39-4.30 (m, 1H), 3.47-3.40 (m, 1H), 2.76-2.67 (m, 2H), 2.30-2.20 (m, 2H), 1.25-1.21 (s, 6H).

6-[8-((S)-3-amino-piperidin-1-yl)-[1,2,4]triazolo[1,5-a]pyrazin-2-ylamino]-3,3-dimethyl-1,3-dihydro-indol-2-one ("C99")

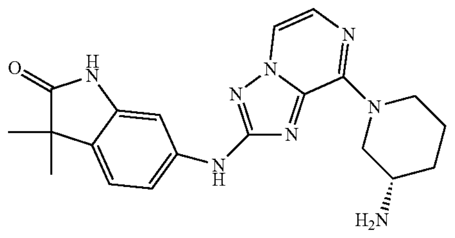 [SMILES: CC1(C)C(=O)Nc2cc(Nc3nc4c(N5CCC[C@H](N)C5)nccn4n3)ccc21]

LCMS purity (Method C): 100%, Rt: min, observed [M+H]=393.2;

$^1$H NMR (500 MHz, DMSO-$d_6$) δ [ppm] 10.33-10.29 (s, 1H), 9.71-9.67 (s, 1H), 8.17-8.12 (d, J=4.3 Hz, 1H), 7.58-7.53 (d, J=4.3 Hz, 1H), 7.31-7.26 (d, J=2.0 Hz, 1H), 7.23-7.17 (m, 1H), 7.17-7.11 (m, 1H), 4.97-4.91 (d, J=13.3 Hz, 1H), 4.73-4.66 (m, 1H), 3.53-3.46 (m, 1H), 3.44-3.40 (s, 2H), 2.10-2.03 (m, 1H), 1.89-1.82 (m, 1H), 1.70-1.57 (m, 2H), 1.24-1.20 (s, 6H).

3,3-dimethyl-6-[8-(2-phenyl-pyrrolidin-1-yl)-[1,2,4]triazolo[1,5-a]pyrazin-2-ylamino]-1,3-dihydro-indol-2-one ("C100")

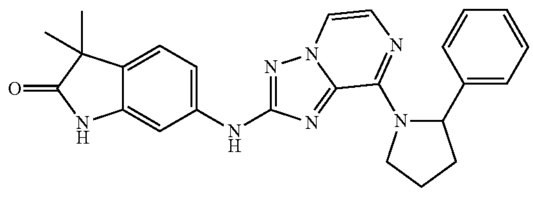 [SMILES: CC1(C)C(=O)Nc2cc(Nc3nc4c(N5CCCC5c5ccccc5)nccn4n3)ccc21]

LCMS purity (Method C): 100%, Rt: 2.41 min, observed [M+H]=440.2;

$^1$H NMR (500 MHz, DMSO-$d_6$) δ [ppm] 10.37-10.20 (s, 1H), 9.56-9.43 (s, 1H), 7.97-7.88 (d, J=4.4 Hz, 1H), 7.54-7.33 (d, J=4.9 Hz, 1H), 7.32-7.03 (m, 8H), 4.52-3.93 (m, 1H), 2.45-2.28 (m, 1H), 2.12-1.95 (m, 1H), 1.95-1.82 (m, 2H), 1.30-1.16 (d, J=2.3 Hz, 6H).

3,3-dimethyl-6-{8-[methyl-(tetrahydro-pyran-4-yl)-amino]-[1,2,4]triazolo[1,5-a]pyrazin-2-ylamino}-1,3-dihydro-indol-2-one ("C101")

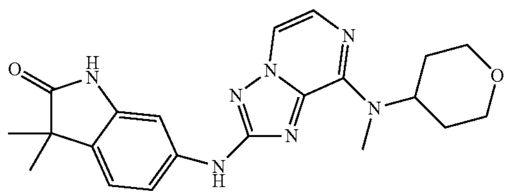 [SMILES: CN(c1nccn2nc(Nc3ccc4c(c3)NC(=O)C4(C)C)nc12)C1CCOCC1]

LCMS purity (Method C): 100%, Rt: 1.79 min, observed [M+H]=408.2;

$^1$H NMR (400 MHz, DMSO-$d_6$) δ [ppm] 10.30-10.25 (s, 1H), 9.58-9.53 (s, 1H), 8.07-8.01 (d, J=4.3 Hz, 1H), 7.57-7.51 (d, J=4.4 Hz, 1H), 7.36-7.29 (m, 1H), 7.23-7.12 (m, 2H), 5.48-5.37 (m, 1H), 4.05-3.96 (m, 2H), 3.55-3.42 (m, 2H), 3.34-3.29 (s, 3H), 2.00-1.85 (m, 2H), 1.74-1.65 (m, 2H), 1.30-1.21 (s, 6H).

3-[2-(3,3-dimethyl-2-oxo-2,3-dihydro-1H-indol-6-ylamino)-[1,2,4]triazolo[1,5-a]pyrazin-8-yl]-benzenesulfonamide ("C102")

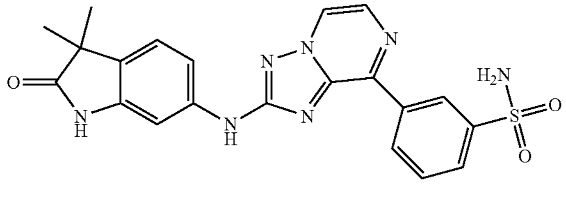 [SMILES: CC1(C)C(=O)Nc2cc(Nc3nc4c(-c5cccc(S(N)(=O)=O)c5)nccn4n3)ccc21]

LCMS purity (Method D): 100%, Rt: 1.92 min, observed [M+H]=450.0.

3,3-dimethyl-6-[8-(1,4,6,7-tetrahydro-imidazo[4,5-c]pyridin-5-yl)-[1,2,4]triazolo[1,5-a]pyrazin-2-ylamino]-1,3-dihydro-indol-2-one ("C103")

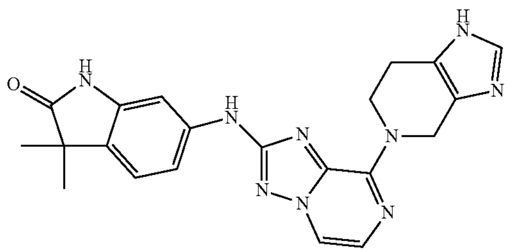 [SMILES: CC1(C)C(=O)Nc2cc(Nc3nc4c(N5CCc6[nH]cnc6C5)nccn4n3)ccc21]

LCMS purity (Method C): 100%, Rt: 1.67 min, observed [M+H]=416.2;

$^1$H NMR (500 MHz, DMSO-$d_6$) δ [ppm] 11.88-11.82 (m, 1H), 10.32-10.28 (s, 1H), 9.72-9.68 (s, 1H), 8.15-8.09 (m, 1H), 7.60-7.55 (d, J=4.3 Hz, 1H), 7.54-7.48 (s, 1H), 7.33-7.21 (m, 2H), 7.19-7.13 (d, J=8.1 Hz, 1H), 5.06-5.00 (m, 2H), 4.53-4.49 (s, 1H), 4.49-4.43 (m, 1H), 3.21-3.16 (d, J=5.3 Hz, 2H), 2.85-2.70 (m, 1H), 1.26-1.22 (s, 6H).

3,3-dimethyl-6-{8-[4-(2-oxo-imidazolidin-1-yl)-piperidin-1-yl]-[1,2,4]triazolo[1,5-a]pyrazin-2-ylamino}-1,3-dihydro-indol-2-one ("C104")

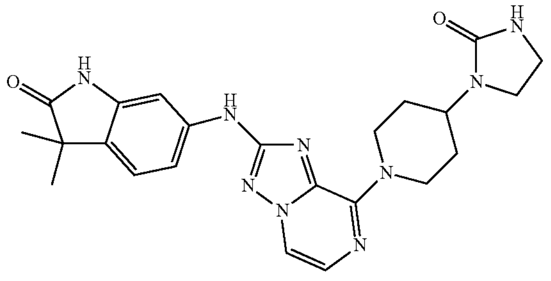 [SMILES: CC1(C)C(=O)Nc2cc(Nc3nc4c(N5CCC(N6CCNC6=O)CC5)nccn4n3)ccc21]

LCMS purity (Method C): 100%, Rt: 1.71 min, observed [M+H]=462.2;

$^1$H NMR (400 MHz, DMSO-$d_6$) δ [ppm] 10.30-10.25 (s, 1H), 9.69-9.64 (s, 1H), 8.11-8.05 (d, J=4.4 Hz, 1H), 7.57-7.51 (d, J=4.3 Hz, 1H), 7.31-7.26 (d, J=1.9 Hz, 1H), 7.23-7.10 (m, 2H), 6.25-6.20 (s, 1H), 5.36-5.28 (d, J=13.0 Hz, 2H), 3.90-3.80 (m, 1H), 3.34-3.17 (m, 8H), 3.13-3.01 (m, 2H), 1.73-1.65 (m, 3H), 1.25-1.20 (s, 6H).

6-[8-(3,3-difluoro-pyrrolidin-1-yl)-[1,2,4]triazolo[1,5-a]pyrazin-2-ylamino]-3,3-dimethyl-1,3-dihydro-indol-2-one ("C105")

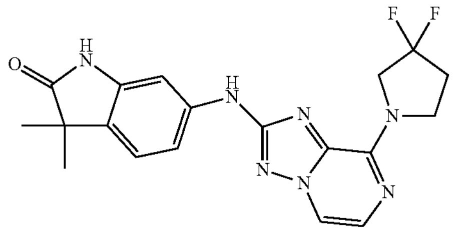 [SMILES: CC1(C)C(=O)Nc2cc(Nc3nc4c(N5CCC(F)(F)C5)nccn4n3)ccc21]

LCMS purity (Method C): 100%, Rt: 2.0 min, observed [M+H]=400.2;

$^1$H NMR (400 MHz, DMSO-$d_6$) δ [ppm] 10.33-10.28 (s, 1H), 9.66-9.61 (s, 1H), 8.13-8.07 (d, J=4.4 Hz, 1H), 7.58-7.52 (d, J=4.4 Hz, 1H), 7.35-7.29 (d, J=1.9 Hz, 1H), 7.25-7.12 (m, 2H), 4.38-4.27 (m, 2H), 4.20-4.11 (m, 2H), 2.67-2.50 (m, 5H), 1.26-1.21 (s, 6H).

5-[2-(3,3-dimethyl-2-oxo-2,3-dihydro-1H-indol-6-ylamino)-[1,2,4]triazolo[1,5-a]pyrazin-8-yl]-4,5,6,7-tetrahydro-pyrazolo[1,5-a]pyrazine-3-carboxylic acid ethyl ester ("C106")

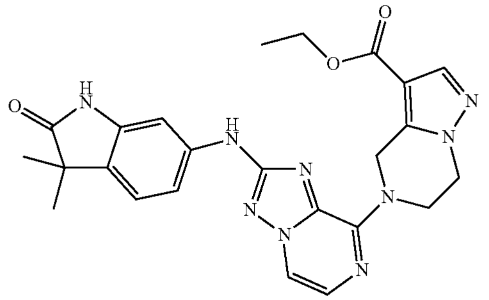 [SMILES: CCOC(=O)c1cnn2c1CN(c1nccn3nc(Nc4ccc5c(c4)NC(=O)C5(C)C)nc13)CC2]

LCMS purity (Method C): 100%, Rt: 2.25 min, observed [M+H]=488.2.

3,3-dimethyl-6-[8-(1-methyl-piperidin-3-ylamino)[1,2,4]triazolo[1,5-a]yrazin-2-ylamino]-1,3-dihydro-indol-2-one ("C107")

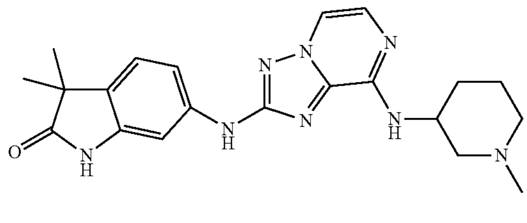 [SMILES: CN1CCCC(Nc2nccn3nc(Nc4ccc5c(c4)NC(=O)C5(C)C)nc23)C1]

LCMS purity (Method C): 100%, Rt: 1.31 min, observed [M+H]=407.2;

$^1$H NMR (400 MHz, DMSO-$d_6$) δ [ppm] 10.27-10.22 (s, 1H), 9.53-9.48 (s, 1H), 8.17-8.12 (s, 1H), 7.99-7.93 (d, J=4.5 Hz, 1H), 7.49-7.43 (d, J=4.5 Hz, 1H), 7.29-7.17 (m, 2H), 7.17-7.10 (d, J=8.1 Hz, 1H), 6.74-6.67 (d, J=8.2 Hz, 1H), 4.26-4.21 (s, 1H), 3.20-3.15 (s, 1H), 2.76-2.68 (d, J=10.4 Hz, 1H), 2.26-2.21 (s, 3H), 1.73-1.68 (s, 2H), 1.64-1.55 (d, J=17.6 Hz, 1H), 1.25-1.20 (s, 6H).

7-[2-(3,3-dimethyl-2-oxo-2,3-dihydro-1H-indol-6-ylamino)-[1,2,4]triazolo[1,5-a]pyrazin-8-yl]-1,3,7-triaza-spiro[4.4]nonane-2,4-dione ("C108")

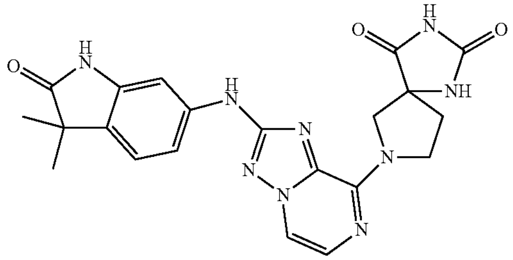 [SMILES: CC1(C)C(=O)Nc2cc(Nc3nc4c(N5CCC6(C5)NC(=O)NC6=O)nccn4n3)ccc21]

LCMS purity (Method C): 100%, Rt: 1.47 min, observed [M+H]=448.2;

$^1$H NMR (400 MHz, DMSO-$d_6$) δ [ppm] 10.89-10.84 (s, 1H), 10.30-10.25 (s, 1H), 9.61-9.56 (s, 1H), 8.51-8.46 (s, 1H), 8.05-7.99 (d, J=4.4 Hz, 1H), 7.54-7.48 (d, J=4.4 Hz, 1H), 7.31-7.25 (d, J=2.0 Hz, 1H), 7.24-7.10 (m, 2H), 4.13-4.08 (s, 4H), 2.45-2.31 (m, 1H), 2.23-2.12 (m, 1H), 1.25-1.20 (s, 6H).

Synthesis of 3,7,9-triazaspiro[4.4]nonane-6,8-dione

3-Oxo-pyrrolidine-1-carboxylic acid tert-butyl ester (1 eq.) and potassium cyanide (1.3 eq) are dissolved in ethanol before ammonium carbonate (8 eq.) in water is added. The mixture is heated to 90° C. for 2 h and monitored by LCMS. Upon completion, the solvent is removed in vacuum. The residue is diluted with water and the product filtered off. Boc-deprotection under standard conditions gives the desired hydantoine as HCl-salt ready for further modifications.

2-[2-(3,3-dimethyl-2-oxo-2,3-dihydro-1H-indol-6-ylamino)-[1,2,4]triazolo[1,5-a]pyrazin-8-yl]-2,5,7-triaza-spiro[3.4]octane-6,8-dione ("C109")

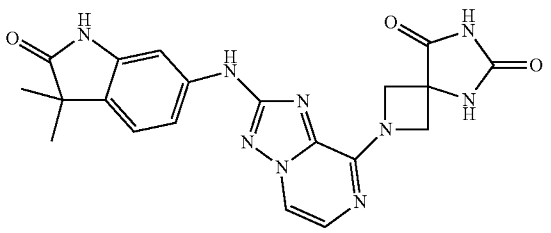 [SMILES: CC1(C)C(=O)Nc2cc(Nc3nc4c(N5CC6(C5)NC(=O)NC6=O)nccn4n3)ccc21]

LCMS purity (Method C): 100%, Rt: 1.49 min, observed [M+H]=434.2;

$^1$H NMR (400 MHz, DMSO-$d_6$) δ [ppm] 10.90-10.85 (s, 1H), 10.32-10.27 (s, 1H), 9.70-9.65 (s, 1H), 8.63-8.58 (s, 1H), 8.14-8.08 (d, J=4.5 Hz, 1H), 7.57-7.51 (d, J=4.5 Hz, 1H), 7.44-7.39 (d, J=1.8 Hz, 1H), 7.19-7.09 (m, 2H), 4.66-4.61 (s, 2H), 4.46-4.41 (s, 2H), 1.24-1.19 (s, 6H).

Synthesis of 2,6,8-triazaspiro[3.4]octane-5,7-dione

3-Oxo-azetidine-1-carboxylic acid tert-butyl ester (1 eq.) and potassium cyanide (1.3 eq) are dissolved in ethanol before ammonium carbonate (8 eq.) in water is added. The mixture is heated to 90° C. for 19 h and monitored by LCMS. Upon completion, the solvent is removed in vacuum. The residue is diluted with water and the product filtered off. Boc-deprotection under standard conditions gives the desired hydantoine as HCl-salt ready for further modifications.

7-[2-(3,3-dimethyl-2-oxo-2,3-dihydro-1H-indol-6-ylamino)-[1,2,4]triazolo[1,5-a]pyrazin-8-yl]-1,3,7-triaza-spiro[4.5]decane-2,4-dione ("C110")

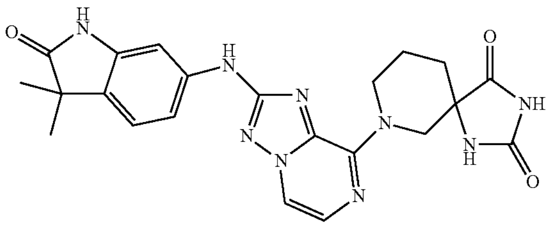 [SMILES: CC1(C)C(=O)Nc2cc(Nc3nc4c(N5CCCC6(C5)NC(=O)NC6=O)nccn4n3)ccc21]

LCMS purity (Method C): 100%, Rt: 1.61 min, observed [M+H]=462.2;

$^1$H NMR (400 MHz, DMSO-$d_6$) δ [ppm] 10.78-10.72 (d, J=1.7 Hz, 1H), 10.25-10.20 (s, 1H), 9.66-9.61 (s, 1H), 8.47-8.42 (d, J=1.8 Hz, 1H), 8.10-8.04 (d, J=4.3 Hz, 1H), 7.55-7.49 (d, J=4.3 Hz, 1H), 7.37-7.32 (s, 2H), 7.28-7.07 (m, 7H), 5.05-4.97 (d, J=13.1 Hz, 1H), 4.85-4.80 (s, 1H), 4.21-4.16 (s, 1H), 3.87-3.79 (d, J=13.1 Hz, 1H), 1.88-1.73 (m, 3H), 1.25-1.20 (s, 6H).

Synthesis of 2,4,9-triazaspiro[4.5]decane-1,3-dione

3-Oxo-piperidine-1-carboxylic acid tert-butyl ester and potassium cyanide (1.3 eq) are dissolved in ethanol before ammonium carbonate (8 eq.) in water is added. The mixture is heated to 90° C. for 2 h and monitored by LCMS. Upon completion, the solvent is removed in vacuum. The residue is diluted with water and the product filtered off. Boc-deprotection under standard conditions gives the desired hydantoine as HCl-salt ready for further modifications.

1H-indol-6-yl)-[8-(1-methyl-1H-pyrazol-4-yl)-[1,2,4]triazolo[1,5-a]pyrazin-2-yl]-amine ("C111")

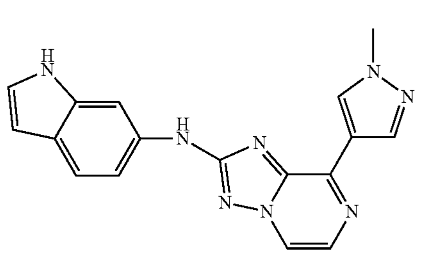 [SMILES: Cn1cc(-c2nccn3nc(Nc4ccc5cc[nH]c5c4)nc23)cn1]

The title compound is synthesized by amination of 8-(1-methyl-1H-pyrazol-4-yl)-[1,2,4]triazolo[1,5-a]pyrazin-2-ylamine using general procedure 2.

LCMS purity (Method D): 100%, Rt: 1.91 min, observed [M+H]=331.1;

$^1$H NMR (500 MHz, DMSO-$d_6$) δ [ppm] 10.99-10.94 (t, J=2.2 Hz, 1H), 9.76-9.72 (s, 1H), 8.70-8.64 (m, 2H), 8.43-8.39 (s, 1H), 8.06-7.99 (m, 2H), 7.48-7.42 (d, J=8.5 Hz, 1H), 7.27-7.18 (m, 2H), 6.37-6.32 (m, 1H), 4.02-3.98 (s, 3H).

2,2,2-trifluoro-1-{6-[8-(1-methyl-1H-pyrazol-4-yl)-[1,2,4]triazolo[1,5-a]pyrazin-2-ylamino]-1H-indol-3-yl}-ethanone ("C112")

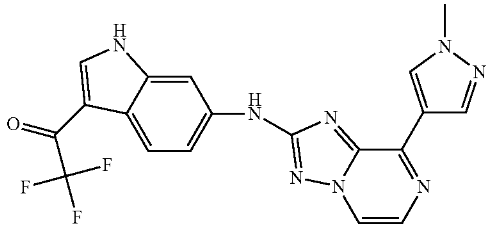 [SMILES: Cn1cc(-c2nccn3nc(Nc4ccc5c(C(=O)C(F)(F)F)c[nH]c5c4)nc23)cn1]

8-(1-Methyl-1H-pyrazol-4-yl)-[1,2,4]triazolo[1,5-a]pyrazin-2-ylamine is reacted with 1-(6-bromo-1H-indol-3-yl)-2,2,2-trifluoro-ethanone, available by reaction of 6-bromo-1H-indole (1 eq.) with TFA (1.6 eq) in DMF at 120° C. for 1 h, under conditions described in general procedure 2.

LCMS purity (Method D): 100%, Rt: 2.10 min, observed [M+H]=427.1;

$^1$H NMR (500 MHz, DMSO-$d_6$) δ [ppm] 12.65-12.61 (s, 1H), 10.12-10.08 (s, 1H), 8.72-8.67 (m, 2H), 8.45-8.37 (m, 2H), 8.26-8.21 (d, J=1.9 Hz, 1H), 8.11-8.05 (m, 2H), 7.58-7.51 (m, 1H), 4.03-3.99 (s, 3H).

1,1,1-trifluoro-2-{6-[8-(1-methyl-1H-pyrazol-4-yl)-[1,2,4]triazolo[1,5-a]pyrazin-2-ylamino]-1H-indol-3-yl}-propan-2-ol ("C113")

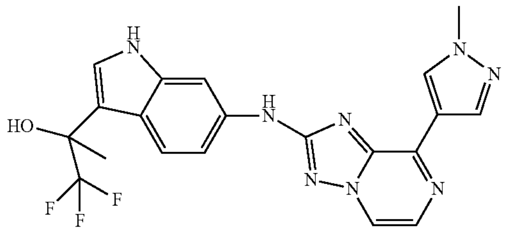 [SMILES: Cn1cc(-c2nccn3nc(Nc4ccc5c(C(C)(O)C(F)(F)F)c[nH]c5c4)nc23)cn1]

1-(6-Bromo-1H-indol-3-yl)-2,2,2-trifluoro-ethanone is treated with methylmagnesiumchloride at −78° C. to rt to obtain 2-(6-bromo-1H-indol-3-yl)-1,1,1-trifluoro-propan-2-ol, which is coupled with 8-(1-methyl-1H-pyrazol-4-yl)-[1,2,4]triazolo[1,5-a]pyrazin-2-ylamine following general procedure 2.

LCMS purity (Method D): 100%, Rt: 1.92 min, observed [M+H]=443.1;

$^1$H NMR (500 MHz, DMSO-$d_6$) δ [ppm] 11.08-11.03 (d, J=2.5 Hz, 1H), 9.77-9.73 (s, 1H), 8.70-8.64 (m, 2H), 8.43-8.39 (d, J=0.7 Hz, 1H), 8.19-8.15 (s, 1H), 8.06-8.02 (d, J=4.3 Hz, 1H), 8.01-7.97 (d, J=1.9 Hz, 1H), 7.70-7.65 (d, J=8.6 Hz, 1H), 7.27-7.19 (m, 2H), 6.26-6.22 (s, 1H), 4.02-3.98 (s, 3H), 1.77-1.73 (s, 3H).

4,4-dimethyl-7-[8-(1-methyl-1H-pyrazol-4-yl)-[1,2,4]triazolo[1,5-a]pyrazin-2-ylamino]-1,4-dihydro-benzo[d][1,3]oxazin-2-one ("C114")

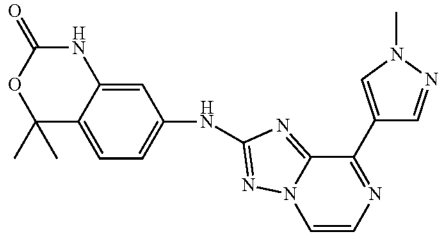 [SMILES: Cn1cc(-c2nccn3nc(Nc4ccc5c(c4)NC(=O)OC5(C)C)nc23)cn1]

7-Bromo-4,4-dimethyl-1,4-dihydro-benzo[d][1,3]oxazin-2-one is obtained by reaction of 2-(2-amino-4-bromo-phenyl)-propan-2-ol (1 eq.) with 1,1'-carbonyldiimidazole (2 eq) in THF at rt for 16 h. The intermediate is isolated and coupled with 8-(1-methyl-1H-pyrazol-4-yl)-[1,2,4]triazolo[1,5-a]pyrazin-2-ylamine following general procedure 2.

LCMS purity (Method C): 100%, Rt: 1.81 min, observed [M+H]=391.2;

$^1$H NMR (500 MHz, DMSO-$d_6$) δ [ppm] 10.28-10.24 (s, 1H), 10.01-9.97 (s, 1H), 8.70-8.63 (m, 2H), 8.42-8.38 (d, J=0.6 Hz, 1H), 8.09-8.04 (d, J=4.3 Hz, 1H), 7.40-7.31 (m, 2H), 7.23-7.17 (d, J=8.4 Hz, 1H), 4.02-3.98 (s, 3H), 1.61-1.57 (s, 6H).

(2,2-dioxo-2,3-dihydro-1H-2I6-benzo[c]isothiazol-5-yl)-[8-(1-methyl-1H-pyrazol-4-yl)-[1,2,4]triazolo[1,5-a]pyrazin-2-yl]-amine ("C115")

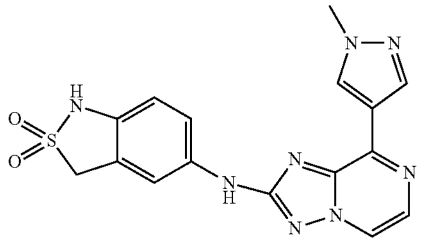 [SMILES: Cn1cc(-c2nccn3nc(Nc4ccc5c(c4)CS(=O)(=O)N5)nc23)cn1]

The title compound is synthesized via amination of 8-(1-methyl-1H-pyrazol-4-yl)-[1,2,4]triazolo[1,5-a]pyrazin-2-ylamine using general procedure 2.

LCMS purity (Method D): 100%, Rt: 1.66 min, observed [M+H]=383.0;

$^1$H NMR (500 MHz, DMSO-$d_6$) δ [ppm] 9.10-9.06 (s, 1H), 8.65-8.61 (m, 2H), 8.37-8.33 (s, 1H), 7.98-7.94 (d, J=4.2 Hz, 1H), 7.31-7.26 (d, J=2.4 Hz, 1H), 7.17-7.11 (m, 1H), 6.28-6.22 (d, J=8.4 Hz, 1H), 4.00-3.96 (s, 3H), 3.73-3.69 (s, 2H).

1,3,3-trimethyl-6-[8-(1-methyl-1H-pyrazol-4-yl)-[1,2,4]triazolo[1,5-a]pyrazin-2-ylamino]-1,3-dihydro-indol-2-one ("C116")

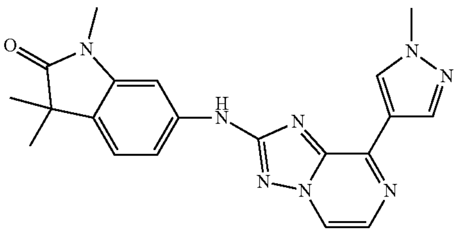 [SMILES: CN1C(=O)C(C)(C)c2ccc(Nc3nc4c(-c5cnn(C)c5)nccn4n3)cc21]

Methylation of "C34" using methyliodide and nButhyllithium gives the title compound as a solid.

LCMS purity (Method C): 100%, Rt: 1.98 min, observed [M+H]=389.2;

$^1$H NMR (500 MHz, DMSO-$d_6$) δ [ppm] 10.01-9.97 (s, 1H), 8.73-8.67 (m, 2H), 8.42-8.38 (s, 1H), 8.10-8.05 (d, J=4.3 Hz, 1H), 7.63-7.59 (d, J=1.8 Hz, 1H), 7.34-7.24 (m, 2H), 4.01-3.97 (s, 3H), 3.22-3.18 (s, 3H), 1.30-1.26 (s, 6H).

(1-methyl-2,2-dioxo-2,3-dihydro-1H-2I6-benzo[c]isothiazol-5-yl)-[8-(1-methyl-1H-pyrazol-4-yl)-[1,2,4]triazolo[1,5-a]pyrazin-2-yl]-amine ("C117")

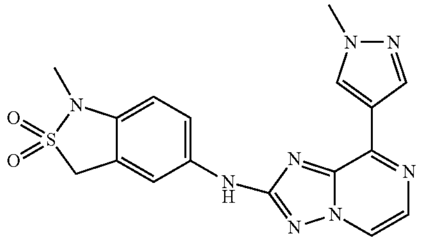 [SMILES: CN1c2ccc(Nc3nc4c(-c5cnn(C)c5)nccn4n3)cc2CS1(=O)=O]

(2,2-Dioxo-2,3-dihydro-1H-2I6-benzo[c]isothiazol-5-yl)-[8-(1-methyl-1H-pyrazol-4-yl)-[1,2,4]triazolo[1,5-a]pyrazin-2-yl]-amine is methylated using MeI and n-butyllithium.

LCMS purity (Method D): 100%, Rt: 1.84 min, observed [M+H]=397.1;

$^1$H NMR (500 MHz, DMSO-$d_6$) δ [ppm] 9.92-9.88 (s, 1H), 8.72-8.64 (m, 2H), 8.39-8.35 (d, J=0.7 Hz, 1H), 8.07-8.02 (d, J=4.3 Hz, 1H), 7.79-7.74 (m, 1H), 7.72-7.65 (dd, J=8.6, 2.3 Hz, 1H), 6.98-6.93 (d, J=8.6 Hz, 1H), 4.72-4.68 (s, 2H), 4.01-3.97 (s, 3H), 3.04-3.00 (s, 3H).

7-[2-(4,4-dimethyl-2-oxo-1,4-dihydro-2H-benzo[d][1,3]oxazin-7-ylamino)-[1,2,4]triazolo[1,5-a]pyrazin-8-yl]-1,3,7-triaza-spiro[4.4]nonane-2,4-dione ("C118")

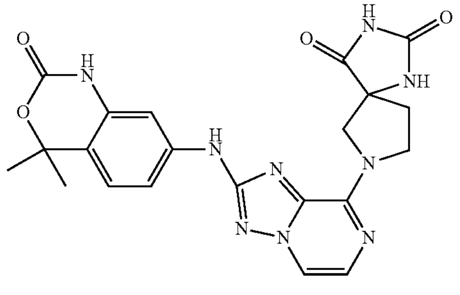 [SMILES: CC1(C)OC(=O)Nc2cc(Nc3nc4c(N5CCC6(C5)NC(=O)NC6=O)nccn4n3)ccc21]

Syntheses of intermediates are described in "C114" and in "C108".

LCMS purity (Method D): 100%, Rt: 1.50 min, observed [M+H]=464.1;

$^1$H NMR (400 MHz, DMSO-$d_6$) δ [ppm] 10.89-10.84 (s, 1H), 10.19-10.14 (s, 1H), 9.73-9.68 (s, 1H), 8.52-8.47 (s, 1H), 8.04-7.98 (d, J=4.4 Hz, 1H), 7.55-7.49 (d, J=4.4 Hz, 1H), 7.30-7.21 (m, 2H), 7.17-7.10 (d, J=8.3 Hz, 1H), 4.14-4.09 (s, 3H), 2.43-2.30 (m, 1H), 2.24-2.13 (m, 1H), 1.59-1.54 (s, 6H), 1.10-1.01 (m, 6H).

4,4-diisopropyl-7-[8-(1-methyl-1H-pyrazol-4-yl)-[1,2,4]triazolo[1,5-a]pyrazin-2-ylamino]-1,4-dihydro-benzo[d][1,3]oxazin-2-one ("C119")

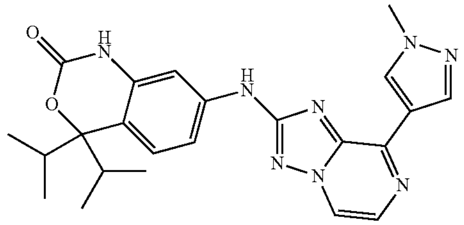 [SMILES: CC(C)C1(C(C)C)OC(=O)Nc2cc(Nc3nc4c(-c5cnn(C)c5)nccn4n3)ccc21]

The title compound is synthesized analogously to "C114". LCMS purity (Method D): 100%, Rt: 2.14 min, observed [M+H]=447.1;

$^1$H NMR (500 MHz, DMSO-$d_6$) δ [ppm] 10.06-10.02 (s, 1H), 10.02-9.98 (s, 1H), 8.70-8.62 (m, 2H), 8.43-8.38 (d, J=0.7 Hz, 1H), 8.09-8.04 (d, J=4.3 Hz, 1H), 7.35-7.29 (m, 2H), 7.07-7.01 (d, J=8.3 Hz, 1H), 4.02-3.98 (s, 3H), 2.41-2.31 (m, 2H), 0.90-0.85 (d, J=6.5 Hz, 6H), 0.84-0.79 (d, J=6.8 Hz, 6H).

7-[8-(1H-indazol-4-yl)-[1,2,4]triazolo[1,5-a]pyrazin-2-ylamino]-4,4-dimethyl-1,4-dihydro-benzo[d][1,3]oxazin-2-one ("C120")

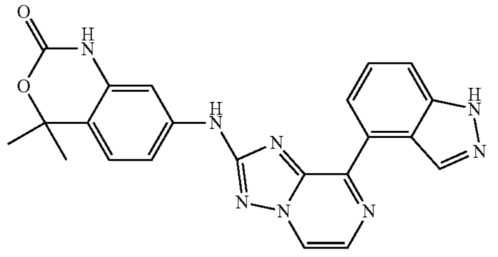 [SMILES: CC1(C)OC(=O)Nc2cc(Nc3nc4c(-c5cccc6[nH]ncc56)nccn4n3)ccc21]

The title compound is synthesized analogously to "C114". LCMS purity (Method C): 100%, Rt: 1.89 min, observed [M+H]=427.2;

$^1$H NMR (500 MHz, DMSO-$d_6$) δ [ppm] 13.32-13.28 (s, 1H), 10.26-10.22 (s, 1H), 10.17-10.13 (s, 1H), 8.97-8.92 (d, J=7.2 Hz, 1H), 8.88-8.82 (m, 2H), 8.40-8.35 (d, J=4.2 Hz, 1H), 7.80-7.74 (d, J=8.3 Hz, 1H), 7.63-7.56 (m, 1H), 7.46-7.40 (m, 1H), 7.34-7.30 (d, J=2.1 Hz, 1H), 7.25-7.19 (d, J=8.4 Hz, 1H), 1.63-1.59 (s, 6H).

6-[8-(2,4-dihydroxy-7,8-dihydro-5H-pyrido[4,3-d]pyrimidin-6-yl)-[1,2,4]triazolo[1,5-a]pyrazin-2-ylamino]-3,3-dimethyl-1,3-dihydro-indol-2-one ("C121")

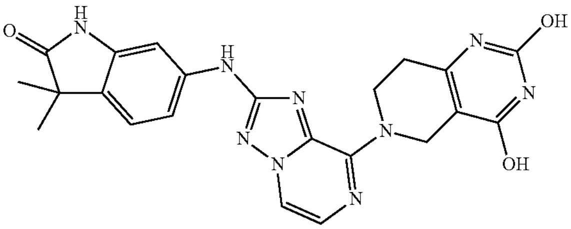 [SMILES: CC1(C)C(=O)Nc2cc(Nc3nc4c(N5CCc6nc(O)nc(O)c6C5)nccn4n3)ccc21]

LCMS purity (Method C): 100%, Rt: 1.66 min, observed [M+H]=460.2;

$^1$H NMR (400 MHz, DMSO-$d_6$) δ [ppm] 11.09-11.04 (s, 1H), 10.89-10.84 (s, 1H), 10.21-10.16 (s, 1H), 9.73-9.68 (s, 1H), 8.18-8.11 (d, J=4.3 Hz, 1H), 7.61-7.55 (d, J=4.4 Hz, 1H), 7.36-7.30 (d, J=2.0 Hz, 1H), 7.26-7.18 (m, 1H), 7.17-7.10 (m, 1H), 4.75-4.70 (s, 2H), 4.37-4.32 (s, 1H), 2.65-2.57 (m, 2H), 1.25-1.20 (s, 6H).

1-[2-(3,3-dimethyl-2-oxo-2,3-dihydro-1H-indol-6-ylamino)-[1,2,4]triazolo[1,5-a]pyrazin-8-yl]-pyrrolidine-3-carboxylic acid methyl ester ("C122")

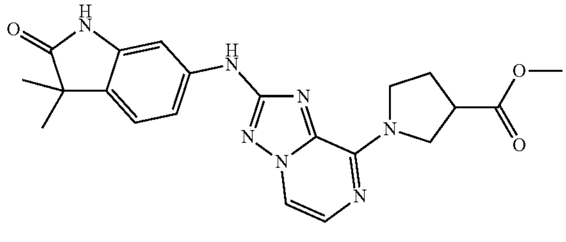 [SMILES: COC(=O)C1CCN(c2nccn3nc(Nc4ccc5c(c4)NC(=O)C5(C)C)nc23)C1]

LCMS purity (Method C): 100%, Rt: 1.64 min, observed [M+H]=422.2;

$^1$H NMR (400 MHz, DMSO-$d_6$) δ [ppm] 10.29-10.24 (s, 1H), 9.62-9.57 (s, 1H), 8.01-7.95 (d, J=4.4 Hz, 1H), 7.52-7.45 (d, J=4.4 Hz, 1H), 7.33-7.27 (d, J=1.9 Hz, 1H), 7.24-7.17 (m, 1H), 7.16-7.09 (m, 1H), 4.21-4.16 (s, 1H), 4.11-4.06 (s, 1H), 4.01-3.96 (s, 1H), 3.93-3.88 (s, 1H), 3.38-3.31 (d, J=7.1 Hz, 1H), 2.35-2.22 (m, 1H), 2.22-2.13 (m, 1H), 1.25-1.20 (s, 6H).

1-[2-(3,3-dimethyl-2-oxo-2,3-dihydro-1H-indol-6-ylamino)-[1,2,4]triazolo[1,5-a]pyrazin-8-yl]-pyrrolidine-3-carboxylic acid amide ("C123")

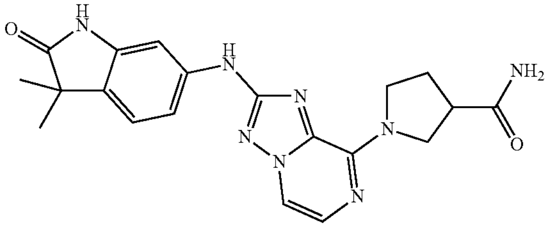 [SMILES: CC1(C)C(=O)Nc2cc(Nc3nc4c(N5CCC(C(N)=O)C5)nccn4n3)ccc21]

LCMS purity (Method C): 100%, Rt: 1.64 min, observed [M+H]=422.2;

$^1$H NMR (400 MHz, DMSO-$d_6$) δ [ppm] 10.29-10.24 (s, 1H), 9.62-9.57 (s, 1H), 8.01-7.95 (d, J=4.4 Hz, 1H), 7.52-7.45 (d, J=4.4 Hz, 1H), 7.33-7.27 (d, J=1.9 Hz, 1H), 7.24-7.17 (m, 1H), 7.16-7.09 (m, 1H), 4.21-4.16 (s, 1H), 4.11-4.06 (s, 1H), 4.01-3.96 (s, 1H), 3.93-3.88 (s, 1H), 3.38-3.31 (d, J=7.1 Hz, 1H), 2.35-2.22 (m, 1H), 2.22-2.13 (m, 1H), 1.25-1.20 (s, 6H).

1-[2-(3,3-dimethyl-2-oxo-2,3-dihydro-1H-indol-6-ylamino)-[1,2,4]triazolo[1,5-a]pyrazin-8-yl]-pyrrolidine-3-carboxylic acid cyclopropylamide ("C124")

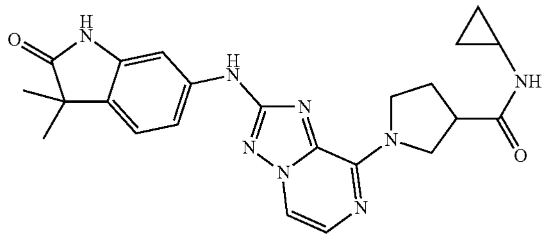 [SMILES: CC1(C)C(=O)Nc2cc(Nc3nc4c(N5CCC(C(=O)NC6CC6)C5)nccn4n3)ccc21]

LCMS purity (Method C): 100%, Rt: 1.54 min, observed [M+H]=447.2;

$^1$H NMR (500 MHz, DMSO-$d_6$) δ [ppm] 10.30-10.26 (s, 1H), 9.59-9.55 (s, 1H), 8.15-8.10 (d, J=4.3 Hz, 1H), 7.97-7.92 (d, J=4.4 Hz, 1H), 7.50-7.45 (d, J=4.4 Hz, 1H), 7.32-7.27 (d, J=2.0 Hz, 1H), 7.23-7.17 (m, 1H), 7.16-7.10 (m, 1H), 3.04-2.97 (t, J=7.7 Hz, 1H), 2.70-2.63 (m, 1H), 2.20-2.04 (m, 2H), 1.24-1.20 (s, 6H), 0.67-0.60 (m, 2H), 0.46-0.39 (m, 2H).

6-[8-((2R,4S)-4-hydroxy-2-phenyl-pyrrolidin-1-yl)-[1,2,4]triazolo[1,5-a]pyrazin-2-ylamino]-3,3-dimethyl-1,3-dihydro-indol-2-one ("C125")

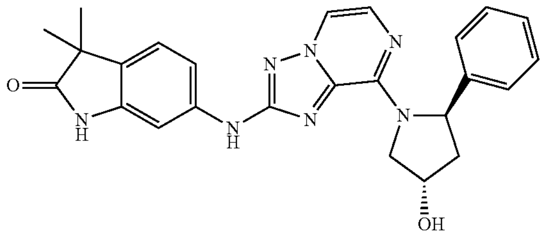 [SMILES: CC1(C)C(=O)Nc2cc(Nc3nc4c(N5C[C@@H](O)C[C@@H]5c5ccccc5)nccn4n3)ccc21]

LCMS purity (Method C): 100%, Rt: 1.87 min, observed [M+H]=456.2;

$^1$H NMR (400 MHz, DMSO-$d_6$) δ [ppm] 10.31-10.26 (s, 1H), 9.59-9.54 (s, 1H), 7.97-7.91 (d, J=4.4 Hz, 1H), 7.40-7.33 (m, 1H), 7.33-7.10 (m, 8H), 5.11-5.05 (d, J=3.7 Hz, 1H), 4.46-4.39 (m, 1H), 4.36-4.31 (s, 2H), 2.47-2.36 (m, 1H), 2.03-1.92 (m, 1H), 1.26-1.21 (s, 6H).

6-[8-((2R,4R)-4-hydroxy-2-phenyl-pyrrolidin-1-yl)-[1,2,4]triazolo[1,5-a]pyrazin-2-ylamino]-3,3-dimethyl-1,3-dihydro-indol-2-one ("C126")

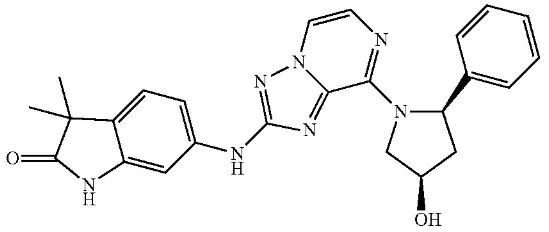 [SMILES: CC1(C)C(=O)Nc2cc(Nc3nc4c(N5C[C@H](O)C[C@@H]5c5ccccc5)nccn4n3)ccc21]

LCMS purity (Method D): 100%, Rt: 1.83 min, observed [M+H]=456.3; $^1$H NMR (400 MHz, DMSO-$d_6$) δ [ppm] 10.29-10.24 (s, 1H), 9.57-9.52 (s, 1H), 7.97-7.91 (d, J=4.4 Hz, 1H), 7.40-7.34 (d, J=4.5 Hz, 1H), 7.32-7.18 (m, 6H), 7.16-7.08 (m, 2H), 4.56-4.51 (s, 1H), 4.48-4.41 (m, 1H), 4.15-4.10 (s, 1H), 2.73-2.61 (m, 1H), 1.93-1.85 (m, 1H), 1.25-1.20 (s, 6H).

7-[2-(4,4-dimethyl-2-oxo-1,2,3,4-tetrahydro-quinolin-7-ylamino)-[1,2,4]triazolo[1,5-a]pyrazin-8-yl]-2,7-diaza-spiro[4.4]nonane-1,3-dione ("C127")

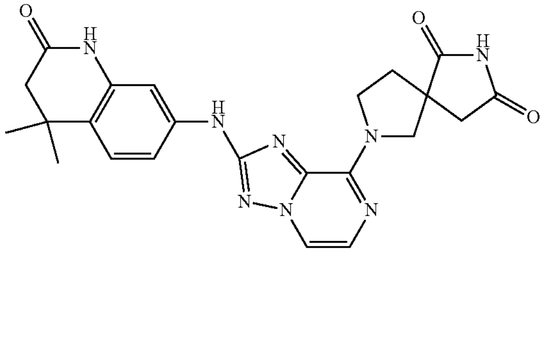 [SMILES: CC1(C)CC(=O)Nc2cc(Nc3nc4c(N5CCC6(CC(=O)NC6=O)C5)nccn4n3)ccc21]

LCMS purity (Method C): 100%, Rt: 1.56 min, observed [M+H]=461.2;

$^1$H NMR (500 MHz, DMSO-$d_6$) δ [ppm] 11.33-11.29 (s, 1H), 10.12-10.08 (s, 1H), 9.57-9.53 (s, 1H), 7.99-7.94 (d, J=4.4 Hz, 1H), 7.51-7.46 (d, J=4.4 Hz, 1H), 7.35-7.31 (s, 2H), 7.27-7.11 (m, 7H), 3.11-3.02 (m, 2H), 2.89-2.81 (m, 1H), 2.81-2.73 (m, 1H), 2.33-2.29 (s, 2H), 1.23-1.16 (m, 6H).

6'-[[8-(1-methylpyrazol-4-yl)-[1,2,4]triazolo[1,5-a]pyrazin-2-yl]amino]spiro[cyclobutane-1,3'-indoline]-2'-one ("C128")

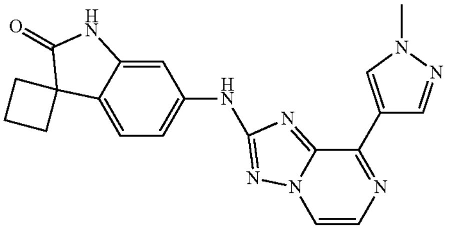 [SMILES: Cn1cc(-c2nccn3nc(Nc4ccc5c(c4)NC(=O)C54CCC4)nc23)cn1]

LCMS purity (Method D): 100%, Rt: 1.91 min, observed [M+H]=387.1;

$^1$H NMR (400 MHz, DMSO-$d_6$) δ [ppm] 10.09-10.04 (s, 1H), 9.76-9.71 (s, 1H), 8.52-8.45 (m, 2H), 8.23-8.18 (s, 1H), 7.90-7.84 (d, J=4.3 Hz, 1H), 7.32-7.25 (d, J=8.1 Hz, 1H), 7.20-7.10 (m, 2H), 3.84-3.79 (s, 3H), 3.13-3.08 (s, 3H), 2.35-2.19 (m, 4H), 2.15-1.95 (m, 3H). [8-(2,7-diaza-spiro[4.4]non-2-yl)-[1,2,4]triazolo[1,5-a]pyrazin-2-yl]-(4,4-dimethyl-1,2,3,4-tetrahydro-quinolin-7-yl)-amine ("C129")

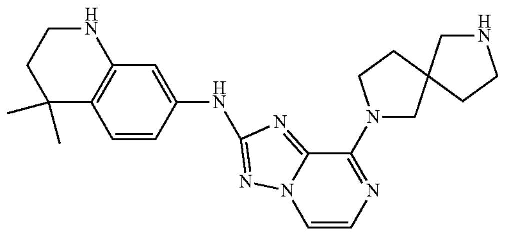 [SMILES: CC1(C)CCNc2cc(Nc3nc4c(N5CCC6(CCNC6)C5)nccn4n3)ccc21]

LCMS purity (Method C): 100%, Rt: 1.38 min, observed [M+H]=419.2.

6-[8-(1,4-dioxa-7-aza-spiro[4.4]non-7-yl)-[1,2,4]triazolo[1,5-a]pyrazin-2-ylamino]-3,3-dimethyl-1,3-dihydro-indol-2-one ("C130")

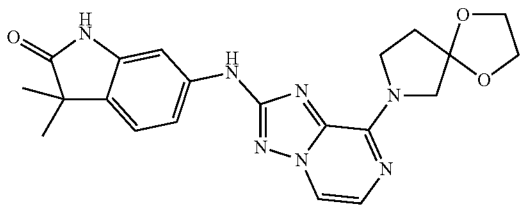 [SMILES: CC1(C)C(=O)Nc2cc(Nc3nc4c(N5CCC6(C5)OCCO6)nccn4n3)ccc21]

LCMS purity (Method C): 100%, Rt: 1.65 min, observed [M+H]=422.2;

$^1$H NMR (500 MHz, DMSO-$d_6$) δ [ppm] 10.30-10.26 (s, 1H), 9.61-9.57 (s, 1H), 8.02-7.97 (d, J=4.4 Hz, 1H), 7.51-7.46 (d, J=4.4 Hz, 1H), 7.31-7.26 (d, J=2.0 Hz, 1H), 7.22-7.17 (d, J=2.0 Hz, 1H), 7.16-7.10 (d, J=8.1 Hz, 1H), 4.00-3.95 (m, 4H), 3.20-3.15 (d, J=5.2 Hz, 3H), 2.20-2.13 (m, 2H), 1.24-1.20 (s, 6H).

N-{1-[2-(3,3-dimethyl-2-oxo-2,3-dihydro-1H-indol-6-ylamino)-[1,2,4]triazolo[1,5-a]pyrazin-8-yl]-pyrrolidin-3-yl}-N-methyl-acetamide ("C131")

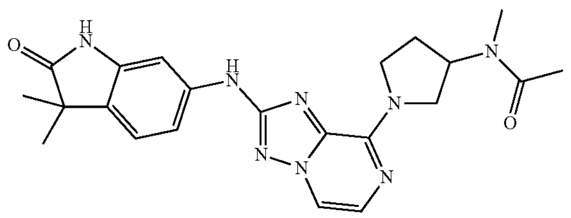 [SMILES: CC(=O)N(C)C1CCN(c2nccn3nc(Nc4ccc5c(c4)NC(=O)C5(C)C)nc23)C1]

LCMS purity (Method C): 100%, Rt: 1.52 min, observed [M+H]=435.2;

$^1$H NMR (500 MHz, DMSO-$d_6$) δ [ppm] 10.29-10.25 (s, 1H), 9.61-9.57 (s, 1H), 8.02-7.96 (m, 1H), 7.52-7.47 (m, 1H), 7.32-7.25 (m, 1H), 7.22-7.16 (m, 1H), 7.16-7.10 (m, 1H), 5.17-5.08 (m, 1H), 4.17-4.13 (s, 2H), 3.81-3.77 (s, 2H), 3.20-3.15 (d, J=5.2 Hz, 1H), 2.95-2.91 (s, 2H), 2.80-2.76 (s, 1H), 2.23-2.17 (d, J=8.7 Hz, 1H), 2.15-2.03 (m, 5H), 1.24-1.20 (s, 6H).

6-[8-(1-methyl-1H-pyrazol-4-yl)-[1,2,4]triazolo[1,5-a]pyrazin-2-ylamino]-pyridine-3-sulfonic acid amide ("C132")

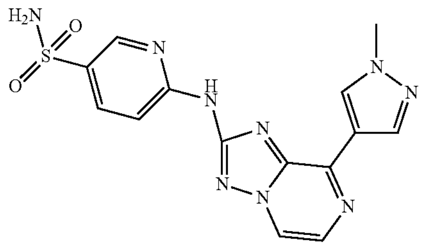 [SMILES: Cn1cc(-c2nccn3nc(Nc4ccc(S(N)(=O)=O)cn4)nc23)cn1]

LCMS purity (Method C): 100%, Rt: 1.49 min, observed [M+H]=372.2;

$^1$H NMR (500 MHz, DMSO-$d_6$) δ [ppm] 11.03-10.99 (s, 1H), 8.80-8.75 (d, J=4.3 Hz, 1H), 8.73-8.64 (m, 2H), 8.43-8.39 (d, J=0.7 Hz, 1H), 8.32-8.26 (m, 1H), 8.25-8.18 (m, 1H), 8.16-8.11 (d, J=4.4 Hz, 1H), 7.41-7.37 (s, 2H), 4.03-3.99 (s, 3H).

8-[2-(3,3-dimethyl-2-oxo-2,3-dihydro-1H-indol-6-ylamino)-[1,2,4]triazolo[1,5-a]pyrazin-8-yl]-2,8-diaza-spiro[4.5]decan-1-one ("C133")

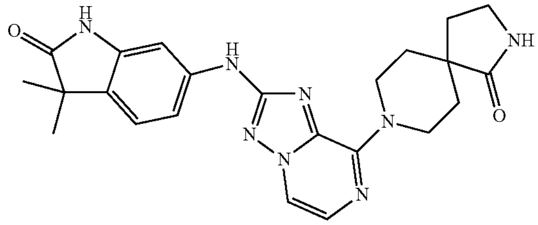 [SMILES: CC1(C)C(=O)Nc2cc(Nc3nc4c(N5CCC6(CCNC6=O)CC5)nccn4n3)ccc21]

LCMS purity (Method C): 100%, Rt: 1.62 min, observed [M+H]=447.2;

$^1$H NMR (500 MHz, DMSO-$d_6$) δ [ppm] 10.31-10.27 (s, 1H), 9.67-9.63 (s, 1H), 8.11-8.06 (d, J=4.3 Hz, 1H), 7.60-7.53

(m, 2H), 7.31-7.26 (d, J=1.9 Hz, 1H), 7.22-7.11 (m, 2H), 4.98-4.91 (m, 1H), 3.46-3.35 (m, 3H), 2.12-2.05 (m, 2H), 1.80-1.70 (m, 2H), 1.53-1.46 (d, J=13.6 Hz, 1H), 1.24-1.20 (s, 6H).

6-{8-[(1-acetyl-piperidin-4-yl)-methyl-amino]-[1,2,4]triazolo[1,5-a]pyrazin-2-ylamino}-3,3-dimethyl-1,3-dihydro-indol-2-one ("C134")

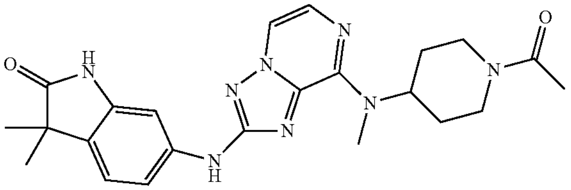 [SMILES: CC(=O)N1CCC(N(C)c2nccn3nc(Nc4ccc5c(c4)NC(=O)C5(C)C)nc23)CC1]

LCMS purity (Method C): 100%, Rt: 1.67 min, observed [M+H]=449.2;

$^1$H NMR (500 MHz, DMSO-$d_6$) δ [ppm] 10.30-10.26 (s, 1H), 9.57-9.53 (s, 1H), 8.07-8.02 (d, J=4.3 Hz, 1H), 7.57-7.52 (d, J=4.3 Hz, 1H), 7.32-7.26 (dd, J=8.1, 2.0 Hz, 1H), 7.23-7.19 (d, J=2.0 Hz, 1H), 7.18-7.12 (d, J=8.1 Hz, 1H), 5.39-5.35 (s, 1H), 4.63-4.55 (m, 1H), 4.01-3.94 (m, 1H), 3.29-3.25 (s, 3H), 3.21-3.11 (m, 1H), 2.67-2.50 (m, 2H), 2.10-2.04 (m, 3H), 1.88-1.74 (m, 3H), 1.72-1.64 (dd, J=12.2, 4.5 Hz, 2H), 1.27-1.21 (s, 7H).

6-{8-[5-((R)-1-amino-ethyl)-2-methoxy-phenyl]-[1,2,4]triazolo[1,5-a]pyrazin-2-ylamino}-3,3-dimethyl-1,3-dihydro-indol-2-one ("C135")

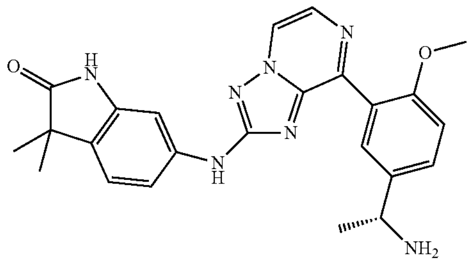 [SMILES: COc1ccc([C@@H](C)N)cc1-c1nccn2nc(Nc3ccc4c(c3)NC(=O)C4(C)C)nc12]

LCMS purity (Method C): 100%, Rt: 1.49 min, observed [M+H]=444.2;

$^1$H NMR (500 MHz, DMSO-$d_6$) δ [ppm] 10.33-10.29 (s, 1H), 9.90-9.86 (s, 1H), 8.91-8.86 (d, J=4.3 Hz, 1H), 8.56-8.51 (d, J=5.6 Hz, 3H), 8.20-8.15 (d, J=4.3 Hz, 1H), 7.73-7.67 (m, 1H), 7.63-7.58 (d, J=2.5 Hz, 2H), 7.43-7.39 (s, 4H), 7.32-7.18 (m, 11H), 7.17-7.11 (d, J=7.9 Hz, 1H), 4.45-4.40 (d, J=6.2 Hz, 1H), 3.81-3.77 (s, 3H), 3.19-3.15 (s, 4H), 1.57-1.52 (d, J=6.8 Hz, 3H), 1.24-1.20 (s, 6H).

(R)-7-[2-(3,3-dimethyl-2-oxo-2,3-dihydro-1H-indol-6-ylamino)-[1,2,4]triazolo[1,5-a]pyrazin-8-yl]-2,7-diaza-spiro[4.4]nonane-1,3-dione ("C136")

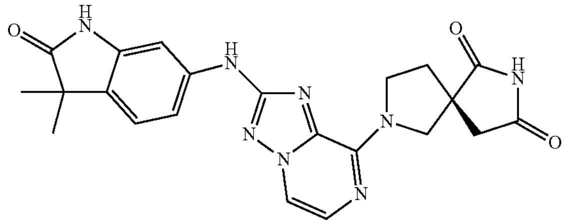 [SMILES: CC1(C)C(=O)Nc2cc(Nc3nc4c(N5CC[C@@]6(CC(=O)NC6=O)C5)nccn4n3)ccc21]

Single enantiomere of "C95"; separation via chiral LCMS chromatography. Absolut configuration not determined.

(S)-7-[2-(3,3-dimethyl-2-oxo-2,3-dihydro-1H-indol-6-ylamino)-[1,2,4]triazolo[1,5-a]pyrazin-8-yl]-2,7-diaza-spiro[4.4]nonane-1,3-dione ("C137")

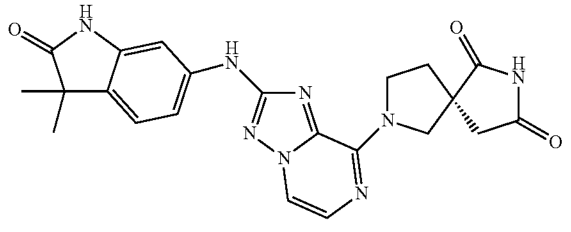 [SMILES: CC1(C)C(=O)Nc2cc(Nc3nc4c(N5CC[C@]6(CC(=O)NC6=O)C5)nccn4n3)ccc21]

Single enantiomere of "C95"; separation via chiral LCMS chromatography. Absolut configuration not determined.

3,3-dimethyl-6-[8-(methyl-piperidin-4-yl-amino)-[1,2,4]triazolo[1,5-a]pyrazin-2-ylamino]-1,3-dihydro-indol-2-one ("C138")

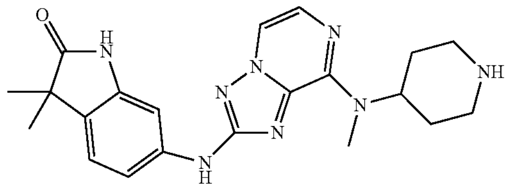 [SMILES: CN(c1nccn2nc(Nc3ccc4c(c3)NC(=O)C4(C)C)nc12)C1CCNCC1]

LCMS purity (Method C): 100%, Rt: 1.40 min, observed [M+H]=407.2;

$^1$H NMR (400 MHz, DMSO-d$_6$) δ [ppm] 10.33-10.28 (s, 1H), 9.60-9.55 (s, 1H), 8.40-8.35 (s, 1H), 8.08-8.02 (d, J=4.3 Hz, 1H), 7.57-7.51 (d, J=4.3 Hz, 1H), 7.34-7.26 (m, 1H), 7.25-7.20 (d, J=2.0 Hz, 1H), 7.19-7.12 (d, J=8.1 Hz, 1H), 5.34-5.29 (s, 1H), 2.91-2.80 (m, 2H), 2.55-2.43 (m, 2H), 1.86-1.78 (d, J=12.1 Hz, 2H), 1.26-1.21 (s, 6H).

6-[8-(6-oxo-2,7-diaza-spiro[4.4]non-2-yl)-[1,2,4]triazolo[1,5-a]pyrazin-2-ylamino]-1,3-dihydro-indol-2-one ("C139")

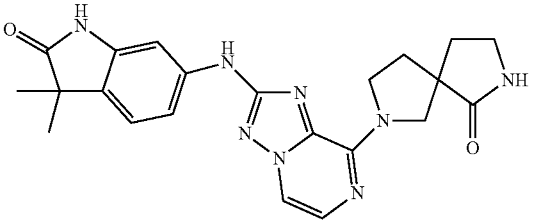 [SMILES: CC1(C)C(=O)Nc2cc(Nc3nc4c(N5CCC6(CCNC6=O)C5)nccn4n3)ccc21]

LCMS purity (Method C): 100%, Rt: 1.60 min, observed [M+H]=433.2.

3,3-dimethyl-6-[8-(8-oxo-2,7-diaza-spiro[4.4]non-2-yl)-[1,2,4]triazolo[1,5-a]pyrazin-2-ylamino]-1,3-dihydro-indol-2-one ("C140")

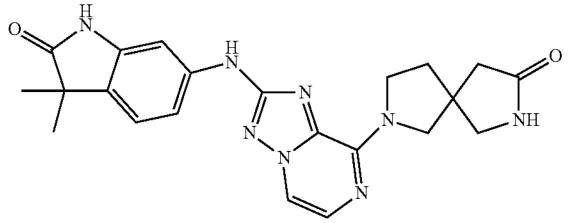 [SMILES: CC1(C)C(=O)Nc2cc(Nc3nc4c(N5CCC6(CNC(=O)C6)C5)nccn4n3)ccc21]

LCMS purity (Method C): 100%, Rt: 1.45 min, observed [M+H]=433.2.

2,4-dimethyl-3-{6-[8-(1-methyl-1H-pyrazol-4-yl)-[1,2,4]triazolo[1,5-a]pyrazin-2-ylamino]-1H-indazol-3-yl}-pentan-3-ol ("C141")

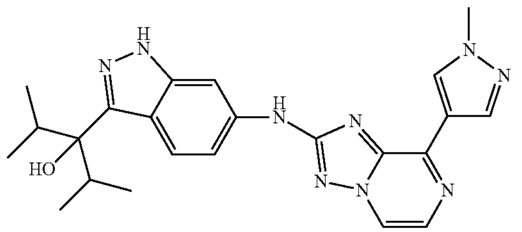 [SMILES: CC(C)C(O)(c1n[nH]c2cc(Nc3nc4c(-c5cnn(C)c5)nccn4n3)ccc12)C(C)C]

LCMS purity (Method C): 100%, Rt: 1.98 min, observed [M+H]=446.2;

$^1$H NMR (500 MHz, DMSO-d$_6$) δ [ppm] 12.53-12.49 (s, 1H), 10.02-9.98 (s, 1H), 8.73-8.67 (m, 2H), 8.44-8.40 (d, J=0.7 Hz, 1H), 8.10-8.03 (m, 2H), 7.98-7.92 (d, J=8.8 Hz, 1H), 7.19-7.13 (dd, J=8.9, 1.9 Hz, 1H), 4.34-4.30 (s, 1H), 4.03-3.99 (s, 3H), 2.38-2.21 (m, 2H), 0.86-0.81 (d, J=6.7 Hz, 6H), 0.81-0.76 (d, J=6.7 Hz, 6H).

2-methyl-1-{6-[8-(1-methyl-1H-pyrazol-4-yl)-[1,2,4]triazolo[1,5-a]pyrazin-2-ylamino]-1H-indazol-3-yl}-propan-1-ol ("C142")

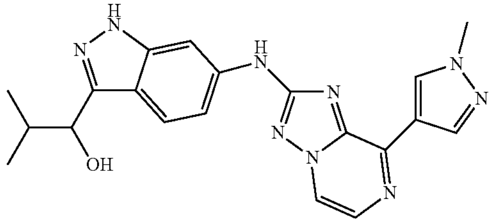 [SMILES: CC(C)C(O)c1n[nH]c2cc(Nc3nc4c(-c5cnn(C)c5)nccn4n3)ccc12]

LCMS purity (Method D): 100%, Rt: 1.77 min, observed [M+H]=404.1;

$^1$H NMR (500 MHz, DMSO-d$_6$) δ [ppm] 12.51-12.47 (s, 1H), 10.07-10.03 (s, 1H), 8.74-8.67 (m, 2H), 8.44-8.40 (s, 1H), 8.12-8.05 (m, 2H), 7.79-7.73 (d, J=8.7 Hz, 1H), 7.25-7.19 (dd, J=8.8, 1.9 Hz, 1H), 5.21-5.16 (d, J=4.5 Hz, 1H), 4.56-4.50 (m, 1H), 4.03-3.99 (s, 3H), 2.20-2.09 (m, 1H), 1.04-0.99 (d, J=6.6 Hz, 3H), 0.78-0.72 (d, J=6.8 Hz, 3H).

6-[8-(4-hydroxy-2-phenyl-pyrrolidin-1-yl)-[1,2,4]triazolo[1,5-a]pyrazin-2-ylamino]-3,3-dimethyl-1,3-dihydro-indol-2-one ("C143")

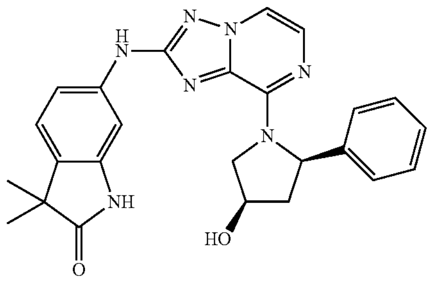 [SMILES: CC1(C)C(=O)Nc2cc(Nc3nc4c(N5C[C@H](O)C[C@@H]5c5ccccc5)nccn4n3)ccc21]

LCMS purity (Method C): 100%, Rt: 1.82 min, observed [M+H]=456.2; (mixture of cis isomers);

$^1$H NMR (500 MHz, DMSO-d$_6$) δ [ppm] 10.28-10.24 (s, 1H), 9.57-9.53 (s, 1H), 8.16-8.12 (s, 1H), 7.96-7.91 (d, J=4.4

Hz, 1H), 7.39-7.34 (d, J=4.4 Hz, 1H), 7.32-7.18 (m, 6H), 7.15-7.07 (m, 2H), 5.64-5.60 (s, 1H), 5.01-4.96 (m, 1H), 4.58-4.50 (s, 1H), 4.48-4.40 (m, 1H), 4.15-4.11 (s, 1H), 3.19-3.15 (s, 1H), 2.71-2.62 (m, 1H), 1.92-1.86 (m, 1H), 1.25-1.21 (d, J=1.5 Hz, 6H).

4,4-dimethyl-7-[8-(1-methyl-1H-pyrazol-4-yl)-[1,2,4]triazolo[1,5-a]pyrazin-2-ylamino]-3,4-dihydro-1H-quinolin-2-one ("C144")

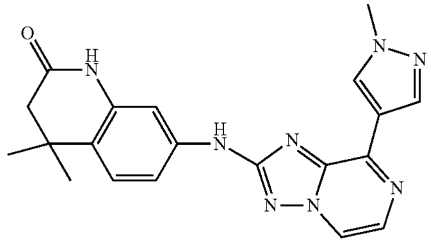 [SMILES: Cn1cc(-c2nccn3nc(Nc4ccc5c(c4)NC(=O)CC5(C)C)nc23)cn1]

LCMS purity (Method C): 100%, Rt: 1.89 min, observed [M+H]=389.2;

$^1$H NMR (500 MHz, DMSO-$d_6$) δ [ppm] 10.23-10.19 (s, 1H), 9.88-9.84 (s, 1H), 8.70-8.62 (m, 2H), 8.42-8.38 (d, J=0.6 Hz, 1H), 8.08-8.03 (d, J=4.3 Hz, 1H), 7.34-7.29 (m, 2H), 7.26-7.20 (d, J=8.1 Hz, 1H), 4.02-3.98 (s, 3H), 2.36-2.32 (s, 2H), 2.11-2.07 (s, 1H), 1.25-1.21 (s, 6H).

The following compounds are obtained analogously to above-mentioned examples

4-[2-(3,5-dimethoxy-phenylamino)-[1,2,4]triazolo[1,5-a]pyrazin-8-yl]-piperazine-1-carboxylic acid tert-butyl ester ("D1");

1-[2-(3,5-dimethoxy-phenylamino)-[1,2,4]triazolo[1,5-a]pyrazin-8-yl]-piperidine-3-carboxylic acid amide ("D2");

(2,3-dimethoxy-phenyl)-[8-(1-methyl-1H-pyrazol-4-yl)-[1,2,4]triazolo[1,5-a]pyrazin-2-yl]-amine ("D3");

{1-[2-(3,5-Dimethoxy-phenylamino)-[1,2,4]triazolo[1,5-a]pyrazin-8-yl]-piperidin-4-yl}-carbamic acid tert-butyl ester ("D4").

The following compounds are obtained analogously

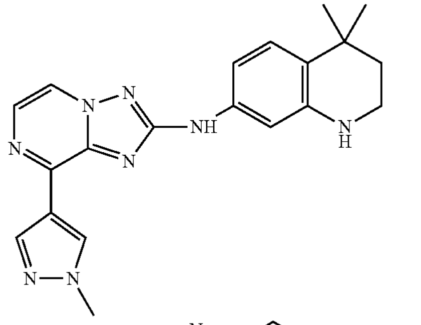

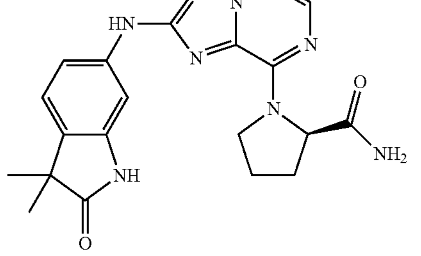

-continued

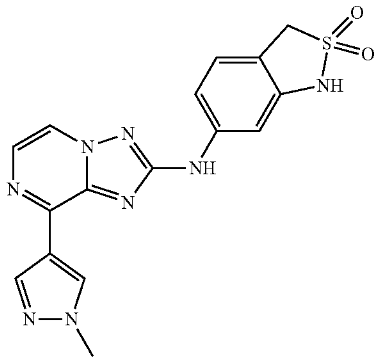

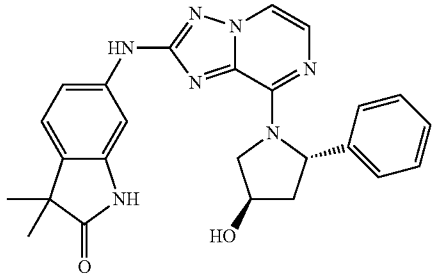

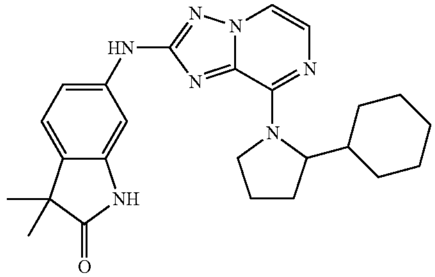

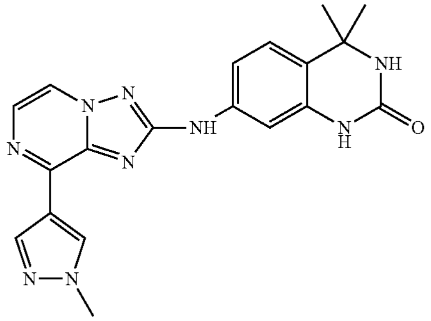

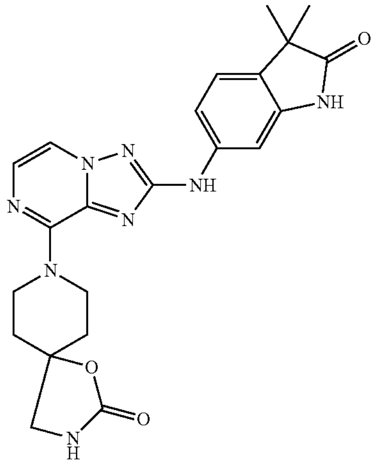

-continued
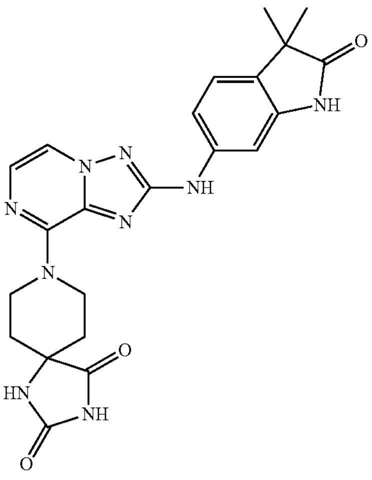
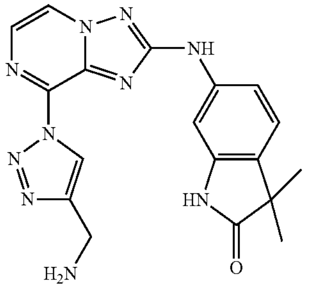
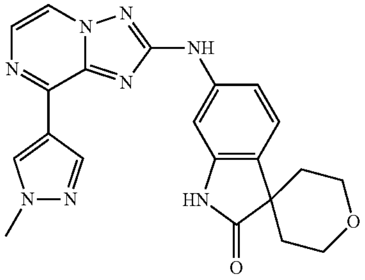
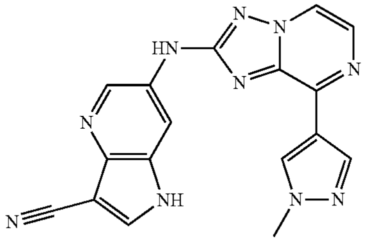
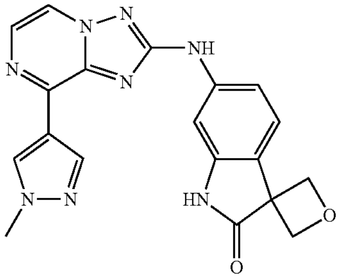
-continued
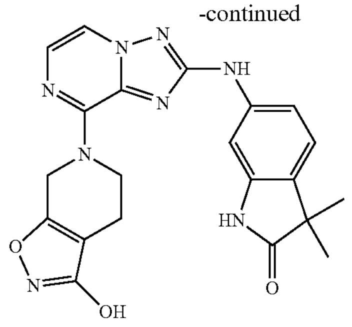
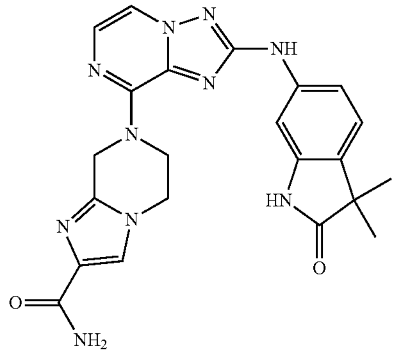
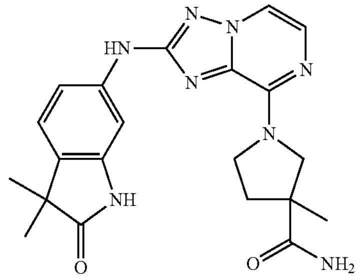
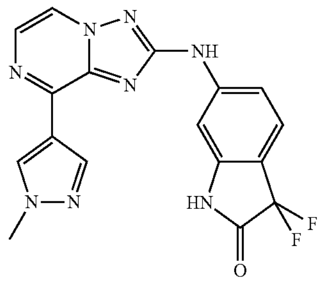
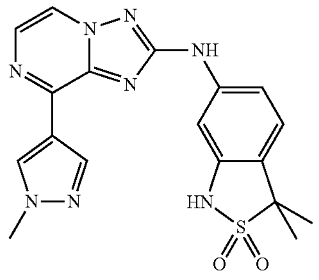

-continued
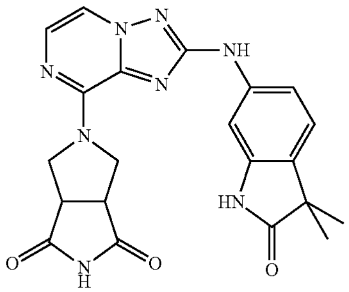
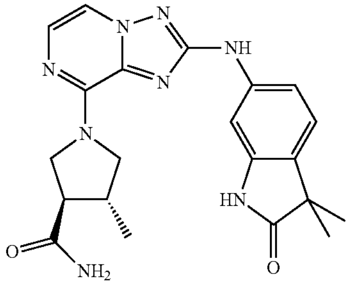
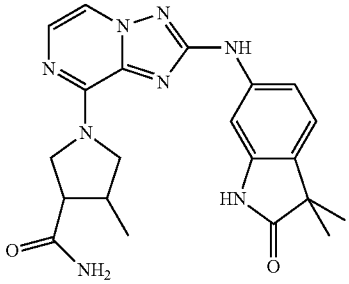
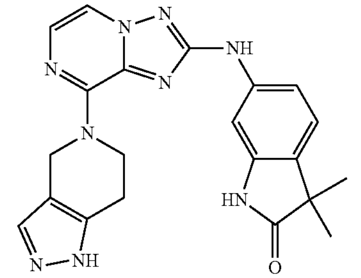
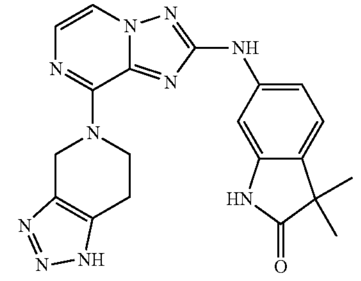
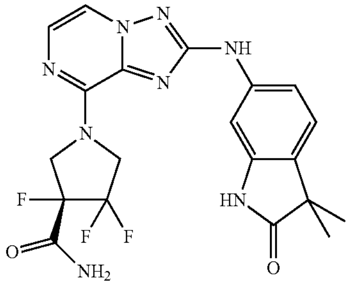
-continued
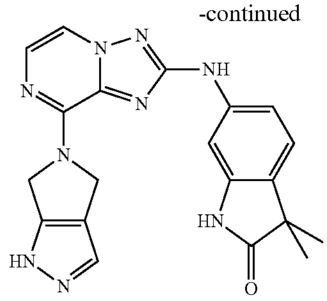
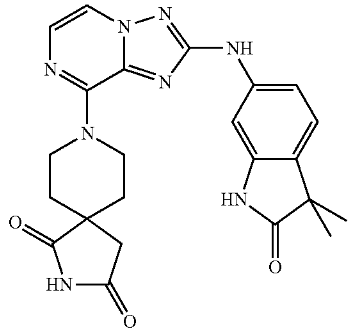
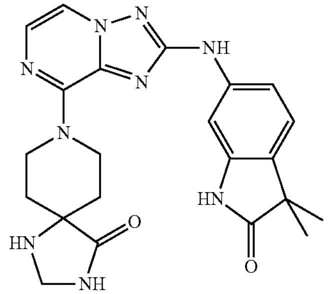
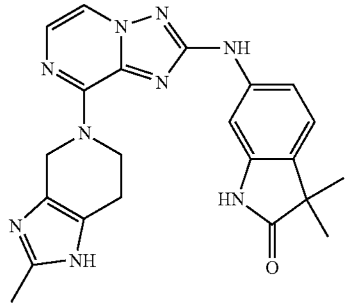
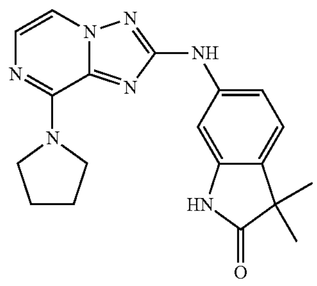

-continued

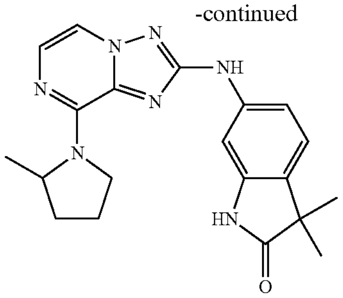

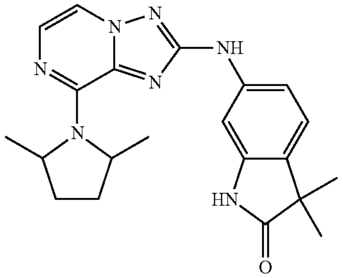

-continued

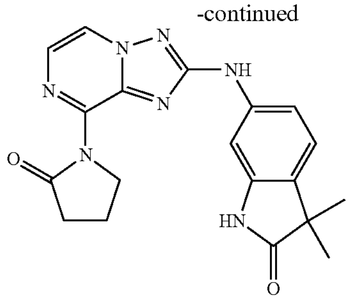

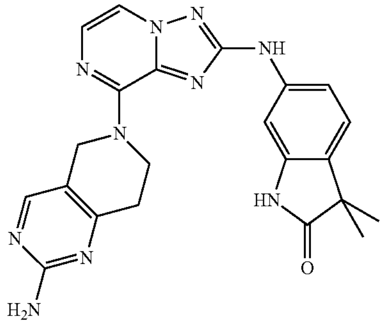

The following compounds are obtained analogously

| nr. | name/structure | LCMS; NMR |
|---|---|---|
| E1 | 6-[8-(2,4-dihydroxy-7,8-dihydro-5H-pyrido[4,3-d]pyrimidin-6-yl)-[1,2,4]triazolo[1,5-a]pyrazin-2-ylamino]-3,3-dimethyl-1,3-dihydro-indol-2-one 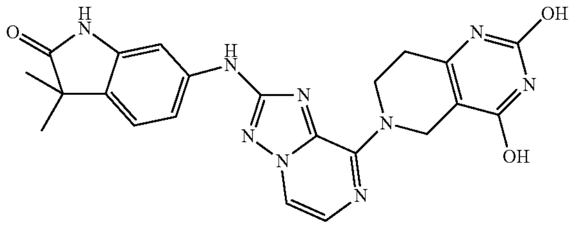 [SMILES: CC1(C)C(=O)Nc2cc(Nc3nc4c(N5CCc6nc(O)nc(O)c6C5)nccn4n3)ccc21] | LCMS (Method C) Rt: 1.688 min, observed [M + H] = 460.2 m/z; $^1$H NMR (400 MHz, DMSO-$d_6$) δ [ppm] 11.07 (s, 1H), 10.86 (s, 1H), 10.19 (s, 1H), 9.70 (s, 1H), 8.14 (d, J = 4.4, 1H), 7.58 (d, J = 4.4, 1H), 7.33 (d, J = 1.9, 1H), 7.22 (dd, J = 8.1, 2.0, 1H), 7.14 (d, J = 8.1, 1H), 4.73 (s, 2H), 4.34 (t, J = 5.8, 2H), 2.61 (t, J = 5.8, 2H), 1.23 (s, 6H) |
| E2 | 1-[2-(3,3-dimethyl-2-oxo-2,3-dihydro-1H-indol-6-ylamino)-[1,2,4]triazolo[1,5-a]pyrazin-8-yl]-pyrrolidine-3-carboxylic acid methyl ester 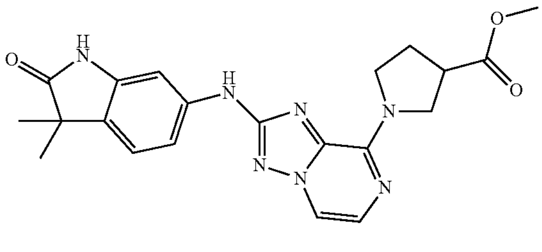 [SMILES: COC(=O)C1CCN(c2nccn3nc(Nc4ccc5c(c4)NC(=O)C5(C)C)nc23)C1] | LCMS (Method C) Rt: 1.636 min, observed [M + H] = 422.2 m/z; $^1$H NMR (400 MHz, DMSO-$d_6$) δ [ppm] 10.27 (s, 1H), 9.59 (s, 1H), 7.98 (d, J = 4.4, 1H), 7.49 (d, J = 4.4, 1H), 7.30 (d, J = 1.9, 1H), 7.21 (dd, J = 8.1, 2.0, 1H), 7.13 (d, J = 8.1, 1H), 4.24-3.86 (m, 4H), 3.67 (s, 3H), 3.38-3.31 (m, 1H), 2.31-2.13 (m, 2H), 1.22 (s, 6H) |

-continued

| nr. | name/structure | LCMS; NMR |
|---|---|---|
| E3 | 1-[2-(3,3-dimethyl-2-oxo-2,3-dihydro-1H-indol-6-ylamino)-[1,2,4]triazolo[1,5-a]pyrazin-8-yl]-pyrrolidine-3-carboxylic acid amide 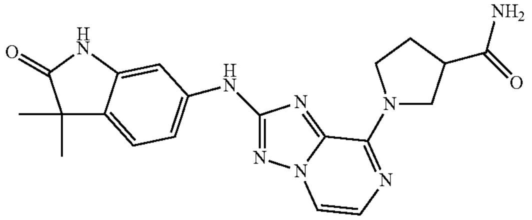 [SMILES: CC1(C)C(=O)Nc2cc(Nc3nc4c(N5CCC(C(N)=O)C5)nccn4n3)ccc21] | LCMS (Method C) Rt: 1.463 min, observed [M + H] = 407.2 m/z. |
| E4 | 1-[2-(3,3-dimethyl-2-oxo-2,3-dihydro-1H-indol-6-ylamino)-[1,2,4]triazolo[1,5-a]pyrazin-8-yl]-pyrrolidine-3-carboxylic acid cyclopropylamide 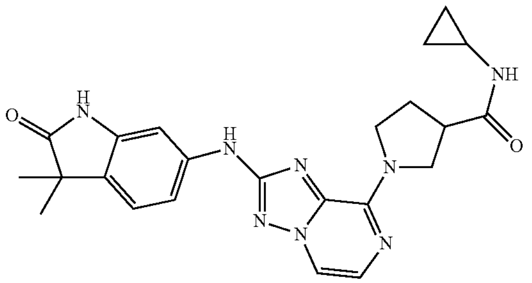 [SMILES: CC1(C)C(=O)Nc2cc(Nc3nc4c(N5CCC(C(=O)NC6CC6)C5)nccn4n3)ccc21] | LCMS (Method C) Rt: 1.569 min, observed [M + H] = 447.3 m/z; $^1$H NMR (500 MHz, DMSO-$d_6$) δ [ppm] 10.28 (s, 1H), 9.57 (s, 1H), 8.12 (d, J = 4.3, 1H), 7.95 (d, J = 4.4, 1H), 7.47 (d, J = 4.4, 1H), 7.30 (d, J = 1.9, 1H), 7.20 (dd, J = 8.1, 2.0, 1H), 7.13 (d, J = 8.1, 1H), 4.23-3.99 (m, 2H), 3.95-3.77 (m, 2H), 3.00 (p, J = 7.7, 1H), 2.70-2.63 (m, 1H), 2.21-2.04 (m, 2H), 1.22 (s, 6H), 0.66-0.61 (m, 2H), 0.44-0.40 (m, 2H). |
| E5 | 6-[8-((2R,4S)-4-hydroxy-2-phenyl-pyrrolidin-1-yl)-[1,2,4]triazolo[1,5-a]pyrazin-2-ylamino]-3,3-dimethyl-1,3-dihydro-indol-2-one 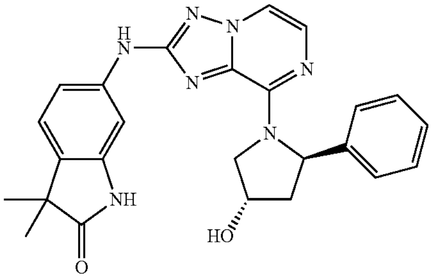 [SMILES: CC1(C)C(=O)Nc2cc(Nc3nc4c(N5C[C@@H](O)C[C@@H]5c5ccccc5)nccn4n3)ccc21] | LCMS (Method D) Rt: 1.87 min, observed [M + H] = 456.2 m/z; $^1$H NMR (400 MHz, DMSO-$d_6$) δ [ppm] 10.29 (s, 1H), 9.57 (s, 1H), 7.94 (d, J = 4.4, 1H), 7.40-7.33 (m, 1H), 7.32-7.28 (m, 1H), 7.25 (d, J = 4.3, 4H), 7.22-7.17 (m, 1H), 7.17-7.11 (m, 2H), 5.64 (s, 1H), 5.08 (d, J = 3.6, 1H), 4.49-4.40 (m, 1H), 4.38-4.25 (m, 2H), 2.47-2.36 (m, 1H), 2.06-1.91 (m, 1H), 1.23 (s, 6H). |
| E6 | 6-[8-(4(2R,4R)-4-hydroxy-2-phenyl-pyrrolidin-1-yl)-[1,2,4]triazolo[1,5-a]pyrazin-2-ylamino]-3,3-dimethyl-1,3-dihydro-indol-2-one 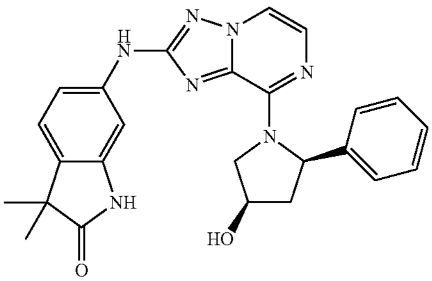 [SMILES: CC1(C)C(=O)Nc2cc(Nc3nc4c(N5C[C@H](O)C[C@@H]5c5ccccc5)nccn4n3)ccc21] | LCMS (Method D) Rt: 1.84 min, observed [M + H] = 456.2 m/z; $^1$H NMR (400 MHz, DMSO-$d_6$) δ [ppm] 10.27 (s, 1H), 9.55 (s, 1H), 7.94 (d, J = 4.4, 1H), 7.37 (d, J = 4.5, 1H), 7.31-7.27 (m, 2H), 7.25-7.19 (m, 4H), 7.15-7.08 (m, 2H), 5.63 (s, 1H), 4.99 (s, 1H), 4.59-4.50 (m, 1H), 4.45 (p, J = 5.5, 1H), 4.20-4.06 (m, 1H), 2.74-2.62 (m, 1H), 1.96-1.84 (m, 1H), 1.23 (s, 6H). |

-continued

| nr. | name/structure | LCMS; NMR |
|---|---|---|
| E7 | 7-[2-(4,4-dimethyl-2-oxo-1,2,3,4-tetrahydro-quinolin-7-ylamino)-[1,2,4]triazolo[1,5-a]pyrazin-8-yl]-2,7-diaza-spiro[4.4]nonane-1,3-dione 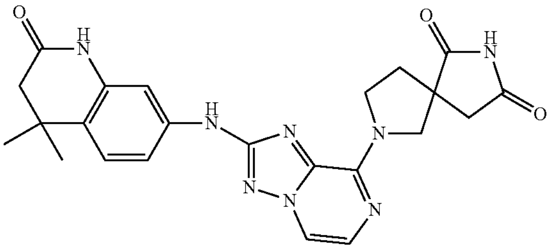 [SMILES: CC1(C)CC(=O)Nc2cc(Nc3nc4c(N5CCC6(CC(=O)NC6=O)C5)nccn4n3)ccc21] | LCMS (Method D) Rt: 1.593 min, observed [M + H] = 461.2 m/z; $^{1}$H NMR (500 MHz, DMSO-$d_6$) δ [ppm] 11.31 (s, 1H), 10.10 (s, 1H), 9.55 (s, 1H), 7.97 (d, J = 4.4, 1H), 7.49 (d, J = 4.4, 1H), 7.33 (s, 2H), 7.13 (s, 1H), 4.25-4.02 (m, 2H), 3.10-3.03 (m, 2H), 2.88-2.74 (m, 2H), 2.34-2.29 (m, 1H), 2.23-2.14 (m, 1H), 1.23-1.17 (m, 8H). |
| E8 | 6'-[[8-(1-methylpyrazol-4-yl)-[1,2,4]triazolo[1,5-a]pyrazin-2-yl]amino]spiro[cyclobutane-1,3'-indoline]-2'-one 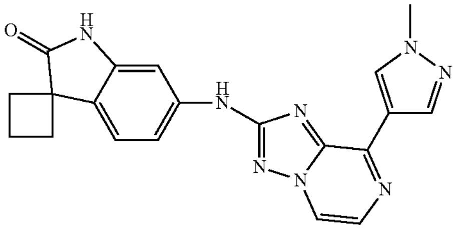 | LCMS (Method C) Rt: 1.906 min, observed [M + H] = 397.2 m/z; $^{1}$H NMR (400 MHz, DMSO-$d_6$) δ [ppm] 10.24 (s, 1H), 9.92 (s, 1H), 8.70-8.63 (m, 2H), 8.39 (s, 1H), 8.05 (d, J = 4.3, 1H), 7.46 (d, J = 8.1, 1H), 7.35 (d, J = 2.0, 1H), 7.32 (dd, J = 8.1, 2.0, 1H), 4.00 (s, 3H), 2.47-2.36 (m, 2H), 2.32-2.22 (m, 2H), 2.22-2.10 (m, 2H). |
| E9 | [8-(2,7-diaza-spiro[4.4]non-2-yl)-[1,2,4]triazolo[1,5-a]pyrazin-2-yl]-(4,4-dimethyl-1,2,3,4-tetrahydro-quinolin-7-yl)-amine 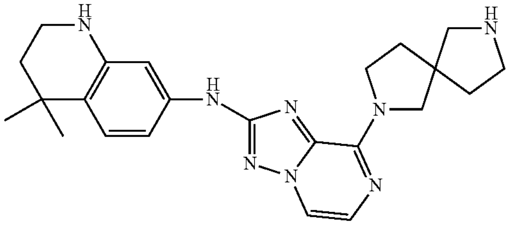 [SMILES: CC1(C)CCNc2cc(Nc3nc4c(N5CCC6(CCNC6)C5)nccn4n3)ccc21] | LCMS (Method C) Rt: 1.373 min, observed [M + H] = 419.3 m/z; X |
| E10 | 6-[8-(1,4-dioxa-7-aza-spiro[4.4]non-7-yl)-[1,2,4]triazolo[1,5-a]pyrazin-2-ylamino]-3,3-dimethyl-1,3-dihydro-indol-2-one 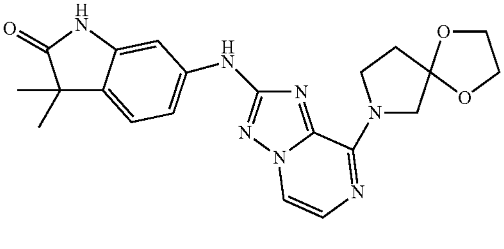 [SMILES: CC1(C)C(=O)Nc2cc(Nc3nc4c(N5CCC6(C5)OCCO6)nccn4n3)ccc21] | LCMS (Method C) Rt: 1.652 min, observed [M + H] = 422.2 m/z; $^{1}$H NMR (500 MHz, DMSO-$d_6$) δ [ppm] 10.28 (s, 1H), 9.59 (s, 1H), 8.00 (d, J = 4.4, 1H), 7.49 (d, J = 4.4, 1H), 7.28 (d, J = 2.0, 1H), 7.20 (dd, J = 8.1, 2.0, 1H), 7.13 (d, J = 8.1, 1H), 4.07 (q, J = 5.3, 1H), 4.01-3.93 (m, 7H), 2.16 (t, J = 7.3, 2H), 1.22 (s, 6H). |

-continued

| nr. | name/structure | LCMS; NMR |
|---|---|---|
| E11 | N-{1-[2-(3,3-dimethyl-2-oxo-2,3-dihydro-1H-indol-6-ylamino)-[1,2,4]triazolo[1,5-a]pyrazin-8-yl]-pyrrolidin-3-yl}-N-methyl-acetamide 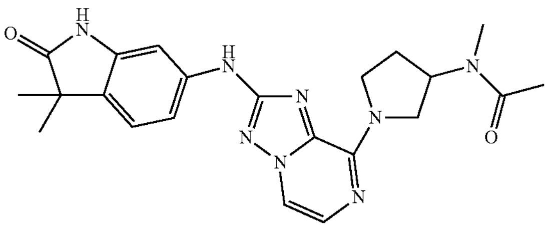 [SMILES: CC(=O)N(C)C1CCN(c2nccn3nc(Nc4ccc5c(c4)NC(=O)C5(C)C)nc23)C1] | LCMS (Method C) Rt: 1.554 min, observed [M + H] = 435.3 m/z; $^1$H NMR (500 MHz, DMSO-$d_6$) δ [ppm] 10.27 (s, 1H), 9.59 (s, 1H), 8.00-7.97 (m, 1H), 7.49 (t, J = 3.9, 1H), 7.31-7.26 (m, 1H), 7.23-7.18 (m, 1H), 7.13 (d, J = 8.1, 1H), 5.17-5.09 (m, 1H), 3.79 (s, 2H), 2.93 (s, 3H), 2.26-2.07 (m, 4H), 2.05 (s, 3H), 1.22 (s, 6H). |
| E12 | 6-[8-(1-methyl-1H-pyrazol-4-yl)-[1,2,4]triazolo[1,5-a]pyrazin-2-ylamino]-pyridine-3-sulfonic acid amide 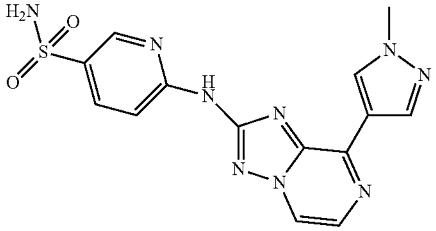 [SMILES: Cn1cc(-c2nccn3nc(Nc4ccc(S(N)(=O)=O)cn4)nc23)cn1] | LCMS (Method C) Rt: 1.485 min, observed [M + H] = 372.1 m/z; $^1$H NMR (500 MHz, DMSO-$d_6$) δ [ppm] 11.01 (s, 1H), 8.77 (d, J = 4.3, 1H), 8.71 (s, 1H), 8.68-8.65 (m, 1H), 8.41 (s, 1H), 8.31-8.27 (m, 1H), 8.21 (dd, J = 8.9, 2.5, 1H), 8.14 (d, J = 4.4, 1H), 7.39 (s, 2H), 4.01 (s, 3H). |
| E13 | 8-[2-(3,3-dimethyl-2-oxo-2,3-dihydro-1H-indol-6-ylamino)-[1,2,4]triazolo[1,5-a]pyrazin-8-yl]-2,8-diaza-spiro[4.5]decan-1-one 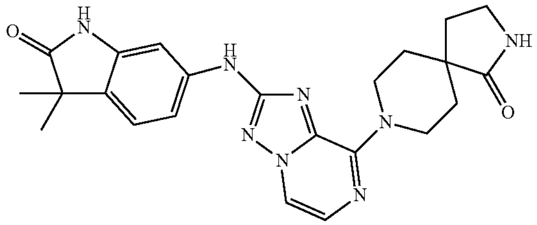 [SMILES: CC1(C)C(=O)Nc2cc(Nc3nc4c(N5CCC6(CCNC6=O)CC5)nccn4n3)ccc21] | LCMS (Method C) Rt: 1.622 min, observed [M + H] = 447.3 m/z; $^1$H NMR (500 MHz, DMSO-$d_6$) δ [ppm] 10.29 (s, 1H), 9.65 (s, 1H), 8.09 (d, J = 4.3, 1H), 7.58 (s, 1H), 7.55 (d, J = 4.3, 1H), 7.29 (d, J = 2.0, 1H), 7.19 (dd, J = 8.1, 2.0, 1H), 7.14 (d, J = 8.1, 1H), 4.98-4.91 (m, 2H), 3.47-3.39 (m, 2H), 3.23 (t, J = 6.8, 2H), 2.12-2.05 (m, 2H), 1.79-1.70 (m, 2H), 1.53-1.46 (m, 2H), 1.22 (s, 6H). |
| E14 | 6-{8-[(1-acetyl-piperidin-4-yl)-methyl-amino]-[1,2,4]triazolo[1,5-a]pyrazin-2-ylamino}-3,3-dimethyl-1,3-dihydro-indol-2-one 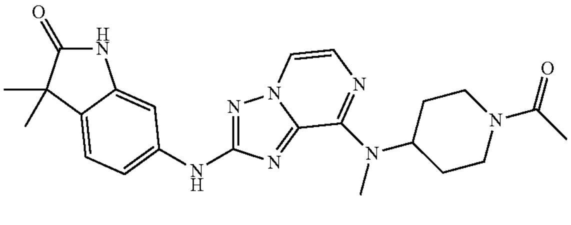 [SMILES: CC(=O)N1CCC(N(C)c2nccn3nc(Nc4ccc5c(c4)NC(=O)C5(C)C)nc23)CC1] | LCMS (Method C) Rt: 1.674 min, observed [M + H] = 449.2 m/z; $^1$H NMR (500 MHz, DMSO-$d_6$) δ [ppm] 10.27 (s, 1H), 9.54 (s, 1H), 8.03 (d, J = 4.3, 1H), 7.53 (d, J = 4.3, 1H), 7.28 (dd, J = 8.1, 2.0, 1H), 7.20 (d, J = 2.0, 1H), 7.14 (d, J = 8.1, 1H), 5.40-5.30 (m, 1H), 4.62-4.55 (m, 1H), 4.00-3.93 (m, 1H), 3.25 (s, 3H), 3.20-3.11 (m, 1H), 2.65-2.57 (m, 1H), 2.05 (s, 3H), 1.88-1.80 (m, 1H), 1.80-1.73 (m, 2H), 1.72-1.61 (m, 1H), 1.22 (s, 6H). |

-continued

| nr. | name/structure | LCMS; NMR |
|---|---|---|
| E15 | 6-{8-[5-((R)-1-amino-ethyl)-2-methoxy-phenyl]-[1,2,4]triazolo[1,5-a]pyrazin-2-ylamino}-3,3-dimethyl-1,3-dihydro-indol-2-one 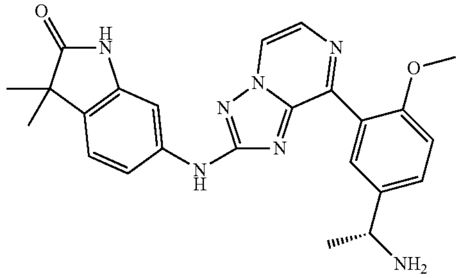 | LCMS (Method C) Rt: 1.443 min, observed [M + H] = 444.2 m/z; $^1$H NMR (500 MHz, DMSO-$d_6$) δ [ppm] 10.31 (s, 1H), 9.88 (s, 1H), 8.88 (d, J = 4.3, 1H), 8.57-8.48 (m, 3H), 8.18 (d, J = 4.3, 1H), 7.70 (dd, J = 8.6, 2.4, 1H), 7.61-7.60 (m, 1H), 7.28-7.23 (m, 3H), 7.14 (d, J = 7.9, 1H), 4.47-4.37 (m, 1H), 3.79 (s, 3H), 1.55 (d, J = 6.8, 3H), 1.22 (s, 6H). |
| E16 | (R)-7-[2-(3,3-dimethyl-2-oxo-2,3-dihydro-1H-indol-6-ylamino)-[1,2,4]triazolo[1,5-a]pyrazin-8-yl]-2,7-diaza-spiro[4.4]nonane-1,3-dione 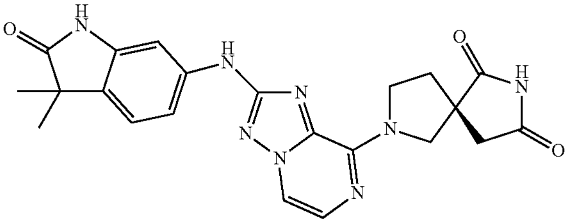 [SMILES: CC1(C)C(=O)Nc2cc(Nc3nc4c(N5CC[C@@]6(CC(=O)NC6=O)C5)nccn4n3)ccc21] | LCMS (Method C) Rt: 1.642 min, observed [M + H] = 447.2 m/z; $^1$H NMR (500 MHz, DMSO-$d_6$) δ [ppm] 11.30 (s, 1H), 10.28 (s, 1H), 9.58 (s, 1H), 7.99 (d, J = 4.4, 1H), 7.49 (d, J = 4.4, 1H), 7.30 (d, J = 2.0, 1H), 7.21-7.16 (m, 1H), 7.13 (d, J = 8.1, 1H), 4.28-3.88 (m, 4H), 2.91-2.73 (m, 2H), 2.36-2.29 (m, 1H), 2.21-2.13 (m, 1H), 1.22 (s, 6H). |
| E17 | 3,3-dimethyl-6-[8-(methyl-piperidin-4-yl-amino)-[1,2,4]triazolo[1,5-a]pyrazin-2-ylamino]-1,3-dihydro-indol-2-one 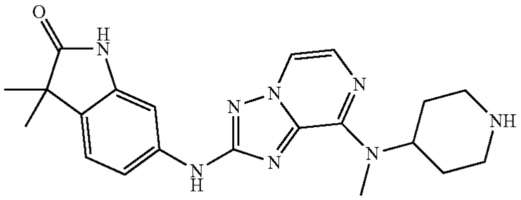 [SMILES: CN(c1nccn2nc(Nc3ccc4c(c3)NC(=O)C4(C)C)nc12)C1CCNCC1] | LCMS (Method C) Rt: 1.407 min, observed [M + H] = 407.2 m/z; $^1$H NMR (500 MHz, DMSO-$d_6$) δ [ppm] 10.30 (s, 1H), 9.56 (s, 1H), 8.36 (s, 1H), 8.04 (d, J = 4.3, 1H), 7.53 (d, J = 4.3, 1H), 7.28 (dd, J = 8.1, 2.0, 1H), 7.21 (d, J = 2.0, 1H), 7.17-7.11 (m, 1H), 5.31 (t, J = 11.7, 1H), 3.33-3.19 (m, 5H), 2.90-2.78 (m, 2H), 2.06-1.90 (m, 2H), 1.87-1.75 (m, 2H), 1.23 (s, 6H). |
| E18 | (S)-7-[2-(3,3-dimethyl-2-oxo-2,3-dihydro-1H-indol-6-ylamino)-[1,2,4]triazolo[1,5-a]pyrazin-8-yl]-2,7-diaza-spiro[4.4]nonane-1,3-dione 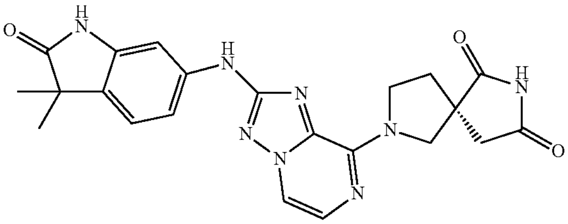 [SMILES: CC1(C)C(=O)Nc2cc(Nc3nc4c(N5CC[C@]6(CC(=O)NC6=O)C5)nccn4n3)ccc21] | LCMS (Method C) Rt: 1.647 min, observed [M + H] = 447.2 m/z; $^1$H NMR (500 MHz, DMSO-$d_6$) δ [ppm] 11.30 (s, 1H), 10.27 (s, 1H), 9.58 (s, 1H), 7.99 (d, J = 4.4, 1H), 7.49 (d, J = 4.4, 1H), 7.30 (d, J = 2.0, 1H), 7.20 (dd, J = 8.1, 2.1, 1H), 7.13 (d, J = 8.1, 1H), 4.28-3.85 (m, 4H), 2.91-2.73 (m, 2H), 2.35-2.28 (m, 1H), 2.22-2.14 (m, 1H), 1.22 (s, 6H). |

-continued

| nr. | name/structure | LCMS; NMR |
|---|---|---|
| E19 | 3,3-dimethyl-6-[8-(6-oxo-2,7-diaza-spiro[4.4]non-2-yl)-[1,2,4]triazolo[1,5-a]pyrazin-2-ylamino]-1,3-dihydro-indol-2-one 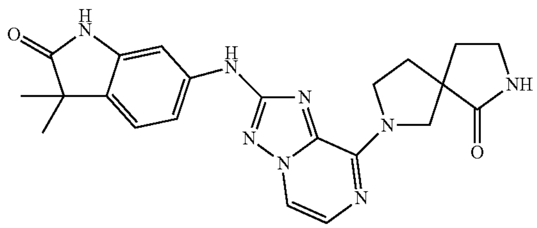 [SMILES: CC1(C)C(=O)Nc2cc(Nc3nc4c(N5CCC6(CCNC6=O)C5)nccn4n3)ccc21] | LCMS (Method D) Rt: 1.65 min, observed [M + H] = 433.1 m/z; $^1$H NMR (500 MHz, DMSO-$d_6$) δ [ppm] 10.28 (s, 1H), 9.58 (s, 1H), 7.97 (d, J = 4.4, 1H), 7.80 (s, 1H), 7.48 (d, J = 4.4, 1H), 7.28 (d, J = 2.0, 1H), 7.20 (dd, J = 8.1, 2.0, 1H), 7.13 (d, J = 8.1, 1H), 4.26-3.82 (m, 4H), 3.28-3.22 (m, 2H), 2.17-2.09 (m, 3H), 2.01-1.94 (m, 1H), 1.22 (s, 6H). |
| E20 | 3,3-dimethyl-6-[8-(8-oxo-2,7-diaza-spiro[4.4]non-2-yl)-[1,2,4]triazolo[1,5-a]pyrazin-2-ylamino]-1,3-dihydro-indol-2-one 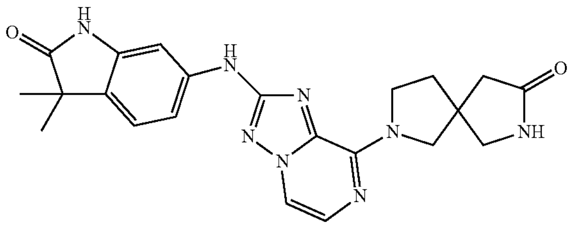 [SMILES: CC1(C)C(=O)Nc2cc(Nc3nc4c(N5CCC6(CNC(=O)C6)C5)nccn4n3)ccc21] | LCMS (Method D) Rt: 1.478 min, observed [M + H] = 433.2 m/z; $^1$H NMR (500 MHz, DMSO-$d_6$) δ [ppm] 10.27 (s, 1H), 9.61 (s, 1H), 7.96 (d, J = 4.4, 1H), 7.67 (s, 1H), 7.47 (d, J = 4.4, 1H), 7.30 (d, J = 2.0, 1H), 7.19 (dd, J = 8.1, 2.0, 1H), 7.13 (d, J = 8.1, 1H), 4.20-3.74 (m, 4H), 3.26 (d, J = 4.7, 2H), 2.29 (s, 2H), 2.05-1.99 (m, 2H), 1.22 (s, 6H). |
| E21 | (4,4-dimethyl-1,2,3,4-tetrahydro-quinolin-7-yl)-[8-(1-methyl-1H-pyrazol-4-yl)-[1,2,4]triazolo[1,5-a]pyrazin-2-yl]-amine 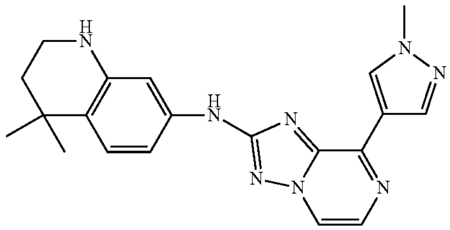 [SMILES: Cn1cc(-c2nccn3nc(Nc4ccc5c(c4)NCCC5(C)C)nc23)cn1] | LCMS (Method D) Rt: 1.649 min, observed [M + H] = 375.3 m/z |
| E22 | (R)-1-[2-(3,3-dimethyl-2-oxo-2,3-dihydro-1H-indol-6-ylamino)-[1,2,4]triazolo[1,5-a]pyrazin-8-yl]-pyrrolidine-2-carboxylic acid amide 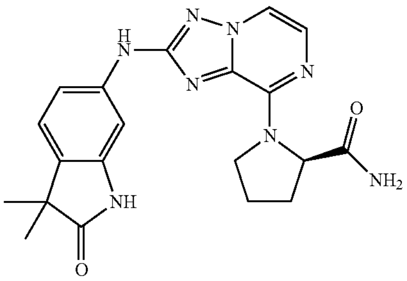 [SMILES: CC1(C)C(=O)Nc2cc(Nc3nc4c(N5CCC[C@@H]5C(N)=O)nccn4n3)ccc21] | LCMS (Method C) Rt: 1.521 min, observed [M + H] = 407.2 m/z; $^1$H NMR (500 MHz, DMSO-$d_6$) δ [ppm] 10.19 (s, 1H), 9.55 (s, 1H), 7.97 (d, J = 4.4, 1H), 7.47 (d, J = 4.4, 1H), 7.44-7.39 (m, 1H), 7.39-7.34 (m, 1H), 7.18 (dd, J = 8.1, 2.0, 1H), 7.12 (d, J = 8.1, 1H), 6.94 (s, 1H), 4.94 (s, 1H), 4.24-3.88 (m, 2H), 2.29-2.19 (m, 1H), 2.12-2.02 (m, 1H), 2.01-1.88 (m, 2H), 1.22 (s, 6H). |

-continued

| nr. | name/structure | LCMS; NMR |
|---|---|---|
| E23 | (2,2-dioxo-2,3-dihydro-1H-2I6-benzo[c]isothiazol-6-yl)-[8-(1-methyl-1H-pyrazol-4-yl)-[1,2,4]triazolo[1,5-a]pyrazin-2-yl]-amine 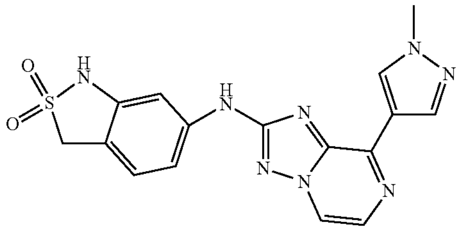 [SMILES: Cn1cc(-c2nccn3nc(Nc4ccc5c(c4)NS(=O)(=O)C5)nc23)cn1] | LCMS (Method D) Rt: 1.679 min, observed [M + H] = 383.2 m/z; $^1$H NMR (400 MHz, DMSO-$d_6$) δ [ppm] 10.51 (s, 1H), 10.04 (s, 1H), 8.69 (d, J = 4.3, 1H), 8.66 (s, 1H), 8.39 (s, 1H), 8.07 (d, J = 4.3, 1H), 7.43 (d, J = 2.0, 1H), 7.27 (dd, J = 8.3, 2.1, 1H), 7.22 (d, J = 8.3, 1H), 4.44 (s, 2H), 4.00 (s, 3H). |
| E24 | 6-[8-((2S,4R)-4-hydroxy-2-phenyl-pyrrolidin-1-yl)-[1,2,4]triazolo[1,5-a]pyrazin-2-ylamino]-3,3-dimethyl-1,3-dihydro-indol-2-one 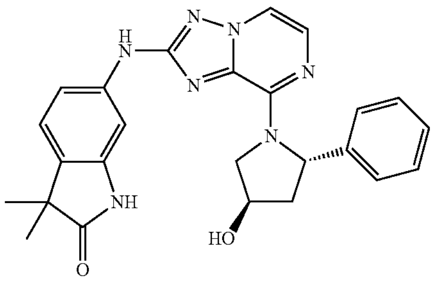 [SMILES: CC1(C)C(=O)Nc2cc(Nc3nc4c(N5C[C@H](O)C[C@H]5c5ccccc5)nccn4n3)ccc21] | LCMS (Method C) Rt: 1.87 min, observed [M + H] = 456.2 m/z; $^1$H NMR (500 MHz, DMSO-$d_6$) δ [ppm] 10.27 (s, 1H), 9.55 (s, 1H), 7.93 (d, J = 4.4, 1H), 7.38-7.33 (m, 1H), 7.31-7.27 (m, 1H), 7.24 (d, J = 4.3, 4H), 7.21-7.17 (m, 1H), 7.15 (q, J = 4.3, 1H), 7.12 (d, J = 8.1, 1H), 5.61 (s, 1H), 5.05 (s, 1H), 4.46-4.39 (m, 1H), 4.33 (s, 1H), 2.45-2.37 (m, 1H), 2.03-1.90 (m, 1H), 1.23 (s, 6H). |
| E25 | 6-[8-(2-cyclohexyl-pyrrolidin-1-yl)-[1,2,4]triazolo[1,5-a]pyrazin-2-ylamino]-3,3-dimethyl-1,3-dihydro-indol-2-one 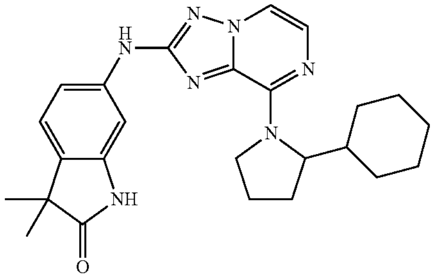 [SMILES: CC1(C)C(=O)Nc2cc(Nc3nc4c(N5CCCC5C5CCCCC5)nccn4n3)ccc21] | LCMS (Method C) Rt: 2.307 min, observed [M + H] = 446.2 m/z; $^1$H NMR (500 MHz, DMSO-$d_6$) δ [ppm] 10.28 (s, 1H), 9.51 (s, 1H), 7.94 (d, J = 4.3, 1H), 7.49 (d, J = 4.4, 1H), 7.30-7.25 (m, 1H), 7.25-7.21 (m, 1H), 7.12 (d, J = 8.1, 1H), 4.78-4.63 (m, 1H), 4.12-3.99 (m, 1H), 3.98-3.86 (m, 1H), 2.00-1.85 (m, 5H), 1.72-1.65 (m, 2H), 1.64-1.51 (m, 3H), 1.22 (s, 6H), 1.15-1.01 (m, 5H). |
| E26 | 4,4-dimethyl-7-[8-(1-methyl-1H-pyrazol-4-yl)-[1,2,4]triazolo[1,5-a]pyrazin-2-ylamino]-3,4-dihydro-1H-quinazolin-2-one 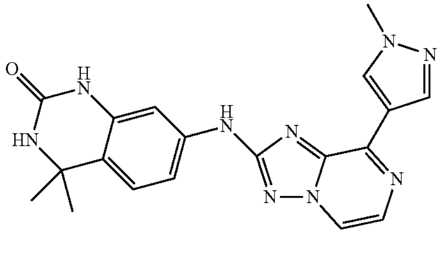 [SMILES: Cn1cc(-c2nccn3nc(Nc4ccc5c(c4)NC(=O)NC5(C)C)nc23)cn1] | LCMS (Method D) Rt: 1.739 min, observed [M + H] = 390.2 m/z; $^1$H NMR (500 MHz, DMSO-$d_6$) δ [ppm] 9.82 (s, 1H), 9.23-9.21 (m, 1H), 8.69 (s, 1H), 8.63 (d, J = 4.3, 1H), 8.39 (s, 1H), 8.05 (d, J = 4.3, 1H), 7.25-7.20 (m, 2H), 7.15-7.12 (m, 1H), 6.83-6.78 (m, 1H), 4.00 (s, 3H), 1.41 (s, 6H). |

-continued

| nr. | name/structure | LCMS; NMR |
|---|---|---|
| E27 | 8-[2-(3,3-dimethyl-2-oxo-2,3-dihydro-1H-indol-6-ylamino)-[1,2,4]triazolo[1,5-a]pyrazin-8-yl]-1-oxa-3,8-diaza-spiro[4.5]decan-2-one 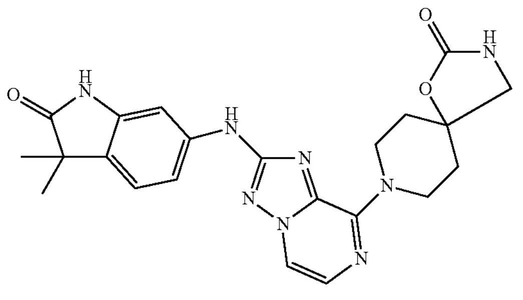 [SMILES: CC1(C)C(=O)Nc2cc(Nc3nc4c(N5CCC6(CC5)CNC(=O)O6)nccn4n3)ccc21] | LCMS (Method D) Rt: 1.636 min, observed [M + H] = 449.2 m/z; $^1$H NMR (500 MHz, DMSO-$d_6$) δ [ppm] 10.28 (s, 1H), 9.68 (s, 1H), 8.11 (d, J = 4.3, 1H), 7.55 (d, J = 4.3, 1H), 7.53 (s, 1H), 7.30 (d, J = 2.0, 1H), 7.18 (dd, J = 8.1, 2.0, 1H), 7.13 (d, J = 8.1, 1H), 4.61-4.50 (m, 2H), 3.91-3.81 (m, 2H), 3.30 (s, 2H), 1.97-1.82 (m, 4H), 1.22 (s, 6H). |
| E28 | 8-[2-(3,3-dimethyl-2-oxo-2,3-dihydro-1H-indol-6-ylamino)-[1,2,4]triazolo[1,5-a]pyrazin-8-yl]-1,3,8-triaza-spiro[4.5]decane-2,4-dione 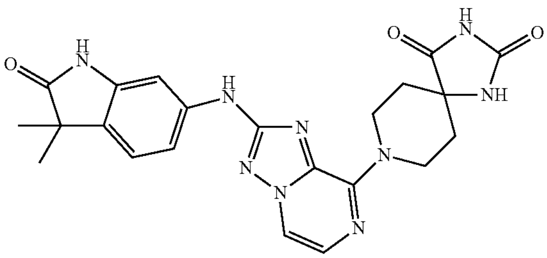 [SMILES: CC1(C)C(=O)Nc2cc(Nc3nc4c(N5CCC6(CC5)NC(=O)NC6=O)nccn4n3)ccc21] | LCMS (Method D) Rt: 1.607 min, observed [M + H] = 462.2 m/z. |
| E29 | 6-[8-((2S,4S)-4-hydroxy-2-phenyl-pyrrolidin-1-yl)-[1,2,4]triazolo[1,5-a]pyrazin-2-ylamino]-3,3-dimethyl-1,3-dihydro-indol-2-one 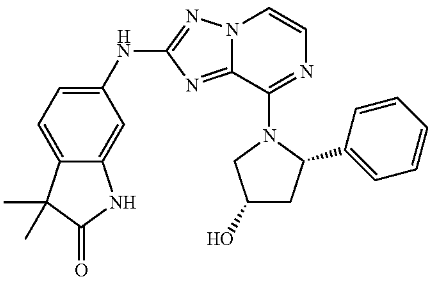 | LCMS (Method C) Rt: 1.594 min, observed [M + H] = 433.1 m/z; $^1$H NMR (500 MHz, DMSO-$d_6$) δ [ppm] 10.26 (s, 1H), 9.54 (s, 1H), 7.93 (d, J = 4.4, 1H), 7.36 (d, J = 4.4, 1H), 7.31-7.26 (m, 2H), 7.26-7.18 (m, 4H), 7.14-7.08 (m, 2H), 5.75-5.51 (m, 1H), 4.98 (d, J = 3.7, 1H), 4.58-4.49 (m, 1H), 4.47-4.40 (m, 1H), 4.20-4.07 (m, 1H), 2.71-2.62 (m, 1H), 1.93-1.85 (m, 1H), 1.26-1.19 (m, 6H). |
| E30 | 6-[8-(3-hydroxymethyl-pyrrolidin-1-yl)-[1,2,4]triazolo[1,5-a]pyrazin-2-ylamino]-3,3-dimethyl-1,3-dihydro-indol-2-one 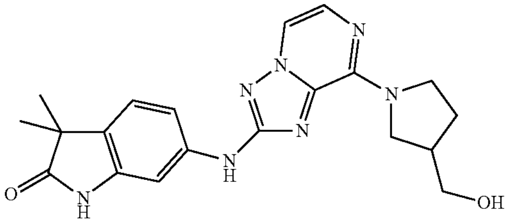 [SMILES: CC1(C)C(=O)Nc2cc(Nc3nc4c(N5CCC(CO)C5)nccn4n3)ccc21] | LCMS (Method C) Rt: 1.439 min, observed [M + H] = 394.2 m/z; $^1$H NMR (500 MHz, DMSO-$d_6$) δ [ppm] 10.28-10.24 (m, 1H), 9.61-9.55 (m, 1H), 7.95-7.91 (m, 1H), 7.49-7.44 (m, 1H), 7.32-7.28 (m, 1H), 7.23-7.19 (m, 1H), 7.14-7.11 (m, 1H), 4.75-4.68 (m, 1H), 4.15-3.92 (m, 2H), 3.87-3.61 (m, 2H), 3.54-3.47 (m, 1H), 3.48-3.40 (m, 1H), 2.48-2.41 (m, 1H), 2.10-2.01 (m, 1H), 1.81-1.71 (m, 1H), 1.26-1.19 (m, 6H). |

-continued

| nr. | name/structure | LCMS; NMR |
| --- | --- | --- |
| E31 | 2 -[2-(3-methoxy-phenylamino)-[1,2,4]triazolo[1,5-a]pyrazin-8-yl]-benzonitrile 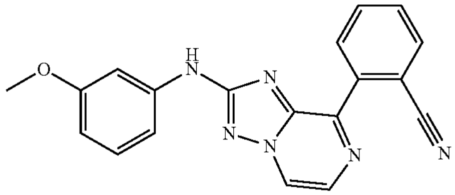 [SMILES: COc1cccc(Nc2nc3c(-c4ccccc4C#N)nccn3n2)c1] | LCMS (Method A) Rt: 4.2 min, observed [M + H] = 343 m/z; $^1$H NMR (400 MHz, DMSO-$d_6$) δ [ppm] 10.10 (s, 1H), 9.03 (d, J = 4.2 Hz, 1H), 8.48-8.46 (m, 1H), 8.31 (dd, J = 10.5, 4.2 Hz, 1H), 8.07 (dd, J = 7.7, 0.9 Hz, 1H), 7.90 (dt, J = 10.7, 1.2 Hz, 1H), 7.74 (dt, J = 10.6, 1.1 Hz, 1H), 7.46-7.45 (m, 1H), 7.21-7.17 (m, 2H), 6.54-6.50 (m, 1H), 3.31 (s, 3H). |
| E32 | 6-[8-(4,6-dihydro-1H-pyrrolo[3,4-c]pyrazol-5-yl)-[1,2,4]triazolo[1,5-a]pyrazin-2-ylamino]-3,3-dimethyl-1,3-dihydro-indol-2-one 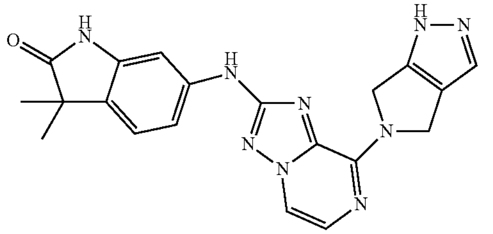 [SMILES: CC1(C)C(=O)Nc2cc(Nc3nc4c(N5Cc6cn[nH]c6C5)nccn4n3)ccc21] | LCMS (Method D) Rt: 1.604 min, observed [M + H] = 402.2 m/z; $^1$H NMR (500 MHz, DMSO-$d_6$) δ [ppm] 13.54-11.99 (m, 1H), 10.31 (s, 1H), 9.63 (s, 1H), 8.05 (d, J = 4.4, 1H), 7.64 (s, 1H), 7.56 (d, J = 4.4, 1H), 7.32 (d, J = 1.9, 1H), 7.23 (dd, J = 8.2, 2.1, 1H), 7.16 (d, J = 8.1, 1H), 5.02 (s, 4H), 1.23 (s, 6H). |
| E33 | 5-[2-(3,3-dimethyl-2-oxo-2,3-dihydro-1H-indol-6-ylamino)-[1,2,4]triazolo[1,5-a]pyrazin-8-yl]-tetrahydro-pyrrolo[3,4-c]pyrrole-1,3-dione 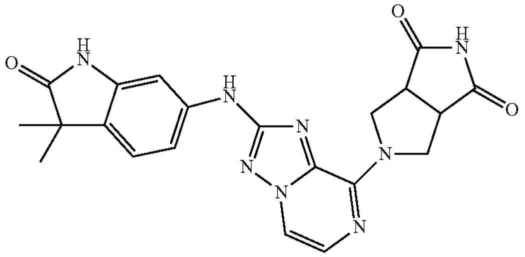 [SMILES: CC1(C)C(=O)Nc2cc(Nc3nc4c(N5CC6C(=O)NC(=O)C6C5)nccn4n3)ccc21] | LCMS (Method D) Rt: 1.594 min, observed [M + H] = 433.2 m/z; $^1$H NMR (500 MHz, DMSO-$d_6$) δ [ppm] 11.36 (s, 1H), 10.25 (s, 1H), 9.70 (s, 1H), 8.14 (d, J = 4.4, 1H), 7.55 (d, J = 4.4, 1H), 7.26 (dd, J = 8.1, 2.0, 1H), 7.23 (d, J = 2.0, 1H), 7.14 (d, J = 8.0, 1H), 4.68 (d, J = 11.7, 2H), 3.75-3.66 (m, 2H), 3.59-3.52 (m, 2H), 1.23 (s, 6H). |
| E34 | formic acid 1-[2-(3,3-dimethyl-2-oxo-2,3-dihydro-1H-indol-6-ylamino)-[1,2,4]triazolo[1,5-a]pyrazin-8-yl] pyrrolidin-3-ylmethyl ester 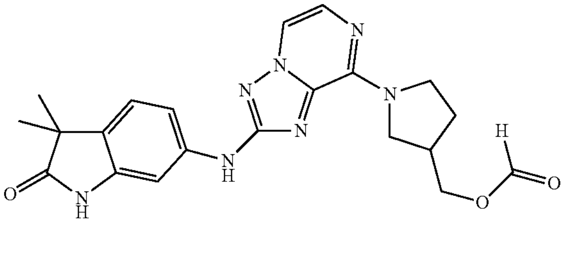 [SMILES: CC1(C)C(=O)Nc2cc(Nc3nc4c(N5CCC(COC=O)C5)nccn4n3)ccc21] | LCMS (Method C) Rt: 1.685 min, observed [M + H] = 422.2 m/z; $^1$H NMR (500 MHz, DMSO-$d_6$) δ [ppm] 10.27 (s, 1H), 9.58 (s, 1H), 8.29 (s, 1H), 7.96 (d, J = 4.4, 1H), 7.48 (d, J = 4.4, 1H), 7.30 (d, J = 2.0 1H), 7.21 (dd, J = 8.1, 2.0, 1H), 7.13 (d, J = 8.1, 1H), 4.30-3.97 (m, 4H), 3.77 (d, J = 87.5, 2H), 2.68 (p, J = 7.2, 1H), 2.19-2.09 (m, 1H), 1.86-1.75 (m, 1H), 1.22 (s, 6H). |

-continued

| nr. | name/structure | LCMS; NMR |
|---|---|---|
| E35 | 8-[2-(3,3-dimethyl-2-oxo-2,3-dihydro-1H-indol-6-ylamino)-[1,2,4]triazolo[1,5-a]pyrazin-8-yl]-1,8-diaza-spiro[4.5]decan-2-one 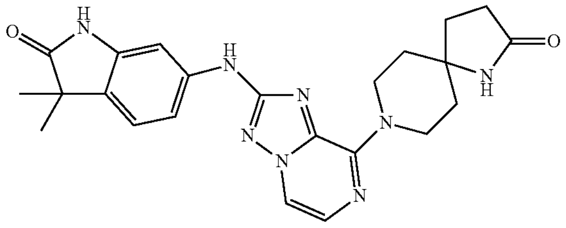 [SMILES: CC1(C)C(=O)Nc2cc(Nc3nc4c(N5CCC6(CCC(=O)N6)CC5)nccn4n3)ccc21] | LCMS (Method D) Rt: 1.654 min, observed [M + H] = 447.3 m/z; $^1$H NMR (500 MHz, DMSO-$d_6$) δ [ppm] 10.28 (s, 1H), 9.66 (s, 1H), 8.09 (d, J = 4.3, 1H), 8.05 (s, 1H), 7.54 (d, J = 4.3, 1H), 7.28 (d, J = 2.0, 1H), 7.19 (dd, J = 8.1, 2.0, 1H), 7.14 (d, J = 8.1, 1H), 4.34-4.25 (m, 2H), 4.09-3.99 (m, 2H), 2.30-2.20 (m, 2H), 1.93 (t, J = 8.0, 2H), 1.69 (t, J = 5.8, 4H), 1.22 (s, 6H). |
| E36 | {2-amino-4-[8-(1-methyl-1H-pyrazol-4-yl)-[1,2,4]triazolo[1,5-a]pyrazin-2-ylamino]-phenyl}-methanesulfonic acid 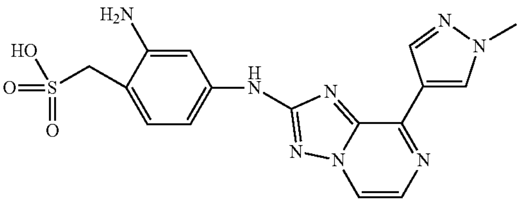 | LCMS (Method D) Rt: 1235 min, observed [M + H] = m/z; $^1$H NMR (400 MHz, DMSO-$d_6$) δ [ppm] 10.25 (s, 1H), 8.72 (s, 1H), 8.69 (d, J = 4.3, 1H), 8.39 (s, 1H), 8.09 (d, J = 4.3, 1H), 7.91 (d, J = 2.3, 1H), 7.64 (dd, J = 8.4, 2.3, 1H), 7.33 (d, J = 8.4, 1H), 4.47 (s, 1H), 4.04-3.95 (m, 5H). |
| E37 | 6-{8-[4-(4,5-dimethyl-1H-imidazol-2-yl)-piperidin-1-yl]-[1,2,4]triazolo[1,5-a]pyrazin-2-ylamino}-3,3-dimethyl-1,3-dihydro-indol-2-one 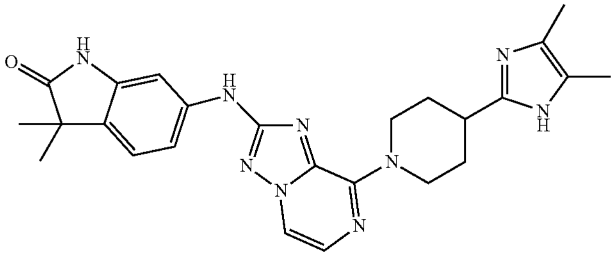 [SMILES: Cc1nc(C2CCN(c3nccn4nc(Nc5ccc6c(c5)NC(=O)C6(C)C)nc34)CC2)[nH]c1C] | LCMS (Method D) Rt: 1.624 min, observed [M + H] = 472.3 m/z; $^1$H NMR (500 MHz, DMSO-$d_6$) δ [ppm] 13.15 (s, 1H), 10.28 (s, 1H), 9.67 (s, 1H), 8.13 (d, J = 4.4, 1H), 7.58 (d, J = 4.3, 1H), 7.27 (d, J = 2.0, 1H), 7.21 (dd, J = 8.1, 2.0, 1H), 7.14 (d, J = 8.1, 1H), 5.26 (d, J = 13.4, 2H), 3.26-3.14 (m, 3H), 2.11 (s, 6H), 2.06-2.00 (m, 2H), 1.88-1.73 (m, 2H), 1.22 (s, 6H). |
| E38 | 1-[2-(3,3-dimethyl-2-oxo-2,3-dihydro-1H-indol-6-ylamino)-[1,2,4]triazolo[1,5-a]pyrazin-8-yl]-piperidine-4-sulfonic acid methylamide 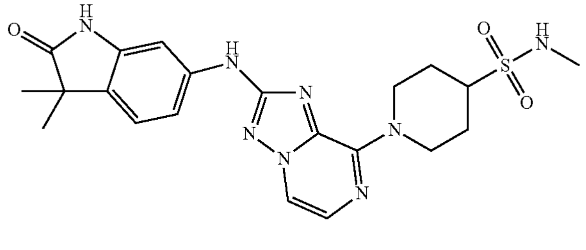 [SMILES: CNS(=O)(=O)C1CCN(c2nccn3nc(Nc4ccc5c(c4)NC(=O)C5(C)C)nc23)CC1] | LCMS (Method D) Rt: 1.713 min, observed [M + H] = 471.2 m/z; $^1$H NMR (500 MHz, DMSO-$d_6$) δ [ppm] 10.29 (s, 1H), 9.67 (s, 1H), 8.12 (d, J = 4.3, 1H), 7.56 (d, J = 4.3, 1H), 7.29 (d, J = 2.0, 1H), 7.20 (dd, J = 8.1, 2.0, 1H), 7.14 (d, J = 8.1, 1H), 6.95 (q, J = 4.8, 1H), 5.33-5.21 (m, 2H), 3.43 (tt, J = 11.9, 3.8, 1H), 3.22-3.10 (m, 2H), 2.62 (d, J = 4.8, 3H), 2.12-2.04 (m, 2H), 1.65 (qd, J = 12.5, 4.2, 2H), 1.22 (s, 6H). |

-continued

| nr. | name/structure | LCMS; NMR |
|---|---|---|
| E39 | 1-[2-(3,3-dimethyl-2-oxo-2,3-dihydro-1H-indol-6-ylamino)-[1,2,4]triazolo[1,5-a]pyrazin-8-yl]-piperidine-4-sulfonic acid amide 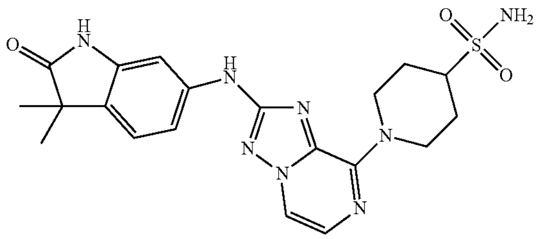 [SMILES: CC1(C)C(=O)Nc2cc(Nc3nc4c(N5CCC(S(N)(=O)=O)CC5)nccn4n3)ccc21] | LCMS (Method D) Rt: 1.623 min, observed [M + H] = 457.2 m/z; $^1$H NMR (500 MHz, DMSO-$d_6$) δ [ppm] 10.28 (s, 1H), 9.68 (s, 1H), 8.12 (d, J = 4.3, 1H), 7.56 (d, J = 4.3, 1H), 7.29 (d, J = 2.0, 1H), 7.20 (dd, J = 8.1, 2.0, 1H), 7.14 (d, J = 8.1, 1H), 6.74 (s, 2H), 5.34-5.25 (m, 2H), 3.22 (tt, J = 11.9, 3.8, 1H), 3.18-3.08 (m, 2H), 2.19-2.09 (m, 2H), 1.67 (qd, J = 12.6, 4.2, 2H), 1.22 (s, 6H). |
| E40 | 1-[2-(3,3-dimethyl-2-oxo-2,3-dihydro-1H-indol-6-ylamino)-[1,2,4]triazolo[1,5-a]pyrazin-8-yl]-piperidine-4-carboxylic acid amide 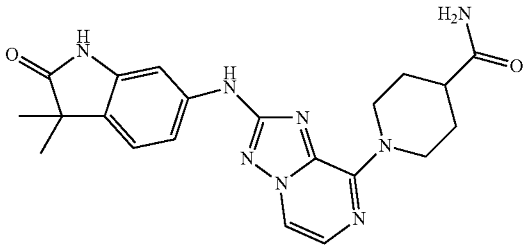 [SMILES: CC1(C)C(=O)Nc2cc(Nc3nc4c(N5CCC(C(N)=O)CC5)nccn4n3)ccc21] | LCMS (Method D) Rt: 1.534 min, observed [M + H] = 421.2 m/z; $^1$H NMR (500 MHz, DMSO-$d_6$) δ [ppm] 10.27 (s, 1H), 9.65 (s, 1H), 8.08 (d, J = 4.4, 1H), 7.54 (d, J = 4.4, 1H), 7.31-7.23 (m, 2H), 7.20 (dd, J = 8.1, 2.0, 1H), 7.13 (d, J = 8.1, 1H), 6.81-6.72 (m, 1H), 5.20-5.08 (m, 2H), 3.15-3.06 (m, 2H), 2.45 (tt, J = 11.5, 3.9, 1H), 1.88-1.78 (m, 2H), 1.68-1.55 (m, 2H), 1.22 (s, 6H). |
| E41 | 3,3-dimethyl-6-(8-pyrrolidin-1-yl-[1,2,4]triazolo[1,5-a]pyrazin-2-ylamino)-1,3-dihydro-indol-2-one 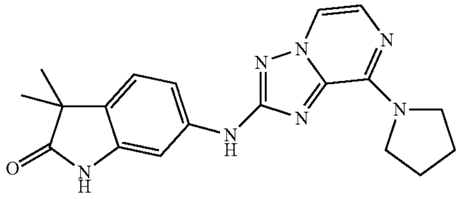 [SMILES: CC1(C)C(=O)Nc2cc(Nc3nc4c(N5CCCC5)nccn4n3)ccc21] | LCMS (Method C) Rt: 1.567 min, observed [M + H] = 364.2 m/z;, $^1$H NMR (500 MHz, DMSO-$d_6$) δ [ppm] 10.28 (s, 1H), 9.55 (s, 1H), 7.92 (d, J = 4.4, 1H), 7.46 (d, J = 4.4, 1H), 7.32 (d, J = 1.9, 1H), 7.19 (dd, J = 8.1, 2.0, 1H), 7.12 (d, J = 8.1, 1H), 4.03-3.77 (m, 4H), 2.03-1.92 (m, 4H), 1.22 (s, 6H). |
| E42 | 3,3-dimethyl-6-[8-(2-methyl-pyrrolidin-1-yl)-[1,2,4]triazolo[1,5-a]pyrazin-2-ylamino]-1,3-dihydro-indol-2-one 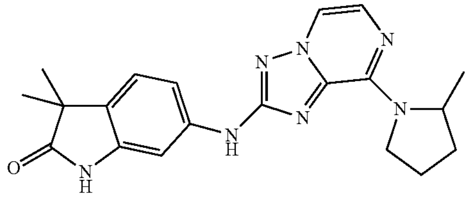 [SMILES: CC1CCCN1c1nccn2nc(Nc3ccc4c(c3)NC(=O)C4(C)C)nc12] | LCMS (Method C) Rt: 1.681 min, observed [M + H] = 378.2 m/z; $^1$H NMR (500 MHz, DMSO-$d_6$) δ [ppm] 10.29 (s, 1H), 9.54 (s, 1H), 7.93 (d, J = 4.4, 1H), 7.48 (d, J = 4.4, 1H), 7.32 (d, J = 2.0, 1H), 7.22 (dd, J = 8.1, 2.0, 1H), 7.12 (d, J = 8.1, 1H), 4.87 (s, 1H), 3.89-3.76 (m, 1H), 3.29 (s, 1H), 2.14-2.01 (m, 2H), 2.02-1.91 (m, 1H), 1.78-1.69 (m, 1H), 1.27 (d, J = 6.3, 3H), 1.22 (s, 6H). |
| E43 | 6-[8-(2,5-dimethyl-pyrrolidin-1-yl)-[1,2,4]triazolo[1,5-a]pyrazin-2-ylamino]-3,3-dimethyl-1,3-dihydro-indol-2-one 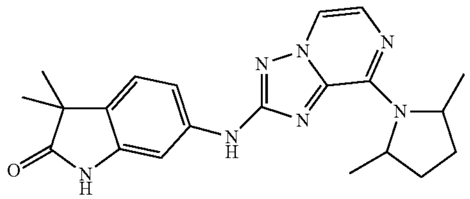 [SMILES: CC1CCC(C)N1c1nccn2nc(Nc3ccc4c(c3)NC(=O)C4(C)C)nc12] | LCMS (Method C) Rt: 1.931 min, observed [M + H] = 392.2 m/z; $^1$H NMR (500 MHz, DMSO-$d_6$) δ [ppm] 10.28 (s, 1H), 9.50 (s, 1H), 7.93 (d, J = 4.3, 1H), 7.49 (d, J = 4.3, 1H), 7.29 (d, J = 2.0, 1H), 7.26 (dd, J = 8.1, 2.0, 1H), 7.12 (d, J = 8.1, 1H), 4.80-4.69 (m, 2H), 2.15-2.03 (m, 2H), 1.85-1.73 (m, 2H), 1.42 (s, 3H), 1.41 (s, 3H), 1.22 (s, 6H). |

-continued

| nr. | name/structure | LCMS; NMR |
|---|---|---|
| E44 | 6-[8-(4-ethyl-4-hydroxy-piperidin-1-yl)-[1,2,4]triazolo[1,5-a]pyrazin-2-ylamino]-3,3-dimethyl-1,3-dihydro-indol-2-one 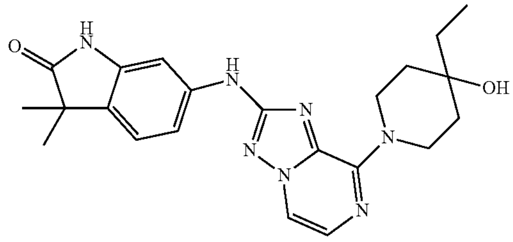 [SMILES: CCC1(O)CCN(c2nccn3nc(Nc4ccc5c(c4)NC(=O)C5(C)C)nc23)CC1] | LCMS (Method D) Rt: 1.701 min, observed [M + H] = 422.2 m/z; $^1$H NMR (500 MHz, DMSO-$d_6$) δ [ppm] 10.27 (s, 1H), 9.62 (s, 1H), 8.04 (d, J = 4.3, 1H), 7.51 (d, J = 4.3, 1H), 7.27 (d, J = 2.0, 1H), 7.20 (dd, J = 8.1, 2.0, 1H), 7.13 (d, J = 8.1, 1H), 4.86-4.76 (m, 2H), 4.20 (s, 1H), 3.56-3.46 (m, 2H),1.61-1.47 (m, 4H), 1.42 (q, J = 7.4, 2H), 1.22 (s, 6H), 0.86 (t, J = 7.5, 3H). |
| E45 | 4,4-dimethyl-7-[8-(2-oxo-1-oxa-3,8-diaza-spiro[4.5]dec-8-yl)-[1,2,4]triazolo[1,5-a]pyrazin-2-ylamino]-3,4-dihydro-1H-quinazolin-2-one 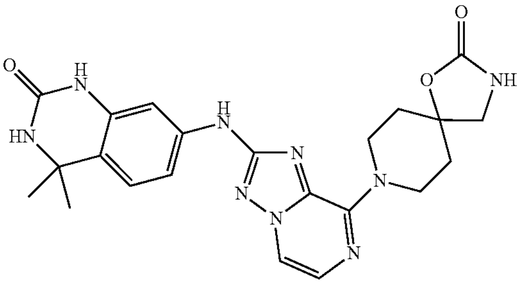 [SMILES: CC1(C)NC(=O)Nc2cc(Nc3nc4c(N5CCC6(CC5)CNC(=O)O6)nccn4n3)ccc21] | LCMS (Method D) Rt: 1.572 min, observed [M + H] = 464.3 m/z. |
| E46 | 4,4-dimethyl-7-[8-(2-oxo-1-oxa-3,8-diaza-spiro[4.5]dec-8-yl)-[1,2,4]triazolo[1,5-a]pyrazin-2-ylamino]-3,4-dihydro-1H-quinolin-2-one 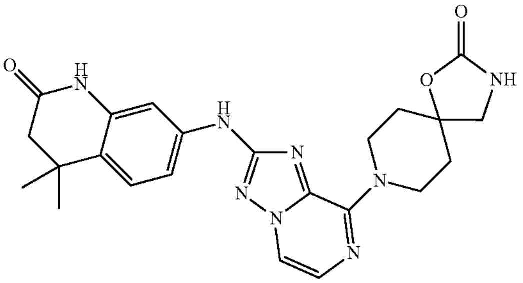 [SMILES: CC1(C)CC(=O)Nc2cc(Nc3nc4c(N5CCC6(CC5)CNC(=O)O6)nccn4n3)ccc21] | LCMS (Method D) Rt: 1.702 min, observed [M + H] = 463.2 m/z. |
| E47 | 4,4-dimethyl-7-[8-(2-oxo-1-oxa-3,8-diaza-spiro[4.5]dec-8-yl)-[1,2,4]triazolo[1,5-a]pyrazin-2-ylamino]-1,4-dihydro-benzo[d][1,3]oxazin-2-one 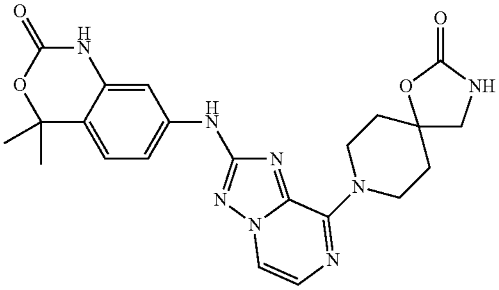 [SMILES: CC1(C)OC(=O)Nc2cc(Nc3nc4c(N5CCC6(CC5)CNC(=O)O6)nccn4n3)ccc21] | LCMS (Method D) Rt: 1.64 min, observed [M + H] = 465.2 m/z. |

-continued

| nr. | name/structure | LCMS; NMR |
| --- | --- | --- |
| E48 | (R)-7-[2-(4,4-dimethyl-2-oxo-1,2,3,4-tetrahydro-quinolin-7-ylamino)-[1,2,4]triazolo[1,5-a]pyrazin-8-yl]-2,7-diaza-spiro[4.4]nonane-1,3-dione 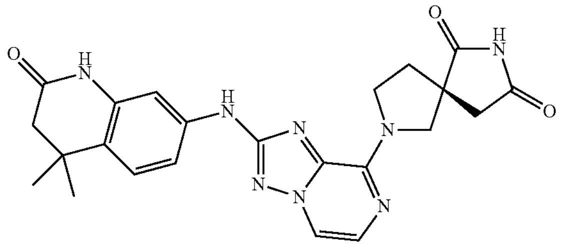 [SMILES: CC1(C)CC(=O)Nc2cc(Nc3nc4c(N5CC[C@@]6(CC(=O)NC6=O)C5)nccn4n3)ccc21] | LCMS (Method D) Rt: 1.593 min, observed [M + H] = 461.2 m/z. |
| E49 | (S)-7-[2-(4,4-dimethyl-2-oxo-1,2,3,4-tetrahydro-quinolin-7-ylamino)-[1,2,4]triazolo[1,5-a]pyrazin-8-yl]-2,7-diaza-spiro[4.4]nonane-1,3-dione 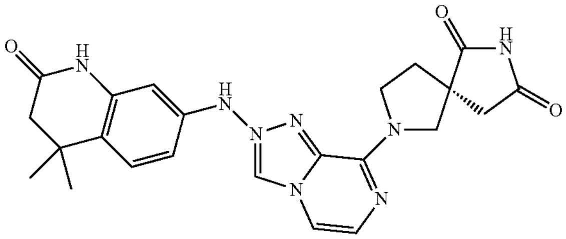 | LCMS (Method D) Rt: 1.593 min, observed [M + H] = 461.2 m/z. |
| E50 | 6-{8-[5-((S)-1-amino-ethyl)-2-methoxy-phenyl]-[1,2,4]triazolo[1,5-a]pyrazin-2-ylamino}-3,3-dimethyl-1,3-dihydro-indol-2-one 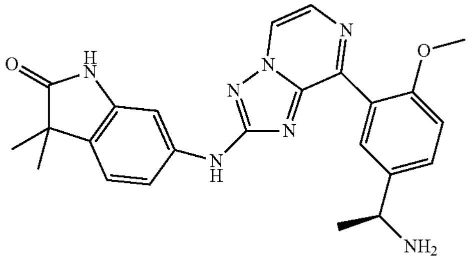 [SMILES: COc1ccc([C@H](C)N)cc1-c1nccn2nc(Nc3ccc4c(c3)NC(=O)C4(C)C)nc12] | LCMS (Method C) Rt: 1.433 min, observed [M + H] = 444.2 m/z; $^{1}H$ NMR (500 MHz, DMSO-$d_6$) δ [ppm] 10.30 (s, 1H), 9.88 (s, 1H), 8.89 (d, J = 4.3, 1H), 8.41 (s, 3H), 8.18 (d, J = 4.4, 1H), 7.67 (dd, J = 8.7, 2.4, 1H), 7.60 (d, J = 2.4, 1H), 7.28-7.26 (m, 1H), 7.25-7.23 (m, 2H), 7.14 (d, J = 8.0, 1H), 4.50-4.39 (m, 1H), 3.79 (s, 3H), 1.54 (d, J = 6.8, 3H), 1.22 (s, 6H). |
| E51 | 3,3-dimethyl-6-[8-((R)-8-oxo-2,7-diaza-spiro[4.4]non-2-yl)-[1,2,4]triazolo[1,5-a]pyrazin-2-ylamino]-1,3-dihydro-indol-2-one 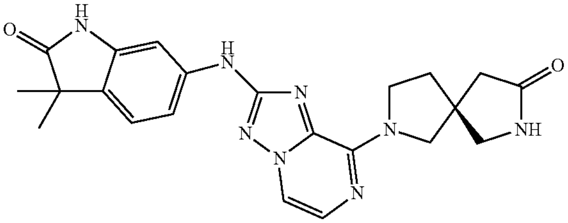 [SMILES: CC1(C)C(=O)Nc2cc(Nc3nc4c(N5CC[C@@]6(CNC(=O)C6)C5)nccn4n3)ccc21] | LCMS (Method C) Rt: 1.533 min, observed [M + H] = 433.2 m/z. |

-continued

| nr. | name/structure | LCMS; NMR |
|---|---|---|
| E52 | 3,3-dimethyl-6-[8-((S)-8-oxo-2,7-diaza-spiro[4.4]non-2-yl)-[1,2,4]triazolo[1,5-a]pyrazin-2-ylamino]-1,3-dihydro-indol-2-one 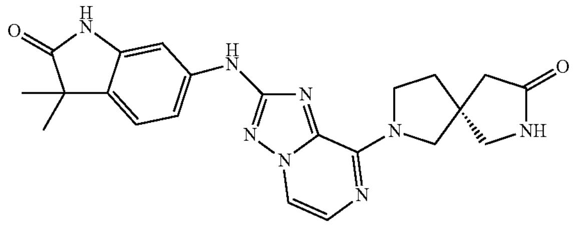 [SMILES: CC1(C)C(=O)Nc2cc(Nc3nc4c(N5CC[C@]6(CNC(=O)C6)C5)nccn4n3)ccc21] | LCMS (Method C) Rt: 1.533 min, observed [M + H] = 433.2 m/z. |
| E53 | 8-[2-(4,4-dimethyl-1,2,3,4-tetrahydro-quinolin-7-ylamino)-[1,2,4]triazolo[1,5-a]pyrazin-8-yl]-1-oxa-3,8-diaza-spiro[4.5]decan-2-one 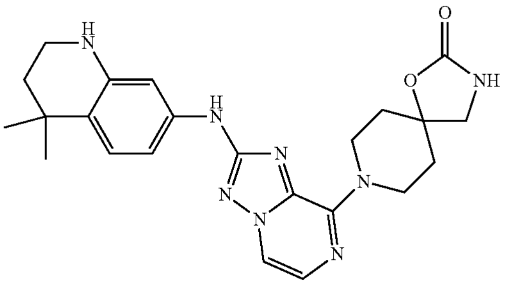 [SMILES: CC1(C)CCNc2cc(Nc3nc4c(N5CCC6(CC5)CNC(=O)O6)nccn4n3)ccc21] | LCMS (Method D) Rt: 1.542 min, observed [M + H] = 449.2 m/z. |
| E54 | 8-[2-(5,5-dimethyl-5,6,7,8-tetrahydro-naphthalen-2-ylamino)-[1,2,4]triazolo[1,5-a]pyrazin-8-yl]-1-oxa-3,8-diaza-spiro[4.5]decan-2-one 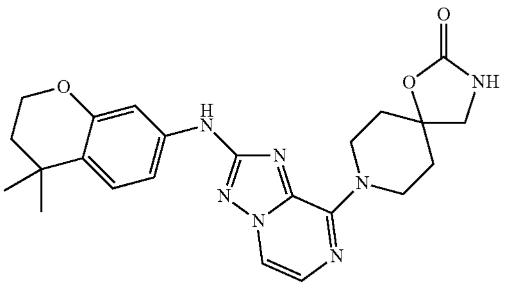 [SMILES: CC1(C)CCOc2cc(Nc3nc4c(N5CCC6(CC5)CNC(=O)O6)nccn4n3)ccc21] | LCMS (Method D) Rt: 2.253 min, observed [M + H] = 448.3 m/z. |
| E55 | 8-[2-(4,4-dimethyl-chroman-7-ylamino)-[1,2,4]triazolo[1,5-a]pyrazin-8-yl]-1-oxa-3,8-diaza-spiro[4.5]decan-2-one 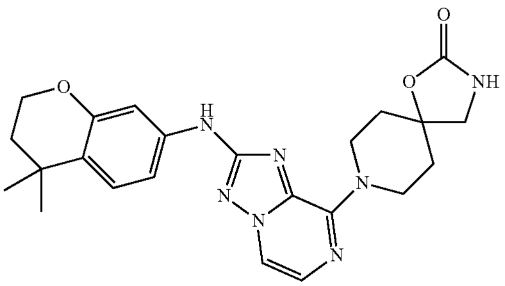 [SMILES: CC1(C)CCOc2cc(Nc3nc4c(N5CCC6(CC5)CNC(=O)O6)nccn4n3)ccc21] | LCMS (Method D) Rt: 2.029 min, observed [M + H] = 450.2 m/z; $^{1}$H NMR (500 MHz, DMSO-$d_6$) δ [ppm] 9.54 (s, 1H), 8.15 (d, J = 4.3, 1H), 7.56-7.49 (m, 2H), 7.18 (d, J = 8.5, 1H) 7.14 (d, J = 2.3, 1H) 7.07 (dd, J = 8.5, 2.3, 1H), 4.56-4.47 (m, 2H), 4.16-4.09 (m, 2H), 3.91-3.81 (m, 2H), 3.31-3.30 (m, 2H), 1.95-1.81 (m, 4H), 1.79-1.72 (m, 2H), 1.26 (s, 6H). |

-continued

| nr. | name/structure | LCMS; NMR |
|---|---|---|
| E56 | 6-[8-(2-amino-7,8-dihydro-5H-pyrido[4,3-d]pyrimidin-6-yl)-[1,2,4]triazolo[1,5-a]pyrazin-2-ylamino]-3,3-dimethyl-1,3-dihydro-indol-2-one 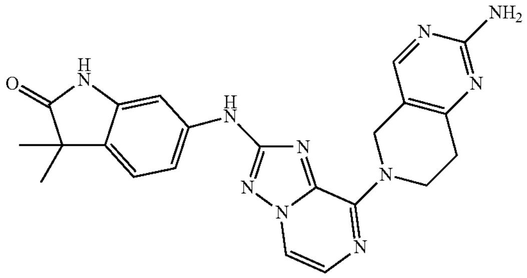 [SMILES: CC1(C)C(=O)Nc2cc(Nc3nc4c(N5CCc6nc(N)ncc6C5)nccn4n3)ccc21] | LCMS (Method D) Rt: 1.644 min, observed [M + H] = 443.2 m/z; $^1$H NMR (500 MHz, DMSO-$d_6$) δ [ppm] 10.31 (s, 1H), 9.69 (s, 1H), 8.17-8.10 (m, 2H), 7.58 (d, J = 4.4, 1H), 7.32 (d, J = 1.9, 1H), 7.21 (dd, J = 8.1, 2.0, 1H), 7.16 (d, J = 8.1, 1H), 6.39 (s, 2H), 4.98 (s, 2H), 4.48 (t, J = 5.9, 2H), 2.82 (t, J = 6.0, 2H), 1.23 (s, 6H). |
| E57 | 6-(8-azepan-1-yl-[1,2,4]triazolo[1,5-a]pyrazin-2-ylamino)-3,3-dimethyl-1,3-dihydro-indol-2-one 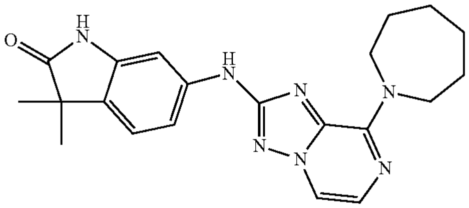 [SMILES: CC1(C)C(=O)Nc2cc(Nc3nc4c(N5CCCCCC5)nccn4n3)ccc21] | LCMS (Method D) Rt: 1.793 min, observed [M + H] = 392.2 m/z. |
| E58 | 3,3-dimethyl-6-[8-(4-methyl-2-oxa-3,9-diaza-spiro[5.5]undec-3-en-9-yl)-[1,2,4]triazolo[1,5-a]pyrazin-2-ylamino]-1,3-dihydro-indol-2-one 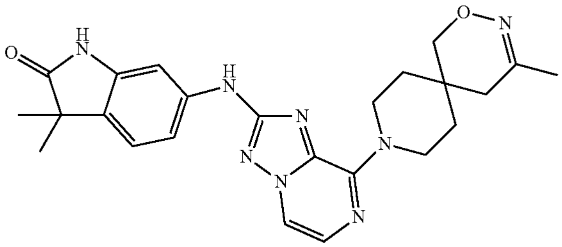 [SMILES: CC1=NOCC2(CCN(c3nccn4nc(Nc5ccc6c(c5)NC(=O)C6(C)C)nc34)CC2)C1] | LCMS (Method D) Rt: 1.616 min, observed [M + H] = 461.3 m/z; $^1$H NMR (500 MHz, DMSO-$d_6$) δ [ppm] 10.27 (s, 1H), 9.66 (s, 1H), 8.08 (d, J = 4.3, 1H), 7.53 (d, J = 4.3, 1H), 7.27 (d, J = 2.0, 1H), 7.19 (dd, J = 8.1, 2.0, 1H), 7.13 (d, J = 8.1, 1H), 4.20-4.04 (m, 4H), 3.80-3.74 (m, 2H), 2.67-2.61 (m, 2H), 1.92-1.86 (m, 3H), 1.78-1.64 (m, 4H), 1.22 (s, 6H). |
| E59 | 3,3-dimethyl-6-{8-[4-(5-trifluoromethyl-1H-imidazol-2-yl)-piperidin-1-ylF [1,2,4]triazolo[1,5-a]pyrazin-2-ylamino}-1,3-dihydro-indol-2-one 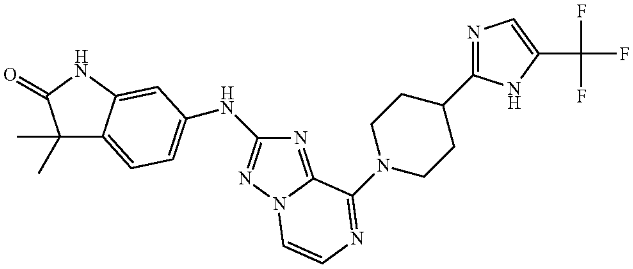 [SMILES: CC1(C)C(=O)Nc2cc(Nc3nc4c(N5CCC(c6ncc(C(F)(F)F)[nH]6)CC5)nccn4n3)ccc21] | LCMS (Method D) Rt: 1.816 min, observed [M + H] = 512.2 m/z; $^1$H NMR (500 MHz, DMSO-$d_6$) δ [ppm] 12.40 (s, 1H), 10.28 (s, 1H), 9.67 (s, 1H), 8.10 (d, J = 4.3, 1H), 7.66-7.62 (m, 1H), 7.56 (d, J = 4.3, 1H), 7.28 (d, J = 2.0, 1H), 7.21 (dd, J = 8.1, 2.0, 1H), 7.14 (d, J = 8.1, 1H), 5.24-5.15 (m, 2H), 3.29-3.21 (m, 2H), 3.10 (tt, J = 11.6, 3.9, 1H), 2.10-1.99 (m, 2H), 1.86-1.72 (m, 2H), 1.22 (s, 6H). |

-continued

| nr. | name/structure | LCMS; NMR |
|---|---|---|
| E60 | 3,3-dimethyl-6-[8-(5-trifluoromethyl-1H-[1,2,4]triazol-3-ylamino)-[1,2,4]triazolo[1,5-a]pyrazin-2-ylamino]-1,3-dihydro-indol-2-one 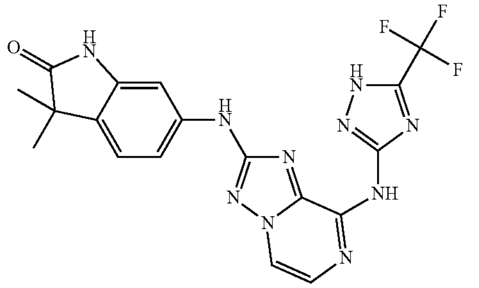 [SMILES: CC1(C)C(=O)Nc2cc(Nc3nc4c(Nc5n[nH]c(C(F)(F)F)n5)nccn4n3)ccc21] | LCMS (Method D) Rt: 1.922 min, observed [M + H] = 445.2 m/z. |
| E61 | 8-[2-(5-methoxy-3aH-indol-6-ylamino)-[1,2,4]triazolo[1,5-a]pyrazin-8-yl]-1-oxa-3,8-diaza-spiro[4.5]decan-2-one 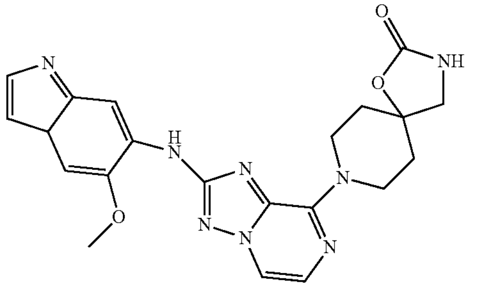 [SMILES: COC1=CC2C=CN=C2C=C1Nc1nc2c(N3CCC4(CC3)CNC(=O)O4)nccn2n1] | LCMS (Method D) Rt: 1.852 min, observed [M + H] = 435.2 m/z; $^1$H NMR (500 MHz, DMSO-$d_6$) δ [ppm] 10.88-10.84 (m, 1H), 8.17-8.15 (m, 1H), 8.12 (d, J = 4.3, 1H), 7.91 (s, 1H), 7.57 (d, J = 4.3, 1H), 7.54 (s, 1H), 7.17 (t, J = 2.7, 1H), 7.13 (s, 1H), 6.34-6.30 (m, 1H), 4.63-4.52 (m, 2H), 3.89 (s, 3H), 3.89-3.84 (m, 2H), 3.30 (s, 2H), 1.98-1.81 (m, 4H). |
| E62 | 6-{8-[(2R,4S)-2-(3-fluoro-phenyl)-4-hydroxy-pyrrolidin-1-yl]-[1,2,4]triazolo[1,5-a]pyrazin-2-ylamino}-3,3-dimethyl-1,3-dihydro-indol-2-one 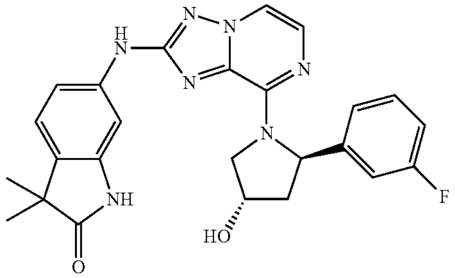 [SMILES: CC1(C)C(=O)Nc2cc(Nc3nc4c(N5C[C@@H](O)C[C@@H]5c5cccc(F)c5)nccn4n3)ccc21] | LCMS (Method C) Rt: 1.944 min, observed [M + H] = 474.2 m/z; $^1$H NMR (400 MHz, DMSO-$d_6$) δ [ppm] 10.02 (s, 1H), 9.24 (s, 1H), 7.89 (d, J = 4.4, 1H), 7.38 (d, J = 4.4, 1H), 7.32-7.24 (m, 2H), 7.20 (dd, J = 8.1, 2.0, 1H), 7.13-7.05 (m, 2H), 7.06-7.01 (m, 1H), 6.96-6.90 (m, 1H), 5.74 (t, J = 7.4, 1H), 4.89-4.80 (m, 1H), 4.51-4.42 (m, 1H), 4.41-4.29 (m, 2H), 2.48-2.41 (m, 1H), 2.08-2.00 (m, 1H), 1.26 (s, 6H). |
| E63 | 8-[2-(3,3-dimethyl-2-oxo-2,3-dihydro-1H-indol-6-ylamino)-[1,2,4]triazolo[1,5-a]pyrazin-8-yl]-2,8-diaza-spiro[4.5]decan-3-one 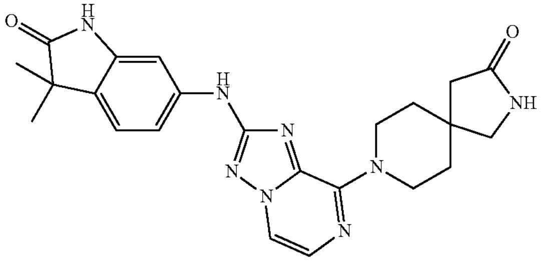 [SMILES: CC1(C)C(=O)Nc2cc(Nc3nc4c(N5CCC6(CC5)CNC(=O)C6)nccn4n3)ccc21] | LCMS (Method C) Rt: 1.687 min, observed [M + H] = 447.2 m/z; $^1$H NMR (500 MHz, DMSO-$d_6$) δ [ppm] 10.29 (s, 1H), 9.66 (s, 1H), 8.08 (d, J = 4.3, 1H), 7.57-7.51 (m, 2H), 7.28 (d, J = 1.9, 1H), 7.20 (dd, J = 8.1, 2.0, 1H), 7.14 (d, J = 8.1, 1H), 4.31-4.22 (m, 2H), 4.01-3.92 (m, 2H), 3.13 (s, 2H), 2.17 (s, 2H), 1.67 (t, J = 5.6, 4H), 1.22 (s, 6H). |

-continued

| nr. | name/structure | LCMS; NMR |
|---|---|---|
| E64 | 6-{8-[(2R,4R)-2-(3-fluoro-phenyl)-4-hydroxy-pyrrolidin-1-yl]-[1,2,4]triazolo[1,5-a]pyrazin-2-ylamino}-3,3-dimethyl-1,3-dihydro-indol-2-one 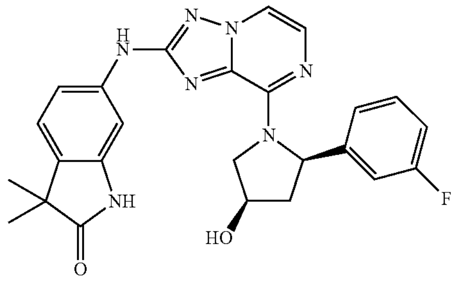 [SMILES: CC1(C)C(=O)Nc2cc(Nc3nc4c(N5C[C@H](O)C[C@@H]5c5cccc(F)c5)nccn4n3)ccc21] | LCMS (Method C) Rt: 1.913 min, observed [M + H] = 474.2 m/z; $^1$H NMR (300 MHz, DMSO-$d_6$) δ [ppm] 10.27 (s, 1H), 9.56 (s, 1H), 7.96 (d, J = 4.4, 1H), 7.39 (d, J = 4.5, 1H), 7.31-7.16 (m, 3H), 7.15-7.04 (m, 3H), 6.92 (td, J = 8.5, 2.6, 1H), 5.65 (s, 1H), 5.14-4.80 (m, 1H), 4.53-4.38 (m, 2H), 4.34-4.08 (m, 1H), 2.71-2.58 (m, 1H), 1.99-1.84 (m, 1H), 1.23 (s, 6H). |
| E65 | 3,3-dimethyl-6-(8-{3[(2,2,2-trifluoro-ethylamino)-methyl]-pyrrolidin-1-yl}-[1,2,4]triazolo[1,5-a]pyrazin-2-ylamino)-1,3-dihydro-indol-2-one 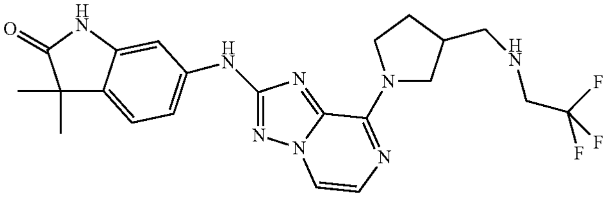 [SMILES: CC1(C)C(=O)Nc2cc(Nc3nc4c(N5CCC(CNCC(F)(F)F)C5)nccn4n3)ccc21] | LCMS (Method D) Rt: 1.551 min, observed [M + H] = 475.2 m/z; $^1$H NMR (500 MHz, DMSO-$d_6$) δ [ppm] 10.26 (s, 1H), 9.57 (s, 1H), 7.93 (d, J = 4.4, 1H), 7.46 (d, J = 4.4, 1H), 7.28 (d, J = 1.9, 1H), 7.22 (dd, J = 8.1, 2.0, 1H), 7.12 (d, J = 8.1, 1H), 4.21-3.95 (m, 2H), 3.93-3.74 (m, 1H), 3.67-3.49 (m, 1H), 3.28-3.22 (m, 1H), 3.17 (d, J = 5.2, 2H), 2.77-2.63 (m, 2H), 2.48-2.37 (m, 1H), 2.16-2.05 (m, 1H), 1.78-1.67(m, 1H), 1.22 (s, 6H). |
| E66 | 6-(8-cyclopentyl-[1,2,4]triazolo[1,5-a]pyrazin-2-ylamino)-3,3-dimethyl-1,3-dihydro-indol-2-one 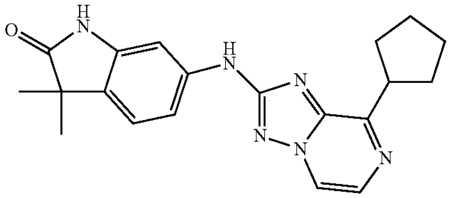 [SMILES: CC1(C)C(=O)Nc2cc(Nc3nc4c(C5CCCC5)nccn4n3)ccc21] | LCMS (Method D) Rt: 2.155 min, observed [M + H] = 363.2 m/z. |
| E67 | 3,3-dimethyl-6-[8-(8-oxa-3-aza-bicyclo[3.2.1]oct-3-yl)-[1,2,4]triazolo[1,5-a]pyrazin-2-ylamino]-1,3-dihydro-indol-2-one 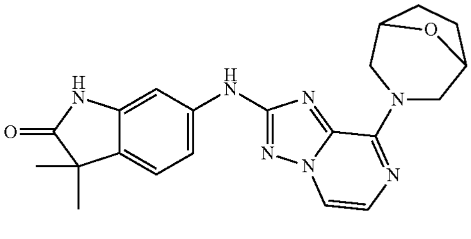 [SMILES: CC1(C)C(=O)Nc2cc(Nc3nc4c(N5CC6CCC(C5)O6)nccn4n3)ccc21] | LCMS (Method D) Rt: 1.873 min, observed [M + H] = 406.2 m/z; $^1$H NMR (500 MHz, DMSO-$d_6$) δ [ppm] 10.28 (s, 1H), 9.66 (s, 1H), 8.10 (d, J = 4.3, 1H), 7.53 (d, J = 4.4, 1H), 7.27 (d, J = 2.0, 1H), 7.18 (dd, J = 8.1, 2.0, 1H), 7.13 (d, J = 8.1, 1H), 4.79 (d, J = 12.9, 2H), 4.50-4.43 (m, 2H), 3.27-3.22 (m, 2H), 1.91-1.77 (m, 4H), 1.22 (s, 6H). |

-continued

| nr. | name/structure | LCMS; NMR |
|---|---|---|
| E68 | 6-(8-[1,4]diazepan-1-yl-[1,2,4]triazolo[1,5-a]pyrazin-2-ylamino)-3,3-dimethyl-1,3-dihydro-indol-2-one 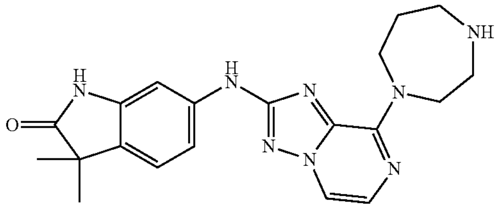 [SMILES: CC1(C)C(=O)Nc2cc(Nc3nc4c(N5CCCNCC5)nccn4n3)ccc21] | LCMS (Method D) Rt: 1.604 min, observed [M + H] = 393.3 m/z; $^1$H NMR (500 MHz, DMSO-d$_6$) δ [ppm] 10.31 (s, 1H), 9.61 (s, 1H), 8.06 (d, J = 4.3, 1H), 7.87 (s, 1H), 7.53 (d, J = 4.3, 1H), 7.30 (d, J = 1.9, 1H), 7.18 (dd, J = 8.2, 2.0, 1H), 7.14 (d, J = 8.1, 1H), 4.33-4.15 (m, 4H), 3.28-3.24 (m, 2H), 3.12-3.06 (m, 2H), 2.06 (p, J = 6.2, 2H), 1.22 (s, 6H). |
| E69 | 3,3-dimethyl-6-(8-piperidin-1-yl-[1,2,4]triazolo[1,5-a]pyrazin-2-ylamino)-1,3-dihydro-indol-2-one 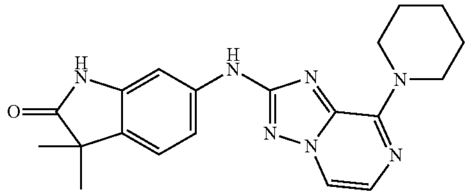 [SMILES: CC1(C)C(=O)Nc2cc(Nc3nc4c(N5CCCCC5)nccn4n3)ccc21] | LCMS (Method D) Rt: 1.759 min, observed [M + H] = 379.2 m/z; $^1$H NMR (500 MHz, DMSO-d$_6$) Rt [ppm] 10.28 (s, 1H), 9.65 (s, 1H), 8.05 (d, J = 4.3, 1H), 7.52 (d, J = 4.3, 1H), 7.27 (d, J = 1.9, 1H), 7.20 (dd, J = 8.1, 2.0, 1H), 7.13 (d, J = 8.1, 1H), 4.13-4.05 (m, 4H), 1.72-1.59 (m, 6H), 1.22 (s, 6H). |
| E70 | 6-[8-(4-hydroxy-4-trifluoromethyl-piperidin-1-yl)-[1,2,4]triazolo[1,5-a]pyrazin-2-ylamino]-3,3-dimethyl-1,3-dihydro-indol-2-one 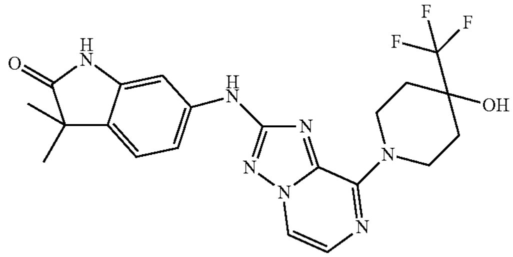 [SMILES: CC1(C)C(=O)Nc2cc(Nc3nc4c(N5CCC(O)(C(F)(F)F)CC5)nccn4n3)ccc21] | LCMS (Method D) Rt: 1.888 min, observed [M + H] = 462.2 m/z; $^1$H NMR (500 MHz, DMSO-d$_6$) δ [ppm] 10.28 (s, 1H), 9.65 (s, 1H), 8.11 (d, J = 4.4, 1H), 7.55 (d, J = 4.3, 1H), 7.28 (d, J = 1.9, 1H), 7.19 (dd, J = 8.1, 2.0, 1H), 7.13 (d, J = 8.1, 1H), 6.12 (s, 1H), 5.15 (d, J = 13.3, 2H), 3.35-3.30 (m, 2H), 1.83-1.73 (m, 4H), 1.22 (s, 6H). |
| E71 | 8-[2-(3,3-dimethyl-2-oxo-2,3-dihydro-1H-indol-6-ylamino)-[1,2,4]triazolo[1,5-a]pyrazin-8-yl]-2-methyl-1,3,8-triaza-spiro[4.5]dec-1-en-4-one 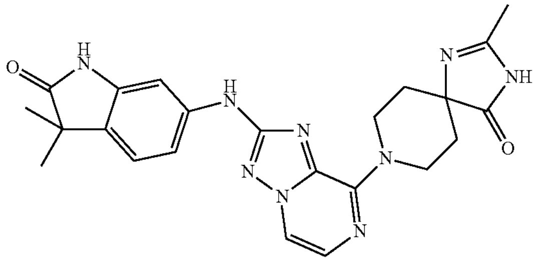 [SMILES: CC1=NC2(CCN(c3nccn4nc(Nc5ccc6c(c5)NC(=O)C6(C)C)nc34)CC2)C(=O)N1] | LCMS (Method D) Rt: 1.61 min, observed [M + H] = 460.3 m/z; $^1$H NMR (500 MHz, DMSO-d$_6$) δ [ppm] 10.80 (s, 1H), 10.29 (s, 1H), 9.69 (s, 1H), 8.12 (d, J = 4.3, 1H), 7.57 (d, J = 4.3, 1H), 7.32 (d, J = 2.0, 1H), 7.18 (dd, J = 8.1, 1.9, 1H), 7.14 (d, J = 8.1, 1H), 5.02 (d, J = 13.6, 2H), 3.67 (t, J = 12.2, 2H), 2.09 (s, 3H), 1.86-1.73 (m, 2H), 1.46 (d, J = 13.2, 2H), 1.23 (s, 6H). |

-continued

| nr. | name/structure | LCMS; NMR |
|---|---|---|
| E72 | 3,3-dimethyl-6-[8-(4-oxo-azepan-1-yl)-[1,2,4]triazolo[1,5-a]pyrazin-2-ylamino]-1,3-dihydro-indol-2-one 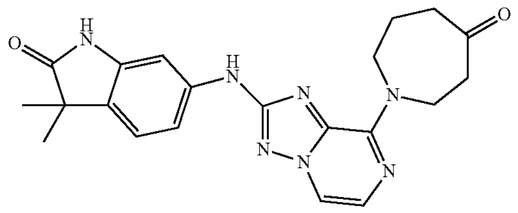 [SMILES: CC1(C)C(=O)Nc2cc(Nc3nc4c(N5CCCC(=O)CC5)nccn4n3)ccc21] | LCMS (Method D) Rt: 1.707 min, observed [M + H] = 406.2 m/z. |
| E73 | 6-[8-(2,3-dihydro-indol-1-yl)-[1,2,4]triazolo[1,5-a]pyrazin-2-ylamino]-3,3-dimethyl-1,3-dihydro-indol-2-one 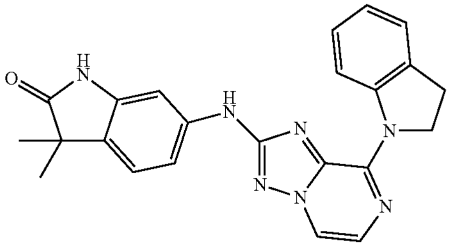 [SMILES: CC1(C)C(=O)Nc2cc(Nc3nc4c(N5CCc6ccccc65)nccn4n3)ccc21] | LCMS (Method D) Rt: 2.386 min, observed [M + H] = 412.2 m/z; $^1$H NMR (500 MHz, DMSO-$d_6$) δ [ppm] 10.32 (s, 1H), 9.70 (s, 1H), 8.39 (d, J = 8.0, 1H), 8.25 (d, J = 4.3, 1H), 7.70 (d, J = 4.3, 1H), 7.35 (d, J = 2.0, 1H), 7.31-7.27 (m, 1H), 7.23 (dd, J = 8.1, 2.0, 1H), 7.21-7.17 (m, 1H), 7.15 (d, J = 8.1, 1H), 7.01-6.95 (m, 1H), 4.88 (t, J = 8.6, 2H), 3.27 (t, J = 8.5, 2H), 1.23 (s, 6H). |
| E74 | 3,3-dimethyl-6-[8-(5-oxo-[1,4]diazepan-1-yl)-[1,2,4]triazolo[1,5-a]pyrazin-2-ylamino]-1,3-dihydro-indol-2-one 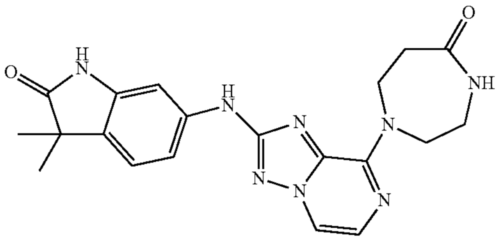 [SMILES: CC1(C)C(=O)Nc2cc(Nc3nc4c(N5CCNC(=O)CC5)nccn4n3)ccc21] | LCMS (Method D) Rt: 1.634 min, observed [M + H] = 407.2 m/z; $^1$H NMR (500 MHz, DMSO-$d_6$) δ [ppm] 10.32 (s, 1H), 9.64 (s, 1H), 8.11 (d, J = 4.3, 1H), 7.65 (t, J = 5.5, 1H), 7.57 (d, J = 4.3, 1H), 7.30 (d, J = 1.9, 1H), 7.18 (dd, J = 8.1, 2.0, 1H), 7.14 (d, J = 8.1, 1H), 4.31-4.24 (m, 4H), 3.31-3.27 (m, 2H), 2.66-2.60 (m, 2H), 1.22 (s, 6H). |
| E75 | 1-[2-(3,3-dimethyl-2-oxo-2,3-dihydro-1H-indol-6-ylamino)-[1,2,4]triazolo[1,5-a]pyrazin-8-yl]-3-methyl-pyrrolidine-3-carboxylic acid amide 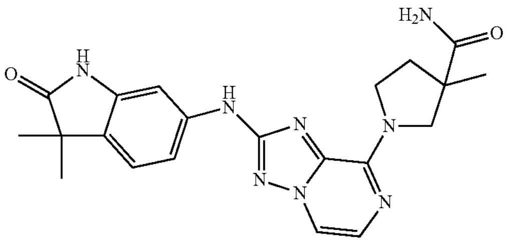 [SMILES: CC1(C(N)=O)CCN(c2nccn3nc(Nc4ccc5c(c4)NC(=O)C5(C)C)nc23)C1] | LCMS (Method D) Rt: 2.022 min, observed [M + H] = 421.2 m/z; $^1$H NMR (500 MHz, DMSO-$d_6$) δ [ppm] 10.26 (s, 1H), 9.59 (s, 1H), 7.94 (d, J = 4.4, 1H), 7.46 (d, J = 4.4, 1H), 7.37 (s, 1H), 7.28 (d, J = 2.0, 1H), 7.21 (dd, J = 8.1, 2.0, 1H), 7.12 (d, J = 8.1, 1H), 6.99 (s, 1H), 4.41-3.65 (m, 4H), 2.41-2.29 (m, 1H), 1.93-1.85 (m, 1H), 1.33 (s, 3H), 1.22 (s, 6H). |

-continued

| nr. | name/structure | LCMS; NMR |
|---|---|---|
| E76 | 6-[8-(1H-indol-3-yl)-[1,2,4]triazolo[1,5-a]pyrazin-2-ylamino]-3,3-dimethyl-1,3-dihydro-indol-2-one 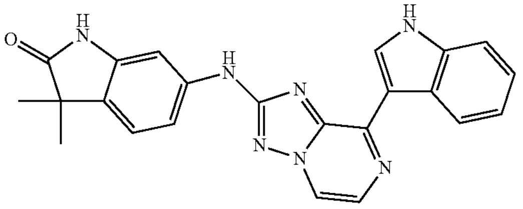 [SMILES: CC1(C)C(=O)Nc2cc(Nc3nc4c(-c5c[nH]c6ccccc56)nccn4n3)ccc21] | LCMS (Method D) Rt: 2.17 min, observed [M + H] = 410.2 m/z; $^1$H NMR (500 MHz, DMSO-$d_6$) δ [ppm] 11.86 (d, J = 2.9, 1H), 10.32 (s, 1H), 9.85 (s, 1H), 8.99 (d, J = 2.8, 1H), 8.71 (d, J = 7.4, 1.4, 1H), 8.57 (d, J = 4.3, 1H), 8.13 (d, J = 4.3, 1H), 7.55 (d, J = 8.2, 1H), 7.38 (d, J = 2.0, 1H), 7.35-7.16 (m, 4H), 1.25 (s, 6H). |
| E77 | 8-[2-(4,4-dimethyl-1,2,3,4-tetrahydro-quinolin-7-ylamino)-[1,2,4]triazolo[1,5-a]pyrazin-8-yl]-2,8-diaza-spiro[4.5]decan-3-one 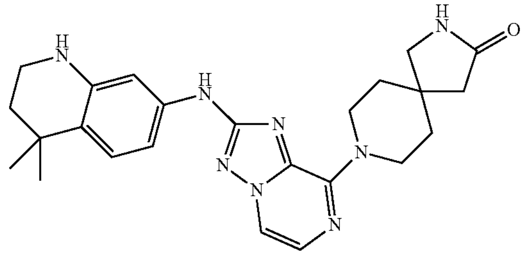 [SMILES: CC1(C)CCNc2cc(Nc3nc4c(N5CCC6(CC5)CNC(=O)C6)nccn4n3)ccc21] | LCMS (Method D) Rt: 1.531 min, observed [M + H] = 447.3 m/z; $^1$H NMR (500 MHz, DMSO-$d_6$) δ [ppm] 9.20 (s, 1H), 8.03 (d, J = 4.3, 1H), 7.53 (s, 1H), 7.50 (d, J = 4.3, 1H), 6.97 (d, J = 8.3, 1H), 6.78-6.69 (m, 2H), 5.59 (s, 1H), 4.30-4.21 (m, 2H), 4.00-3.90 (m, 2H), 3.18-3.15 (m, 2H), 3.12 (s, 2H), 2.15 (s, 2H), 1.66 (t, J = 5.6, 4H), 1.61-1.55 (m, 2H), 1.19 (s, 6H). |
| E78 | 3,3-dimethyl-6-[8-((1R,3R,5S)-8-methyl-8-aza-bicyclo[3.2.1]oct-3-ylamino)-[1,2,4]triazolo[1,5-a]pyrazin-2-ylamino]-1,3-dihydro-indol-2-one 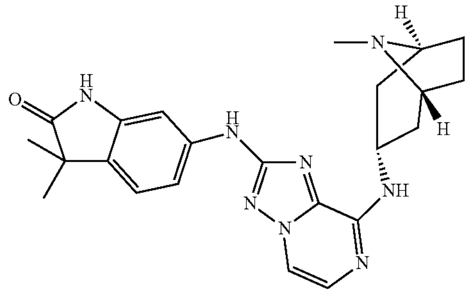 [SMILES: CN1[C@@H]2CC[C@H]1C[C@@H](Nc1nccn3nc(Nc4ccc5c(c4)NC(=O)C5(C)C)nc13)C2] | LCMS (Method D) Rt: 1.563 min, observed [M + H] = 433.3 m/z; $^1$H NMR (500 MHz, DMSO-$d_6$) δ [ppm] 10.28 (s, 1H), 9.56 (s, 1H), 8.05 (d, J = 4.5, 1H), 7.50 (d, J = 4.5, 1H), 7.31-7.23 (m, 2H), 7.14 (d, J = 8.0, 2H), 4.21-4.14 (m, 1H), 3.86-3.82 (m, 2H), 2.66 (s, 3H), 2.48-2.38 (m, 4H), 2.35-2.24 (m, 2H), 2.23-2.17 (m, 2H), 1.22 (s, 6H). |
| E79 | 3,3-dimethyl-6-{8-[(piperidin-3-ylmethyl)-amino]-[1,2,4]triazolo[1,5-a]pyrazin-2-ylamino}-1,3-dihydro-indol-2-one 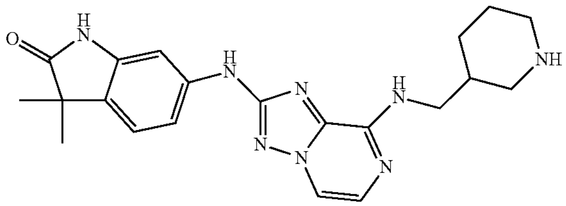 [SMILES: CC1(C)C(=O)Nc2cc(Nc3nc4c(NCC5CCCNC5)nccn4n3)ccc21] | LCMS (Method D) Rt: 1.462 min, observed [M + H] = 407.2 m/z; $^1$H NMR (400 MHz, DMSO-$d_6$) δ [ppm] 10.29 (s, 1H), 9.59 (s, 1H), 9.13 (d, J = 11.2, 1H), 8.99-8.40 (m, 2H), 8.08 (d, J = 5.0, 1H), 7.41 (d, J = 5.0, 1H), 7.34 (dd, J = 8.1, 2.0, 1H), 7.20 (d, J = 2.0, 1H), 7.16 (d, J = 8.1, 1H), 3.62-3.53 (m, 2H), 3.37-3.25 (m, 1H), 3.24-3.08 (m, 1H), 2.85-2.59 (m, 2H), 2.30-2.13 (m, 1H), 1.94-1.71 (m, 2H), 1.72-1.53 (m, 1H), 1.37-1.11 (m, 7H). |

-continued

| nr. | name/structure | LCMS; NMR |
|---|---|---|
| E80 | 6-{8-[(2R,4S)-4-hydroxy-2-(2-trifluoromethyl-phenyl)-pyrrolidin-1-yl]-[1,2,4]triazolo[1,5-a]pyrazin-2-ylamino}-3,3-dimethyl-1,3-dihydro-indol-2-one 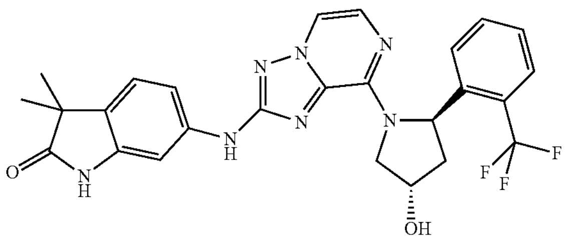 [SMILES: CC1(C)C(=O)Nc2cc(Nc3nc4c(N5C[C@@H](O)C[C@@H]5c5ccccc5C(F)(F)F)nccn4n3)ccc21] | LCMS (Method C) Rt: 2.265 min, observed [M + H] = 524.2 m/z; $^1$H NMR (400 MHz, DMSO-$d_6$) δ [ppm] 10.28 (s, 1H), 9.62 (s, 1H), 7.91 (d, J = 4.4, 1H), 7.69 (d, J = 7.8, 1H), 7.55-7.45 (m, 2H), 7.38 (t, J = 7.5, 1H), 7.32 (d, J = 2.0, 1H), 7.25-7.21 (m, 2H), 7.14 (d, J = 8.1, 1H), 5.72 (t, J = 7.9, 1H), 4.65 (d, J = 11.3, 1H), 4.51-4.41 (m, 2H), 2.47-2.38 (m, 1H), 1.92-1.82 (m, 1H), 1.23 (s, 6H). |
| E81 | 6-[8-(5-methoxy-2,3-dihydro-indol-1-yl)-[1,2,4]triazolo[1,5-a]pyrazin-2-ylamino]-3,3-dimethyl-1,3-dihydro-indol-2-one 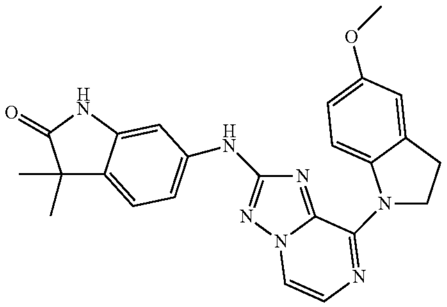 [SMILES: COc1ccc2c(c1)CCN2c1nccn2nc(Nc3ccc4c(c3)NC(=O)C4(C)C)nc12] | LCMS (Method. D) Rt: 2.351 min, observed [M + H] = 442.2 m/z; $^1$H NMR (500 MHz, DMSO-$d_6$) δ [ppm] 10.31 (s, 1H), 9.66 (s, 1H), 8.35 (d, J = 8.9, 1H), 8.16 (d, J = 4.3, 1H), 7.65 (d, J = 4.3, 1H), 7.35 (d, J = 2.0, 1H), 7.21 (dd, J = 8.1, 2.0, 1H), 7.15 (d, J = 8.1, 1H), 6.93 (d, J = 2.7, 1H), 6.77 (dd, J = 8.9, 2.8, 1H), 4.88 (t, J = 8.5, 2H), 3.75 (s, 3H), 3.25 (t, J = 8.5, 2H), 1.23 (s, 6H) |
| E82 | 3,3-dimethyl-6-{8-[(3S,5R)-5-(2-trifluoroinethyl-phenyl)-pyrrolidin-3-yloxy]-[1,2,4]triazolo[1,5-a]pyrazin-2-ylamino}-1,3-dihydro-indol-2-one 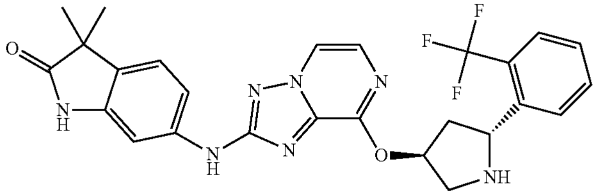 [SMILES: CC1(C)C(=O)Nc2cc(Nc3nc4c(O[C@@H]5CN[C@@H](c6ccccc6C(F)(F)F)C5)nccn4n3)ccc21] | LCMS (Method C) Rt: 1.783 min, observed [M + H] = 524.2 m/z; $^1$H NMR (500 MHz, DMSO-$d_6$) δ [ppm] 10.29 (s, 1H), 9.83 (s, 1H), 8.44 (d, J = 4.5, 1H), 8.01 (d, J = 7.9, 1H), 7.72-7.64 (m, 2H), 7.60 (d, J = 4.5, 1H), 7.45 (t, J = 7.6, 1H), 7.23 (s, 1H), 7.21 (d, J = 2.0, 1H), 7.17 (d, J = 8.0, 1H), 5.72-5.67 (m, 1H), 4.77-4.70 (m, 1H), 3.63 (dd, J = 11.9, 5.2, 1H), 3.21 (dd, J = 11.7, 2.7, 1H), 2.42 (dd, J = 13.8, 6.6, 1H), 1.98-1.89 (m, 1H), 1.23 (s, 6H). |
| E83 | 6-[8-(2-methoxymethyl-pyrrolidin-1-yl)-[1,2,4]triazolo[1,5-a]pyrazin-2-ylamino]-3,3-dimethyl-1,3-dihydro-indol-2-one 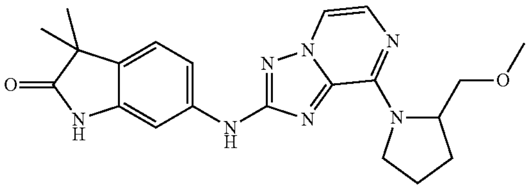 [SMILES: COCC1CCCN1c1nccn2nc(Nc3ccc4c(c3)NC(=O)C4(C)C)nc12] | LCMS (Method C) Rt: 1.868 min, observed [M + H] = 408.2 m/z; $^1$H NMR (400 MHz, DMSO-$d_6$) δ [ppm] 10.26 (s, 1H), 9.53 (s, 1H), 7.97 (d, J = 4.4, 1H), 7.50 (d, J = 4.4, 1H), 7.29-7.23 (m, 2H), 7.12 (d, J = 8.4, 1H), 4.97-4.77 (m, 1H), 4.05-3.94 (m, 1H), 3.93-3.81 (m, 1H), 3.62 (dd, J = 9.2, 3.5, 1H), 3.41-3.36 (m, 1H), 3.27 (s, 3H), 2.13-1.89 (m, 4H), 1.22 (s, 6H). |

-continued

| nr. | name/structure | LCMS; NMR |
|---|---|---|
| E84 | 6-{8-[(2R,4R)-4-hydroxy-2-(2-trifluoromethyl-phenyl)-pyrrolidin-1-yl]-[1,2,4]triazolo[1,5-a]pyrazin-2-ylamino}-3,3-dimethyl-1,3-dihydro-indol-2-one 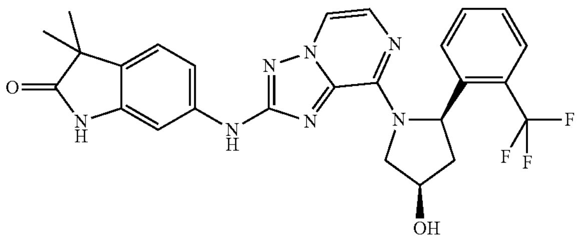 [SMILES: CC1(C)C(=O)Nc2cc(Nc3nc4c(N5C[C@H](O)C[C@@H]5c5ccccc5C(F)(F)F)nccn4n3)ccc21] | LCMS (Method C) Rt: 2.27 min, observed [M + H] = 524.2 m/z; $^1$H NMR (500 MHz, DMSO-$d_6$) δ [ppm] 10.27 (s, 1H), 9.60 (s, 1H), 7.93 (d, J = 4.3, 1H), 7.69-7.65 (m, 1H), 7.60 (d, J = 8.0, 1H), 7.51-7.46 (m, 1H), 7.38-7.34 (m, 1H), 7.27-7.22 (m, 3H), 7.16-7.13 (m, 1H), 5.71-5.63 (m, 1H), 4.61-4.54 (m, 1H), 4.52-4.46 (m, 2H), 2.68-2.60 (m, 1H), 1.82 (dt, J = 12.9, 4.8, 1H), 1.23 (s, 6H). |
| E85 | formic acid (3R,5R)-1-[2-(3,3-dimethyl-2-oxo-2,3-dihydro-1H-indol-6-ylamino)-[1,2,4]triazolo[1,5-a]pyrazin-8-yl]-5-(2-trifluoromethyl-phenyl)-pyrrolidin-3-yl ester 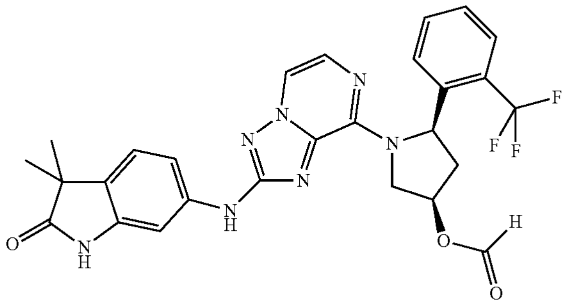 [SMILES: CC1(C)C(=O)Nc2cc(Nc3nc4c(N5C[C@H](OC=O)C[C@@H]5c5ccccc5C(F)(F)F)nccn4n3)ccc21] | LCMS (Method C) Rt: 2.165 min, observed [M + H] = 552.2 m/z; $^1$H NMR (500 MHz, DMSO-$d_6$) δ [ppm] 10.29 (s, 1H), 9.75 (s, 1H), 8.47-8.43 (m, 1H), 8.33 (s, 1H), 7.72 (t, J = 8.4, 1H), 7.69-7.65 (m, 1H), 7.63-7.56 (m, 2H), 7.41 (t, J = 7.6, 1H), 7.26-7.20 (m, 2H), 7.18-7.15 (m, 1H), 5.74-5.68 (m, 1H), 5.34-5.28 (m, 1H), 4.37 (dd, J = 11.7, 5.7, 1H), 4.17-4.10 (m, 1H), 3.11-2.99 (m, 1H), 2.08-1.99 (m, 1H), 1.23 (s, 6H). |
| E86 | (S)-7-[2-(4,4-dimethyl-1,2,3,4-tetrahydro-quinolin-7-ylamino)-[1,2,4]triazolo[1,5-a]pyrazin-8-yl]-2,7-diaza-spiro[4.4]nonan-3-one 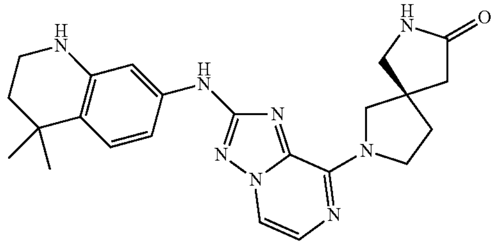 [SMILES: CC1(C)CCNc2cc(Nc3nc4c(N5CC[C@]6(CNC(=O)C6)C5)nccn4n3)ccc21] | LCMS (Method C) Rt: 1.489 min, observed [M + H] = 433.2 m/z; $^1$H NMR (500 MHz, DMSO-$d_6$) δ [ppm] 9.15 (s, 1H), 7.91 (d, J = 4.4, 1H), 7.66 (s, 1H), 7.44 (d, J = 4.4, 1H), 6.96 (d, J = 8.2, 1H), 6.77-6.71 (m, 2H), 5.57 (s, 1H), 4.13-3.83 (m, 4H), 3.25 (d, J = 2.9, 2H), 3.18-3.12 (m, 2H), 2.28 (d, J = 2.7, 2H), 2.01 (td, J = 6.9, 1.7, 2H), 1.62-1.55 (m, 2H), 1.19 (s, 6H). |
| E87 | 6-[8-(2,7-diaza-spiro[4.4]non-2-yl)-[1,2,4]triazolo[1,5-a]pyrazin-2-ylamino]-3,3-dimethyl-1,3-dihydro-indol-2-one 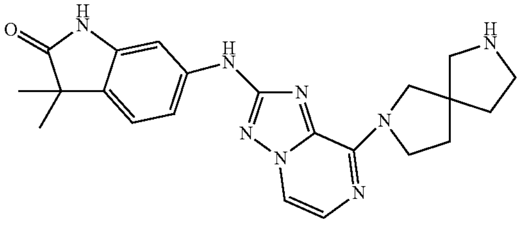 [SMILES: CC1(C)C(=O)Nc2cc(Nc3nc4c(N5CCC6(CCNC6)C5)nccn4n3)ccc21] | LCMS (Method D) Rt: 1.4 min, observed [M + H] = 419.2 m/z; $^1$H NMR (500 MHz, DMSO-$d_6$) δ [ppm] 10.41 (s, 1H), 9.59 (s, 1H), 8.33 (s, 1H), 7.97 (d, J = 4.4, 1H), 7.48 (d, J = 4.4, 1H), 7.34 (d, J = 1.9, 1H), 7.32-7.15 (m, 1H), 7.23-7.09 (m, 2H), 4.20-3.78 (m, 4H), 3.24-3.14 (m, 2H), 3.14-2.98 (m, 2H), 2.10-1.85 (m, 4H), 1.22 (s, 6H). |

-continued

| nr. | name/structure | LCMS; NMR |
|---|---|---|
| E88 | 6-(8-dimethylamino-[1,2,4]triazolo[1,5-a]pyrazin-2-ylamino)-3,3-dimethyl-1,3-dihydro-indol-2-one 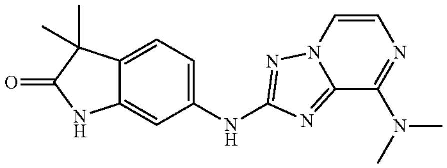 [SMILES: CN(C)c1nccn2nc(Nc3ccc4c(c3)NC(=O)C4(C)C)nc12] | LCMS (Method C) Rt: 1.663 min, observed [M + H] = 338.2 m/z; $^1$H NMR (500 MHz, DMSO-$d_6$) δ [ppm] 10.27 (s, 1H), 9.59 (s, 1H), 8.01 (d, J = 4.3, 1H), 7.51 (d, J = 4.4, 1H), 7.29 (d, J = 2.0, 1H), 7.20 (dd, J = 8.1, 2.0, 1H), 7.13 (d, J = 8.1, 1H), 3.44 (s, 6H), 1.22 (s, 6H). |
| E89 | 6-{8-[(2-dimethylamino-ethyl)-methyl-amino]-[1,2,4]triazolo[1,5-a]pyrazin-2-ylamino}-3,3-dimethyl-1,3-dihydro-indol-2-one 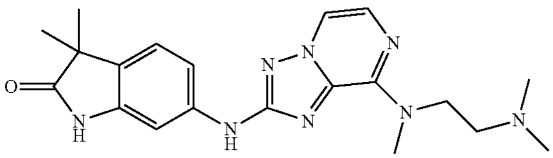 [SMILES: CN(C)CCN(C)c1nccn2nc(Nc3ccc4c(c3)NC(=O)C4(C)C)nc12] | LCMS (Method C) Rt: 1.416 min, observed [M + H] = 395.2 m/z;, $^1$H NMR (500 MHz, DMSO-$d_6$) δ [ppm] 10.27 (s, 1H), 9.54 (s, 1H), 7.99 (d, J = 4.3, 1H), 7.50 (d, J = 4.3, 1H), 7.26-7.21 (m, 2H), 7.12 (d, J = 8.0, 1H), 4.16 (t, J = 6.7, 2H), 3.39 (s, 3H), 2.56 (t, J = 6.7, 2H), 2.21 (s, 6H) 1.22 (s, 6H). |
| E90 | 3,3-dimethyl-6-{8-[methyl-(2-pyridin-2-yl-ethyl)-amino]-[1,2,4]triazolo[1,5-a]pyrazin-2-ylamino}-1,3-dihydro-indol-2-one 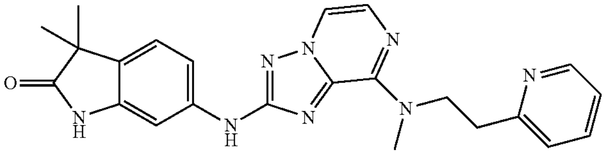 [SMILES: CN(CCc1ccccn1)c1nccn2nc(Nc3ccc4c(c3)NC(=O)C4(C)C)nc12] | LCMS (Method C) Rt: 1.496 min, observed [M + H] = 429.2 m/z; $^1$H NMR (500 MHz, DMSO-$d_6$) δ [ppm] 10.25 (s, 1H), 9.55 (s, 1H), 8.49-8.44 (m, 1H), 7.99 (d, J = 4.3, 1H), 7.64 (td, J = 7.6, 1.9, 1H), 7.51 (d, J = 4.3, 1H), 7.32-7.28 (m, 1H), 7.26-7.21 (m, 2H), 7.21-7.17 (m, 1H), 7.07 (d, J = 7.9, 1H), 4.40 (t, J = 7.4, 2H), 3.32 (s, 3H), 3.15-3.09 (m, 2H), 1.22 (s, 6H). |
| E91 | 3,3-dimethyl-6-{8-[(piperidin-4-ylmethyl)-amino]-[1,2,4]triazolo[1,5-a]pyrazin-2-ylamino}-1,3-dihydro-indol-2-one 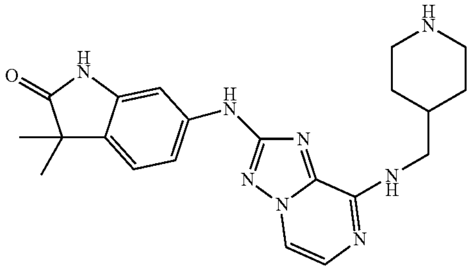 [SMILES: CC1(C)C(=O)Nc2cc(Nc3nc4c(NCC5CCNCC5)nccn4n3)ccc21] | LCMS (Method D) Rt: 1.42 min, observed [M + H] = 407.3 m/z; $^1$H NMR (500 MHz, DMSO-$d_6$) δ [ppm] 10.29 (s, 1H), 9.56 (s, 1H), 9.17-8.22 (m, 3H), 8.06 (d, J = 4.9, 1H), 7.42 (d, J = 4.9, 1H), 7.36-7.30 (m, 1H), 7.19 (d, J = 2.0, 1H), 7.15 (d, J = 8.1, 1H), 3.57-3.44 (m, 2H), 3.33-3.18 (m, 2H), 2.89-2.68 (m, 2H), 2.11-1.94 (m, 1H), 1.95-1.82 (m, 2H), 1.52-1.38 (m, 2H), 1.23 (s, 6H). |
| E92 | 6-(8-diethylamino-[1,2,4]triazolo[1,5-a]pyrazin-2-ylamino)-3,3-dimethyl-1,3-dihydro-indol-2-one 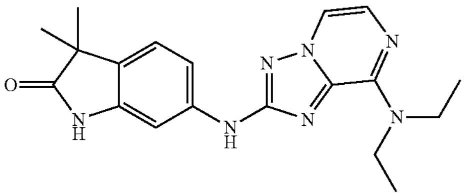 [SMILES: CCN(CC)c1nccn2nc(Nc3ccc4c(c3)NC(=O)C4(C)C)nc12] | LCMS (Method C) Rt: 2.013 min, observed [M + H] = 366.2 m/z; $^1$H NMR (500 MHz, DMSO-$d_6$) δ [ppm] 10.27 (s, 1H), 9.54 (s, 1H), 7.96 (d, J = 4.3, 1H), 7.50 (d, J = 4.3, 1H), 7.28 (d, J = 2.0, 1H), 7.23 (dd, J = 8.1, 2.0, 1H), 7.13 (d, J = 8.1, 1H), 3.96 (q, J = 6.9, 4H), 1.28-1.17 (m, 12H). |

-continued

| nr. | name/structure | LCMS; NMR |
|---|---|---|
| E93 | 4,4-dimethyl-7-[8-(2-phenyl-pyrrolidin-1-yl)-[1,2,4]triazolo[1,5-a]pyrazin-2-ylamino]-3,4-dihydro-1H-quinolin-2-one 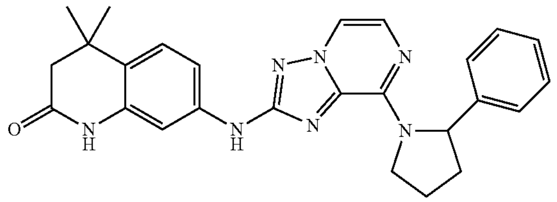 [SMILES: CC1(C)CC(=O)Nc2cc(Nc3nc4c(N5CCCC5c5ccccc5)nccn4n3)ccc21] | LCMS (Method C) Rt: 2.23 min, observed [M + H] = 454.2 m/z; $^{1}$H NMR (500 MHz, DMSO-$d_6$) δ [ppm] 10.11 (s, 1H), 9.47 (s, 1H), 7.91 (d, J = 4.4, 1H), 7.41 (s, 1H), 7.30-7.03 (m, 8H), 4.33 (t, J = 5.1, 1H), 3.49-3.41 (m, 1H), 2.45-2.38 (m, 1H), 2.32 (s, 2H), 2.07-1.96 (m, 1H), 1.95-1.85 (m, 2H), 1.21 (d, J = 5.6, 6H), 1.06 (t, J = 7.0, 1H). |
| E94 | 6-[8-((cis2)-4-hydroxymethyl-2-phenyl-pyrrolidin-1-yl)-[1,2,4]triazolo[1,5-a]pyrazin-2-ylamino]-3,3-dimethyl-1,3-dihydro-indol-2-one 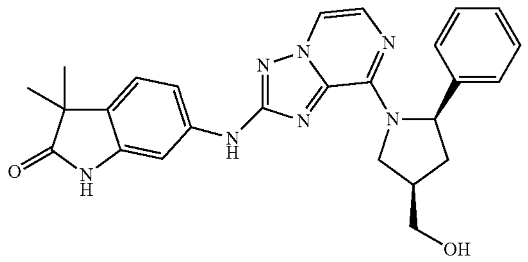 [SMILES: CC1(C)C(=O)Nc2cc(Nc3nc4c(N5C[C@H](CO)C[C@@H]5c5ccccc5)nccn4n3)ccc21] | LCMS (Method C) Rt: 1.902 min, observed [M + H] = 470.2 m/z; $^{1}$H NMR (500 MHz, DMSO-$d_6$) δ [ppm] 10.26 (s, 1H), 9.61 (s, 1H), 7.93 (d, J = 4.4, 1H), 7.37-7.32 (m, 1H), 7.32-7.27 (m, 1H), 7.27-7.18 (m, 5H), 7.16-7.10 (m, 2H), 5.54 (s, 1H), 4.67 (t, J = 5.1, 1H), 3.98-3.87 (m, 1H), 3.52-3.37 (m, 3H), 2.65-2.55 (m, 1H), 1.69-1.59 (m, 1H), 1.22 (s, 6H), 1.06 (t, J = 7.0, 1H). |
| E95 | 6-[8-((cis1)-4-hydroxymethyl-2-phenyl-pyrrolidin-1-yl)-[1,2,4]triazolo[1,5-a]pyrazin-2-ylamino]-3,3-dimethyl-1,3-dihydro-indol-2-one 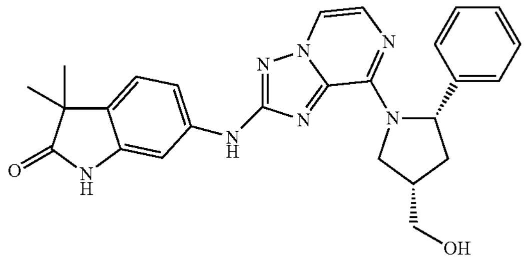 [SMILES: CC1(C)C(=O)Nc2cc(Nc3nc4c(N5C[C@@H](CO)C[C@H]5c5ccccc5)nccn4n3)ccc21] | LCMS (Method C) Rt: 1.902 min, observed [M + H] = 470.2 m/z; $^{1}$H NMR (500 MHz, $CDCl_3$) δ [ppm] 8.31-8.20 (s, 1H), 7.59-7.53 (d, J = 4.4 Hz, 1H), 7.45-7.39 (s, 1H), 7.31-7.26 (d, J = 4.4 Hz, 1H), 7.22-7.15 (m, 4H), 7.13-7.06 (m, 1H), 7.02-6.93 (m, 2H), 6.83-6.77 (m, 1H), 5.65-5.53 (s, 1H), 4.82-4.67 (m, 1H), 4.07-3.92 (m, 1H), 3.69-3.50 (m, 2H), 2.61-2.49 (m, 2H), 1.81-1.68 (m, 1H), 1.62-1.46 (s, 1H), 1.24-1.13 (m, 6H). |
| E96 | 7-[8-(4-hydroxy-2-phenyl-pyrrolidin-1-yl)-[1,2,4]triazolo[1,5-a]pyrazin-2-ylamino]-4,4-dimethyl-3,4-dihydro-1H-quinolin-2-one 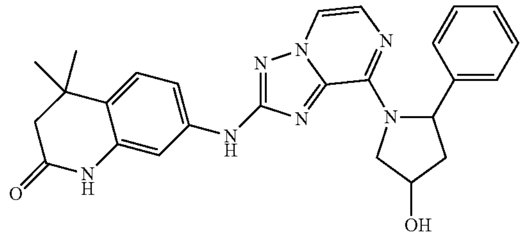 [SMILES: CC1(C)CC(=O)Nc2cc(Nc3nc4c(N5CC(O)CC5c5ccccc5)nccn4n3)ccc21] | LCMS (Method C) Rt: 2.003 min, observed [M + H] = 470.3 m/z; $^{1}$H NMR (500 MHz, DMSO-$d_6$) δ [ppm] 10.12 (s, 1H), 9.56-9.50 (m, 1H), 7.91 (d, J = 4.4, 1H), 7.51-7.27 (m, 2H), 7.27-7.14 (m, 8H), 5.60 (s, 1H), 5.06 (d, J = 3.7, 1H), 4.45-4.40 (m, 1H), 4.39-4.33 (m, 1H), 2.44-2.37 (m, 1H), 2.35-2.28 (m, 2H), 2.02-1.91 (m, 1H), 1.22 (s, 3H), 1.21 (s, 3H). |

-continued

| nr. | name/structure | LCMS; NMR |
|---|---|---|
| E97 | 6-[8-((trans1)-4-hydroxymethyl-2-phenyl-pyrrolidin-1-yl)-[1,2,4]triazolo[1,5-a]pyrazin-2-ylamino]-3,3-dimethyl-1,3-dihydro-indol-2-one 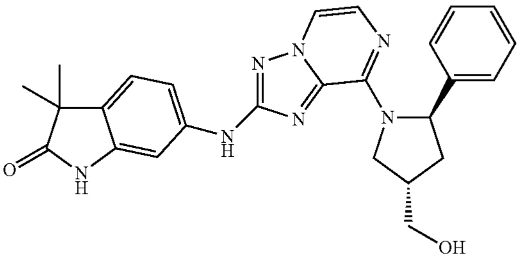 [SMILES: CC1(C)C(=O)Nc2cc(Nc3nc4c(N5C[C@@H](CO)C[C@@H]5c5ccccc5)nccn4n3)ccc21] | LCMS (Method C) Rt: 1.902 min, observed [M + H] = 470.2 m/z; $^{1}$H NMR (500 MHz, $CDCl_3$) δ [ppm] 7.64-7.56 (m, 1H), 7.43-7.35 (d, J = 4.6 Hz, 1H), 7.28-7.22 (m, 2H), 7.21-7.15 (m, 3H), 7.03-6.94 (d, J = 8.0 Hz, 1H), 6.80-6.63 (m, 2H), 6.17-5.84 (s, 1H), 4.51-4.32 (s, 1H), 4.09-3.99 (m, 1H), 3.99-3.90 (m, 1H), 3.76-3.69 (m, 1H), 3.69-3.61 (m, 1H), 2.81-2.70 (m, 1H), 2.62-2.49 (m, 1H), 2.28-2.04 (m, 2H), 1.37-1.33 (s, 1H), 1.20-1.17 (d, J = 3.2 Hz, 6H). |
| E98 | 6-[8-((trans2)-4-hydroxymethyl-2-phenyl-pyrrolidin-1-yl)-[1,2,4]triazolo[1,5-a]pyrazin-2-ylamino]-3,3-dimethyl-1,3-dihydro-indol-2-one 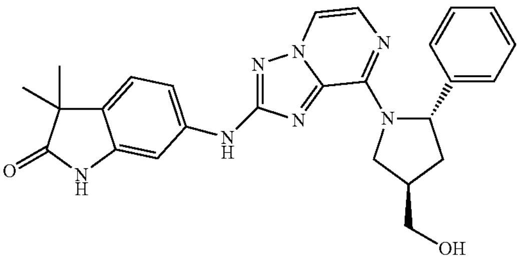 [SMILES: CC1(C)C(=O)Nc2cc(Nc3nc4c(N5C[C@H](CO)C[C@H]5c5ccccc5)nccn4n3)ccc21] | LCMS (Method C) Rt: 1.902 min, observed [M + H] = 470.2 m/z; |
| E99 | (8-azepan-1-yl-[1,2,4]triazolo[1,5-a]pyrazin-2-yl)-(3,3-dimethyl-2,3-dihydro-1H-indol-6-yl)-amine 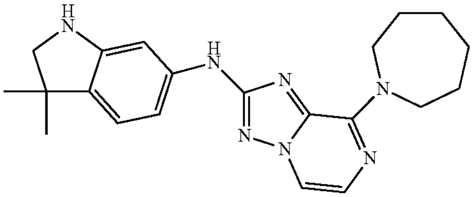 [SMILES: CC1(C)CNc2cc(Nc3nc4c(N5CCCCCC5)nccn4n3)ccc21] | LCMS (Method D) Rt: 1.529 min, observed [M + H] = 378.3 m/z; $^{1}$H NMR (500 MHz, DMSO-$d_6$) δ [ppm] 11.48 (s, 2H), 10.02 (s, 1H), 8.07 (d, J = 4.6, 1H), 7.79 (s, 1H), 7.63-7.57 (m, 1H), 7.51 (d, J = 4.6, 1H), 7.35 (d, J = 8.4, 1H), 4.15 (s, 4H), 3.47 (s, 2H), 1.90-1.82 (m, 4H), 1.60-1.49 (m, 4H), 1.34 (s, 6H). |
| E100 | 6-[8-(6-chloro-3,3-dimethyl-2,3-dihydro-indol-1-yl)-[1,2,4]triazolo[1,5-a]pyrazin-2-ylamino]-3,3-dimethyl-1,3-dihydro-indol-2-one 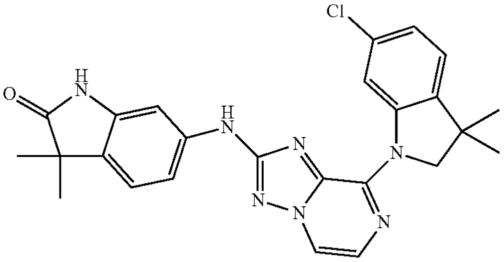 [SMILES: CC1(C)CN(c2nccn3nc(Nc4ccc5c(c4)NC(=O)C5(C)C)nc23)c2cc(Cl)ccc21] | LCMS (Method D) Rt: 2.685 min, observed [M + H] = 474.2 m/z. |

-continued

| nr. | name/structure | LCMS; NMR |
|---|---|---|
| E101 | (R)-7-[2-(4,4-dimethyl-1,2,3,4-tetrahydro-quinolin-7-ylamino)-[1,2,4]triazolo[1,5-a]pyrazin-8-yl]-2,7-diaza-spiro[4.4]nonan-3-one 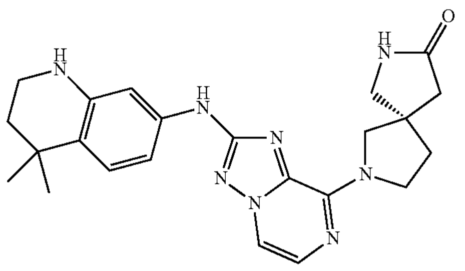 [SMILES: CC1(C)CCNc2cc(Nc3nc4c(N5CC[C@@]6(CNC(=O)C6)C5)nccn4n3)ccc21] | LCMS (Method C) Rt: 1.463 min, observed [M + H] = 433.2 m/z; $^1$H NMR (500 MHz, DMSO-$d_6$) δ [ppm] 9.15 (s, 1H), 7.91 (d, J = 4.4, 1H), 7.66 (s, 1H), 7.44 (d, J = 4.4, 1H), 6.96 (d, J = 8.3, 1H), 6.78-6.71 (m, 2H), 5.56 (s, 1H), 3.98-3.85 (m, 2H), 3.28-3.22 (m, 2H), 3.20-3.12 (m, 4H), 2.33-2.23 (m, 2H), 2.05-1.99 (m, 2H), 1.61-1.56 (m, 2H), 1.19 (s, 6H). |
| E102 | 6-[8-(6-amino-2,3-dihydro-indol-1-yl)-[1,2,4]triazolo[1,5-a]pyrazin-2-ylamino]-3,3-dimethyl-1,3-dihydro-indol-2-one 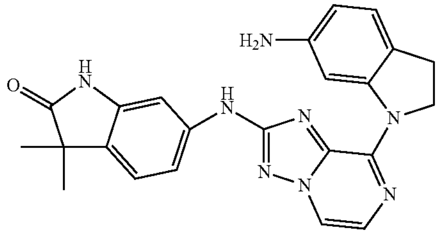 [SMILES: CC1(C)C(=O)Nc2cc(Nc3nc4c(N5CCc6ccc(N)cc65)nccn4n3)ccc21] | LCMS (Method D) Rt: 1.686 min, observed [M + H] = 427.2 m/z; $^1$H NMR (500 MHz, DMSO-$d_6$) δ [ppm] 10.69-9.89 (m, 4H), 9.75 (s, 1H), 8.45 (d, J = 1.9, 1H), 8.33 (d, J = 4.3, 1H), 7.70 (d, J = 4.3, 1H), 7.40-7.34 (m, 2H), 7.23 (dd, J = 8.1, 2.0, 1H), 7.16 (d, J = 8.1, 1H), 7.00 (dd, J = 7.8, 2.0, 1H), 4.95 (t, J = 8.6, 2H), 3.30 (t, J = 8.6, 2H), 1.23 (s, 6H). |
| E103 | N-{2-[2-(3,3-dimethyl-2-oxo-2,3-dihydro-1H-indol-6-ylamino)-[1,2,4]triazolo[1,5-a]pyrazin-8-ylamino]-ethyl}-acetamide 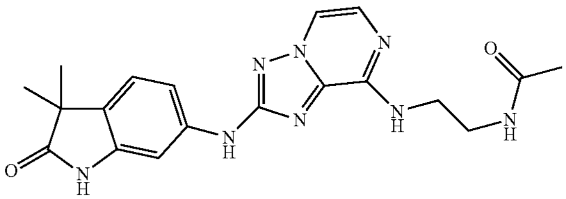 [SMILES: CC(=O)NCCNc1nccn2nc(Nc3ccc4c(c3)NC(=O)C4(C)C)nc12] | LCMS (Method C) Rt: 1.51 min, observed [M + H] = 395.2 m/z; $^1$H NMR (500 MHz, DMSO-$d_6$) δ [ppm] 10.24 (s, 1H), 9.48 (s, 1H), 7.99 (t, J = 5.7, 1H), 7.95 (d, J = 4.5, 1H), 7.44 (d, J = 4.5, 1H), 7.30 (dd, J = 8.1, 2.0, 1H), 7.26 (t, J = 5.7, 1H), 7.20 (d, J = 2.0, 1H), 7.13 (d, J = 8.1, 1H), 3.53 (q, J = 6.2, 2H), 3.35-3.30 (m, 2H), 1.81 (s, 3H), 1.22 (s, 6H). |
| E104 | N-[2-(3,3-dimethyl-2-oxo-2,3-dihydro-1H-indol-6-ylamino)-[1,2,4]triazolo[1,5-a]pyrazin-8-yl]-methanesulfonamide 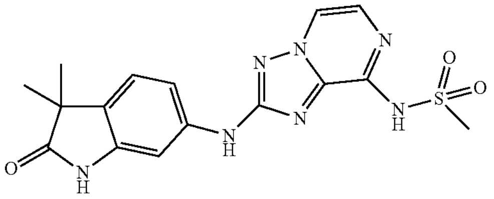 [SMILES: CC1(C)C(=O)Nc2cc(Nc3nc4c(NS(C)(=O)=O)nccn4n3)ccc21] | LCMS (Method C) Rt: 1.576 min, observed [M + H] = 388 m/z; $^1$H NMR (500 MHz, DMSO-$d_6$) δ [ppm] 12.30-10.69 (m, 1H), 10.29 (s, 1H), 9.75 (s, 1H), 8.79-6.80 (m, 5H), 3.64-2.83 (m, 3H), 1.23 (s, 6H). |

-continued

| nr. | name/structure | LCMS; NMR |
|---|---|---|
| E105 | 6-[(S)-8-(2,7-diaza-spiro[4.4]non-2-yl)-[1,2,4]triazolo[1,5-a]pyrazin-2-ylamino]-3,3-dimethyl-1,3-dihydro-indol-2-one 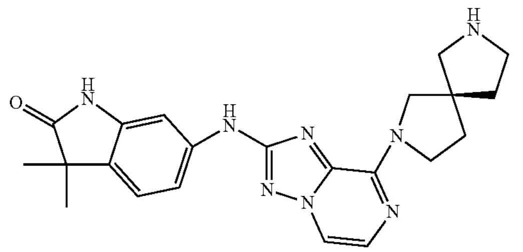 [SMILES: CC1(C)C(=O)Nc2cc(Nc3nc4c(N5CC[C@]6(CCNC6)C5)nccn4n3)ccc21] | LCMS (Method D) Rt: 1.397 min, observed [M + H] = 419.2 m/z. |
| E106 | 6-[(R)-8-(2,7-diaza-spiro[4.4]non-2-yl)-[1,2,4]triazolo[1,5-a]pyrazin-2-ylamino]-3,3-dimethyl-1,3-dihydro-indol-2-one 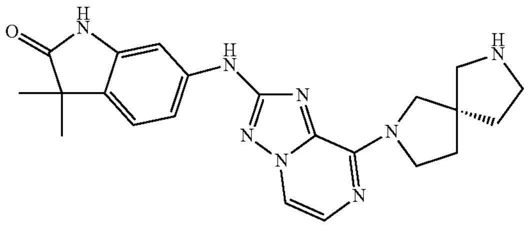 [SMILES: CC1(C)C(=O)Nc2cc(Nc3nc4c(N5CC[C@@]6(CCNC6)C5)nccn4n3)ccc21] | LCMS (Method D) Rt: 1.399 min, observed [M + H] = 419.3 m/z. |
| E107 | 3-cyano-N-[2-(3,3-dimethyl-2-oxo-2,3-dihydro-1H-indol-6-ylamino)-[1,2,4]triazolo[1,5-a]pyrazin-8-yl]-benzenesulfonamide 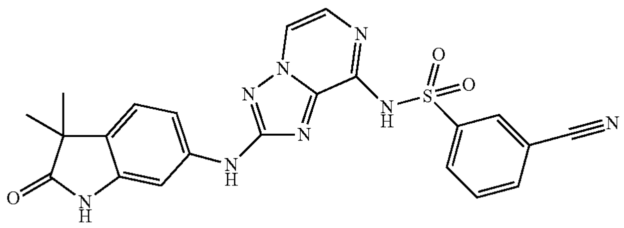 [SMILES: CC1(C)C(=O)Nc2cc(Nc3nc4c(NS(=O)(=O)c5cccc(C#N)c5)nccn4n3)ccc21] | LCMS (Method C) Rt: 1,812 (UV) min, observed [M + H] = m/z;, $^{1}H$ NMR (500 MHz, DMSO-$d_6$) δ [ppm] 12.21 (s, 1H), 10.29 (s, 1H), 9.79 (s, 1H), 8.42-8.38 (m, 1H), 8.26 (d, J = 8.0, 1H), 8.19-8.06 (m, 2H), 7.80 (t, J = 7.9, 1H), 7.35-7.23 (m, 1H), 7.21-7.12 (m, 3H), 1.22 (s, 6H). |
| E108 | 6-[8-(3,4-dihydro-2H-quinolin-1-yl)-[1,2,4]triazolo[1,5-a]pyrazin-2-ylamino]-3,3-dimethyl-1,3-dihydro-indol-2-one 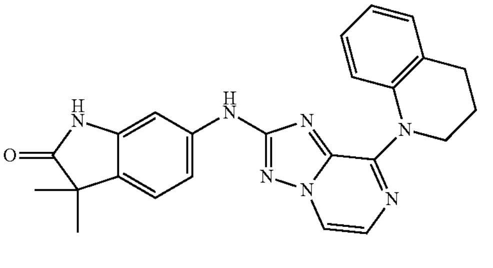 [SMILES: CC1(C)C(=O)Nc2cc(Nc3nc4c(N5CCCc6ccccc65)nccn4n3)ccc21] | LCMS (Method C) Rt: 2.226 min, observed [M + H] = 426.2 m/z; $^{1}H$ NMR (500 MHz, DMSO-$d_6$) δ [ppm] 10.24 (s, 1H), 9.73 (s, 1H), 8.39 (d, J = 4.3, 1H), 7.67 (d, J = 4.3, 1H), 7.24-7.18 (m, 2H), 7.15 (dd, J = 7.5, 1.4, 1H), 7.10 (d, J = 8.0, 1H), 7.06-6.99 (m, 2H), 6.98-6.93 (m, 1H), 4.18-4.12 (m, 2H), 2.83 (t, J = 6.6, 2H), 2.00-1.93 (m, 2H), 1.22 (s, 6H). |

-continued

| nr. | name/structure | LCMS; NMR |
|---|---|---|
| E109 | 1-methyl-1H-imidazole-4-sulfonic acid [2-(3,3-dimethyl-2-oxo-2,3-dihydro-1H-indol-6-ylamino)-[1,2,4]triazolo[1,5-a]pyrazin-8-yl]-amide 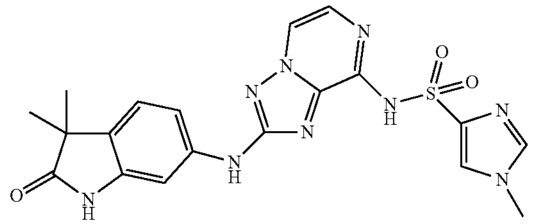 [SMILES: Cn1cnc(S(=O)(=O)Nc2nccn3nc(Nc4ccc5c(c4)NC(=O)C5(C)C)nc23)c1] | LCMS (Method C) Rt: 1.512 min, observed [M + H] = 454 m/z; $^{1}H$ NMR (400 MHz, DMSO-$d_6$) δ [ppm] 10.31 (s, 1H), 9.73 (s, 1H), 8.06 (s, 1H), 7.82 (s, 1H), 7.77-7.72 (m, 1H), 7.37 (s, 1H), 7.24 (s, 1H), 7.20-7.05 (m, 2H), 3.70 (s, 3H), 1.22 (s, 6H). |
| E110 | 6-[8-(2-amino-ethylamino)-[1,2,4]triazolo[1,5-a]pyrazin-2-ylamino]-3,3-dimethyl-1,3-dihydro-indol-2-one 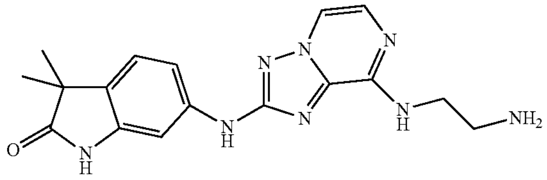 [SMILES: CC1(C)C(=O)Nc2cc(Nc3nc4c(NCCN)nccn4n3)ccc21] | LCMS (Method C) Rt: 1.404 min, observed [M + H] = 353.2 m/z; $^{1}H$ NMR (400 MHz, DMSO-$d_6$) δ [ppm] 10.29 (s, 1H), 9.47 (s, 1H), 8.35 (s, 1H), 7.97 (d, J = 4.5, 1H), 7.45 (d, J = 4.5, 1H), 7.36 (t, J = 5.7, 1H), 7.29 (dd, J = 8.1, 2.0, 1H), 7.23 (d, J = 2.0, 1H), 7.13 (d, J = 8.1, 1H), 3.61 (q, J = 6.0, 2H), 2.96 (t, J = 6.2, 2H), 1.22 (s, 6H). |
| E111 | N-[2-(3,3-dimethyl-2-oxo-2,3-dihydro-1H-indol-6-ylamino)-[1,2,4]triazolo[1,5-a]pyrazin-8-yl]-benzenesulfonamide 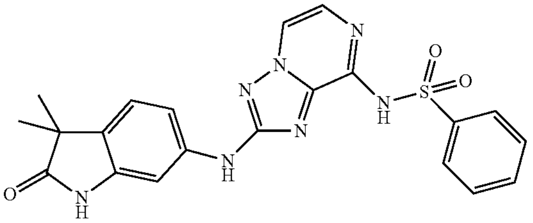 [SMILES: CC1(C)C(=O)Nc2cc(Nc3nc4c(NS(=O)(=O)c5ccccc5)nccn4n3)ccc21] | LCMS (Method C) Rt: 1.828 min, observed [M + H] = 450 m/z; $^{1}H$ NMR (400 MHz, DMSO-$d_6$) δ [ppm] 12.10 (s, 1H), 10.28 (s, 1H), 9.75 (s, 1H), 8.12-7.88 (m, 3H), 7.67-7.52 (m, 3H), 7.32-7.06 (m, 4H), 1.22 (s, 6H). |
| E112 | 3,3-dimethyl-6-[8-(2-oxo-1-oxa-3,7-diaza-spiro[4.4]non-7-yl)-[1,2,4]triazolo[1,5-a]pyrazin-2-ylamino]-1,3-dihydro-indol-2-one 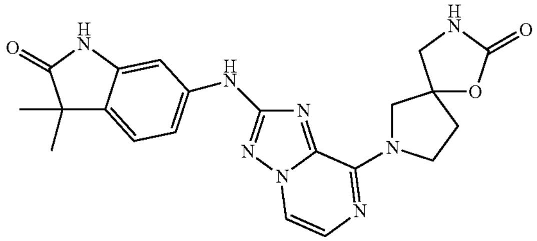 | LCMS (Method C) Rt: 2.068 min, observed [M + H] = 425.2 m/z; $^{1}H$ NMR (500 MHz, DMSO-$d_6$) δ [ppm] 10.33 (s, 1H), 10.02 (s, 1H), 9.37-9.34 (m, 1H), 8.80 (d, J = 4.2, 1H), 8.70 (dd, J = 9.0, 1.6, 1H), 8.28-8.26 (m, 1H), 8.21 (d, J = 4.2, 1H), 7.82 (d, J = 9.0, 1H), 7.37-7.32 (m, 2H), 7.21 (d, J = 8.0, 1H), 4.12 (s, 3H), 1.25 (s, 6H). |

-continued

| nr. | name/structure | LCMS; NMR |
|---|---|---|
| E113 | 1-[2-(3,3-dimethyl-2-oxo-2,3-dihydro-1H-indol-6-ylamino)-[1,2,4]triazolo[1,5-a]pyrazin-8-yl]-piperidine-3-carboxylic acid amide 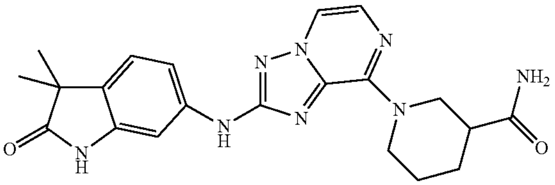 [SMILES: CC1(C)C(=O)Nc2cc(Nc3nc4c(N5CCCC(C(N)=O)C5)nccn4n3)ccc21] | LCMS (Method C) Rt: 1.685 min, observed [M + H] = 421.2 m/z; $^1$H NMR (500 MHz, DMSO-$d_6$) δ [ppm] 10.22 (s, 1H), 9.68 (s, 1H), 8.08 (d, J = 4.3, 1H), 7.54 (d, J = 4.3, 1H), 7.34 (s, 1H), 7.27 (d, J = 2.0, 1H), 7.22 (dd, J = 8.1, 2.0, 1H), 7.13 (d, J = 8.1, 1H), 6.88 (s, 1H), 5.22 (d, J = 13.6, 1H), 5.11 (d, J = 13.1, 1H), 3.16-3.09 (m, 1H), 3.07-2.99 (m, 1H), 2.41 (tt, J = 11.3, 3.8, 1H), 1.99-1.92 (m, 1H), 1.82-1.74 (m, 1H), 1.74-1.63 (m, 1H), 1.59-1.47 (m, 1H), 1.22 (s, 6H). |
| E114 | 3,3-dimethyl-6-[8-(1-methyl-1H-indazol-5-yl)-[1,2,41triazolo[1,5-a]pyrazin-2-ylamino]-1,3-dihydro-indol-2-one 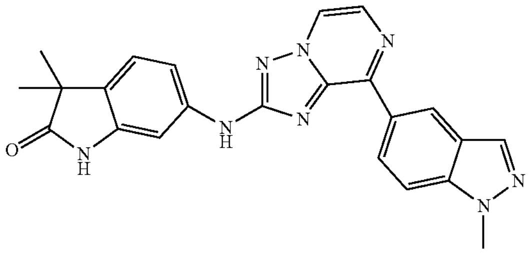 [SMILES: Cn1ncc2cc(-c3nccn4nc(Nc5ccc6c(c5)NC(=O)C6(C)C)nc34)ccc21] | LCMS (Method C) Rt: 2.068 min, observed [M + H] = 425.2 m/z; $^1$H NMR (500 MHz, DMSO-$d_6$) δ [ppm] 10.33 (s, 1H), 10.02 (s, 1H), 9.37-9.34 (m, 1H), 8.80 (d, J = 4.2, 1H), 8.70 (dd, J = 9.0, 1.6, 1H), 8.28-8.26 (m, 1H), 8.21 (d, J = 4.2, 1H), 7.82 (d, J = 9.0, 1H), 7.37-7.32 (m, 2H), 7.21 (d, J = 8.0, 1H), 4.12 (s, 3H), 1.25 (s, 6H). |
| E115 | 3,3-Dimethyl-6-(8-quinolin-3-yl-[1,2,4]triazolo[1,5-a]pyrazin-2-ylamino)-1,3-dihydro-indol-2-one 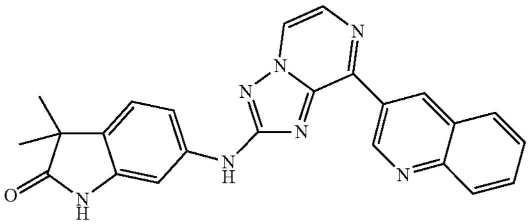 [SMILES: CC1(C)C(=O)Nc2cc(Nc3nc4c(-c5cnc6ccccc6c5)nccn4n3)ccc21] | LCMS (Method C) Rt: 2.115 min, observed [M + H] = 422.2 m/z; $^1$H NMR (500 MHz, DMSO-$d_6$) δ [ppm] 10.35 (s, 1H), 10.08 (s, 1H), 10.05 (d, J = 2.2, 1H), 9.65 (d, J = 2.2, 1H), 8.95 (d, J = 4.2, 1H), 8.32 (d, J = 4.2, 1H), 8.18-8.15 (m, 1H), 8.15-8.11 (m, 1H), 7.91-7.86 (m, 1H), 7.77-7.71 (m, 1H), 7.38 (dd, J = 8.1, 2.0, 1H), 7.33 (d, J = 1.9, 1H), 7.23 (d, J = 8.0, 1H), 1.25 (s, 6H). |
| E116 | 6-[8-(3,4-Dihydro-2H-pyrano[2,3-b]pyridin-6-yl)-[1,2,4]triazolo[1,5-a]pyrazin-2-ylamino]-3,3-dimethyl-1,3-dihydro-indol-2-one 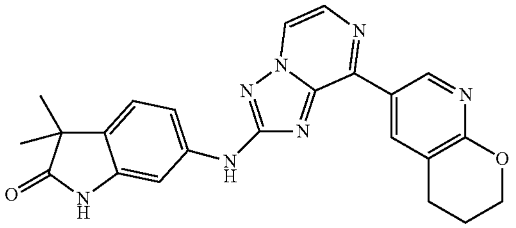 [SMILES: CC1(C)C(=O)Nc2cc(Nc3nc4c(-c5cnc6c(c5)CCCO6)nccn4n3)ccc21] | LCMS (Method C) Rt: 1.953 min, observed [M + H] = 428.2 m/z; $^1$H NMR (500 MHz, DMSO-$d_6$) δ [ppm] 10.31 (s, 1H), 9.98 (s, 1H), 9.37 (d, J = 2.4, 1H), 8.81 (d, J = 4.2, 1H), 8.73-8.69 (m, 1H), 8.18 (d, J = 4.2, 1H), 7.33 (dd, J = 8.1, 2.0, 1H), 7.29 (d, J = 2.0, 1H), 7.20 (d, J = 8.1, 1H), 4.40-4.36 (m, 2H), 2.92 (t, J = 6.4, 2H), 2.04-1.96 (m, 2H), 1.24 (s, 6H). |

-continued

| nr. | name/structure | LCMS; NMR |
|---|---|---|
| E117 | 6-[[8-[3-[[2-[(3,3-dimethyl-2-oxo-indolin-6-yl)amino]-[1,2,4]triazolo[1,5-a]pyrazin-8-yl]amino]propylamino]-[1,2,4]triazolo[1,5-a]pyrazin-2-yl]amino]-3,3-dimethyl-indolin-2-one 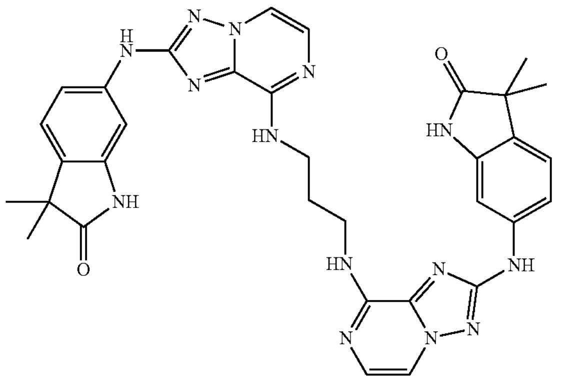 [SMILES: CC1(C)C(=O)Nc2cc(Nc3nc4c(NCCCNc5nccn6nc(Nc7ccc8c(c7)NC(=O)C8(C)C)nc56)nccn4n3)ccc21] | LCMS (Method C) Rt: 1.766 min, observed [M + H] = 659.2 m/z; $^1$H NMR (500 MHz, DMSO-$d_6$) δ [ppm] 10.25 (s, 2H), 9.45 (s, 2H), 7.93 (d, J = 4.5, 2H), 7.50 (t, J = 6.1, 2H), 7.48 (d, J = 4.5, 2H), 7.31 (dd, J = 8.1, 2.0, 2H), 7.20 (d, J = 2.0, 2H), 7.14 (d, J = 8.1, 2H), 3.58 (q, J = 6.4, 4H), 1.94 (p, J = 6.5, 2H), 1.23 (s, 12H). |
| E118 | 4-amino-N-[2-(3,3-dimethyl-2-oxo-2,3-dihydro-1H-indol-6-ylamino)-[1,2,4]triazolo[1,5-a]pyrazin-8-yl] benzenesulfonamide 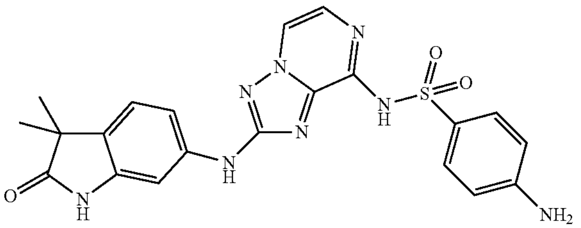 [SMILES: CC1(C)C(=O)Nc2cc(Nc3nc4c(NS(=O)(=O)c5ccc(N)cc5)nccn4n3)ccc21] | LCMS (Method C) Rt: 1.619 min, observed [M + H] = 465 m/z; $^1$H NMR (400 MHz, DMSO-$d_6$) δ, [ppm] 11.80 (s, 1H), 7.40-7.09 (m, 4H), 5.92 (s, 2H), 1.22 (s, 6H), 8.23-7.79 (m, 1H), 10.28 (s, 1H), 9.67 (s, 1H), 7.70-7.57 (m, 2H), 6.62-6.55 (m, 2H). |
| E119 | 6-[8-(6-dimethylamino-2,3-dihydro-indol-1-yl)-[1,2,4]triazolo[1,5-a]pyrazin-2-ylamino]-3,3-dimethyl-1,3-dihydro-indol-2-one 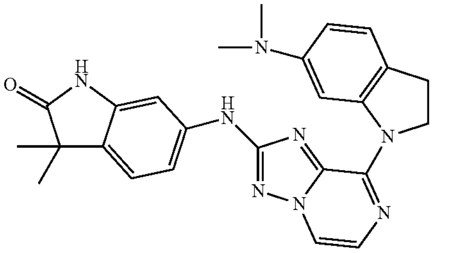 [SMILES: CN(C)c1ccc2c(c1)N(c1nccn3nc(Nc4ccc5c(c4)NC(=O)C5(C)C)nc13)CC2] | LCMS (Method D) Rt: 1.79 min, observed [M + H] = 455.2 m/z; $^1$H NMR (500 MHz, DMSO-$d_6$) δ [ppm] 10.31 (s, 1H), 9.68 (s, 1H), 8.21 (d, J = 4.3, 1H), 7.98 (d, J = 2.3, 1H), 7.69 (d, J = 4.3, 1H), 7.34 (d, J = 2.0, 1H), 7.24-7.20 (m, 1H), 7.15 (d, J = 8.1, 1H), 7.08 (d, J = 8.2, 1H), 6.37 (dd, J = 8.2, 2.4, 1H), 4.84 (t, J = 8.3, 2H), 3.13 (t, J = 8.3, 2H), 2.89 (s, 6H), 1.23 (s, 6H). |
| E120 | 2-[2-(3,3-dimethyl-2-oxo-2,3-dihydro-1H-indol-6-ylamino)-[1,2,4]triazolo[1,5-a]pyrazin-8-yl]-6-oxa-2,9-diaza-spiro[4.5]decan-8-one 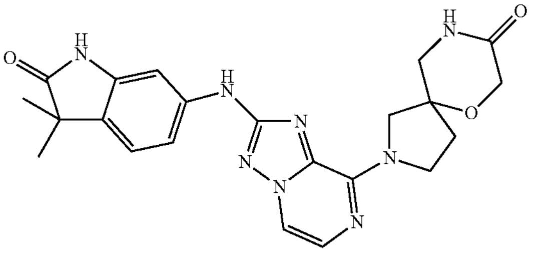 [SMILES: CC1(C)C(=O)Nc2cc(Nc3nc4c(N5CCC6(CNC(=O)CO6)C5)nccn4n3)ccc21] | LCMS (Method D) Rt: 1.48 min, observed [M + H] = 449.2 m/z. |

-continued

| nr. | name/structure | LCMS; NMR |
|---|---|---|
| E121 | 6-fluoro-4,4-dimethyl-7-[8-(1-methyl-1H-pyrazol-4-yl)-[1,2,4]triazolo[1,5-a]pyrazin-2-ylamino]-3,4-dihydro-1H-quinolin-2-one 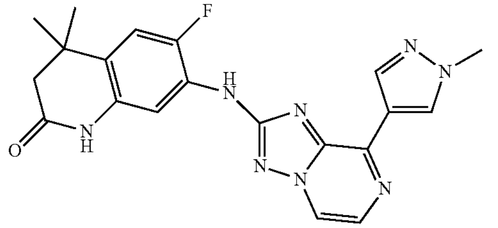 [SMILES: Cn1cc(-c2nccn3nc(Nc4cc5c(cc4F)C(C)(C)CC(=O)N5)nc23)cn1] | LCMS (Method D) Rt: 1.94 min, observed [M + H] = 407.2 m/z; $^1$H NMR (500 MHz, DMSO-$d_6$) δ [ppm] 10.26 (s, 1H), 9.40 (s, 1H), 8.69 (s, 1H), 8.63 (d, J = 4.3, 1H), 8.39 (s, 1H), 8.06 (d, J = 4.3, 1H), 7.66 (d, J = 7.6, 1H), 7.17 (d, J = 11.9, 1H), 3.98 (s, 3H), 2.35 (s, 2H), 1.23 (s, 6H). |
| E122 | 6-[8-(3-amino-propylamino)-[1,2,4]triazolo[1,5-a]pyrazin-2-ylamino]-3,3-dimethyl-1,3-dihydro-indol-2-one 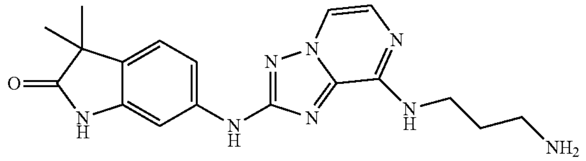 [SMILES: CC1(C)C(=O)Nc2cc(Nc3nc4c(NCCCN)nccn4n3)ccc21] | LCMS (Method C) Rt: 1.35 min, observed [M + H] = 367.2 m/z; $^1$H NMR (500 MHz, DMSO-$d_6$) δ [ppm] 10.37 (s, 1H), 9.47 (s, 1H), 7.95 (d, J = 4.5, 1H), 7.58-7.47 (m, 1H), 7.45 (d, J = 4.5, 1H), 7.29-7.24 (m, 2H), 7.13 (d, J = 8.0, 1H), 3.55 (t, J = 6.6, 2H), 2.82 (t, J = 7.1, 2H), 1.87 (p, J = 6.8, 2H), 1.22 (s, 6H). |
| E123 | 3,3-dimethyl-6-[8-(pyrrolidin-3-yloxy)-[1,2,4]triazolo[1,5-a]pyrazin-2-ylamino]-1,3-dihydro-indol-2-one 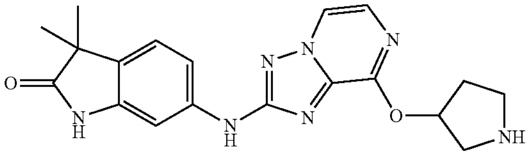 [SMILES: CC1(C)C(=O)Nc2cc(Nc3nc4c(OC5CCNC5)nccn4n3)ccc21] | LCMS (Method C) Rt: 1.328 min, observed [M + H] = 380.2 m/z; $^1$H NMR (500 MHz, DMSO-$d_6$) δ [ppm] 10.30 (s, 1H), 9.76 (s, 1H), 8.44 (d, J = 4.5, 1H), 7.60 (d, J = 4.5, 1H), 7.24 (d, J = 1.9, 1H), 7.19 (dd, J = 8.1, 2.0, 1H) 7.15 (d, J = 8.1, 1H), 5.65-5.60 (m, 1H), 3.34 (dd, J = 12.8, 5.5, 1H), 3.17-3.13 (m, 1H), 3.12-3.00 (m, 2H), 2.24-2.14 (m, 1H), 2.08-2.01 (m, 1H), 1.22 (s, 6H). |
| E124 | 2-[2-(3,3-dimethyl-2-oxo-2,3-dihydro-1H-indol-6-ylamino)-[1,2,4]triazolo[1,5-a]pyrazin-8-yl]-1,2,3,4-tetrahydro-isoquinoline-7-carbonitrile 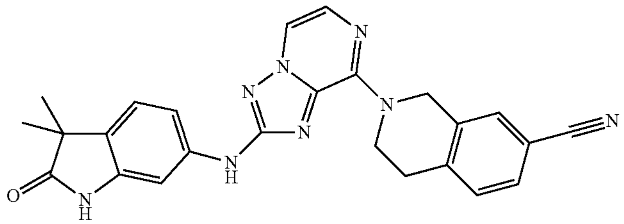 [SMILES: CC1(C)C(=O)Nc2cc(Nc3nc4c(N5CCc6ccc(C#N)cc6C5)nccn4n3)ccc21] | LCMS (Method C) Rt: 2.268 min, observed [M + H] = 451.2 m/z; $^1$H NMR (500 MHz, DMSO-$d_6$) δ [ppm] 10.31 (s, 1H), 9.70 (s, 1H), 8.14 (d, J = 4.3, 1H), 7.80-7.76 (m, 1H), 7.64 (dd, J = 7.4, 1.3, 1H), 7.59 (d, J = 4.4, 1H), 7.41 (d, J = 7.9, 1H), 7.31 (d, J = 1.9, 1H), 7.22 (dd, J = 8.1, 2.0, 1H), 7.15 (d, J = 8.1, 1H), 5.18 (s, 2H), 4.51 (t, J = 5.9, 2H), 3.07 (t, J = 5.9, 2H),1.23 (s, 6H). |
| E125 | 2-[2-amino-4-(8-azepan-1-yl-[1,2,4]triazolo[1,5-a]pyrazin-2-ylamino)-phenyl]-propan-2-ol 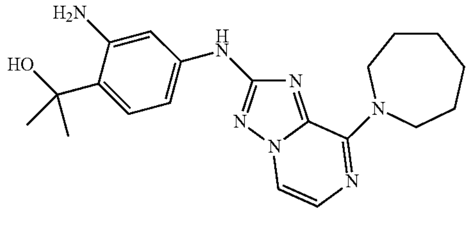 [SMILES: CC(C)(O)c1ccc(Nc2nc3c(N4CCCCCC4)nccn3n2)cc1N] | LCMS (Method D) Rt: 1.442 min, observed [M + H] = 382.3 m/z; $^1$H NMR (400 MHz, DMSO-$d_6$) δ [ppm] 9.18 (s, 1H), 7.93 (d, J = 4.3, 1H), 7.47 (d, J = 4.3, 1H), 6.89 (d, J = 8.3, 1H), 6.87-6.80 (m, 2H), 5.30 (s, 2H), 5.06 (s, 1H), 4.14-4.05 (m, 4H), 1.85-1.76 (m, 4H), 1.58-1.51 (m, 4H), 1.48 (s, 6H). |

-continued

| nr. | name/structure | LCMS; NMR |
| --- | --- | --- |
| E126 | (8-azepan-1-yl-[1,2,4]triazolo[1,5-a]pyrazin-2-yl)-(4,4-dimethyl-2-trifluoromethyl-1,4-dihydro-2H-benzo[d][1,3]oxazin-7-yl)-amine 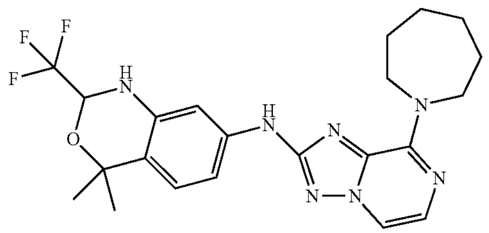 | LCMS (Method D) Rt: 1.585 min, observed [M + H] = 480.3 m/z; X |
| E127 | 1-{1-[2-amino-4-(8-azepan-1-yl-[1,2,4]triazolo[1,5-a]pyrazin-2-ylamino)-phenyl]-1-methyl-ethoxy}-2,2,2-trifluoro-ethanol 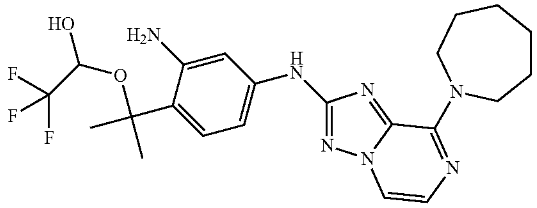 [SMILES: CC(C)(OC(O)C(F)(F)F)c1ccc(Nc2nc3c(N4CCCCCC4)nccn3n2)cc1N] | LCMS (Method D) Rt: 2.1 min, observed [M + H] = 462.2 m/z. |
| E128 | 2-[2-(3,3-dimethyl-2-oxo-2,3-dihydro-1H-indol-6-ylamino)-[1,2,4]triazolo[1,5-a]pyrazin-8-yl]-1,2,3,4-tetrahydro-isoquinoline-7-carboxylic acid amide 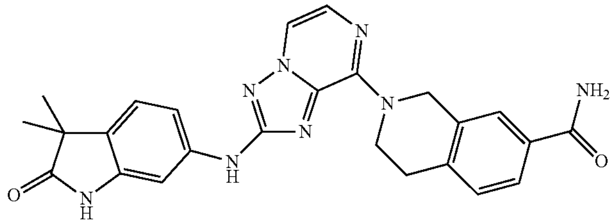 [SMILES: CC1(C)C(=O)Nc2cc(Nc3nc4c(N5CCc6ccc(C(N)=O)cc6C5)nccn4n3)ccc21] | LCMS (Method C) Rt: 1.832 min, observed [M + H] = 469.2 m/z; $^{1}$H NMR (500 MHz, DMSO-$d_6$) δ [ppm] 10.29 (s, 1H), 9.70 (s, 1H), 8.11 (d, J = 4.4, 1H), 7.90 (s, 1H), 7.76 (s, 1H), 7.69 (d, J = 7.9, 1H), 7.58 (d, J = 4.4, 1H), 7.33-7.21 (m, 4H), 7.15 (d, J = 8.1, 1H), 5.25 (s, 2H), 4.50-4.42 (m, 2H), 3.06-3.00 (m, 2H), 1.23 (s, 6H). |
| E129 | 2,3-dihydro-1H-indole-6-carboxylic acid [2-(3,3-dimethyl-2-oxo-2,3-dihydro-1H-indol-6-ylamino)-[1,2,4]triazolo[1,5-a]pyrazin-8-yl]-amide 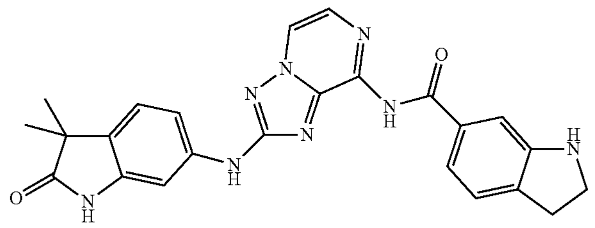 [SMILES: CC1(C)C(=O)Nc2cc(Nc3nc4c(NC(=O)c5ccc6c(c5)NCC6)nccn4n3)ccc21] | LCMS (Method C) Rt: 1.446 min, observed [M + H] = 455.2 m/z; $^{1}$H NMR (500 MHz, DMSO-$d_6$) δ [ppm] 10.78 (s, 1H), 10.28 (s, 1H), 9.95 (s, 1H), 8.76 (d, J = 4.4, 1H), 7.93 (d, J = 4.4, 1H), 7.42-7.35 (m, 1H), 7.27-7.27 (m, 1H), 7.26-7.25 (m, 1H), 7.23-7.22 (m, 1H), 7.18-7.13 (m, 2H), 7.11 (d, J = 1.3, 1H), 3.50 (t, J = 8.6, 2H), 3.00 (t, J = 8.6, 2H), 1.23 (s, 6H). |

-continued

| nr. | name/structure | LCMS; NMR |
|---|---|---|
| E130 | 6-[8-(5-Chloro-spiro[indole-3,3'-pyrrolidin]-1-yl)-[1,2,4]triazolo[1,5-a]pyrazin-2-ylamino]-3,3-dimethyl-1,3-dihydro-indol-2-one 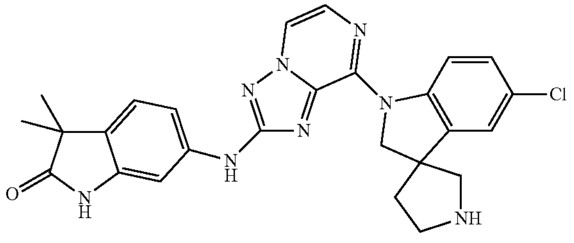 [SMILES: CC1(C)C(=O)Nc2cc(Nc3nc4c(N5CC6(CCNC6)c6cc(Cl)ccc65)nccn4n3)ccc21] | LCMS (Method C) Rt: 2.091 min, observed [M + H] = 501.2 m/z; $^1$H NMR (500 MHz, DMSO-$d_6$) δ [ppm] 10.29 (s, 1H), 9.72 (s, 1H), 8.11 (d, J = 4.8, 1H), 7.48 (d, J = 4.9, 1H), 7.36-7.32 (m, 1H), 7.27-7.21 (m, 1H), 7.19 (dd, J = 8.1, 2.0, 1H), 7.17-7.12 (m, 2H), 6.79 (d, J = 8.4, 1H), 4.50-3.77 (m, 4H), 3.65-3.57 (m, 2H), 2.45-2.37 (m, 1H), 2.29-2.22 (m, 1H), 1.21 (s, 6H). |
| E131 | 1-[2-(3,3-Dimethyl-2-oxo-2,3-dihydro-1H-indol-6-ylamino)-[1,2,4]triazolo[1,5-a]pyrazin-8-yl]-2,3-dihydro-1H-indole-6-carboxylic acid amide 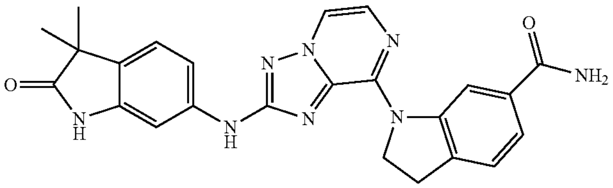 [SMILES: CC1(C)C(=O)Nc2cc(Nc3nc4c(N5CCc6ccc(C(N)=O)cc65)nccn4n3)ccc21] | LCMS (Method D) Rt: 1.911 min, observed [M + H] = 455.2 m/z; $^1$H NMR (500 MHz, DMSO-$d_6$) δ [ppm] 10.31 (s, 1H), 9.71 (s, 1H), 8.80-8.76 (m, 1H), 8.29 (d, J = 4.3, 1H), 7.85 (s, 1H), 7.75 (d, J = 4.3, 1H), 7.49 (dd, J = 7.7, 1.4, 1H), 7.36 (d, J = 2.0, 1H), 7.33 (d, J = 7.7, 1H), 7.25 (s, 1H), 7.22 (dd, J = 8.1, 2.0, 1H), 7.16 (d, J = 8.1, 1H), 4.90 (t, J = 8.6, 2H), 3.32-3.28 (m, 2H), 1.23 (s, 6H). |
| E132 | 6-[8-(6,7-Dihydro-4H-pyrazolo[5,1-c][1,4]oxazin-2-yl)-[1,2,4]triazolo[1,5-a]pyrazin-2-ylamino]-3,3-dimethyl-1,3-dihydro-indol-2-one 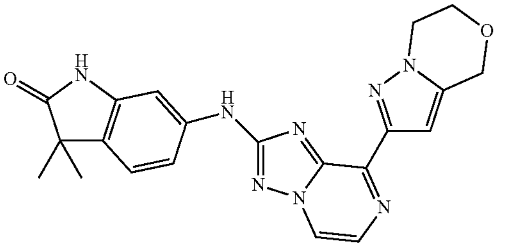 [SMILES: CC1(C)C(=O)Nc2cc(Nc3nc4c(-c5cc6n(n5)CCOC6)nccn4n3)ccc21] | LCMS (Method D) Rt: 1.761 min, observed [M + H] = 417.2 m/z; $^1$H NMR (400 MHz, DMSO-$d_6$) δ [ppm] 10.32 (s, 1H), 10.03 (s, 1H), 8.79 (d, J = 4.3, 1H), 8.12 (d, J = 4.2, 1H), 7.37 (d, J = 2.0, 1H), 7.29 (dd, J = 8.1, 2.0, 1H), 7.18 (d, J = 8.1, 1H), 7.15 (s, 1H), 4.93 (s, 2H), 4.27 (t, J = 5.3, 2H), 4.15 (t, J = 5.2, 2H), 1.24 (s, 6H). |
| E133 | 8-(1-methyl-1H-pyrazol-4-yl)-[1,2,4]triazolo[1,5-a]pyrazin-2-ylamine 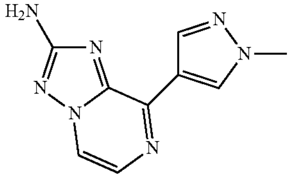 [SMILES: Cn1cc(-c2nccn3nc(N)nc23)cn1] | LCMS (Method C) Rt: 1133 min, observed [M + H] = 216.2 m/z; $^1$H NMR (400 MHz, DMSO-$d_6$) δ [ppm] 8.59 (s, 1H), 8.49 (d, J = 4.3, 1H), 8.30 (s, 1H), 7.92 (d, J = 4.3, 1H), 6.42 (s, 2H), 3.95 (s, 3H). |
| E134 | 1-[2-(3,3-dimethyl-2-oxo-2,3-dihydro-1H-indol-6-ylamino)-[1,2,4]triazolo[1,5-a]pyrazin-8-yl]-2,3-dihydro-1H-indole-6-carbonitrile 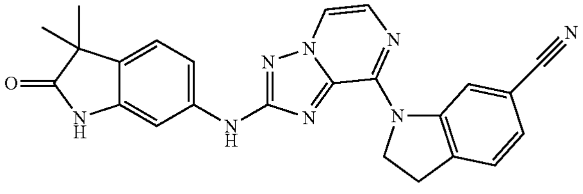 [SMILES: CC1(C)C(=O)Nc2cc(Nc3nc4c(N5CCc6ccc(C#N)cc65)nccn4n3)ccc21] | LCMS (Method C) Rt: 2.394 min, observed [M + H] = 437.2 m/z; $^1$H NMR (500 MHz, DMSO-$d_6$) δ [ppm] 10.31 (s, 1H), 9.74 (s, 1H), 8.69-8.67 (m, 1H), 8.34 (d, J = 4.3, 1H), 7.80 (d, J = 4.4, 1H), 7.49 (d, J = 7.4, 1H), 7.42 (dd, J = 7.6, 1.5, 1H), 7.35 (d, J = 2.0, 1H), 7.22 (dd, J = 8.1, 2.0, 1H), 7.15 (d, J = 8.1, 1H), 4.93 (t, J = 8.7, 2H), 3.37 (t, J = 8.6, 2H), 1.23 (s, 6H). |

-continued

| nr. | name/structure | LCMS; NMR |
|---|---|---|
| E135 | 6-[8-(1-aza-bicyclo[2.2.2]oct-3-ylamino)-[1,2,4]triazolo[1,5-a]pyrazin-2-ylamino]-3,3-dimethyl-1,3-dihydro-indol-2-one 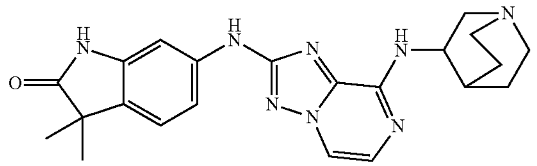 [SMILES: CC1(C)C(=O)Nc2cc(Nc3nc4c(NC5CN6CCC5CC6)nccn4n3)ccc21] | LCMS (Method C) Rt: 1.428 min, observed [M + H] = 419.2 m/z; X |
| E136 | 6-[8-((4aS,8aS)-4a-hydroxy-octahydro-isoquinolin-2-yl)-[1,2,4]triazolo[1,5-a]pyrazin-2-ylamino]-3,3-dimethyl-1,3-dihydro-indol-2-one 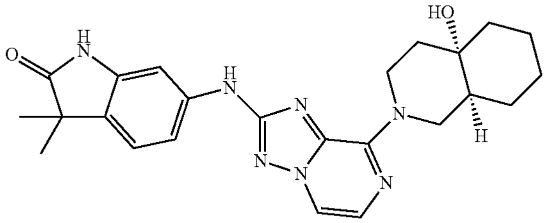 [SMILES: CC1(C)C(=O)Nc2cc(Nc3nc4c(N5CC[C@@]6(O)CCCC[C@H]6C5)nccn4n3)ccc21] | LCMS (Method C) Rt: 1.958 min, observed [M + H] = 448.2 m/z; $^1$H NMR (400 MHz, DMSO-$d_6$) δ [ppm] 10.29 (s, 1H), 9.60 (s, 1H), 8.01 (d, J = 4.3, 1H), 7.49 (d, J = 4.3, 1H), 7.26 (d, J = 1.9, 1H), 7.21 (dd, J = 8.1, 2.0, 1H), 7.13 (d, J = 8.1, 1H), 4.78-4.54 (m, 2H), 4.38 (s, 1H), 3.92-3.65 (m, 2H), 2.05-1.95 (m, 1H), 1.74-1.46 (m, 6H), 1.41-1.24 (m, 4H), 1.22 (s, 6H). |
| E137 | 3,3-dimethyl-6-[8-(2-methyl-2,3-dihydro-indol-1-yl)-[1,2,4]triazolo[1,5-a]pyrazin-2-ylamino]-1,3-dihydro-indol-2-one 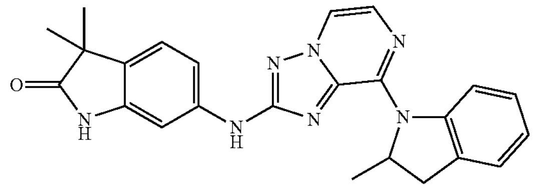 [SMILES: CC1Cc2ccccc2N1c1nccn2nc(Nc3ccc4c(c3)NC(=O)C4(C)C)nc12] | LCMS (Method C) Rt: 2.574 min, observed [M + H] = 426.2 m/z; $^1$H NMR (500 MHz, DMSO-$d_6$) δ [ppm] 10.34 (s, 1H), 9.71 (s, 1H), 8.44-8.40 (m, 1H), 8.27 (d, J = 4.3, 1H), 7.72 (d, J = 4.3, 1H), 7.34 (d, J = 2.0, 1H), 7.33-7.29 (m, 1H), 7.26 (dd, J = 8.1, 2.0, 1H), 7.24-7.18 (m, 1H), 7.16 (d, J = 8.1, 1H), 7.00 (td, J = 7.4, 1.0, 1H), 6.03-5.95 (m, 1H), 3.54-3.47 (m, 1H), 2.86-2.80 (m, 1H), 1.31 (d, J = 6.2, 3H), 1.23 (s, 6H). |
| E138 | 6-[8-(4-dimethylaminomethyl-4-hydroxy-azepan-1-yl)-[1,2,4]triazolo[1,5-a]pyrazin-2-ylamino]-3,3-dimethyl-1,3-dihydro-indol-2-one 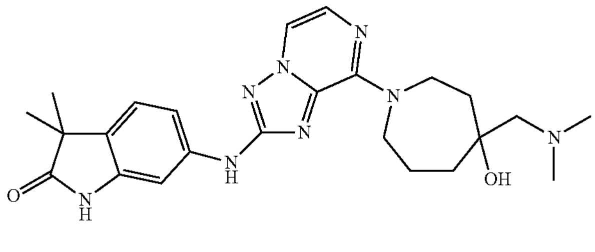 [SMILES: CN(C)CC1(O)CCCN(c2nccn3nc(Nc4ccc5c(c4)NC(=O)C5(C)C)nc23)CC1] | LCMS (Method C) Rt: 1.371 min, observed [M + H] = 465.3 m/z; $^1$H NMR (500 MHz, DMSO-$d_6$) δ [ppm] 10.24 (s, 1H), 9.55 (s, 1H), 7.95 (d, J = 4.3, 1H), 7.49 (d, J = 4.3, 1H), 7.32 (d, J = 2.0, 1H), 7.21 (dd, J = 8.1, 2.0, 1H), 7.12 (d, J = 8.1, 1H), 4.57-4.17 (m, 3H), 3.86-3.65 (m, 3H), 2.26 (s, 6H), 2.15-2.05(m, 1H), 1.88-1.64 (m, 4H), 1.46-1.39 (m, 1H), 1.22 (s, 6H). |

-continued

| nr. | name/structure | LCMS; NMR |
|---|---|---|
| E139 | 6-[8-(6-dimethylamino-pyridin-3-yl)-[1,2,4]triazolo[1,5-a]pyrazin-2-ylamino]-3,3-dimethyl-1,3-dihydro-indol-2-one 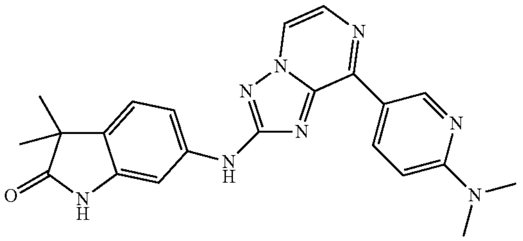 [SMILES: CN(C)c1ccc(-c2nccn3nc(Nc4ccc5c(c4)NC(=O)C5(C)C)nc23)cn1] | LCMS (Method C) Rt: 1.557 min, observed [M + H] = 415.2 m/z; $^1$H NMR (500 MHz, DMSO-$d_6$) δ [ppm] 10.32 (s, 1H), 9.91 (s, 1H), 9.51 (d, J = 2.4, 1H), 8.76 (dd, J = 9.1, 2.4, 1H), 8.69 (d, J = 4.3, 1H), 8.11 (d, J = 4.3, 1H), 7.33-7.29 (m, 2H), 7.22-7.17 (m, 1H), 6.84 (d, J = 9.0, 1H), 3.16 (s, 6H), 1.24 (s, 6H). |
| E140 | 6-[8-(1-tert-butyl-1H-pyrazol-4-yl)-[1,2,4]triazolo[1,5-a]pyrazin-2-ylamino]-3,3-dimethyl-1,3-dihydro-indol-2-one 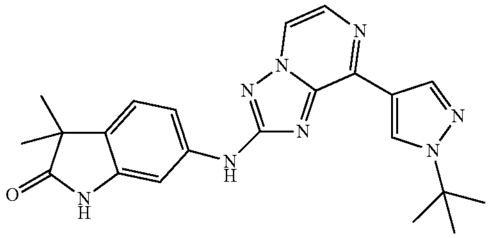 [SMILES: CC1(C)C(=O)Nc2cc(Nc3nc4c(-c5cnn(C(C)(C)C)c5)nccn4n3)ccc21] | LCMS (Method C) Rt: 2.05 min, observed [M + H] = 417.2 m/z; $^1$H NMR (500 MHz, DMSO-$d_6$) δ [ppm] 10:34 (s, 1H), 9.87 (s, 1H), 8.74 (s, 1H), 8.66 (d, J = 4.3, 1H), 8.46 (s, 1H), 8.05 (d, J = 4.3, 1H), 7.35 (d, J = 2.0, 1H), 7.32 (dd, J = 8.1, 2.0, 1H), 7.19 (d, J = 8.0, 1H), 1.63 (s, 9H), 1.24 (s, 6H). |
| E141 | 2-[2-(3,3-dimethyl-2-oxo-2,3-dihydro-1H-indol-6-ylamino)-[1,2,4]triazolo[1,5-a]pyrazin-8-yl]-2,8-diaza-spiro[4.5]decan-1-one 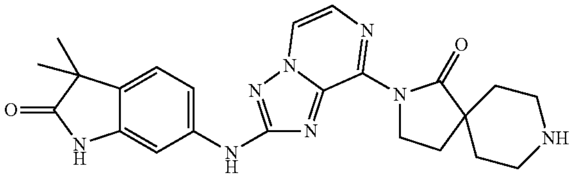 [SMILES: CC1(C)C(=O)Nc2cc(Nc3nc4c(N5CCC6(CCNCC6)C5=O)nccn4n3)ccc21] | LCMS (Method C) Rt: 1.274 min, observed [M + H] = 447.2 m/z; $^1$H NMR (500 MHz, DMSO-$d_6$) δ [ppm] 10.31 (s, 1H), 9.95 (s, 1H), 8.78 (d, J = 4.3, 1H), 8.33 (s, 1H), 7.94 (d, J = 4.3, 1H), 7.29 (dd, J = 8.1, 2.0, 1H), 7.26 (d, J = 2.0, 1H), 7.16 (d, J = 8.1, 1H), 4.03 (t, J = 6.9, 2H), 3.12 (dt, J = 12.7, 4.2, 2H), 2.89-2.80 (m, 2H), 2.22 (t, J = 6.9, 2H), 1.91-1.81 (m, 2H), 1.66-1.60 (m, 2H), 1.23 (s, 6H). |
| E142 | 6-[8-(2,3-dihydro-benzo[1,4]dioxin-6-yl)-[1,2,4]triazolo[1,5-a]pyrazin-2-ylamino]-3,3-dimethyl-1,3-dihydro-indol-2-one 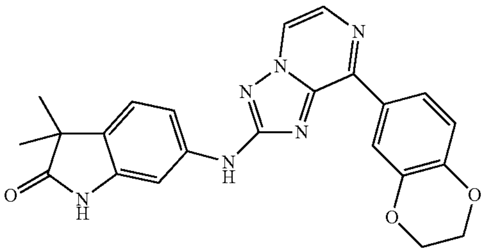 [SMILES: CC1(C)C(=O)Nc2cc(Nc3nc4c(-c5ccc6c(c5)OCCO6)nccn4n3)ccc21] | LCMS (Method C) Rt: 2.172 min, observed [M + H] = 429.1 m/z; $^1$H NMR (500 MHz, DMSO-$d_6$) δ [ppm] 10.31 (s, 1H), 10.00 (s, 1H), 8.77 (d, J = 4.2, 1H), 8.33 (d, J = 2.1, 1H), 8.29 (dd, J = 8.6, 2.1, 1H), 8.15 (d, J = 4.3, 1H), 7.33-7.29 (m, 2H), 7.20-7.17 (m, 1H), 7.07 (d, J = 8.5, 1H), 4.37-4.30 (m, 4H), 1.24 (s, 6H). |

-continued

| nr. | name/structure | LCMS; NMR |
|---|---|---|
| E143 | 3,3-dimethyl-6-[8-(1,4,4-trimethyl-1,2,3,4-tetrahydro-quinolin-6-yl)-[1,2,4]triazolo[1,5-a]pyrazin-2-ylamino]-1,3-dihydro-indol-2-one 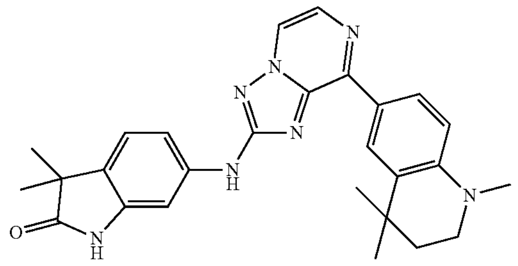 [SMILES: CN1CCC(C)(C)c2cc(-c3nccn4nc(Nc5ccc6c(c5)NC(=O)C6(C)C)nc34)ccc21] | LCMS (Method C) Rt: 2.549 min, observed [M + H] = 468.2 m/z; $^1$H NMR (500 MHz, DMSO-$d_6$) δ [ppm] 10.30 (s, 1H), 9.83 (s, 1H), 8.63 (d, J = 2.2, 1H), 8.60 (d, J = 4.2, 1H), 8.57 (dd, J = 8.8, 2.2, 1H), 8.08 (d, J = 4.2, 1H), 7.45 (dd, J = 8.1, 2.0, 1H), 7.26 (d, J = 2.0, 1H), 7.16 (d, J = 8.1, 1H), 6.72 (d, J = 8.9, 1H), 3.37-3.36 (m, 2H), 3.00 (s, 3H), 1.80-1.74 (m, 2H), 1.33 (s, 6H), 1.24 (s, 6H). |
| E144 | 3,3-dimethyl-6-[8-(4-methyl-3,4-dihydro-2H-pyrido[3,2-b][1,4]oxazin-7-yl)-[1,2,4]triazolo[1,5-a]pyrazin-2-ylamino]-1,3-dihydro-indol-2-one 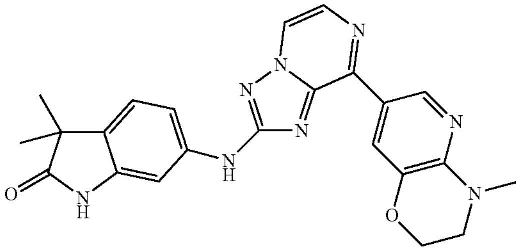 [SMILES: CN1CCOc2cc(-c3nccn4nc(Nc5ccc6c(c5)NC(=O)C6(C)C)nc34)cnc21] | LCMS (Method C) Rt: 1.817 min, observed [M + H] = 443.2 m/z; $^1$H NMR (500 MHz, DMSO-$d_6$) δ [ppm] 10.30 (s, 1H), 9.92 (s, 1H), 9.17 (d, J = 2.0, 1H), 8.69 (d, J = 4.2, 1H), 8.16 (d, J = 2.0, 1H), 8.10 (d, J = 4.2, 1H), 7.33 (dd, J = 8.1, 2.0, 1H), 7.25 (d, J = 2.0, 1H), 7.19 (d, J = 8.1, 1H), 4.31-4.23 (m, 2H), 3.57 (t, J = 4.6, 2H), 3.17 (s, 3H), 1.24 (s, 6H). |
| E145 | 6-{8-[1-(2-hydroxy-ethyl)-1H-pyrazol-4-yl]-[1,2,4]triazolo[1,5-a]pyrazin-2-ylamino)-3,3-dimethyl-1,3-dihydro-indol-2-one 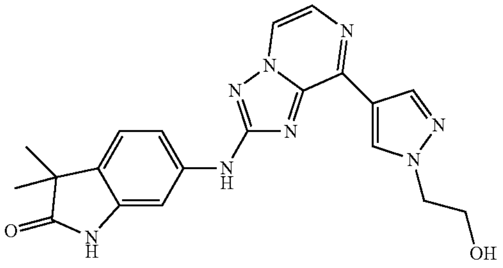 [SMILES: CC1(C)C(=O)Nc2cc(Nc3nc4c(-c5cnn(CCO)c5)nccn4n3)ccc21] | LCMS (Method C) Rt: 1.623 min, observed [M + H] = 405.1 m/z; $^1$H NMR (400 MHz, DMSO-$d_6$) δ [ppm] 10.33 (s, 1H), 9.92 (s, 1H), 8.71 (s, 1H), 8.67 (d, J = 4.3, 1H), 8.41 (s, 1H), 8.05 (d, J = 4.3, 1H), 7.39 (d, J = 2.0, 1H), 7.30 (dd, J = 8.1, 2.0, 1H), 7.19 (d, J = 8.1, 1H), 5.01 (t, J = 5.2, 1H), 4.30 (t, J = 5.4, 2H), 3.82 (q, J = 5.4, 2H), 1.24 (s, 6H). |
| E146 | 6-[8-(8,8-dimethyl-5,6,7,8-tetrahydro-naphthalen-2-yl)-[1,2,4]triazolo[1,5-a]pyrazin-2-ylamino]-3,3-dimethyl-1,3-dihydro-indol-2-one 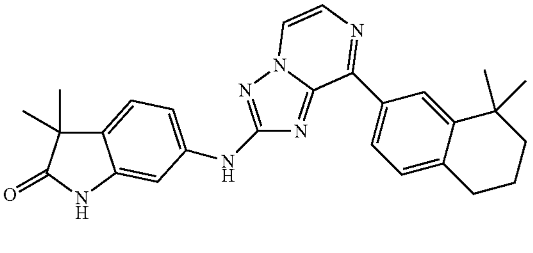 [SMILES: CC1(C)CCCc2ccc(-c3nccn4nc(Nc5ccc6c(c5)NC(=O)C6(C)C)nc34)cc21] | LCMS (Method C) Rt: 2.777 min, observed [M + H] = 453.2 m/z; $^1$H NMR (500 MHz, DMSO-$d_6$) δ [ppm] 10.30 (s, 1H), 9.91 (s, 1H), 8.80 (d, J = 4.2, 1H), 8.77 (d, J = 1.8, 1H), 8.47 (dd, J = 8.1, 1.8, 1H), 8.20 (d, J = 4.2, 1H), 7.47 (dd, J = 8.1, 2.0, 1H), 7.27-7.24 (m, 2H), 7.17 (d, J = 8.1, 1H), 2.83 (t, J = 6.3, 2H), 1.85-1.78 (m, 2H), 1.73-1.69 (m, 2H), 1.37 (s, 6H), 1.24 (s, 6H). |

-continued

| nr. | name/structure | LCMS; NMR |
|---|---|---|
| E147 | 6-[8-(3,3-dimethyl-indan-5-yl)-[1,2,4]triazolo[1,5-a]pyrazin-2-ylamino]-3,3-dimethyl-1,3-dihydro-indol-2-one 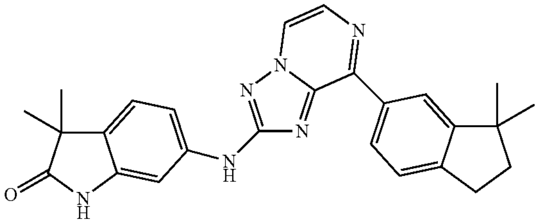 [SMILES: CC1(C)CCc2ccc(-c3nccn4nc(Nc5ccc6c(c5)NC(=O)C6(C)C)nc34)cc21] | LCMS (Method C) Rt: 2.676 min, observed [M + H] = 439.2 m/z; $^1$H NMR (400 MHz, DMSO-$d_6$) δ [ppm] 10.33 (s, 1H), 9.94 (s, 1H), 8.80 (d, J = 4.2, 1H), 8.66 (dd, J = 7.9, 1.7, 1H), 8.45 (d, J = 1.6, 1H), 8.20 (d, J = 4.2, 1H), 7.42 (d, J = 7.9, 1H), 7.39 (dd, J = 8.1, 2.0, 1H), 7.30 (d, J = 2.0, 1H), 7.18 (d, J = 8.1, 1H), 2.96 (t, J = 7.2, 2H), 1.97 (t, J = 7.2, 2H), 1.32 (s, 6H), 1.24 (s, 6H). |
| E148 | 3,3-dimethyl-6-{8-[1-(tetrahydro-pyran-4-yl)-1H-pyrazol-4-yl]-[1,2,4]triazolo[1,5-a]pyrazin-2-ylamino}-1,3-dihydro-indol-2-one 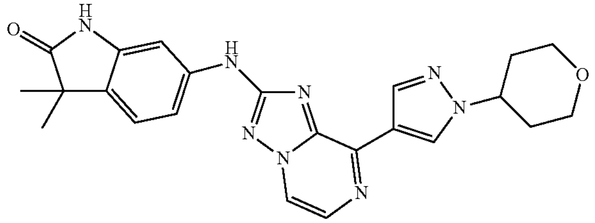 [SMILES: CC1(C)C(=O)Nc2cc(Nc3nc4c(-c5cnn(C6CCOCC6)c5)nccn4n3)ccc21] | LCMS (Method D) Rt: 1.891 min, observed [M + H] = 445.2 m/z. |
| E149 | 6-(8-isoxazol-4-yl-[1,2,4]triazolo[1,5-a]pyrazin-2-ylamino)-3,3-dimethyl-1,3-dihydro-indol-2-one 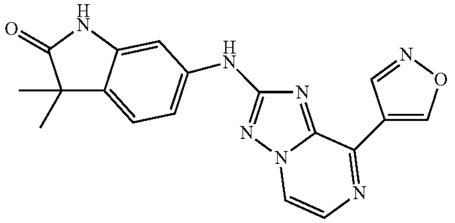 [SMILES: CC1(C)C(=O)Nc2cc(Nc3nc4c(-c5cnoc5)nccn4n3)ccc21] | LCMS (Method D) Rt: 1.691 min, observed [M + H] = 362.2 m/z. |
| E150 | 3,3-dimethyl-6-[8-(1-piperidin-4-yl-1H-pyrazol-4-yl)-[1,2,4]triazolo[1,5-a]pyrazin-2-ylamino]-1,3-dihydro-indol-2-one 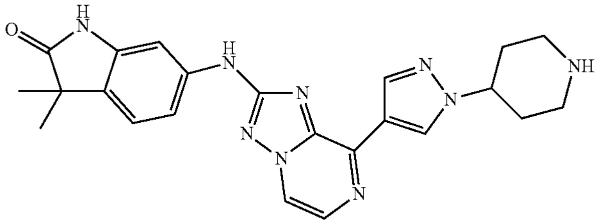 [SMILES: CC1(C)C(=O)Nc2cc(Nc3nc4c(-c5cnn(C6CCNCC6)c5)nccn4n3)ccc21] | LCMS (Method D) Rt: 1.608 min, observed [M + H] = 444.2 m/z. |
| E151 | 3-{[2-(3,3-dimethyl-2-oxo-2,3-dihydro-1H-indol-6-ylamino)-[1,2,4]triazolo[1,5-a]pyrazin-8-yl]-methyl-amino}-benzamide 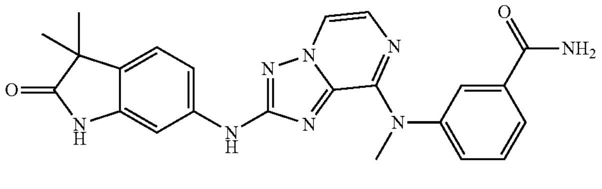 [SMILES: CN(c1cccc(C(N)=O)c1)c1nccn2nc(Nc3ccc4c(c3)NC(=O)C4(C)C)nc12] | LCMS (Method C) Rt: 1.714 min, observed [M + H] = 443.2 m/z. |

-continued

| nr. | name/structure | LCMS; NMR |
|---|---|---|
| E152 | 6-{8-[4-(bis-trifluoromethyl-amino)-phenyl]-[1,2,4]triazolo[1,5-a]pyrazin-2-ylamino}-3,3-dimethyl-1,3-dihydro-indol-2-one 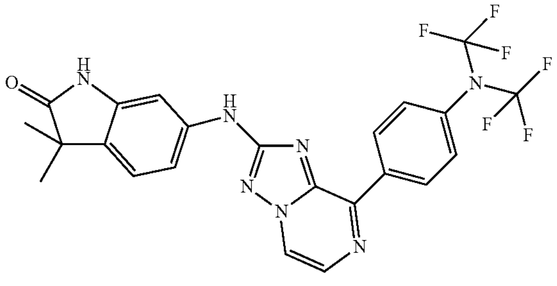 [SMILES: CC1(C)C(=O)Nc2cc(Nc3nc4c(-c5ccc(N(C(F)(F)F)C(F)(F)F)cc5)nccn4n3)ccc21] | LCMS (Method C) Rt: 2.679 min, observed [M + H] = 522.1 m/z. |
| E153 | 3,3-dimethyl-6-[8-((S)-8-trifluoromethyl-2,7-diaza-spiro[4.4]non-2-yl)-[1,2,4]triazolo[1,5-a]pyrazin-2-ylamino]-1,3-dihydro-indol-2-one 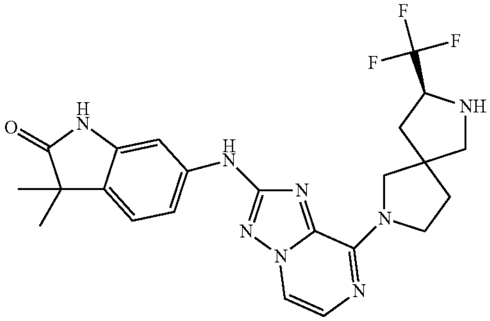 [SMILES: CC1(C)C(=O)Nc2cc(Nc3nc4c(N5CCC6(CN[C@H](C(F)(F)F)C6)C5)nccn4n3)ccc21] | LCMS (Method D) Rt: 1.497 min, observed [M + H] = 487.2 m/z. |
| E154 | 8-[2-(4,4-dimethyl-1,2,3,4-tetrahydro-quinolin-7-ylamino)-[1,2,4]triazolo[1,5-a]pyrazin-8-yl]-hexahydro-pyrazino[1,2-a]pyrazine-1,4-dione 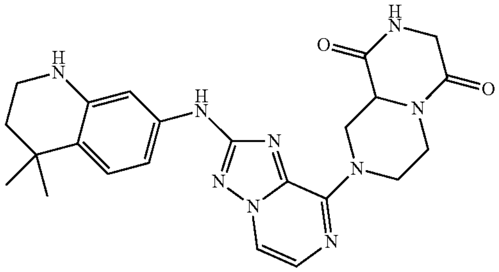 [SMILES: CC1(C)CCNc2cc(Nc3nc4c(N5CCN6C(=O)CNC(=O)C6C5)nccn4n3)ccc21] | LCMS (Method D) Rt: 1.560 min, observed [M + H] = 462.3 m/z. |
| E155 | 5,5-dimethyl-8-[5-(1-methyl-1H-pyrazol-4-yl)-[1,2,4]triazolo[1,5-c]pyrimidin-2-ylamino]-1,3,4,5-tetrahydro-benzo[b]azepin-2-one 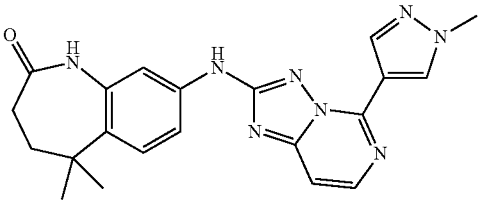 [SMILES: Cn1cc(-c2nccc3nc(Nc4ccc5c(c4)NC(=O)CCC5(C)C)nn23)cn1] | LCMS (Method D) Rt: 1.938 min, observed [M + H] = 403.2 m/z. |

Pharmacological Data

TABLE 1

Syk and GCN2 inhibition of some representative compounds of the formula I

| Compound No. | $IC_{50}$ SYK (enzyme assay) | $IC_{50}$ GCN2 (enzyme assay) | Compound No. | $IC_{50}$ SYK (enzyme assay) | $IC_{50}$ GCN2 (enzyme assay) |
|---|---|---|---|---|---|
| "C1" | C | | "C75" | AA | |
| "C2" | B | C | "C76" | B | |
| "C3" | B | | "C77" | AA | |
| "C4" | | | "C78" | B | C |
| "C5" | A | | "C79" | B | |
| "C6" | B | B | "C80" | A | C |
| "C7" | B | | "C81" | AA | C |
| "C8" | C | C | "C82" | A | B |
| "C9" | | | "C83" | A | C |
| "C10" | | | "C84" | A | C |
| "C11" | B | | "C85" | AA | C |
| "C12" | A | C | "C86" | B | C |
| "C13" | C | | "C87" | A | |
| "C14" | C | B | "C88" | B | C |
| "C15" | C | | "C89" | B | |
| "C16" | B | C | "C90" | AA | |
| "C17" | B | | "C91" | AA | C |
| "C18" | B | C | "C92" | AA | |
| "C19" | | | "C93" | B | |
| "C20" | B | | "C94" | AA | C |
| "C21" | B | C | "C95" | AA | C |
| "C22" | | | "C96" | A | |
| "C23" | B | C | "C97" | B | |
| "C24" | C | | "C98" | AA | |
| "C25" | | | "C99" | AA | C |
| "C26" | B | C | "C100" | B | |
| "C27" | | | "C101" | A | C |
| "C28" | C | B | "C102" | AA | |
| "C29" | A | C | "C103" | AA | C |
| "C30" | B | B | "C104" | B | C |
| "C31" | C | | "C105" | AA | C |
| "C32" | B | C | "C106" | B | |
| "C33" | A | B | "C107" | B | |
| "C34" | AA | C | "C108" | AA | C |
| "C35" | C | | "C109" | A | |
| "C36" | B | B | "C110" | B | |
| "C37" | | | "C111" | A | B |
| "C38" | A | B | "C112" | B | C |
| "C39" | | | "C113" | AA | B |
| "C40" | | | "C114" | AA | B |
| "C41" | C | C | "C115" | A | C |
| "C42" | B | | "C116" | | |
| "C43" | B | C | "C117" | A | B |
| "C44" | | | "C118" | AA | C |
| "C45" | C | C | "C119" | A | C |
| "C46" | B | | "C120" | AA | B |
| "C47" | | | "C121" | | |
| "C48" | C | B | "C122" | | |
| "C49" | B | C | "C123" | | |
| "C50" | B | C | "C124" | | |
| "C51" | C | C | "C125" | | |
| "C52" | | | "C126" | | |
| "C53" | B | | "C127" | | |
| "C54" | C | | "C128" | | |
| "C55" | B | C | "C129" | | |
| "C56" | B | C | "C130" | | |
| "C57" | C | B | "C131" | | |
| "C58" | B | B | "C132" | | |
| "C59" | C | B | "C133" | | |
| "C60" | B | B | "C134" | | |
| "C61" | A | B | "C135" | | |
| "C62" | A | | "C136" | | |
| "C63" | A | B | "C137" | | |
| "C64" | B | B | "C138" | | |
| "C65" | A | C | "C139" | | |
| "C66" | A | C | "C140" | | |
| "C67" | AA | B | "C141" | AA | B |
| "C68" | B | | "C142" | A | B |
| "C69" | A | B | "C143" | A | |

TABLE 1-continued

Syk and GCN2 inhibition of some representative compounds of the formula I

| Compound No. | $IC_{50}$ SYK (enzyme assay) | $IC_{50}$ GCN2 (enzyme assay) | Compound No. | $IC_{50}$ SYK (enzyme assay) | $IC_{50}$ GCN2 (enzyme assay) |
|---|---|---|---|---|---|
| "C70" | A | B | "C144" | AA | B |
| "C71" | A | B | "D1" | C | |
| "C72" | AA | B | "D2" | B | |
| "C73" | A | C | "D3" | | |
| "C74" | A | C | | | |
| "E1" | AA | | "E11" | B | |
| "E2" | AA | | "E12" | | |
| "E3" | AA | | "E13" | AA | |
| "E4" | A | | "E14" | A | |
| "E5" | A | | "E15" | | |
| "E6" | A | | "E16" | AA | |
| "E7" | AA | | "E17" | A | |
| "E8" | AA | | "E18" | AA | |
| "E9" | AA | | "E19" | A | |
| "E10" | A | | "E20" | AA | |
| "E21" | AA | | "E31" | AA | |
| "E22" | B | | "E32" | AA | |
| "E23" | A | | "E33" | A | |
| "E24" | C | | "E34" | A | |
| "E25" | | | "E35" | AA | |
| "E26" | AA | | "E36" | A | |
| "E27" | AA | | "E37" | A | |
| "E28" | AA | | "E38" | A | |
| "E29" | C | | "E39" | AA | |
| "E30" | C | | "E40" | AA | |
| "E41" | AA | | "E51" | | |
| "E42" | AA | | "E52" | A | |
| "E43" | AA | | "E53" | AA | |
| "E44" | AA | | "E54" | AA | |
| "E45" | AA | | "E55" | AA | |
| "E46" | AA | | "E56" | AA | |
| "E47" | AA | | "E57" | AA | |
| "E48" | AA | | "E58" | A | |
| "E49" | AA | | "E59" | AA | |
| "E50" | | | "E60" | B | |
| "E61" | C | | "E71" | A | |
| "E62" | B | | "E72" | AA | |
| "E63" | AA | | "E73" | AA | |
| "E64" | B | | "E74" | AA | |
| "E65" | A | | "E75" | AA | |
| "E66" | B | | "E76" | AA | |
| "E67" | AA | | "E77" | AA | |
| "E68" | AA | | "E78" | A | |
| "E69" | AA | | "E79" | B | |
| "E70" | AA | | "E80" | | |
| "E81" | AA | | "E91" | AA | |
| "E82" | C | | "E92" | AA | |
| "E83" | B | | "E93" | B | |
| "E84" | | | "E94" | | |
| "E85" | C | | "E95" | AA | |
| "E86" | A | | "E96" | B | |
| "E87" | AA | | "E97" | B | |
| "E88" | AA | | "E98" | A | |
| "E89" | B | | "E99" | AA | |
| "E90" | B | | "E100" | B | |
| "E101" | AA | | "E111" | B | |
| "E102" | AA | | "E112" | AA | |
| "E103" | B | | "E113" | AA | |
| "E104" | C | | "E114" | AA | |
| "E105" | AA | | "E115" | AA | |
| "E106" | AA | | "E116" | AA | |
| "E107" | | | "E117" | C | |
| "E108" | B | | "E118" | C | |
| "E109" | | | "E119" | A | |
| "E110" | B | | "E120" | B | |
| "E121" | B | | "E131" | AA | |
| "E122" | B | | "E132" | B | |
| "E123" | C | | "E133" | | |
| "E124" | AA | | "E134" | AA | |
| "E125" | AA | | "E135" | AA | |
| "E126" | AA | | "E136" | AA | |
| "E127" | B | | "E137" | AA | |

TABLE 1-continued

Syk and GCN2 inhibition of some representative compounds of the formula I

| Compound No. | $IC_{50}$ SYK (enzyme assay) | $IC_{50}$ GCN2 (enzyme assay) | Compound No. | $IC_{50}$ SYK (enzyme assay) | $IC_{50}$ GCN2 (enzyme assay) |
|---|---|---|---|---|---|
| "E128" | AA | | "E138" | A | |
| "E129" | B | | "E139" | AA | |
| "E130" | B | | "E140" | AA | |
| "E141" | A | | "E150" | AA | |
| "E142" | AA | | "E151" | B | |
| "E143" | A | | "E152" | C | |
| "E144" | AA | | "E153" | AA | |
| "E145" | AA | | "E154" | AA | |
| "E146" | B | | "E155" | AA | |
| "E147" | | | | | |
| "E148" | AA | | | | |
| "E149" | AA | | | | |

IC:
<0.1 μM = AA;
0.1-0.3 μM = A;
0.3-3 μM = B;
3-50 μM = C

The following examples relate to medicaments:

Example A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B

Suppositories

A mixture of 20 g of an active ingredient of the formula I with 100 g of soya lecithin and 1400 g of cocoa butter is melted, poured into moulds and allowed to cool. Each suppository contains 20 mg of active ingredient.

Example C

Solution

A solution is prepared from 1 g of an active ingredient of the formula I, 9.38 g of $NaH_2PO_4.2H_2O$, 28.48 g of $Na_2HPO_4.12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D

Ointment 500 mg of an active ingredient of the formula I are mixed with 99.5 g of Vaseline under aseptic conditions.

Example E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F

Dragees

Tablets are pressed analogously to Example E and subsequently coated in a conventional manner with a coating of sucrose, potato starch, talc, tragacanth and dye.

Example G

Capsules 2 kg of active ingredient of the formula I are introduced into hard gelatine capsules in a conventional manner in such a way that each capsule contains 20 mg of the active ingredient.

Example H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:

1. Compound selected from the group 3,3-dimethyl-6-[8-(2-oxa-6-aza-spiro[3.4]oct-6-yl)-[2,4]triazolo[1,5-a]pyrazin-2-ylamino]-1,3-dihydro-indol-2-one ("C81"), 3,3-dimethyl-6-[8-(2-oxa-6-aza-spiro[3.3]hept-6-yl)-[1,2,4]triazolo[1,5-a]pyrazin-2-ylamino]-1,3-dihydro-indol-2-one ("C91"), 3,3-dimethyl-6-[8-(2-oxa-6-aza-spiro[3.5]non-6-yl)-[1,2,4]triazolo[1,5-a]pyrazin-2-ylamino]-1,3-dihydro-indol-2-one ("C92"), 7-[2-(3,3-dimethyl-2-oxo-2,3-dihydro-1H-indol-6-ylamino)-[1,2,4]triazolo[1,5-a]pyrazin-8-yl]-2,7-diaza-spiro[4.4]nonane-1,3-dione ("C95"), 7-[2-(3,3-dimethyl-2-oxo-2,3-dihydro-1H-indol-6-ylamino)-[1,2,4]triazolo[1,5-a]pyrazin-8-yl]-1,3,7-triaza-spiro[4.4]nonane-2,4-dione ("C108"), 2-[2-(3,3-dimethyl-2-oxo-2,3-dihydro-1H-indol-6-ylamino)-[1,2,4]triazolo[1,5-a]pyrazin-8-yl]-2,5,7-triaza-spiro[3.4]octane-6,8-dione ("C109"), 7-[2-(3,3-dimethyl-2-oxo-2,3-dihydro-1H-indol-6-ylamino)-[1,2,4]triazolo[1,5-a]pyrazin-8-yl]-1,3,7-triaza-spiro[4.5]decane-2,4-dione ("C110"), 7-[2-(4,4-dimethyl-2-oxo-1,4-dihydro-2H-benzo[d][1,3]oxazin-7-ylamino)-[1,2,4]triazolo[1,5-a]pyrazin-8-yl]-1,3,7-triaza-spiro[4.4]nonane-2,4-dione ("C118"), 7-[2-(4,4-dimethyl-2-oxo-1,2,3,4-tetrahydro-quinolin-7-ylamino)-[1,2,4]triazolo[1,5-a]pyrazin-8-yl]-2,7-diaza-spiro[4.4]nonane-1,3-dione ("C127"), 6'-[[8-(1-methylpyrazol-4-yl)-[1,2,4]triazolo[1,5-a]pyrazin-2-yl]amino]spiro[cyclobutane-1,3'-indoline]-2'-one ("C128"),

[8-(2,7-diaza-spiro[4.4]non-2-yl)-[1,2,4]triazolo[1,5-a]pyrazin-2-yl]-(4,4-dimethyl-1,2,3,4-tetrahydro-quinolin-7-yl)-amine ("C129"), 6-[8-(1,4-dioxa-7-aza-spiro[4.4]non-7-yl)-[1,2,4]triazolo[1,5-a]pyrazin-2-ylamino]-3,3-dimethyl-1,3-dihydro-indol-2-one ("C130"), 8-[2-(3,3-dimethyl-2-oxo-2,3-dihydro-1H-indol-6-ylamino)-[1,2,4]triazolo[1,5-a]pyrazin-8-yl]-2,8-diaza-spiro[4.5]decan-1-one ("C133"), (R)-7-[2-(3,3-dimethyl-2-oxo-2,3-dihydro-1H-indol-6-ylamino)-[1,2,4]triazolo[1,5-a]pyrazin-8-yl]-2,7-diaza-spiro[4.4]nonane-1,3-dione ("C136"), (S)-7-[2-(3,3-dimethyl-2-oxo-2,3-dihydro-1H-indol-6-ylamino)-[1,2,4]triazolo[1,5-a]pyrazin-8-yl]-2,7-diaza-spiro[4.4]nonane-1,3-dione ("C137"), 6-[8-(6-oxo-2,7-diaza-spiro[4.4]non-2-yl)-[1,2,4]triazolo[1,5-a]pyrazin-2-ylamino]-1,3-dihydro-indol-2-one ("C139"), 3,3-dimethyl-6-[8-(8-oxo-2,7-diaza-spiro[4.4]non-2-yl)-[1,2,4]triazolo[1,5-a]pyrazin-2-ylamino]-1,3-dihydro-indol-2-one ("C140"),

| nr. | name |
|---|---|
| E7 | 7-[2-(4,4-dimethyl-2-oxo-1,2,3,4-tetrahydro-quinolin-7-ylamino)-[1,2,4]triazolo[1,5-a]pyrazin-8-yl]-2,7-diaza-spiro[4.4]nonane-1,3-dione |
| E8 | 6'-[[8-(1-methylpyrazol-4-yl)-[1,2,4]triazolo[1,5-a]pyrazin-2-yl]amino]spiro[cyclobutane-1,3'-indoline]-2'-one |
| E9 | [8-(2,7-diaza-spiro[4.4]non-2-yl)-[1,2,4]triazolo[1,5-a]pyrazin-2-yl]-(4,4-dimethyl-1,2,3,4-tetrahydro-quinolin-7-yl)-amine |
| E10 | 6-[8-(1,4-dioxa-7-aza-spiro[4.4]non-7-yl)-[1,2,4]triazolo[1,5-a]pyrazin-2-ylamino]-3,3-dimethyl-1,3-dihydro-indol-2-one |
| E13 | 8-[2-(3,3-dimethyl-2-oxo-2,3-dihydro-1H-indol-6-ylamino)-[1,2,4]triazolo[1,5-a]pyrazin-8-yl]-2,8-diaza-spiro[4.5]decan-1-one |
| E16 | (R)-7-[2-(3,3-dimethyl-2-oxo-2,3-dihydro-1H-indol-6-ylamino)-[1,2,4]triazolo[1,5-a]pyrazin-8-yl]-2,7-diaza-spiro[4.4]nonane-1,3-dione |
| E18 | (S)-7-[2-(3,3-dimethyl-2-oxo-2,3-dihydro-1H-indol-6-ylamino)-[1,2,4]triazolo[1,5-a]pyrazin-8-yl]-2,7-diaza-spiro[4.4]nonane-1,3-dione |
| E19 | 3,3-dimethyl-6-[8-(6-oxo-2,7-diaza-spiro[4.4]non-2-yl)-[1,2,4]triazolo[1,5-a]pyrazin-2-ylamino]-1,3-dihydro-indol-2-one |
| E20 | 3,3-dimethyl-6-[8-(8-oxo-2,7-diaza-spiro[4.4]non-2-yl)-[1,2,4]triazolo[1,5-a]pyrazin-2-ylamino]-1,3-dihydro-indol-2-one |
| E27 | 8-[2-(3,3-dimethyl-2-oxo-2,3-dihydro-1H-indol-6-ylamino)-[1,2,4]triazolo[1,5-a]pyrazin-8-yl]-1-oxa-3,8-diaza-spiro[4.5]decan-2-one |
| E28 | 8-[2-(3,3-dimethyl-2-oxo-2,3-dihydro-1H-indol-6-ylamino)-[1,2,4]triazolo[1,5-a]pyrazin-8-yl]-1,3,8-triaza-spiro[4.5]decane-2,4-dione |
| E35 | 8-[2-(3,3-dimethyl-2-oxo-2,3-dihydro-1H-indol-6-ylamino)-[1,2,4]triazolo[1,5-a]pyrazin-8-yl]-1,8-diaza-spiro[4.5]decan-2-one |
| E45 | 4,4-dimethyl-7-[8-(2-oxo-1-oxa-3,8-diaza-spiro[4.5]dec-8-yl)-[1,2,4]triazolo[1,5-a]pyrazin-2-ylamino]-3,4-dihydro-1H-quinazolin-2-one |
| E46 | 4,4-dimethyl-7-[8-(2-oxo-1-oxa-3,8-diaza-spiro[4.5]dec-8-yl)-[1,2,4]triazolo[1,5-a]pyrazin-2-ylamino]-3,4-dihydro-1H-quinolin-2-one |
| E47 | 4,4-dimethyl-7-[8-(2-oxo-1-oxa-3,8-diaza-spiro[4.5]dec-8-yl)-[1,2,4]triazolo[1,5-a]pyrazin-2-ylamino]-1,4-dihydro-benzo[d][1,3]oxazin-2-one |
| E48 | (R)-7-[2-(4,4-dimethyl-2-oxo-1,2,3,4-tetrahydro-quinolin-7-ylamino)-[1,2,4]triazolo[1,5-a]pyrazin-8-yl]-2,7-diaza-spiro[4.4]nonane-1,3-dione |
| E49 | (S)-7-[2-(4,4-dimethyl-2-oxo-1,2,3,4-tetrahydro-quinolin-7-ylamino)-[1,2,4]triazolo[1,5-a]pyrazin-8-yl]-2,7-diaza-spiro[4.4]nonane-1,3-dione |
| E51 | 3,3-dimethyl-6-[8-((R)-8-oxo-2,7-diaza-spiro[4.4]non-2-yl)-[1,2,4]triazolo[1,5-a]pyrazin-2-ylamino]-1,3-dihydro-indol-2-one |
| E52 | 3,3-dimethyl-6-[8-((S)-8-oxo-2,7-diaza-spiro[4.4]non-2-yl)-[1,2,4]triazolo[1,5-a]pyrazin-2-ylamino]-1,3-dihydro-indol-2-one |

-continued

| nr. | name |
|---|---|
| E53 | 8-[2-(4,4-dimethyl-1,2,3,4-tetrahydro-quinolin-7-ylamino)-[1,2,4]triazolo[1,5-a]pyrazin-8-yl]-1-oxa-3,8-diaza-spiro[4.5]decan-2-one |
| E54 | 8-[2-(5,5-dimethyl-5,6,7,8-tetrahydro-naphthalen-2-ylamino)-[1,2,4]triazolo[1,5-a]pyrazin-8-yl]-1-oxa-3,8-diaza-spiro[4.5]decan-2-one |
| E55 | 8-[2-(4,4-dimethyl-chroman-7-ylamino)-[1,2,4]triazolo[1,5-a]pyrazin-8-yl]-1-oxa-3,8-diaza-spiro[4.5]decan-2-one |
| E58 | 3,3-dimethyl-6-[8-(4-methyl-2-oxa-3,9-diaza-spiro[5.5]undec-3-en-9-yl)-[1,2,4]triazolo[1,5-a]pyrazin-2-ylamino]-1,3-dihydro-indol-2-one |
| E61 | 8-[2-(5-methoxy-3aH-indol-6-ylamino)-[1,2,4]triazolo[1,5-a]pyrazin-8-yl]-1-oxa-3,8-diaza-spiro[4.5]decan-2-one |
| E63 | 8-[2-(3,3-dimethyl-2-oxo-2,3-dihydro-1H-indol-6-ylamino)-[1,2,4]triazolo[1,5-a]pyrazin-8-yl]-2,8-diaza-spiro[4.5]decan-3-one |
| E71 | 8-[2-(3,3-dimethyl-2-oxo-2,3-dihydro-1H-indol-6-ylamino)-[1,2,4]triazolo[1,5-a]pyrazin-8-yl]-2-methyl-1,3,8-triaza-spiro[4.5]dec-1-en-4-one |
| E77 | 8-[2-(4,4-dimethyl-1,2,3,4-tetrahydro-quinolin-7-ylamino)-[1,2,4]triazolo[1,5-a]pyrazin-8-yl]-2,8-diaza-spiro[4.5]decan-3-one |
| E86 | (S)-7-[2-(4,4-dimethyl-1,2,3,4-tetrahydro-quinolin-7-ylamino)-[1,2,4]triazolo[1,5-a]pyrazin-8-yl]-2,7-diaza-spiro[4.4]nonan-3-one |
| E87 | 6-[8-(2,7-diaza-spiro[4.4]non-2-yl)-[1,2,4]triazolo[1,5-a]pyrazin-2-ylamino]-3,3-dimethyl-1,3-dihydro-indol-2-one |
| E101 | (R)-7-[2-(4,4-dimethyl-1,2,3,4-tetrahydro-quinolin-7-ylamino)-[1,2,4]triazolo[1,5-a]pyrazin-8-yl]-2,7-diaza-Spiro[4.4]nonan-3-one |
| E105 | 6-[(S)-8-(2,7-diaza-spiro[4.4]non-2-yl)-[1,2,4]triazolo[1,5-a]pyrazin-2-ylamino]-3,3-dimethyl-1,3-dihydro-indol-2-one |
| E106 | 6-[(R)-8-(2,7-diaza-spiro[4.4]non-2-yl)-[1,2,4]triazolo[1,5-a]pyrazin-2-ylamino]-3,3-dimethyl-1,3-dihydro-indol-2-one |
| E112 | 3,3-dimethyl-6-[8-(2-oxo-1-oxa-3,7-diaza-spiro[4.4]non-7-yl)-[1,2,4]triazolo[1,5-a]pyrazin-2-ylamino]-1,3-dihydro-indol-2-one |
| E120 | 2-[2-(3,3-dimethyl-2-oxo-2,3-dihydro-1H-indol-6-ylamino)-[1,2,4]triazolo[1,5-a]pyrazin-8-yl]-6-oxa-2,9-diaza-spiro[4.5]decan-8-one |
| E130 | 6-[8-(5-Chloro-spiro[indole-3,3'-pyrrolidin]-1-yl)-[1,2,4]triazolo[1,5-a]pyrazin-2-ylamino]-3,3-dimethyl-1,3-dihydro-indol-2-one |
| E141 | 2-[2-(3,3-dimethyl-2-oxo-2,3-dihydro-1H-indol-6-ylamino)-[1,2,4]triazolo[1,5-a]pyrazin-8-yl]-2,8-diaza-spiro[4.5]decan-1-one |
| E153 | 3,3-dimethyl-6-[8-((S)-8-trifluoromethyl-2,7-diaza-spiro[4.4]non-2-yl)-[1,2,4]triazolo[1,5-a]pyrazin-2-ylamino]-1,3-dihydro-indol-2-one |

and pharmaceutically acceptable solvates, salts, tautomers and stereoisomers thereof, including mixtures thereof in all ratios.

2. A medicament comprising at least one compound according to claim 1 and/or pharmaceutically acceptable salts, solvates, tautomers and stereoisomers thereof, including mixtures thereof in all ratios, and optionally a pharmaceutically acceptable carrier, excipient or vehicle.

3. A medicament comprising at least one compound according to claim 1, including mixtures thereof in all ratios, and at least one further medicament active ingredient.

4. A set (kit) consisting of separate packs of (a) an effective amount of a compound according to claim 1, including mixtures thereof in all ratios, and (b) an effective amount of a further medicament active ingredient.

* * * * *